(12) United States Patent
Wilson et al.

(10) Patent No.: US 12,338,451 B2
(45) Date of Patent: Jun. 24, 2025

(54) COMPOSITIONS USEFUL IN TREATMENT OF METACHROMATIC LEUKODYSTROPHY

(71) Applicant: The Trustees of the University of Pennsylvania, Philadelphia, PA (US)

(72) Inventors: James M. Wilson, Philadelphia, PA (US); Juliette Hordeaux, Philadelphia, PA (US)

(*) Notice: Subject to any disclaimer, the term of this patent is extended or adjusted under 35 U.S.C. 154(b) by 713 days.

(21) Appl. No.: 17/608,493

(22) PCT Filed: May 2, 2020

(86) PCT No.: PCT/US2020/031207
§ 371 (c)(1),
(2) Date: Nov. 3, 2021

(87) PCT Pub. No.: WO2020/227166
PCT Pub. Date: Nov. 12, 2020

(65) Prior Publication Data
US 2022/0228170 A1 Jul. 21, 2022

Related U.S. Application Data

(60) Provisional application No. 62/843,091, filed on May 3, 2019.

(51) Int. Cl.
| C12N 15/86 | (2006.01) |
| A61K 47/02 | (2006.01) |
| A61K 48/00 | (2006.01) |
| A61P 25/28 | (2006.01) |
| C12N 9/16 | (2006.01) |

(52) U.S. Cl.
CPC .............. *C12N 15/86* (2013.01); *A61K 47/02* (2013.01); *A61P 25/28* (2018.01); *C12N 9/16* (2013.01); *C12Y 301/06001* (2013.01); *A61K 48/00* (2013.01); *C12N 2750/14121* (2013.01); *C12N 2750/14122* (2013.01); *C12N 2750/14143* (2013.01); *C12N 2750/14171* (2013.01); *C12N 2830/42* (2013.01); *C12N 2830/50* (2013.01)

(58) Field of Classification Search
CPC ................................ C12N 15/86; A61P 25/28
See application file for complete search history.

(56) References Cited

U.S. PATENT DOCUMENTS

| 5,139,941 A | 8/1992 | Muzyczka et al. |
| 5,741,683 A | 4/1998 | Zhou et al. |
| 6,057,152 A | 5/2000 | Samulski et al. |
| 6,204,059 B1 | 3/2001 | Samulski et al. |
| 6,268,213 B1 | 7/2001 | Samulski et al. |
| 6,491,907 B1 | 12/2002 | Rabinowitz et al. |
| 6,596,535 B1 | 7/2003 | Carter |
| 6,660,514 B1 | 12/2003 | Zolotukhin et al. |
| 6,951,753 B2 | 10/2005 | Shenk et al. |
| 7,094,604 B2 | 8/2006 | Snyder et al. |
| 7,125,717 B2 | 10/2006 | Carter |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,439,065 B2 | 10/2008 | Ferrari et al. |
| 7,456,683 B2 | 11/2008 | Takano et al. |
| 7,588,772 B2 | 9/2009 | Kay et al. |
| 7,906,111 B2 | 3/2011 | Wilson et al. |
| 8,734,809 B2 | 5/2014 | Gao et al. |
| 8,927,514 B2 | 1/2015 | Chatterjee et al. |
| 2008/0003211 A1 | 1/2008 | Fogh et al. |
| 2013/0045186 A1 | 2/2013 | Gao et al. |
| 2014/0206755 A1 | 7/2014 | Bancel et al. |
| 2015/0344911 A1 | 12/2015 | Chatterjee et al. |
| 2018/0071373 A1 | 3/2018 | McIvor et al. |
| 2020/0056159 A1 | 2/2020 | Wilson et al. |

FOREIGN PATENT DOCUMENTS

| JP | 2013-538788 | 10/2013 |
| WO | WO 2000/026393 | 5/2000 |
| WO | WO 2002/098455 | 12/2002 |
| WO | WO-2003/042397 | 5/2003 |
| WO | WO-2005/033321 | 4/2005 |
| WO | WO-2006/110689 | 10/2006 |

(Continued)

OTHER PUBLICATIONS

Hordeaux, Juliette, et al. "Efficacy and safety of a Krabbe disease gene therapy." Human gene therapy 33.9-10 (2022): 499-517. (Year: 2022).*

Ellison, Stuart, H. Parker, and B. Bigger. "Advances in therapies for neurological lysosomal storage disorders." Journal of Inherited Metabolic Disease 46.5 (2023): 874-905. (Year: 2023).*

Absoud et al., "Paediatric UK demyelinating disease longitudinal study (PUDDLS)," BMC Pediatrics, vol. 11(1):68, Jul. 2011.

Audentes, "Audentes announces continuing positive data from first dose cohort of ASPIRO, a Phase 1/2 clinical trial of AT132 in patients with X-linked myotubular myopathy," May 2018.

Bartus et al., "Parkinson's disease gene therapy: Success by design meets failure by efficacy," Mol Ther., vol. 22(3): 487-497, Mar. 2014.

(Continued)

*Primary Examiner* — Kevin K Hill
*Assistant Examiner* — Allison Marie Johnson
(74) *Attorney, Agent, or Firm* — HOWSON & HOWSON LLP; Cathy A Kodroff

(57) ABSTRACT

Provided is a recombinant adeno-associated virus (rAAV) having an AAVhu68 capsid and a vector genome which comprises a nucleic acid sequence encoding a functional human arylsulfatase A (ARSA). Also provided are a production system useful for producing the rAAV, a pharmaceutical composition comprising the rAAV, and a method of treating a subject having metachromatic leukodystrophy, or ameliorating symptoms of metachromatic leukodystrophy, or delaying progression of metachromatic leukodystrophy via administering an effective amount of rAAV to a subject in need thereof.

28 Claims, 11 Drawing Sheets

Specification includes a Sequence Listing.

(56) References Cited

FOREIGN PATENT DOCUMENTS

| | | |
|---|---|---|
| WO | WO-2011/126808 | 10/2011 |
| WO | WO 2011/163650 | 12/2011 |
| WO | WO-2013/096899 | 6/2013 |
| WO | WO-2016/049230 | 3/2016 |
| WO | WO-2017/160360 | 9/2017 |
| WO | WO-2018/160582 | 9/2018 |
| WO | WO-2020/132455 | 6/2020 |

OTHER PUBLICATIONS

Bell et al., "Analysis of tumors arising in male B6C3F1 mice with and without AAV vector delivery to liver," Mol Ther., vol. 14(1):34-44, Jul. 2006.

Bell et al., "No evidence for tumorigenesis of AAV vectors in a large-scale study in mice," Mol Ther., vol. 12(2):299-306, Aug. 2005.

Bell et al., "The AAV9 receptor and its modification to improve in vivo lung gene transfer in mice," J Clin Invest., vol. 121:2427-2435, Jun. 2011.

Bevan et al., "Systemic gene delivery in large species for targeting spinal cord, brain, and peripheral tissues for pediatric disorders," Mol Ther., vol. 19(11):1971-80, Nov. 2011.

Biffi et al., "Correction of metachromatic leukodystrophy in the mouse model by transplantation of genetically modified hematopoietic stem cells," J Clin Invest., vol. 113(8):1118-29, Apr. 2004.

Biffi, "Hematopoietic stem cell gene therapy for storage disease: Current and new indications," Mol Ther., vol. 25(5):1155-1162, May 2017.

Blobel et al., "Transfer of proteins across membranes. I. Presence of proteolytically processed and unprocessed nascent immunoglobulin light chains on membrane-bound ribosomes of murine myeloma," J Cell Biol., vol. 67 (3): 835-51, Dec. 1975.

Boucher et al., "Long-term outcomes after allogeneic hematopoietic stem cell transplantation for metachromatic leukodystrophy: the largest single-institution cohort report," Orphanet J Rare Dis., vol. 10:94, Aug. 2015.

Bryant et al., "Lessons learned from the clinical development and market authorization of Glybera," Hum Gene Ther Clin Dev., vol. 24(2):55-64, Jun. 2013.

Buning et al., "Recent developments in adeno-associated virus vector technology," J. Gene Med. 10:717-733, May 2008.

Calcedo et al., "Worldwide epidemiology of neutralizing antibodies to adeno-associated viruses," J Infect Dis., vol. 199(3):381-90, Feb. 2009.

Carter, Handbook of Parvoviruses (ed., P. Tijsser), CRC Press, pp. 155-168, Jan. 1990.

Castle et al., "Long-distance axonal transport of AAV9 is driven by dynein and kinesin-2 and is trafficked in a highly motile Rab7-positive compartment," Mol Ther., vol. 22(3):554-566, Mar. 2014.

Cearley et al., "Expanded repertoire of AAV vector serotypes mediate unique patterns of transduction in mouse brain," Mol Ther., vol. 16(10):1710-8, Oct. 2008.

Cesani et al., "Characterization of new arylsulfatase A gene mutations reinforces genotype-phenotype correlation in metachromatic leukodystrophy," Hum Mutat., vol. 30(10):E936-45, Oct. 2009.

Chandler et al., "Vector design influences hepatic genotoxicity after adeno-associated virus gene therapy," J Clin Invest., vol. 125(2):870-80, Feb. 2015.

Ciesielska et al., "Cerebral infusion of AAV9 vector-encoding non-self proteins can elicit cell-mediated immune responses," Mol Ther., vol. 21(1):158-66, Jan. 2013.

Colle et al., "Efficient intracerebral delivery of AAV5 vector encoding human ARSA in non-human primate," Hum Mol Genet., vol. 19(1):147-58, Jan. 2010.

Couto et al., "Direct exposure of mouse spermatozoa to very high concentrations of a serotype-2 adeno-associated virus gene therapy vector fails to lead to germ cell transduction," Hum Gene Ther., vol. 15(3):287-91, Mar. 2004.

Dekaban, "Changes in brain weights during the span of human life: relation of brain weights to body heights and body weights," Ann Neurol., vol. 4(4):345-56, Oct. 1978.

Deverman et al., "Cre-dependent selection yields AAV variants for widespread gene transfer to the adult brain," Nat Biotechnol., vol. 34(2):204-9, Feb. 2016.

Donsante et al., "Observed incidence of tumorigenesis in long-term rodent studies of rAAV vectors," Gene Ther., vol. 8(17):1343-6, Sep. 2001.

Ellinwood et al., "Safe, efficient, and reproducible gene therapy of the brain in the dog models of Sanfilippo and Hurler syndromes," Mol Ther., vol. 19(2):251-9, Feb. 2011.

Ferla et al., "Non-clinical safety and efficacy of an AAV2/8 vector administered intravenously for treatment of Mucopolysaccharidosis Type VI," Mol Ther Methods Clin Dev., Vo.1 6:143-158, Jul. 2017.

Fisher et al., "Transduction with recombinant adeno-associated virus for gene therapy is limited by leading-strand synthesis," J. Virol., vol. 70:520-532, Jan. 1996.

Flanigan, "Update on Phase I/II Gene Transfer Clinical Trial of Systemic Gene Transfer of scAAV9.Ula.hSGSH for MPSIIIA (Sanfilippo Syndrome) (Abstract/Agenda Summary)," Voyager Therapeutics Corporate Presentation, ASGCT Annual Meeting, May 2018.

Foust et al., "Intravascular AAV9 preferentially targets neonatal neurons and adult astrocytes," Nat Biotechnol., vol. 27(1):59-65, Jan. 2009.

Frate et al., "Human iPSC-based models highlight defective glial and neuronal differentiation from neural progenitor cells in metachromatic leukodystrophy," Cell Death Dis., vol. 9(6):698, Jun. 2018.

Gallo et al., "Late onset MLD with normal nerve conduction associated with two novel missense mutations in the ASA gene," J Neurol Neurosurg Psychiatry, vol. 75(4): 655-7, Apr. 2004.

Gao et al., "Clades of adeno-associated viruses are widely disseminated in human tissues," J Virol., vol. 78(12):6381-8, Jun. 2004.

Gao et al., "Adeno-associated viruses undergo substantial evolution in primates during natural infections," Proc. Natl. Acad. Sci. U.S.A., vol. 100 (10):6081-6086, May 2003.

GenBank, "AB448736.1—*Homo sapiens* ARSA mRNA for arylsulfatase A, complete cds," Aug. 2011.

GenBank, "AK092752.1—*Homo sapiens* cDNA FLJ35433 fis, clone SMINT2002314, highly similar to Arylsulfatase a Precursor (EC 3.1.6.8)," Jan. 2008.

GenBank, "AK098659.1—*Homo sapiens* cDNA FLJ25793 fis, clone TST06976, highly similar to Arylsulfatase a Precursor (EC 3.1.6. 8)," Sep. 2006.

GenBank, "AK301098.1—*Homo sapiens* cDNA FLJ57896 complete cds, highly similar to Arylsulfatase A precursor (EC 3.1.6.8)," Jul. 2008.

Genbank, "AK310564.1—*Homo sapiens* cDNA, FLJ17606," Jan. 2008.

GenBank, "AK315011.1—*Homo sapiens* cDNA, FLJ95943, *Homo sapiens* arylsulfatase A (ARSA), mRNA," May 2008.

GenBank, "BC014210.2—*Homo sapiens* arylsulfatase A, mRNA (cDNA clone MGC:20637 IMAGE:4763974), complete cds," Jul. 2006.

GenBank, "BI770997.1—03055340F1 NIH_MGC_122 *Homo sapiens* cDNA clone IMAGE:5204985 5', mRNA sequence," Sep. 2001.

Genbank, "BM818814.1—K-EST0086413 S18N669761 *Homo sapiens* cDNA clone S18N669761-16-A05 5', mRNA sequence," Feb. 2011.

Genbank, "BP306351.1—BP306351 Sugano cDNA library, macrophage *Homo sapiens* cDNA clone MPG07168 5', mRNA sequence," Feb. 2011.

Genbank, "BQ184813.1—UI-E-EJ1-ajt-f-17-0-UI.s1 UI-E-EJ1 *Homo sapiens* cDNA clone UI-E-EJ1-ajt-f-17-0-UI 3', mRNA sequence," Jan. 2011.

Genbank, "BU632196.1—UI-H-FE1-bea-1-05-0-UI.s1 NCI_CGAP_FE1 *Homo sapiens* cDNA clone UI-H-FE1-bea-1-05-0-UI 3', mRNA sequence," Jan. 2011.

Genbank, "BX648618.1—*Homo sapiens* mRNA; cDNA DKFZp686G12235 (from clone DKFZp686G12235)," Oct. 2008.

(56) References Cited

OTHER PUBLICATIONS

Genbank, "CA423492.1—UI-H-FE1-bec-f-15-0-UI.s1 NCI CGAP FE1 *Homo sapiens* cDNA clone UI-H-FE1-bec-f-15-0-UI 3', mRNA sequence," Jan. 2011.
Genbank, "CN409235.1—17000600004063 GRN_PRENEU *Homo sapiens* cDNA 5', mRNA sequence," Feb. 2011.
Genbank, "CR456383.1—*Homo sapiens* ARSA full length open reading frame (ORF) cDNA clone (cDNA clone C22ORF:pGEM. ARSA. V2)," Oct. 2008.
Genbank, "DA844740.1—DA844740 PLACE6 *Homo sapiens* cDNA clone PLACE6012731 5', mRNA sequence," Feb. 2011.
Genbank, "DB028013.1—DB028013 TESTI2 *Homo sapiens* cDNA clone TESTI2010741 5', mRNA sequence," Feb. 2011.
Genbank, "GQ891416.1—*Homo sapiens* clone HEL-S-137 epididymis secretory sperm binding protein mRNA, complete cds," Sep. 2018.
GenBank, "K03104.1—Human cytomegalovirus major immediate-early gene, enhancer," Aug. 1993.
Genbank, "KU177918.1—*Homo sapiens* arylsulfatase A isoform 1 (ARSA) mRNA, partial cds," Dec. 2015.
Genbank, "KU177919.1—*Homo sapiens* arylsulfatase A isoform 2 (ARSA) mRNA, complete cds, alternatively spliced," Dec. 2015.
GenBank, "NC_001401—Adeno-associated virus—2, complete genome," Aug. 2018.
Genbank, "NM_000487.5—*Homo sapiens* arylsulfatase A (ARSA), transcript variant 1, mRNA," Nov. 2018.
Genbank, "NM_001085425.2—*Homo sapiens* arylsulfatase A (ARSA), transcript variant 2, mRNA," Mar. 2019.
Genbank, "NM_001085426.2—*Homo sapiens* arylsulfatase A (ARSA), transcript variant 3, mRNA," Mar. 2019.
Genbank, "NM_001085427.2—*Homo sapiens* arylsulfatase A (ARSA), transcript variant 4, mRNA," Mar. 2019.
Genbank, "NM_001085428.2—*Homo sapiens* arylsulfatase A (ARSA), transcript variant 5, mRNA," Mar. 2019.
Genbank, "NM_001362782.1—*Homo sapiens* arylsulfatase A (ARSA), transcript variant 6, mRNA," Mar. 2019.
GenBank, "NP_000478.3—arylsulfatase A isoform a precursor [*Homo sapiens*]," Jun. 2022.
GenBank, "V00882.1—Rabbit (*O. cuniculus*) gene for beta-globin," Nov. 2006.
GenBank, "X00182.1—Gallus gallus cytoplasmic beta-actin gene," Nov. 2006.
Genbank, "X52151.1—*Homo sapiens* arylsulphatase A mRNA, complete cds," Oct. 2008.
GeneCards.org, "ARSA Gene—Arylsulfatase A," Dec. 2010, retrieved on Jul. 22, 2022 from genecards.org/cgi-bin/carddisp.pl?gene=ARSA.
Gieselmann et al., "Arylsulfatase A pseudodeficiency: loss of a polyadenylation signal and N-glycosylation site," Proc Natl Acad Sci U S A., vol. 86(23):9436-40, Dec. 1989.
Gil-Farina et al., "Recombinant AAV integration is not associated with hepatic genotoxicity in nonhuman primates and patients," Mol Ther., vol. 24(6):1100-1105, Jun. 2016.
Godel et al., "Human dorsal-root-ganglion perfusion measured in-vivo by MRI," Neuroimage, vol. 141:81-87, Nov. 2016.
Gombash et al., "Systemic gene delivery transduces the enteric nervous system of guinea pigs and cynomolgus macaques," Gene Ther., vol. 24(10):640-648, Oct. 2017.
Gomez-Ospina, "Arylsulfatase A Deficiency," GeneReviews (eds. Adam et al.), Seattle, WA: University of Washington, Seattle, May 2016.
Graham et al., "Characteristics of a human cell line transformed by DNA from human adenovirus type 5," J Gen Virol., vol. 36(1):59-74, Jul. 1977.
Gray et al., "Global CNS gene delivery and evasion of anti-AAV-neutralizing antibodies by intrathecal AAV administration in non-human primates," Gene Ther., vol. 20(4):450-9, Apr. 2013.
Gray et al., "Preclinical differences of intravascular AAV9 delivery to neurons and glia: a comparative study of adult mice and nonhuman primates," Mol Ther., vol. 19(6):1058-69, Jun. 2011.

Greig et al., "Non-clinical study examining AAV8.TBG.hLDLR vector-associated toxicity in chow-fed wild-type and LDLR(+/−) Rhesus macaques," Hum Gene Ther Clin Dev., vol. 28(1):39-50, Mar. 2017.
Greiger et al., "Adeno-associated virus as a gene therapy vector: Vector development, production and clinical applications," Adv. Biochem. Engin/Biotechnol., vol. 99: 119-145, Oct. 2005.
Grimm et al., "Titration of AAV-2 particles via a novel capsid ELISA: packaging of genomes can limit production of recombinant AAV-2," Gene Therapy, vol. 6:1322-1330, Jul. 1999.
Gu et al., "Absence of PTHrP nuclear localization and carboxyl terminus sequences leads to abnormal brain development and function," PLoS One, vol. 7(7):e41542, Jul. 2012.
Gurda et al., "Evaluation of AAV-mediated gene therapy for central nervous system disease in canine Mucopolysaccharidosis VII," Mol Ther., vol. 24(2):206-216, Feb. 2016 (ePub Oct. 2015).
Guvenet et al., "A simple composite phenotype scoring system for evaluating mouse models of cerebellar ataxia," J Vis Exp., vol. 39, May 2010.
Hageman et al., "Clinical symptoms of adult metachromatic leukodystrophy and arylsulfatase A pseudodeficiency," Arch Neurol., vol. 52(4):408-13, Apr. 1995.
Haurigot et al., "Whole body correction of mucopolysaccharidosis IIIA by intracerebrospinal fluid gene therapy," J Clin Invest., Aug. 2013.
Hess et al., "Phenotype of arylsulfatase A-deficient mice: relationship to human metachromatic leukodystrophy," Proc Natl Acad Sci U S A., vol. 93(25):14821-6, Dec. 1996.
Hinderer et al., "Evaluation of intrathecal routes of administration for adeno-associated viral vectors in large animals," Hum Gene Ther., vol. 29(1):15-24, Jan. 2018.
Hinderer et al., "Widespread gene transfer in the central nervous system of cynomolgus macaques following delivery of AAV9 into the cisterna magna," Mol Ther Methods Clin Dev., vol. 1:14051, Dec. 2014.
Hordeaux et al., "The GPI-Linked Protein LY6A Drives AAV-PHP.B Transport across the Blood-Brain Barrier," Molec Ther., May 2019.
Hordeaux et al., "Toxicology study of intra-cisterna magna adeno-associated virus 9 expressing human alpha-L-iduronidase in Rhesus macaques," Mol Ther Methods Clin Dev., vol. 10:79-88, Jul. 2018.
Iannaccone et al., "The PedsQL in pediatric patients with Spinal Muscular Atrophy: feasibility, reliability, and validity of the Pediatric Quality of Life Inventory Generic Core Scales and Neuromuscular Module," Neuromuscular disorders : NMD., vol. 19(12): 805-812, Dec. 2009.
Jabbehdari et al., "The clinical features and diagnosis of Metachromatic leukodystrophy: A case series of Iranian Pediatric Patients," Iran J Child Neurol., vol. 9(3):57-61, Jun. 2015.
Jakob et al., "No evidence for germ-line transmission following prenatal and early postnatal AAV-mediated gene delivery," J Gene Med., vol. 7(5):630-7, May 2005.
Janson et al., "Clinical protocol. Gene therapy of Canavan disease: AAV-2 vector for neurosurgical delivery of aspartoacylase gene (ASPA) to the human brain," Hum Gene Ther., vol. 13(11):1391-412, Jul. 2002.
Jin et al., "Direct Liquid Chromatography/Mass Spectrometry Analysis for Complete Characterization of Recombinant Adeno-Associated Virus Capsid Proteins," Hu Gene Therapy Methods, vol. 28(5):255-267, Oct. 2017 (ePub Jun. 2017).
Josenby et al., "Longitudinal construct validity of the GMFM-88 total score and goal total score and the GMFM-66 score in a 5-year follow-up study," Phys Ther., vol. 89(4):342-50, Apr. 2009.
Kehrer et al., "Development and reliability of a classification system for gross motor function in children with metachromatic leukodystrophy," Dev Med Child Neurol., vol. 53(2):156-60, Feb. 2011.
Kehrer et al., "Language and cognition in children with metachromatic leukodystrophy: onset and natural course in a nationwide cohort," Orphanet J Rare Dis., vol. 9:18, Feb. 2014.
Kreysing et al., "High residual arylsulfatase A (ARSA) activity in a patient with late-infantile metachromatic leukodystrophy," Am J Hum Genet., vol. 53(2):339-46, Aug. 1993.

(56) References Cited

OTHER PUBLICATIONS

Kruse et al., "Alterations of brain metabolites in metachromatic leukodystrophy as detected by localized proton magnetic resonance spectroscopy in vivo," J Neurol., vol. 241(2):68-74, Dec. 1993.
Kumperscak et al., "Adult metachromatic leukodystrophy: disorganized schizophrenia-like symptoms and postpartum depression in 2 sisters," J Psychiatry Neurosci., vol. 30(1):33-6, Jan. 2005.
Lawlor et al., "Efficient gene delivery and selective transduction of glial cells in the mammalian brain by AAV serotypes isolated from nonhuman primates," Mol Ther., vol. 17(10):1692-702, Oct. 2009.
Li et al., "Adeno-associated virus capsid antigen presentation is dependent on endosomal escape," J Clin Invest., vol. 123(3):1390-401, Mar. 2013.
Li et al., "Assessing the potential for AAV vector genotoxicity in a murine model," Blood, vol. 117(12):3311-9, Mar. 2011.
Lock et al., "Absolute determination of single-stranded and self-complementary adeno-associated viral vector genome titers by droplet digital PCR," Hum Gene Ther Methods, vol. 25(2):115-25, Apr. 2014 (ePub Feb. 2014).
Lock et al., "Rapid, Simple, and Versatile Manufacturing of Recombinant Adeno-Associated Viral Vectors at Scale," Human Gene Therapy, vol. 21:1259-1271, Oct. 2010.
Lugowska et al., "Population carrier rates of pathogenic ARSA gene mutations: is metachromatic leukodystrophy underdiagnosed?" PLoS One, vol. 6(6):e20218, Jun. 2011.
Mahmood et al., "Metachromatic leukodystrophy: a case of triplets with the late infantile variant and a systematic review of the literature," J Child Neurol., vol. 25(5):572-80, May 2010.
Marcao et al., "Adult onset metachromatic leukodystrophy without electroclinical peripheral nervous system involvement: a new mutation in the ARSA gene," Arch Neurol., vol. 62(2):309-13, Feb. 2005.
Martin et al., "Neurodevelopmental outcomes of umbilical cord blood transplantation in metachromatic leukodystrophy," Biol Blood Marrow Transplant, vol. 19(4):616-24, Apr. 2013.
Martin et al., "Toward a better understanding of brain lesions during metachromatic leukodystrophy evolution," AJNR Am J Neuroradiol., vol. 33(9):1731-9, Oct. 2012.
Matthes et al., "Efficacy of enzyme replacement therapy in an aggravated mouse model of metachromatic leukodystrophy declines with age," Hum Mol Genet., vol. 21(11):2599-609, Jun. 2012.
Matzner et al., "Enzyme replacement improves ataxic gait and central nervous system histopathology in a mouse model of metachromatic leukodystrophy," Mol Ther., vol. 17(4):600-6, Apr. 2009.
Matzner et al., "Enzyme replacement improves nervous system pathology and function in a mouse model for metachromatic leukodystrophy," Hum Mol Genet., vol. 14(9):1139-52, May 2005.
McCarty et al., "Integration of adeno-associated virus (AAV) and recombinant AAV vectors," Annu Rev Genet., vol. 38:819-45, Aug. 2004.
McCarty et al., "Self-complementary recombinant adeno-associated virus (scAAV) vectors promote efficient transduction independently of DNA synthesis," Gene Therapy, vol. 8(16):1248-1254, Aug. 2001.
Melnick et al., "Association of 20 milli-micron particles with adenoviruses," J Bacteriol., vol. 90(1):271-4, 1965.
Mendell et al., "Single-dose gene-replacement therapy for spinal muscular atrophy," N Engl J Med., vol. 377(18):1713-1722, Nov. 2017.
Miller, "Glybera and the future of gene therapy in the European Union," Nat Rev Drug Discov., vol. 11(5):419, May 2012.
Mittermeyer et al., "Long-term evaluation of a Phase 1 study of AADC gene therapy for Parkinson's disease," Hum Gene Ther., vol. 23(4):377-81, Apr. 2012.
Nathwani et al., "Adenovirus-associated virus vector-mediated gene transfer in hemophilia B," N Engl J Med., vol. 365(25):2357-65, Dec. 2011.
Nault et al., "Wild-type AAV Insertions in Hepatocellular Carcinoma Do Not Inform Debate Over Genotoxicity Risk of Vectorized AAV," Mol Ther., vol. 24(4):660-1, Apr. 2016.

OMIM.org, "# 250100: Metachromatic Leukodystrophy," Jun. 1986 (last edit Sep. 2021), retrieved Jul. 22, 2022 from omim.org/entry/250100.
OMIM.org, "# 607574: Arylsulfatase A; ARSA," Feb. 2003 (last update May 2008), retrieved Jul. 22, 2022 from omim.org/entry/607574.
Palisano et al., "Stability of the gross motor function classification system," Dev Med Child Neurol., vol. 48(6):424-8, Jun. 2006.
Passini et al., "Intracranial delivery of CLN2 reduces brain pathology in a mouse model of classical late infantile neuronal ceroid lipofuscinosis," J Neurosci., vol. 26(5):1334-42, Feb. 2006.
Patil et al., "Developing therapeutic approaches for metachromatic leukodystrophy," Drug Des Devel Ther., vol. 7:729-45, Aug. 2013.
Penaud-Budloo et al., "Adeno-associated virus vector genomes persist as episomal chromatin in primate muscle," J Virol., vol. 82(16):7875-85, Aug. 2008.
Piguet et al., "Correction of brain oligodendrocytes by AAVrh. 10 intracerebral gene therapy in metachromatic leukodystrophy mice," Hum Gene Ther., vol. 23(8):903-14, Aug. 2012.
Pinto et al., "Prevalence of lysosomal storage diseases in Portugal," Eur J Hum Genet., vol. 12(2):87-92, Feb. 2004.
Polten et al., "Molecular basis of different forms of metachromatic leukodystrophy," N Engl J Med., vol. 324(1):18-22, Jan. 1991.
Rafi et al., "Extended normal life after AAVrh10-mediated gene therapy in the mouse model of Krabbe disease," Mol Ther., vol. 20(11):2031-42, Nov. 2012.
Ramakrishnan et al., "Increasing sulfatide synthesis in myelin-forming cells of arylsulfatase A-deficient mice causes demyelination and neurological symptoms reminiscent of human metachromatic leukodystrophy," J Neurosci., vol. 27(35):9482-90, Aug. 2007.
Rangarajan et al., "AAV5-Factor VIII gene transfer in severe hemophilia A," N Engl J Med., vol. 377(26):2519-2530, Dec. 2017.
Regenxbio, "Regenxbio reports fourth quarter and full-year 2018 financial results and recent operational highlights," Feb. 2019.
Rosas et al., "Patterns of scAAV vector insertion associated with oncogenic events in a mouse model for genotoxicity," Mol Ther., vol. 20(11):2098-2110, Nov. 2012.
Rosenberg et al., "Gene therapy for metachromatic leukodystrophy," J Neurosci Res., vol. 94(11):1169-79, Nov. 2016.
Samaranch et al., "Strong cortical and spinal cord transduction after AAV7 and AAV9 delivery into the cerebrospinal fluid of nonhuman primates," Hum Gene Ther., vol. 24(5):526-32, May 2013.
Sands, "A Hitchhiker's guide to the blood-brain barrier: in trans delivery of a therapeutic enzyme," Mol Ther., vol. 22(3):483-484, Mar. 2014.
Saunders et al., "Cisternal or suboccipital puncture: A report of 2019 punctures," New England Journal of Medicine, vol. 201:166-168, 1929.
Schuster et al., "Biodistribution of adeno-associated virus serotype 9 (AAV9) vector after intrathecal and intravenous delivery in mouse," Front Neuroanat., vol. 8:42, Jun. 2014.
Sessa et al., "Lentiviral haemopoietic stem-cell gene therapy in early-onset metachromatic leukodystrophy: an ad-hoc analysis of a non-randomised, open-label, phase 1/2 trial," Lancet, vol. 388(10043):476-87, Jul. 2016.
Sommer et al., "Quantification of adeno-associated virus particles and empty capsids by optical density measurement," Molec. Ther., vol. 7:122-128, Jan. 2003.
Spark, "European Commission approves Spark Therapeutics' Luxturna® (voretigene neparvovec), a one-time gene therapy for inherited retinal disease caused by confirmed biallelic RPE65 mutations," 2018.
Strolin et al., "Demyelination load as predictor for disease progression in juvenile metachromatic leukodystrophy," Ann Clin Transl Neurol., vol. 4(6):403-410, May 2017.
Stroobants et al., "Intracerebroventricular enzyme infusion corrects central nervous system pathology and dysfunction in a mouse model of metachromatic leukodystrophy," Hum Mol Genet., vol. 20(14):2760-9, Jul. 2011.
Tardieu et al., "Intracerebral administration of adeno-associated viral vector serotype rh. 10 carrying human SGSH and SUMF1

(56) References Cited

OTHER PUBLICATIONS cDNAs in children with mucopolysaccharidosis type IIIA disease: results of a phase I/II trial," Hum Gene Ther., vol. 25(6):506-16, Jun. 2014.
Thomson et al., "A comprehensive comparison of multiple sequence alignments," Nucl. Acids. Res., vol. 27(13):2682-2690, Jul. 1999.
UNIPROT.org, "P15289 . ARSA_HUMAN," Feb. 1991, retrieved Jul. 22, 2022 from uniprot.org/uniprot/P15289.
Van Egmond et al., "Improvement of white matter changes on neuroimaging modalities after stem cell transplant in metachromatic leukodystrophy," JAMA Neurol., vol. 70(6): 779-82, Jun. 2013.
Varni et al., "The PedsQL Infant Scales: feasibility, internal consistency reliability, and validity in healthy and ill infants," Qual Life Res., vol. 20(1):45-55, Feb. 2011.
Vite et al., "Effective gene therapy for an inherited CNS disease in a large animal model," Ann Neurol., vol. 57(3):355-64, Mar. 2005.
Wang et al., "Lysosomal storage diseases: diagnostic confirmation and management of presymptomatic individuals," Genet Med., vol. 13(5):457-84, May 2011.
Wijnhoven et al., "Assessment of gross motor development in the WHO Multicentre Growth Reference Study," Food Nutr Bull., vol. 25(1 Suppl):S37-45, Mar. 2004.
Wobus et al., "Monoclonal antibodies against the adeno-associated virus type 2 (AAV-2) capsid: epitope mapping and identification of capsid domains involved in AAV-2-cell interaction and neutralization of AAV-2 infection," J. Virol., vol. 74:9281-9293, Oct. 2000.
Worgall et al., "Treatment of late infantile neuronal ceroid lipofuscinosis by CNS administration of a serotype 2 adeno-associated virus expressing CLN2 cDNA," Hum Gene Ther., vol. 19(5):463-74, May 2008.
Zanta-Boussif et al., "Validation of a mutated PRE sequence allowing high and sustained transgene expression while abrogating WHV-X protein synthesis: application to the gene therapy of WAS," Gene Therapy, vol. 16:605-619, May 2009.
Zerah et al., "Intracerebral Gene Therapy Using AAVrh. 10-hARSA Recombinant Vector to Treat Patients with Early-Onset Forms of Metachromatic Leukodystrophy: Preclinical Feasibility and Safety Assessments in Nonhuman Primates," Hum Gene Ther Clin Dev., vol. 26(2):113-24, Jun. 2015.
Zhang et al., "Adenovirus-adeno-associated virus hybrid for large-scale recombinant adeno-associated virus production," Human Gene Therapy, vol. 20:922-929, Sep. 2009.
U.S. Appl. No. 62/226,357, filed Dec. 11, 2015.
U.S. Appl. No. 62/322,071, filed Apr. 13, 2016.
U.S. Appl. No. 62/783,956, filed Dec. 21, 2018.
International Preliminary Report on Patentability issued on International Patent Application No. PCT/US2020/031207, dated Nov. 2, 2021.
International Search Report issued on International Patent Application No. PCT/US2020/031207, dated Aug. 14, 2020.
Abbott, "Blood-brain barrier structure and function and the challenges for CNS drug delivery," J Inherit Metab Dis., vol. 36(3):437-49, May 2013.
Albers et al., "Test Review: Bayley, N. (2006). Bayley Scales of Infant and Toddler Development—Third Edition. San Antonio, TX: Harcourt Assessment," J of Psychoed Assess. 25(2):180-190, Jun. 2007.
Alotaibi et al., "The efficacy of GMFM-88 and GMFM-66 to detect changes in gross motor function in children with cerebral palsy (CP): a literature review," Disabil Rehabil., vol. 36(8):617-27, 2014 (ePub Jun. 2013).
Arbour et al., "Variable onset of metachromatic leukodystrophy in a Vietnamese family," Pediatr Neurol., vol. 23(2):173-6, Aug. 2000.
Aubourg, "Gene therapy for leukodystrophy: progress, challenges and opportunities," Exp Opin Orph Drugs, vol. 4(4):359-367, Feb. 2016.
Batzios et al., "Developing treatment options for metachromatic leukodystrophy," Mol Genet Metab., vol. 105(1):56-63, Jan. 2012 (ePub Oct. 2011).
Baumann et al., "Motor and psycho-cognitive clinical types in adult metachromatic leukodystrophy: genotype/phenotype relationships?" J Physiol Paris., vol. 96(3-4):301-6, Apr. 2002.
Bell et al., "Motor neuron transduction after intracisternal delivery of AAV9 in a cynomolgus macaque," Hum Gene Ther Methods, vol. 26(2):43-4, Apr. 2015.
Biffi et al., "Lentiviral hematopoietic stem cell gene therapy benefits metachromatic leukodystrophy," Science, vol. 341(6148):1233158, Aug. 2013.
Biffi et al., "Metachromatic leukodystrophy—mutation analysis provides further evidence of genotype-phenotype correlation," Clin Genet., vol. 74(4):349-57, Oct. 2008.
Bisgaard et al., "Chromosomal deletion unmasking a recessive disease: 22q13 deletion syndrome and metachromatic leukodystrophy," Clin Genet., vol. 75(2):175-9, Feb. 2009.
Böhringer et al., "Enzymatic characterization of novel arylsulfatase A variants using human arylsulfatase A-deficient immortalized mesenchymal stromal cells," Hum Mutat., vol. 38(11):1511-1520, Nov. 2017 (Epub Sep. 2017).
Bredius et al., "Early marrow transplantation in a pre-symptomatic neonate with late infantile metachromatic leukodystrophy does not halt disease progression," Bone Marrow Transplant, vol. 39(5):309-10, Mar. 2007.
Cameron et al., "Multifocal slowing of nerve conduction in metachromatic leukodystrophy," Muscle Nerve, vol. 29(4):531-6, Apr. 2004.
Cesani et al., "Mutation Update of ARSA and PSAP Genes Causing Metachromatic Leukodystrophy," Hum Mutat., vol. 37(1):16-27, Jan. 2016.
Chen et al., "Outcome of Early Juvenile Onset Metachromatic Leukodystrophy After Unrelated Cord Blood Transplantation: A Case Series and Review of the Literature," J Child Neurol., vol. 31(3):338-44, Mar. 2016.
Clarke et al., "Marked clinical difference between two sibs affected with juvenile metachromatic leukodystrophy," Am J Med Genet., vol. 33(1):10-3, May 1989.
Dali et al., "Brain N-acetylaspartate levels correlate with motor function in metachromatic leukodystrophy," Neurology, vol. 75(21):1896-903, Nov. 2010.
De Hosson et al., "Adult metachromatic leukodystrophy treated by allo-SCT and a review of the literature," Bone Marrow Transplant, vol. 46(8):1071-6, Aug. 2011.
Ding et al., "Long-term neuroimaging follow-up on an asymptomatic juvenile metachromatic leukodystrophy patient after hematopoietic stem cell transplantation: evidence of myelin recovery and ongoing brain maturation," Am J Med Genet A., vol. 158a(1):257-6.
Duyff et al., "Late-presenting metachromatic leukodystrophy," Lancet, vol. 348(9038):1382-3, Nov. 1996.
Fumagalli et al., "Update on safety and efficacy of lentiviral hematopoietic stem cell gene therapy (HSC-GT) for metachromatic leukodystrophy (MLD)," Eur J of Paed Neurol., vol. 21:e20, Jun. 2017.
Garavelli et al., "Massive hemobilia and papillomatosis of the gallbladder in metachromatic leukodystrophy: a life-threatening condition," Neuropediatrics, vol. 40(6):284-6, Dec. 2009.
Ghosh et al., "Mannose 6-phosphate receptors: new twists in the tale," Nat Rev Mol Cell Biol., vol. 4(3):202-12, Mar. 2003.
Gieselmann et al., "Advances in the molecular genetics of metachromatic leukodystrophy," J Inherit Metab Dis., vol. 13(4):560-71, Jul. 1990.
Gieselmann et al., "Metachromatic leukodystrophy: Molecular genetics and an animal model," J Inherit Metab Dis., vol. 21(5):564-74, Aug. 1998.
Gieselmann et al., "Metachromatic leukodystrophy—an update," Neuropediatrics, vol. 41(1):1-6, Feb. 2010.
Giugliani et al., "Safety of intrathecal delivery of recombinant human arylsulfatase A in children with late-infantile metachromatic leukodystrophy: A post hoc analysis of responders and non-responders," Molec Genet Metab., vol. 123(2):S54, Feb. 2018.
Groeschel et al., "Metachromatic leukodystrophy: natural course of cerebral MRI changes in relation to clinical course," J Inherit Metab Dis., vol. 34(5):1095-102, Oct. 2011.
Heim et al., "Leukodystrophy incidence in Germany," Am J Med Genet., vol. 71(4):475-8, Sep. 1997.

(56) References Cited

OTHER PUBLICATIONS

Hyde et al., "Psychiatric disturbances in metachromatic leukodystrophy. Insights into the neurobiology of psychosis," Arch Neurol., vol. 49(4):401-6, Apr. 1992.
Kapaun et al., "Slow progression of juvenile metachromatic leukodystrophy 6 years after bone marrow transplantation," J Child Neurol., vol. 14(4):222-8, Apr. 1999.
Kaplitt et al., "Safety and tolerability of gene therapy with an adeno-associated virus (AAV) borne GAD gene for Parkinson's disease: an open label, phase I trial," Lancet, vol. 369(9579):2097-105, Jun. 2007.
Kay et al., "Evidence for gene transfer and expression of factor IX in haemophilia B patients treated with an AAV vector," Nat Genet., vol. 24(3):257-61, Mar. 2000.
Kim et al., "Gallbladder abnormalities in children with metachromatic leukodystrophy.," J Surg Res., vol. 208:187-191, Feb. 2017.
Krageloh-Mann et al., "Juvenile metachromatic leukodystrophy 10 years post transplant compared with a non-transplanted cohort," Bone Marrow Transplant, vol. 48(3):369-75, Mar. 2013.
Krivit et al., "Treatment of late infantile metachromatic leukodystrophy by bone marrow transplantation," N Engl J Med., vol. 322(1):28-32, Jan. 1990.
Largo et al., "Early development of locomotion: Significance of prematurity, cerebral palsy and sex," Dev Med Child Neurol., vol. 27(2):183-91, Apr. 1985.
Lee-Vaupel et al., "A simple chromogenic assay for arylsulfatase A," Clin Chim Acta. vol. 164(2):171-80, Apr. 1987.
McFadden et al., "Pathology of the gallbladder in a child with metachromatic leukodystrophy," Pediatr Dev Pathol., vol. 18(3):228-30, May 2015.
Morena et al., "A new analytical bench assay for the determination of arylsulfatase a activity toward galactosyl-3-sulfate ceramide: implication for metachromatic leukodystrophy diagnosis," Anal Chem., vol. 86(1):473-81, Jan. 2014 (Epub Dec. 2013).
Navarro et al., "Late juvenile metachromatic leukodystrophy treated with bone marrow transplantation; a 4-year follow-up study," Neurology, vol. 46(1):254-6, Jan. 1996.
Perusi et al., "Mutations associated with very late-onset metachromatic leukodystrophy," Clin Genet., vol. 55(2):130, Feb. 1999.
Pilz et al., "Adult metachromatic leukodystrophy. I. Clinical manifestation in a female aged 44 years, previously diagnosed in the preclinical state," Eur Neurol., vol. 15(6):301-7, Jan. 1977 (accepted Jul. 1976).
Poorthuis et al., "The frequency of lysosomal storage diseases in the Netherlands," Hum Genet., vol. 105(1-2):151-6, Jul. 1999.
Rauschka et al., "Late-onset metachromatic leukodystrophy: genotype strongly influences phenotype," Neurology, vol. 67(5):859-63, Sep. 2006.
Regis et al., "Contribution of arylsulfatase A mutations located on the same allele to enzyme activity reduction and metachromatic leukodystrophy severity," Hum Genet., vol. 110(4):351-5, Apr. 2002.
Rodriguez-Waitkus et al., "Metachromatic leukodystrophy and its effects on the gallbladder: a case report," Ultrastruct Pathol., vol. 35(6):271-6, Dec. 2011.
Russell et al., "The gross motor function measure: a means to evaluate the effects of physical therapy," Dev Med Child Neurol., vol. 31(3):341-52, Jun. 1989.
Sevin et al., "Enzyme, cell and gene-based therapies for metachromatic leukodystrophy," J Inherit Metab Dis., vol. 30(2):175-83, Apr. 2007.
Sevin et al., "Intracerebral gene therapy in children with metachromatic leukodystrophy: Results of a phase I/II trial (abstract)," Molec Genet Metab., vol. 123(2):S129, Feb. 2018.
Skorupa et al., Sustained production of beta-glucuronidase from localized sites after AAV vector gene transfer results in widespread distribution of enzyme and reversal of lysosomal storage lesions in a large volume of brain in mucopolysaccharidosis VII.
Smith et al., "Haematopoietic stem cell transplantation does not retard disease progression in the psycho-cognitive variant of late-onset metachromatic leukodystrophy," J Inherit Metab Dis., vol. 33(Suppl 3: S47): 1-5, Dec. 2010.
Solders et al., "Hematopoietic SCT: a useful treatment for late metachromatic leukodystrophy," Bone Marrow Transplant, vol. 49(8):1046-51, Aug. 2014.
Toda et al., "Lysosulfatide (sulfogalactosylsphingosine) accumulation in tissues from patients with metachromatic leukodystrophy," J Neurochem, vol. 55(5):1585-91, Nov. 1990.
Tylki-Szymanska et al., "Late juvenile metachromatic leukodystrophy (MLD) in three patients with a similar clinical course and identical mutation on one allele," Clin Genet., vol. 50(5):287-92, Nov. 1996.
Van Rappard et al., "Gallbladder and the risk of polyps and carcinoma in metachromatic leukodystrophy," Neurology, vol. 87(1):103-11, Jul. 2016.
Van Rappard et al., "Metachromatic leukodystrophy: Disease spectrum and approaches for treatment," Best Pract Res Clin Endocrinol Metab., vol. 29(2):261-73, Mar. 2015.
Van Rappard et al., "Slowly Progressive Psychiatric Symptoms: Think Metachromatic Leukodystrophy," J Am Acad Child Adolesc Psychiatry, vol. 57(2):74-76, Feb. 2018.
Virgens et al., "Genotypic characterization of Brazilian patients with infantile and juvenile forms of metachromatic leukodystrophy," Gene, vol. 568(1):69-75, Aug. 2015.
Von Bülow et al., "Crystal structure of an enzyme-substrate complex provides insight into the interaction between human arylsulfatase A and its substrates during catalysis," J Mol Biol., vol. 305(2):269-77, Jan. 2001.
WHO, "Reliability of motor development data in the WHO Multicentre Growth Reference Study," Acta Paediatr Suppl., vol. 450:47-55, Apr. 2006.
Zafeiriou et al., "Neurophysiology and MRI in late-infantile metachromatic leukodystrophy," Pediatr Neurol., vol. 21(5):843-6, Nov. 1999.
Peng, L., & Suzuki, K., Ultrastructural study of neurons in metachromatic leukodystrophy. Clin Neuropathol. Sep.-Oct. 1987;6(5):224-30. Abstract only.
Hironaka et al., Enzyme replacement in the CSF to treat metachromatic leukodystrophy in mouse model using single intracerebroventricular injection of self-complementary AAV1 vector. Sci Rep. vol. 5:13104. pp. 1-12. Aug. 2015.
Kurai, T., & Shimada, T., Recombinant adeno-associated virus-mediated gene delivery to the central nervous system. J Nippon Med Sch. Jun. 2007;74(3):188-9.
Consolaro et al., Chapter 5—Assessment Tools in Juvenile Idiopathic Arthritis, Handbook of Systemic Autoimmune Diseases (eds. Cimaz Lehman), Elsevier, vol. 11:107-127, Jan. 2016.
Dali et al., Sulfatide levels correlated with severity of neuropathy in metachromatic leukodystrophy, Ann Clin Transl Neurol., vol. 2(5):518-33, May 2015.
Herndon et al., Brain weight does not decrease with age in adult rhesus monkeys, Neurobiol Aging, vol. 19(3):267-72, May 1998.
Hinderer et al., Delivery of an adeno-associated virus vector into cerebrospinal fluid attendates central nervous system disease in Mucopolysaccharidosis Type II mice, Hum Gene Ther., vol. 27(11):906-915, Nov. 2016.
Kehrer et al., The natural course of gross motor deterioration in metachromatic leukodystrophy, Dev Med Child Neurol., vol. 53(9):850-855, Sep. 2011(a).
Mandel et al., Clinical trails in neurological disorders using AAV vectors: promises and challenges, Curr Opin Mol Ther., vol. 6(5):482-90, Oct. 2004.
Sambrook et al., Molecular Cloning. A Laboratory Manual ($2^{nd}$ ed.), Cold Spring Harbor Laboratory, New York, pp. 165-166, Jan. 1989.
Office action dated Feb. 9, 2024 issued in Canadian Patent Application No. 3,135,539 and Response filed Jun. 10, 2024.
Office Action dated Sep. 7, 2023 issued in Chinese Patent Application No. 202080048744.4.
Office Action dated Jun. 6, 2024 issued in Chinese Patent Application No. 202080048744.4.
Office Action dated Mar. 1, 2024 issued in Colombian Patent Application No. NC2021/0016323.
Office Action dated Jun. 5, 2024 issued in Japanese Patent Application No. 2021-564955.

(56) References Cited

OTHER PUBLICATIONS

Substantive Examination Report dated Jul. 21, 2023 issued in Saudi Arabian Patent Application No. 521430755.

* cited by examiner

ATGGGAGCCCCTAGATCTCTGCTGCTGGCTCTGGCTGCTGGACTGGCAG
TTGCCAGACCTCCTAACATCGTGCTGATCTTCGCCGACGATCTCGGCTA
CGGCGATCTGGGCTGTTACGGACACCCCAGCAGCACCACACCTAACCT
GGATCAACTTGCCGCTGGCGGCCTGAGATTCACCGATTTCTACGTGCCC
GTGTCTCTGTGCACCCCTTCTAGAGCTGCTCTGCTGACAGGCAGACTCC
CTGTGCGGATGGGAATGTATCCTGGCGTGCTGGTGCCTAGCTCTAGAGG
CGGACTGCCTCTGGAAGAAGTGACAGTTGCCGAAGTGCTGGCCGCCAG
AGGATATCTGACTGGCATGGCCGGAAAGTGGCACCTCGGAGTTGGACC
AGAAGGCGCTTTTCTGCCTCCTCACCAGGGCTTCCACCGGTTTCTGGGC
ATCCCTTACTCTCACGATCAGGGCCCCTGCCAGAACCTGACCTGTTTTC
CTCCTGCCACACCTTGCGACGGCGGCTGTGATCAAGGACTGGTGCCAAT
TCCTCTGCTGGCCAACCTGAGCGTGGAAGCTCAACCTCCTTGGCTGCCA
GGACTGGAAGCCCGGTATATGGCCTTCGCTCACGACCTGATGGCCGAC
GCTCAGAGACAGGACAGACCATTCTTCCTGTACTACGCCAGCCACCAC
ACACACTACCCTCAGTTTAGCGGCCAGAGCTTCGCCGAGAGATCTGGC
AGAGGACCTTTCGGCGACAGCCTGATGGAACTGGATGCCGCTGTGGGC
ACACTGATGACAGCCATCGGAGATCTGGGACTGCTGGAAGAGACACTG
GTCATCTTCACCGCCGACAACGGCCCCGAGACAATGAGAATGAGCAGA
GGCGGCTGTAGCGGCCTGCTGAGATGTGGCAAGGGCACCACATATGAA
GGCGGCGTGAGAGAACCTGCTCTGGCCTTTTGGCCTGGCCATATTGCTC
CAGGCGTGACACACGAGCTGGCCTCTTCTCTGGATCTGCTGCCTACACT
GGCAGCTCTTGCTGGTGCTCCCCTGCCTAATGTGACCCTGGATGGCTTC
GATCTGAGCCCACTGCTGCTCGGCACAGGCAAGTCTCCAAGACAGAGC
CTGTTCTTCTACCCTAGCTACCCCGACGAAGTGCGGGGAGTGTTTGCCG
TGCGGACCGGAAAGTATAAGGCCCACTTCTTCACCCAAGGCAGCGCCC
ACTCTGACACCACAGCTGATCCTGCTTGTCACGCCAGCTCTAGCCTGAC
AGCCCATGAACCTCCACTGCTGTACGACCTGAGCAAGGACCCCGGCGA
GAACTACAATCTGCTTGGCGGAGTTGCCGGCGCTACACCTGAAGTTCTG
CAGGCCCTGAAACAGCTCCAGCTGCTGAAAGCCCAGCTGGACGCTGCC
GTGACATTTGGACCTAGTCAGGTGGCCAGAGGCGAGGATCCTGCTCTG
CAGATCTGTTGTCACCCTGGCTGCACACCCAGACCTGCCTGCTGTCATT
GTCCTGATCCACACGCC

FIG. 1

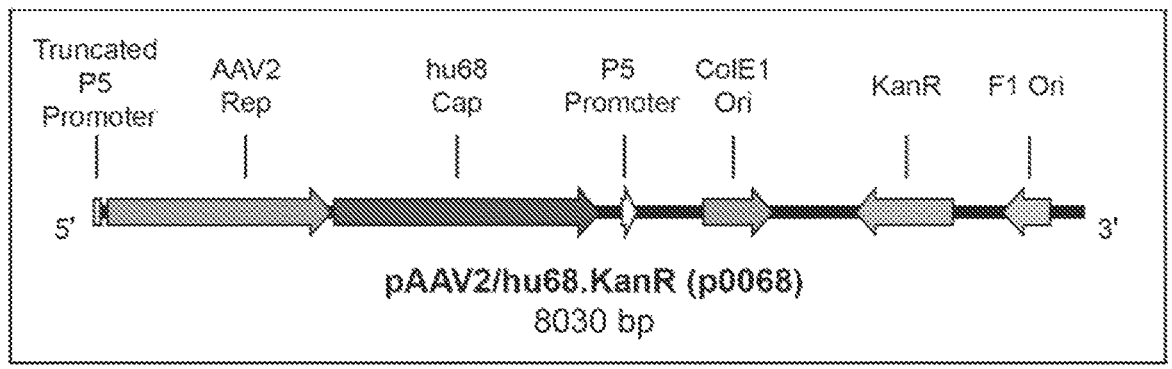
FIG. 4
FIG. 5A
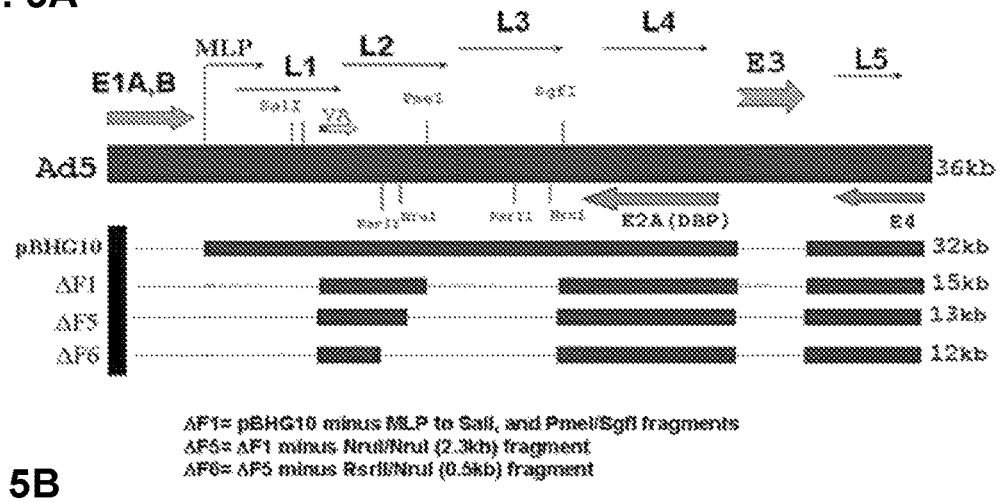
FIG. 5B

FIG. 9B
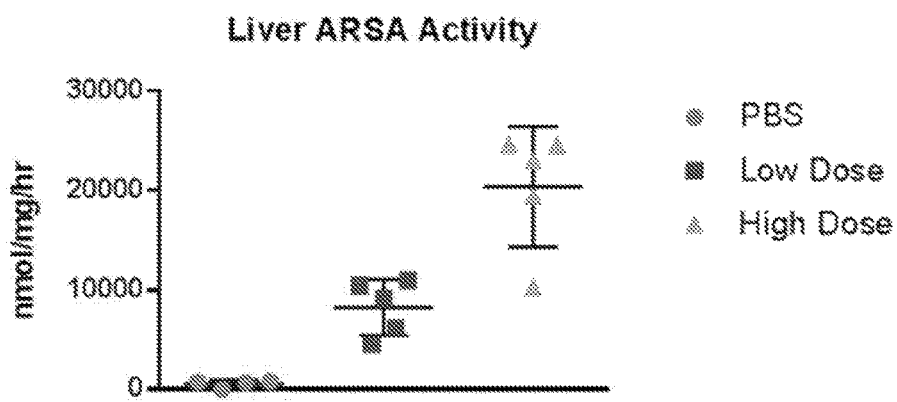
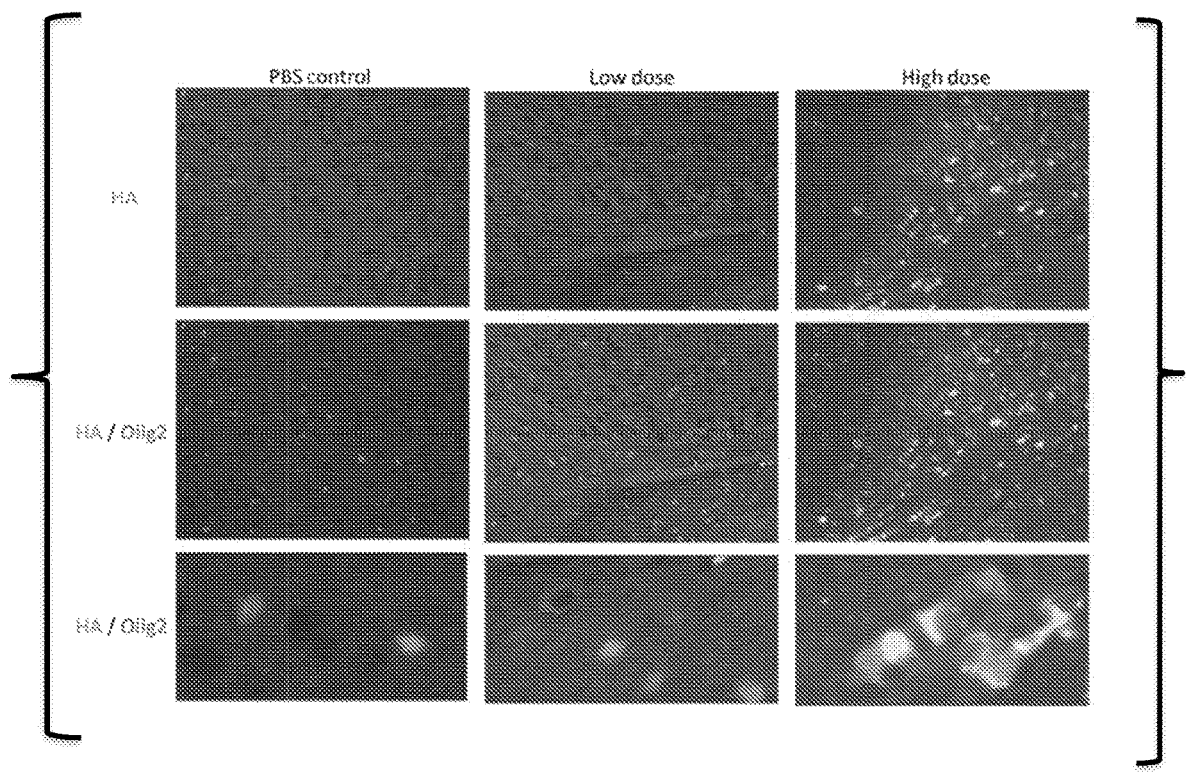
FIG. 10

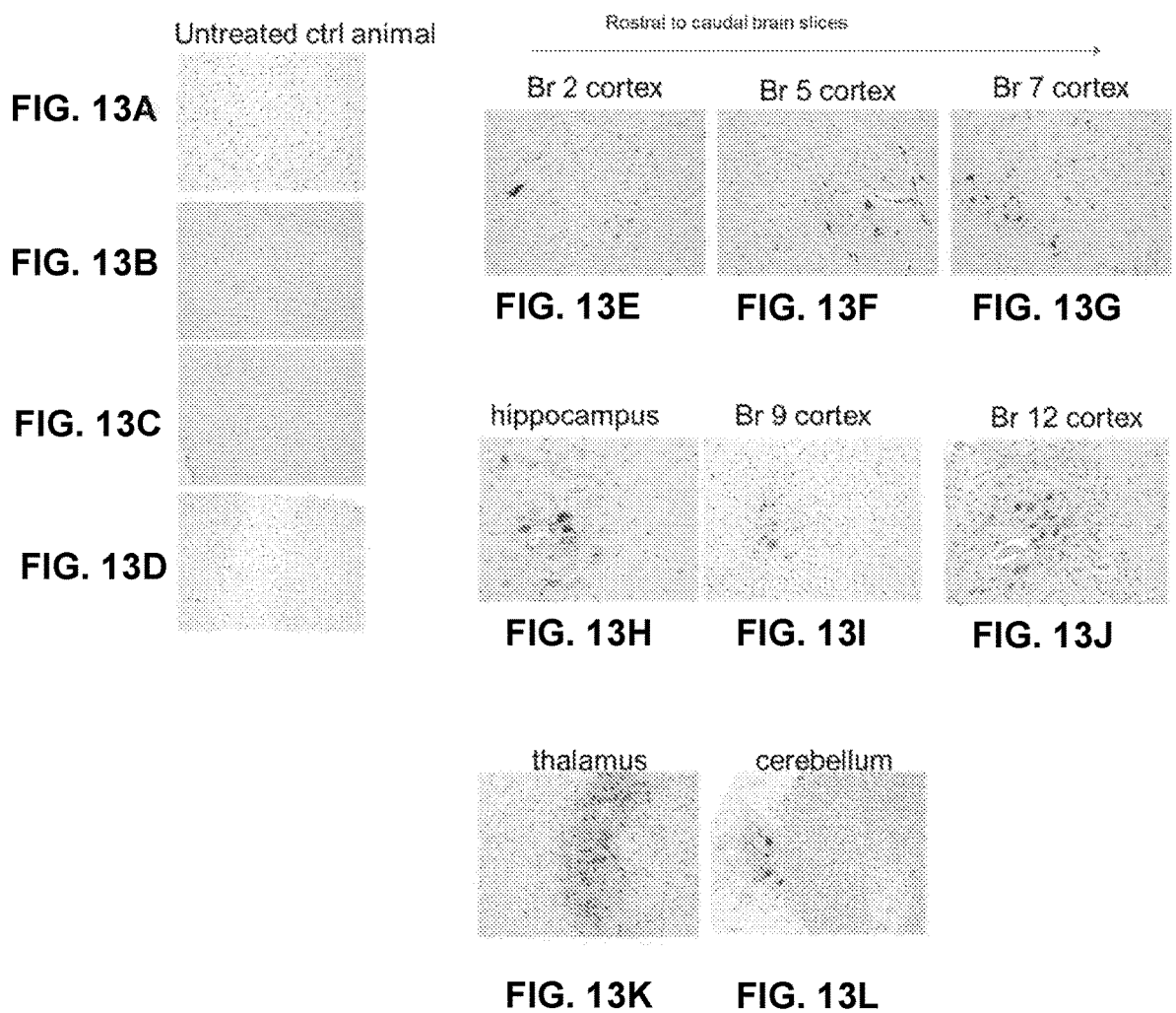

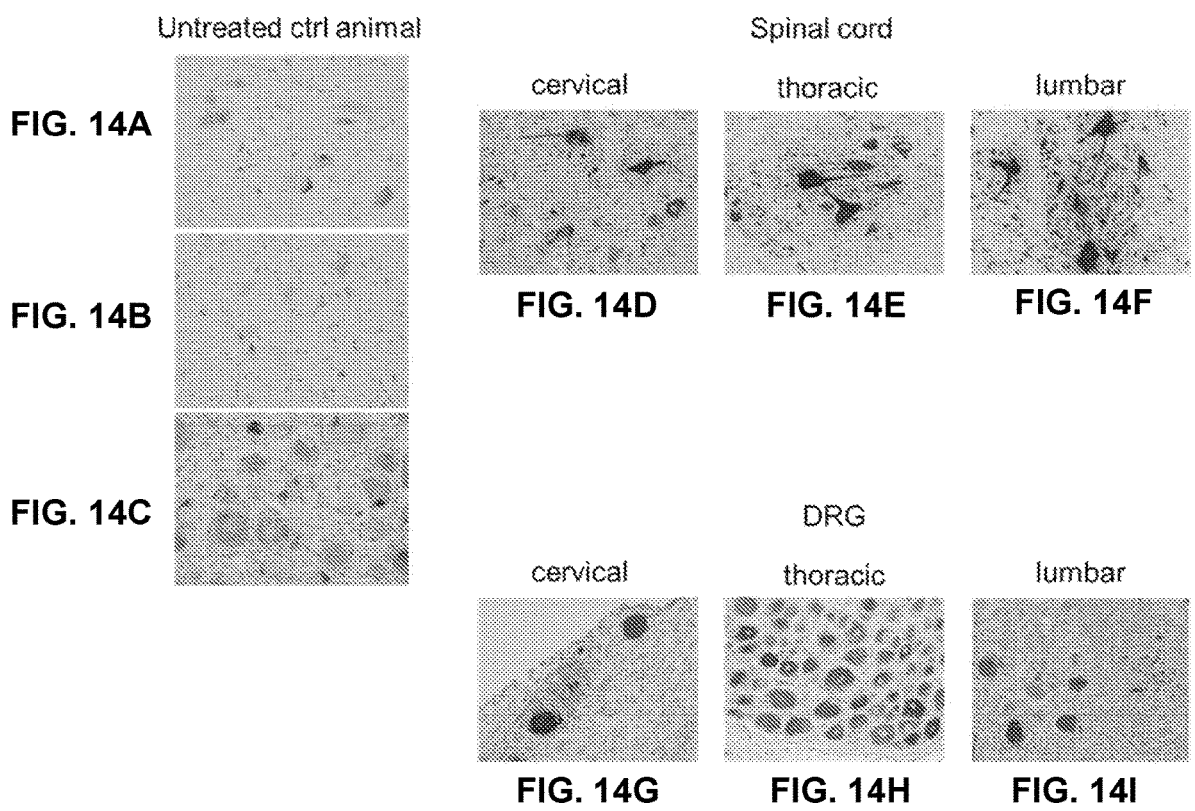

COMPOSITIONS USEFUL IN TREATMENT OF METACHROMATIC LEUKODYSTROPHY

CROSS-REFERENCE TO RELATED APPLICATIONS

This application is a National Stage Entry under 35 U.S.C. 371 of International Patent Application No. PCT/US2020/031207, filed May 2, 2020, which claims priority to U.S. Provisional Patent Application No. 62/843,091, filed May 3, 2019, which is incorporated herein by reference.

BACKGROUND OF THE INVENTION

Metachromatic Leukodystrophy (MLD) is a monogenic autosomal recessive sphingolipid storage disease caused by mutations in the gene encoding the lysosomal enzyme ARSA (Von Figura et al., 2001; Gieselmann and Krageloh-Mann, 2010). ARSA deficiency leads to accumulation of its natural substrates, which are sulfated galactosphingolipids (galactosylceramide-3-O-sulfate and galactosylsphingosine-3-O-sulfate), commonly referred to as sulfatides. Sulfatides accumulate within the lysosomes of oligodendrocytes, microglia, and certain types of neurons in the Central Nervous System (CNS), in addition to Schwann cells and macrophages in the Peripheral Nervous System (PNS) (Peng and Suzuki, 1987). While the PNS and CNS are mainly affected, sulfatide storage also occurs in visceral organs; most notably, the kidney, liver (Toda et al., 1990), and gallbladder (Rodriguez-Waitkus et al., 2011; McFadden and Ranganathan, 2015).

MLD patients (i.e., those who carry a mutation on both alleles) typically have ARSA enzyme activity that is 0-10% of control values in synthetic substrate-based assays. ARSA mutation carriers, who have a single mutated ARSA allele and one normal allele, are clinically unaffected and usually have ARSA enzyme activity that is approximately 10% of control values, while asymptomatic individuals with pseudodeficiency (PD, another genetically distinct form of ARSA deficiency) alleles have ARSA enzyme activity that is approximately 10-20% of healthy controls (Gomez-Ospina, 2017). Clinically, three forms of MLD can be distinguished based on age of symptom onset that span a broad continuous spectrum of disease severity: a rapidly progressive severe late infantile form, a juvenile form, and a late onset slowly progressive adult form comprising 50-60%, 20-30%, and 15-20% of MLD diagnoses, respectively (Gomez-Ospina, 2017, Wang et al., 2011). Infantile MLD is considered an orphan disease. Late infantile MLD has an onset before 30 months of age and is the most severe form of the disease. The late infantile form has a uniform clinical presentation and a rapidly progressive, predictable disease course. Juvenile MLD is characterized by an age of onset between the age of 30 months and 16 years with a median age of onset of 6 years 2 months (Kehrer et al., 2011a) to 10 years (Mahmood et al., 2010), depending on the study. In order to better characterize the clinical phenotype, a subset of juvenile MLD patients has been described, referred to as early juvenile MLD, who have a clinical onset ≤6 years of age and who have a similar, although less rapid, initial disease evolution compared to children with late infantile MLD (Biffi et al., 2008; Chen et al., 2016; Sessa et al., 2016). The early juvenile and late infantile phenotypes are collectively referred to as early onset MLD (Sessa et al., 2016). In late juvenile MLD patients (i.e., those with symptom onset between 7-16 years of age), behavioral issues, attention deficit, or cognitive decline usually develops first, sometimes in combination with gait disturbances.

There is no approved curative or disease-modifying therapy for MLD. Since MLD is caused by defective ARSA, various investigational approaches aim to correct the biochemical defect by replacing functional ARSA in affected neural tissue of the CNS. Enzyme replacement therapy (ERT) and hematopoietic stem cell transplantation (HSCT) rely on providing normal enzyme to ARSA-deficient cells, while gene therapy approaches are based on the overexpression of wild-type ARSA in different cell types (Patil and Maegawa, 2013). The efficacy of Hematopoietic Stem Cell Transplantation (HSCT) using umbilical cord blood (UCB), allogeneic peripheral blood stem cells, or allogeneic bone marrow depends on the MLD phenotype and the timing of intervention relative to the disease state of the patient (Patil and Maegawa, 2013; van Rappard et al., 2015). Bone marrow transplant (BMT) requires availability of a human leukocyte antigen-matched sibling donor for the best outcome (Boucher et al., 2015) and carries risks of transplant- and conditioning-related complications, such as graft versus host disease (GvHD), infections, and death. Umbilical Cord Blood (UCB) transplantation provides an alternative to BMT with the advantage of quicker availability, lower risk of GvHD, lower mortality, higher rates of full-donor chimerism, and better correction of enzymatic defect (Batzios and Zafeiriou, 2012; Martin et al., 2013). However, BMT is not widely available in Europe. Brain engraftment is slow, often taking many months for cells to engraft, migrate to the CNS, differentiate, and restore enzyme levels. Moreover, physiological enzyme levels achieved with HSCT may not be sufficient to correct the deficit throughout the CNS. This may explain why transplant is not efficacious in rapidly progressive early onset MLD, and may not correct or stabilize all aspects of the disease even when performed pre-symptomatically (de Hosson et al., 2011; Martin et al., 2013; Boucher et al., 2015).

Thus, there remains a substantial unmet need for fast-onset therapies that can halt or prevent disease progression in these patients.

In addition to HSCT, various other cell-based approaches exist that (over) express ARSA and deliver enzyme to affected cells and treat the neurological manifestations of MLD, including microencapsulated recombinant cells, oligodendrocyte and neural progenitor cells, and embryonic stem cells. These cell therapies have shown considerable clearance of sulfatide storage in animal models (Patil and Maegawa, 2013), but are still untested in humans.

Ex vivo lentiviral gene therapy has been attempted which combines hematopoictic stem cell transplant with gene therapy (HSC-GT) (Biffi et al., 2013) by transducing autologous CD34+ cells with a human ARSA-encoding lentiviral vector and re-administering the gene-corrected cells to the patient. While this therapy is promising for patients identified at a pre-symptomatic stage (after diagnosis in an older affected sibling), it has not been shown to be efficacious in patients who are already symptomatic. Unfortunately, most new MLD diagnoses are made after symptom onset because newborn screening is not yet available, making it an unlikely therapeutic option for many MLD patients. Additionally, there are risks inherent to the myeloablative conditioning regimen and risk of insertional mutagenesis associated with these integrating vectors.

A pharmacological-toxicological study in NHPs demonstrated significant dose-limiting toxicity (Zerah et al., 2015) due to brain inflammation (encephalitis) localized around injection sites. A Phase 1/2 clinical study to assess safety and efficacy of AAVrh10-mediated ARSA gene transfer in the brain of children affected with early onset MLD is ongoing (NCT01801709) (Aubourg, 2016) likewise involved intra-cerebral vector administration at 12 sites in the white matter of the brain (Zerah et al., 2015). Results of the trial have not been published, except in abstract form, with preliminary reports suggesting lack of efficacy at preventing onset or stopping disease progression (Sevin et al., 2018). The reasons for the lack of efficacy have not been discussed by the sponsor of the trial. In addition to AAVrh10-mediated gene therapy, an intra-cerebrally delivered lentiviral gene therapy is also recruiting patients with any form of MLD (NCT03725670).

Enzyme replacement therapy (ERT) is now the Standard of Care (SOC) for several Lysosomal Storage Diseases (LSDs) (Sands, 2014) and relies on the ability of cells to take up infused enzyme via mannose-6-phosphate receptors (Ghosh et al., 2003). In MLD, ERT reduces sulfatide storage in the kidneys, peripheral nerves, and CNS in Arsa-mice (Matzner et al., 2005). In an aggravated MLD mouse model with immune tolerance to human ARSA and supra-normal sulfatide synthesis, improvements in MLD symptoms and reduction in sulfatide storage was seen only in mice treated at early time points, suggesting that IV-administered ERT may not work in patients with advanced symptoms (Matthes et al., 2012). In the same model, continuous IT infusion of recombinant ARSA to bypass the BBB (Stroobants et al., 2011) resulted in complete reversal of sulfatide storage and correction of CNS dysfunction, while other non-clinical studies in mice result in reduced sulfatide storage and improved functional outcomes (Matzner et al., 2009; Piguet et al., 2012). However, in humans, the extent of metabolic correction with ERT will unlikely be sufficient and timely to arrest the rapid cerebral demyelination that occurs in early onset MLD (Rosenberg et al., 2016). Since the BBB restricts access to the CNS of most large proteins, it is believed that ERT will likely only work when delivered directly to the CNS (Abbott, 2013), and the short half-life will require frequent administration. This hypothesis is bearing out in ERT clinical trials that attempted to overcome these limitation through frequent high dose IV administration (NCT00681811) or IT injection (Giugliani et al., 2018). However, results in late infantile MLD patients with IV-administered ERT have been disappointing (NCT00418561), along with IT-administered ERT in early onset and late juvenile MLD (NCT01510028).

Small molecule-based treatments can potentially overcome limitations of current therapies for MLD (e.g., by crossing the BBB) and may also address different pathogenic mechanisms of the disease. Warfarin (Coumadin) is an anti-coagulant that has been tested as a substrate-reducing agent in a small cohort of late infantile MLD patients. There was no beneficial effect on urinary sulfatide levels or levels of the brain biomarkers N-acetylaspartate and myo-inositol (Patil and Maegawa, 2013).

The limited benefit, restricted population, short therapeutic window, and associated risks of HSCT and HSC-GT combined with the overall disappointing non-clinical results obtained with other investigational approaches represent a significant unmet clinical need for other viable treatment options, especially for early onset MLD patients.

What is desirable are alternative therapeutics for treatment of conditions associated with abnormal ARSA gene and/or Metachromatic Leukodystrophy.

SUMMARY OF THE INVENTION

Provided herein is a therapeutic, recombinant, and replication-defective adeno-associated virus (rAAV) which is useful for treating a disease associated with an Arylsulfatase A gene (ARSA) mutation (for example, Metachromatic Leukodystrophy, i.e., MLD, or ARSA pseudodeficiency) in a subject in need thereof. The rAAV is desirably replication-defective and carries a vector genome comprising inverted terminal repeats (ITR) and a nucleic acid sequence encoding a functional human Arylsulfatase A (hARSA) under the control of regulatory sequences which direct the hARSA expression in a target cell. In certain embodiment, the rAAV further comprises an AAVhu68 capsid in which the vector genome is packaged. In certain embodiments, the vector genome is entirely exogenous to the AAVhu68 capsid, as it contains no AAVhu68 genomic sequences.

In certain embodiments, the functional hARSA has a signal peptide and a sequence of amino acid (aa) 19 to aa 507 of SEQ ID NO: 2. In certain embodiments, the native hARSA signal peptide is used, e.g., aa 1 to aa 18 of SEQ ID NO: 2. In certain embodiment, the signal peptide is aa 1 to aa 20 of SEQ ID NO: 4. In certain embodiment, the functional hARSA has an amino acid sequence of SEQ ID NO: 2 or SEQ ID NO: 4.

In certain embodiments, the hARSA coding sequence is about 95% to 100% identical to nucleotide (nt) 55 to nt 1521 of SEQ ID NO: 1. In certain embodiments, the hARSA-coding sequence is SEQ ID NO: 1 or SEQ ID NO: 3. In a further embodiment, the hARSA coding sequence encodes a sequence of amino acid (aa) 19 to aa 507 of SEQ ID NO: 2. In yet a further embodiment, the hARSA coding sequence encodes a sequence of SEQ ID NO: 2 or SEQ ID NO: 4.

In certain embodiments, the regulatory sequences comprise one or more of the following: a regulatory element derived from the chicken β-actin (BA) promoter and human cytomegalovirus immediate-early enhancer (CMV IE) (for example, CB7 promoter, nt 198 to nt 862 of SEQ ID NO: 5), a chimeric intron consisting of a chicken BA splice donor and a rabbit β-globin (rBG) splice acceptor element (for example, CI, nt 956 to nt 1928 of SEQ ID NO: 5), and polyadenylation (PolyA) signal derived from the rBG gene (for example, rBG, nt 3539 to nt 3665 of SEQ ID NO: 5). In certain embodiments, the vector genome has a sequence of nucleotide (nt) 1 to nt 3883 of SEQ ID NO: 5. In certain embodiments, the rAAV or a composition comprising the rAAV is administrable to a subject in need thereof to ameliorate symptoms of a disease associated with an ARSA mutation (for example, MLD) and/or to delay progression of a disease associated with an ARSA mutation (for example, MLD).

In another aspect, a production system useful for producing the rAAV is provided. In this system, cells which comprise a nucleic acid sequence encoding an AAVhu68 capsid protein are cultured, a vector genome as described herein and sufficient AAV rep functions and helper functions to permit packaging of the vector genome into the AAV capsid.

In one aspect, provided herein is a vector which is useful for treating a disease associated with an ARSA mutation (for example, MLD) in a subject in need thereof. The vector carries a nucleic acid sequence encoding a functional human Arylsulfatase A (hARSA) under the control of regulatory sequences which direct the hARSA expression in a target cell. In certain embodiments, the hARSA-coding sequence is about 95% to 100% identical to SEQ ID NO: 1. Additionally or alternatively, the function hARSA protein has an amino acid sequence of SEQ ID NO: 2. In certain embodiments, the hARSA coding sequence is SEQ ID NO: 1. In certain embodiments, the vector or a composition comprising the vector is administrable to a subject in need thereof to ameliorate symptoms of a disease associated with an ARSA mutation (for example, MLD), and/or to delay progression of a disease associated with an ARSA mutation (for example, MLD).

In a further aspect, provided herein is a composition comprising a rAAV or a vector as described herein and an aqueous suspension media. In certain embodiments, the aqueous composition is provided which comprises a formulation buffer and the rAAV or vector as described. In certain embodiments, the formulation buffer comprises: an artificial cerebrospinal fluid comprising buffered saline and one or more of sodium, calcium, magnesium, potassium, or mixtures thereof; and a surfactant. In certain embodiments, the formulation buffer comprises about 0.0005% to about 0.001% surfactant. In certain embodiments, the composition is at a pH of 7.2 to 7.8.

In another aspect, a method of treating a subject having a disease associated with an ARSA mutation (for example, MLD), or ameliorating symptoms of a disease associated with an ARSA mutation (for example, MLD), or delaying progression of a disease associated with an ARSA mutation (for example, MLD) is provided. The method comprises administrating an effective amount of a rAAV or a vector as described herein to a subject in need thereof. In certain embodiments, the vector or rAAV is administrable to a patient via an intra-cisterna *magna* injection (ICM), for example, CT-guided sub-occipital injection into the cisterna *magna*. In certain embodiments, a vector or a composition is provided which is administrable to a patient having Metachromatic Leukodystrophy who is 7 years of age or younger, or who is 6 years of age or younger. In certain embodiments, the method involves delivering the rAAV or the vector to a human patient in a single dose.

These and other aspects of the invention are apparent from the following detailed description of the invention.

BRIEF DESCRIPTION OF THE DRAWINGS

FIG. 1 provides the engineered hARSA coding sequence (SEQ ID NO: 1, i.e., nt 7 to nt 1527 of SEQ ID NO: 3 and nt 1968 to nt 3488 of SEQ ID NO: 5).

FIG. 4 provides a linear map of the trans plasmid pAAV2/hu68.KanR. AAV2, adeno-associated virus serotype 2; AAVhu68, adeno-associated virus serotype hu68; bp, base pairs; Cap, capsid; KanR, kanamycin resistance; Ori, origin of replication; Rep, replicase.

FIGS. 5A and 5B provide an adenovirus helper plasmid pAdDeltaF6 (KanR). FIG. 5A shows derivation of the helper plasmid pAdAF6 from parental plasmid pBHG10 through intermediates pAdAF1 and pAdAF5. FIG. 5B shows that the ampicillin resistance gene in pAdAF6 was replaced by the kanamycin resistance gene to generate pAdAF6 (Kan).

FIGS. 9A to 9B show ARSA enzyme activity in the liver and serum of mice following intracerebroventricular administration of the AAVhu68.CB7.CI.hARSAco.rBG vector. Six-week-old C57BL6/J wild type mice received a single ICV injection of the AAVhu68.CB7.CI.hARSAco.rBG vector into the right ventricle at a dose of either $1.00 \times 10^{10}$ GC (low dose) or $1.00 \times 10^{11}$ GC (high dose) (N=5/group). Age-matched C57BL6/J wild type mice were ICV-administered PBS into the right ventricle as a control (N=4). Mice were necropsied 21 days later, and ARSA enzyme activity in the FIG. 9A serum and FIG. 9B liver was measured based upon the rate of hydrolysis of the chromogenic substrate, 4-nitrocatechol sulfate (nmol/mg/hr). ARSA, arylsulfatase A (protein); GC, genome copies; ICV, intracerebroventricular; N, number of animals; PBS, phosphate-buffered saline.

FIG. 10 shows delivery of ARSA to Neurons and Oligodendrocytes in the brain following intracerebroventricular administration of AAVhu68.CB7.CI.hARSAcoHA.rBG in mice. Six-week-old C57BL6/J wild type mice received a single ICV injection of AAVhu68.CB7.CI.hARSAcoHA.rBG into the right ventricle at a dose of either $1.00 \times 10^{10}$ GC (low dose) or $1.00 \times 10^{11}$ GC (high dose) (N=5/group). Age-matched C57BL6/J wild type mice were ICV-administered PBS into the right ventricle as a control (N=5). Mice were necropsied 21 days later, and brain tissue was obtained. Tissues were sectioned and immunostained to visualize ARSA (green: anti-HA primary antibody detected with a fluorescein isothiocyanate-conjugated secondary antibody) and oligodendrocytes (red: anti-OLIG2 primary antibody detected with a tetramethylrhodamine-conjugated secondary antibody). Representative images of the brain cortex are shown at 20× magnification with 500 ms exposure. Cropped and zoomed-in views (bottom row) show oligodendrocytes from the subcortical white matter expressing ARSA. ARSA, arylsulfatase A (protein); GC, genome copies; HA, hemagglutinin; ICV, intracerebroventricular; N, number of animals; OLIG2, oligodendrocyte transcription factor 2; PBS, phosphate-buffered saline.

FIG. 13A-13L show human ARSA expression in the brain of nonhuman primates following intra-cisterna magna administration of AAVhu68.CB7.CI.hARSAco.rBG. Adult cynomolgus macaques received a single ICM administration of AAVhu68.CB7.CI.hARSAco.rBG at a dose of $3.00 \times 10^{13}$ GC (HD) (N=2). Untreated age-matched cynomolgus macaques served as a control (N=2). Animals were necropsied 42+2 days after AAVhu68.CB7.CI.hARSAco.rBG administration, and brains were obtained for immunohistochemical staining using an antibody recognizing human ARSA (brown precipitate). Representative images of sections through the brain's cortex (FIG. 13E, FIG. 13F, FIG. 13G, FIG. 13I, and FIG. 13J), hippocampus (FIG. 13H), thalamus (FIG. 13K), and cerebellum (FIG. 13L) for one AAVhu68.CB7.CI.hARSAco.rBG-treated animal is shown, along with sections from an untreated control for signal comparison (FIG. 13A, FIG. 13B, FIG. 13C, and FIG. 13D). ARSA, arylsulfatase A (protein); GC, genome copies; HD, high dose; ICM, intra-cisterna magna; N, number of animals.

FIG. 14A, FIG. 14B, FIG. 14C, FIG. 14D, FIG. 14E, FIG. 14F, FIG. 14G, FIG. 14H, and FIG. 14I provide human ARSA expression in the spinal cord and dorsal root ganglia of nonhuman primates following intra-cisterna magna administration of AAVhu68.CB7.CI.hARSAco.rBG. Adult cynomolgus macaques received a single ICM administration of AAVhu68.CB7.CI.hARSAco.rBG at a dose of $3.00 \times 10^{13}$ GC (HD) (N=2). Untreated age-matched cynomolgus macaques served as a control (N=2). Animals were necropsied 42+2 days after AAVhu68.CB7.CI.hARSAco.rBG administration, and sections of the cervical, thoracic, and lumbar spinal cord and DRG were obtained for immunohistochemical staining using an antibody recognizing human ARSA (brown precipitate). Representative images of sections for one AAVhu68.CB7.CI.hARSAco.rBG-treated animal (FIG. 14D, FIG. 14E, FIG. 14F, FIG. 14G, FIG. 14H, and FIG. 14I) is shown, along with sections from an untreated control for signal comparison (FIG. 14A, FIG. 14B, and FIG. 14C). ARSA, arylsulfatase A (protein); GC, genome copies; HD, high dose; ICM, intra-cisterna magna; N, number of animals.

DETAILED DESCRIPTION OF THE INVENTION

Figure 2:
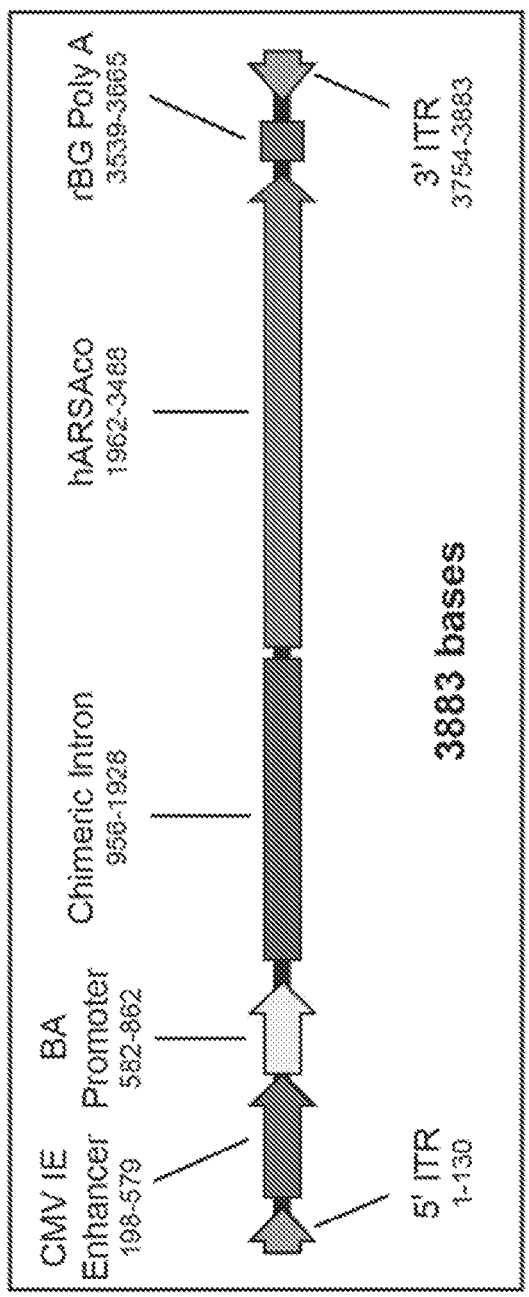
FIG. 2 provides a linear map of the AAV.CB7.CI.hARSAco.rBG vector genome. The vector genome is to express an engineered version of human ARSA (hARSAco) under the control of the ubiquitous CB7 promoter. CB7 is composed of a hybrid between a CMV IE enhancer and a chicken BA promoter. ARSA, arylsulfatase A; BA, B-actin; CMV IE, cytomegalovirus immediate-early; ITR, inverted terminal repeats; PolyA, polyadenylation; and rBG, rabbit β-globin.

Compositions and methods for treating a disease caused by mutation(s) in the Arylsulfatase A (ARSA) gene and/or deficiencies in normal levels of functional Arylsulfatase A (e.g., Metachromatic Leukodystrophy (MLD)) are provided herein. In certain embodiments, also provided are compositions and methods for treating disease(s) or symptom(s) caused by mutation(s) in the ARSA gene and/or deficiencies in normal levels of functional Arylsulfatase A. An effective amount of a recombinant adeno-associated virus (rAAV) having an AAVhu68 capsid and packaged therein a vector genome encoding a functional human Arylsulfatase A (hARSA) protein is delivered to a subject in need. Desirably, this rAAV is formulated with an aqueous buffer. In certain embodiments, the suspension is suitable for intrathecal injection. In certain embodiments, the rAAV vector is termed as AAVhu68.hARSAco, in which the hARSA coding sequence is an engineered hARSA coding sequence (termed as "hARSAco" or "hARSA" unless specified, for example, nucleotide (nt) 55 to nt 1521 of SEQ ID NO: 1, SEQ ID NO: 3, or a sequence at least about 95% to about 99.9% identical thereto). In certain embodiment, the hARSAco is SEQ ID NO: 1. In certain embodiment, the hARSAco is SEQ ID NO: 3. In certain embodiments, the rAAV vector is termed AAVhu68.CB7.hARSAco, in which the engineered hARSA coding sequence is under the control of regulatory sequences which include a chicken beta actin promoter with a cytomegalovirus enhancer (CB7; SEQ ID NO: 16). In certain embodiments, the compositions are delivered via an intracisterna *magna* injection (ICM).

Nucleic acid sequences encoding capsid of a clade F adeno-associated virus (AAV), which is termed herein AAVhu68, are utilized in the production of the AAVhu68 capsid and recombinant AAV (rAAV) carrying the vector genome. Additional details relating to AAVhu68 are provided in WO 2018/160582 and in this detailed description. The AAVhu68 vectors described herein are well suited for delivery of the vector genome comprising the engineered hARSA coding sequence to cells within the central nervous system (CNS), including brain, hippocampus, motor cortex, cerebellum, and motor neurons, and the peripheral nervous system (PNS), including nerves and ganglia outside the brain and the spinal cord. These vectors may be used for targeting other cells within the CNS and/or PNS and certain other tissues and cells, for example, kidney or liver or gallbladder.

1. Arylsulfatase A (hARSA)

Arylsulfatase A (ARSA) has an enzymatic activity of hydrolyzing cerebroside sulfate (i.e., the following reaction: a cerebroside 3-sulfate+$H_2O$=a cerebroside+sulfate). Two isoforms of human ARSA (hARSA) protein (UniProtKB-P15289, ARSA_HUMAN) have been identified: P51608-1, SEQ ID NO: 2; and P51608-2, SEQ ID NO: 15. Throughout this specification, reference to ARSA is hARSA unless otherwise specified.

As used herein, a functional hARSA protein refers to an isoform, a natural variant, a variant, a polymorph, or a truncation of a hARSA protein which has at least about 10% of the enzymatic activity (i.e., enzyme activity) of the wildtype hARSA protein (for example, P51608-1, SEQ ID NO: 2; or P51608-2, SEQ ID NO: 15). See, OMIM #607574 (omim.org/entry/607574), genecards.org/cgi-bin/carddisp.pl?gene=ARSA and uniprot.org/uniprot/P15289, each of the webpages is incorporated herein by reference in its entirety. In certain embodiments, the functional hARSA protein has at least about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 100%, 1.5-fold, 2-fold, 3-fold, 4-fold, 5-fold, 10-fold or more of the enzymatic activity of the wildtype hARSA protein (for example, P51608-1, SEQ ID NO: 2; or P51608-2, SEQ ID NO: 15). In certain embodiments, the functional hARSA protein has about 10% to about 15%, about 10% to about 20%, about 10% to about 25%, about 10% to about 30%, about 10% to about 50%, about 10% to about 75%, about 10% to about 90%, about 10% to about 100%, about 10% to about 3-fold, about 15% to about 20%, about 15% to about 25%, about 15% to about 30%, about 15% to about 50%, about 15% to about 75%, about 15% to about 90%, about 15% to about 100%, about 15% to about 3-fold, about 20% to about 25%, about 20% to about 30%, about 20% to about 50%, about 20% to about 75%, about 20% to about 90%, about 20% to about 100%, about 20% to about 3-fold, about 25% to about 30%, about 25% to about 50%, about 25% to about 75%, about 25% to about 90%, about 25% to about 100%, about 25% to about 3-fold, about 50% to about 75%, about 50% to about 90%, about 50% to about 100%, about 50% to about 3-fold, about 75% to about 90%, about 75% to about 100%, or about 75% to about 3-fold of the enzymatic activity of the wildtype hARSA protein (for example, P51608-1, SEQ ID NO: 2; or P51608-2, SEQ ID NO: 15). Method(s) of measuring the hARSA enzymatic activity (for example, via synthetic substrate-based assays and/or via sulfatide loading assay) can be found in the Examples as well as in various publications, such as Kreysing et al., High residual arylsulfatase A (ARSA) activity in a patient with late-infantile metachromatic leukodystrophy. Am J Hum Genet. 1993 August;53 (2): 339-46.; Lee-Vaupel M and Conzelmann E. A simple chromogenic assay for arylsulfatase A. Clin Chim Acta. 1987 Apr. 30;164 (2): 171-80; Böhringer et al., Enzymatic characterization of novel arylsulfatase A variants using human arylsulfatase A-deficient immortalized mesenchymal stromal cells. Hum Mutat. 2017 November;38 (11): 1511-1520. doi: 10.1002/humu.23306. Epub 2017 Sep. 6; and Francesco Morena, et al., A new analytical bench assay for the determination of arylsulfatase a activity toward galactosyl-3-sulfate ceramide: implication for metachromatic leukodystrophy diagnosis. Anal Chem. 2014 Jan. 7;86 (1): 473-81. doi: 10.1021/ac4023555. Epub 2013 Dec. 11.

In certain embodiments, the functional hARSA protein comprises (i) a signal peptide, and (ii) an amino acid sequence of amino acid (aa) 19 to aa 507 of SEQ ID NO: 2 or an amino acid sequence at least about 90% (e.g., at least about 90%, 91%, 92%, 93%, 94%, 95%, 96%, 97%, 98%, 99%, or 99.9%) identical thereto. In certain embodiments, the functional hARSA protein comprises (i) a signal peptide, and (ii) an amino acid sequence of SEQ ID NO: 15 (i.e., aa 85 to aa 507 of SEQ ID NO: 2) or an amino acid sequence at least about 90% (e.g., at least about 90%,: 91%, 92%, 93%, 94%, 95%, 96%, 97%, 98%, 99%, or 99.9%) identical thereto. In certain embodiments, the functional hARSA protein comprises (i) a signal peptide, (ii) an amino acid sequence of amino acid (aa) 19 to aa 444 of SEQ ID NO: 2 or an amino acid sequence at least about 90% (e.g., at least about 90%, 91%, 92%, 93%, 94%, 95%, 96%, 97%, 98%, 99%, or 99.9%) identical thereto, and (iii) an amino acid sequence of aa 448 to aa 507 of SEQ ID NO: 2 or an amino acid sequence at least about 90% (e.g., at least about 90%, 91%, 92%, 93%, 94%, 95%, 96%, 97%, 98%, 99%, or 99.9%) identical thereto. In a further embodiment, the amino acid sequence of (ii) may be linked to the amino acid sequence of (iii) by disulfide bond(s). Other chemical bond(s) may be utilized, for example, covalent bond, and noncovalent bond (including hydrogen, ionic, hydrophobic, and Van Der Waals bonding). In yet a further embodiment, the link between the amino acid sequences of (ii) and (iii) is formed by a combination of the bonds described. In another embodiment, the link between the amino acid sequences of (ii) and (iii) is a peptide linker (see, e.g., parts.igem.org/Protein_domains/Linker). In certain embodiments, the functional hARSA protein comprises (i) a signal peptide, (ii) an amino acid sequence of amino acid (aa) 85 to aa 444 of SEQ ID NO: 2 or an amino acid sequence at least about 90% (e.g., at least about 90%, 91%, 92%, 93%, 94%, 95%, 96%, 97%, 98%, 99%, or 99.9%) identical thereto, and (iii) an amino acid sequence of aa 448 to aa 507 of SEQ ID NO: 2 or an amino acid sequence at least about 90% (e.g., at least about 90%, 91%, 92%, 93%, 94%, 95%, 96%, 97%, 98%, 99%, or 99.9%) identical thereto. In a further embodiment, the amino acid sequence of (ii) may be linked to the amino acid sequence of (iii) by disulfide bond(s). Other chemical bond(s) may be utilized, for example, covalent bond, and noncovalent bond (including hydrogen, ionic, hydrophobic, and Van Der Waals bonding). In yet a further embodiment, the link between the amino acid sequences of (ii) and (iii) is formed by a combination of the bonds described. In another embodiment, the link between the amino acid sequences of (ii) and (iii) is a peptide linker (see, e.g., parts.igem.org/Protein_domains/-Linker). In certain embodiments, the functional hARSA protein comprises (i) a signal peptide, and (ii) an amino acid sequence of amino acid (aa) 23 to aa 348 of SEQ ID NO: 2 or an amino acid sequence at least about 90% (e.g., at least about 90%, 91%, 92%, 93%, 94%, 95%, 96%, 97%, 98%, 99%, or 99.9%) identical thereto. In certain embodiments, the functional hARSA protein comprises (i) a signal peptide, and (ii) an amino acid sequence of amino acid (aa) 19 to aa 448 of SEQ ID NO: 2 or an amino acid sequence at least about 90% (e.g., at least about 90%, 91%, 92%, 93%, 94%, 95%, 96%, 97%, 98%, 99%, or 99.9%) identical thereto. In certain embodiments, the functional hARSA protein comprises (i) a signal peptide, and (ii) an amino acid sequence of amino acid (aa) 448 to aa 507 of SEQ ID NO: 2 or an amino acid sequence at least about 90% (e.g., at least about 90%, 91%, 92%, 93%, 94%, 95%, 96%, 97%, 98%, 99%, or 99.9%) identical thereto. In certain embodiments, the functional hARSA protein with the identity specified has its modifications outside of the aa 85 to aa 507 based on the numbering in SEQ ID NO: 2, and/or outside of any one or more of the aa 29, 69, 123, 125, 150, 229, 281, 282 based on the numbering in SEQ ID NO: 2, and/or outside of any of hARSA conserved domain(s) (for example, the sulfatase domain with Pfam: PF00884), and/or outside of aa 19 to aa 444 based on the numbering in SEQ ID NO: 2, and/or outside of aa 448 to aa 507 based on the numbering in SEQ ID NO: 2, and/or outside of aa 23 to aa 348 based on the numbering in SEQ ID NO: 2 or any combination thereof. See. e.g., von Bülow R et al, Crystal structure of an enzyme-substrate complex provides insight into the interaction between human arylsulfatase A and its substrates during catalysis, J Mol Biol. 2001 Jan. 12;305 (2): 269-77.

In certain embodiments, the functional hARSA protein has an amino acid sequence of SEQ ID NO: 2 or an amino acid sequence at least about 90% (e.g., at least about 90%, 91%, 92%, 93%, 94%, 95%, 96%, 97%, 98%, 99%, or 99.9%) identical thereto. In certain embodiment, the functional hARSA protein has an amino acid sequence of SEQ ID NO: 4 or an amino acid sequence at least about 90% (e.g., at least about 90%, 91%, 92%, 93%, 94%, 95%, 96%, 97%, 98%, 99%, or 99.9%) identical thereto.

As used herein, a signal peptide (sometimes referred to as signal sequence, targeting signal, localization signal, localization sequence, transit peptide, leader sequence or leader peptide) is a short peptide (usually 15-30 amino acids long) present at the N-terminus of the majority of newly synthesized proteins that are destined towards the secretory pathway (Blobel G, Dobberstein B (December 1975). "Transfer of proteins across membranes. I. Presence of proteolytically processed and unprocessed nascent immunoglobulin light chains on membrane-bound ribosomes of murine myeloma". J Cell Biol. 67 (3): 835-51). These proteins include those that reside either inside certain organelles (the endoplasmic reticulum, golgi or endosomes), secreted from the cell, or inserted into most cellular membranes. In certain embodiments, the signal peptide has an amino acid sequence of aa 1 to aa 18 of SEQ ID NO: 2 or an amino acid sequence of aa 1 to aa 20 of SEQ ID NO: 4. In certain embodiments, the signal peptide is from another protein which is secreted by a CNS cell (for example, a neuron), a PNS cell, or another cell (such as a kidney cell, or a liver cell). The signal peptide is preferably of human origin or a derivative of a human signal peptide, and is be about 15 to about 30 amino acids, preferably about 17 to 25 amino acids, or about 18 amino acids in length. In certain embodiments, the signal peptide is the native signal peptide (amino acids 1 to 18 of SEQ ID NO: 2). In certain embodiments, the functional hARSA protein comprises an exogenous leader sequence in the place of the native signal peptide. In another embodiment, the signal peptide may be from a human IL2 or a mutated signal peptide. In another embodiment, a human serpinF1 secretion signal may be used as a signal peptide. Such chimeric hARSA proteins comprising an exogenous signal peptide and the mature portion of the hARSA (e.g., aa 19 to 507 of SEQ ID NO:2, aa 19 to aa 444 of SEQ ID NO: 2, aa 85 to aa 507 of SEQ ID NO: 2, aa 23 to aa 348 of SEQ ID NO: 2, or aa 448 to 507 of SEQ ID NO: 2) is included in the various embodiments described herein when reference is made to a functional hARSA protein.

Provided herein is a nucleic acid sequence encoding a functional hARSA protein, termed as hARSA coding sequence or ARSA coding sequence or hARSA or ARSA. In certain embodiments, the hARSA coding sequence is a modified or engineered (hARSA or hARSAco). In certain embodiments, the hARSA coding sequence has a sequence of nucleotide (nt) 55 to nt 1521 of SEQ ID NO: 1, or a sequence at least 95% to 99.9% identical thereto. In certain embodiments, the hARSA coding sequence is nt 55 to nt 1521 of SEQ ID NO: 1 or a nucleic acid sequence at least about 70% (e.g., at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.9%) identical thereto. In certain embodiments, the hARSA coding sequence is SEQ ID NO: 1 or a sequence at least 95% to 99.9% identical thereto. In certain embodiments, the hARSA coding sequence is SEQ ID NO: 1 or a nucleic acid sequence at least about 70% (e.g., at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.9%) identical thereto. In certain embodiments, the hARSA coding sequence is SEQ ID NO: 3 or a sequence at least 95% to 99.9% identical thereto. In certain embodiments, the hARSA coding sequence is SEQ ID NO: 3 or a nucleic acid sequence at least about 70% (e.g., at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.9%) identical thereto.

Transcript variants of hARSA (which is also hARSA coding sequence) can be found as NCBI Reference Sequences NM_000487.5, NM_001085425.2, NM_001085426.2, NM_001085427.2, NM_001085428.2, NM_001362782.1, AB448736.1, AK092752.1, AK098659.1, AK301098.1, AK310564.1, AK315011.1, BC014210.2, BI770997.1, BM818814.1, BP306351.1, BQ184813.1, BU632196.1, BX648618.1, CA423492.1, CN409235.1, CR456383.1, DA844740.1, DB028013.1, GQ891416.1, KUI77918.1, KU177919.1, and X52151.1. Each of the NCBI Reference Sequences is incorporated herein by reference in its entirety. In certain embodiments, the modified or engineered hARSA coding sequence shares less than about 70%, 75%, 80%, 85%, 90%, 91%, 92%, 93%, 94%, 95%, 96%, 97%, 98%, 99%, or 99.9% identity to one of the NCBI Reference Sequences. In certain embodiments, the modified or engineered hARSA coding sequence shares about 50%, 60%, 70%, 75%, 80%, 85%, 90%, 91%, 92%, 93%, 94%, 95%, 96%, 97%, 98%, 99%, or 99.9% identity to one of the NCBI Reference Sequences. A "nucleic acid" or a "nucleotide", as described herein, can be RNA, DNA, or a modification thereof, and can be single or double stranded, and can be selected, for example, from a group including: nucleic acid encoding a protein of interest, oligonucleotides, nucleic acid analogues, for example peptide-nucleic acid (PNA), pseudocomplementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

The term "percent (%) identity", "sequence identity", "percent sequence identity", or "percent identical" in the context of nucleic acid sequences refers to the residues in the two sequences which are the same when aligned for correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired.

Percent identity may be readily determined for amino acid sequences over the full-length of a protein, polypeptide, about 32 amino acids, about 330 amino acids, or a peptide fragment thereof or the corresponding nucleic acid sequence coding sequences. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence.

Alignments are performed using any of a variety of publicly or commercially available Multiple Sequence Alignment Programs. Sequence alignment programs are available for amino acid sequences, e.g., the "Clustal X", "Clustal Omega" "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27 (13): 2682-2690 (1999).

Multiple sequence alignment programs are also available for nucleic acid sequences. Examples of such programs include, "Clustal W", "Clustal Omega", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

II. Metachromatic Leukodystrophy (MLD)

Provided herein are rAAV, vector, methods and compositions useful in treating a disease or an abnormal condition caused by mutation(s) of Arylsulfatase A (ARSA) gene and/or deficiencies in normal levels of functional Arylsulfatase A, termed as "disease" herein, for example, Metachromatic leukodystrophy (MLD). See, e.g., omim.org/entry/250100.

Metachromatic Leukodystrophy (MLD) can be classified into the following types: early onset MLD which includes infantile MLD (typically begins equal to or earlier than 30 months of age) and early juvenile MLD (usually begins between 30 months of age to 6 years of age (including 6 years); juvenile MLD which includes early juvenile MLD and late juvenile MLD (usually begins between 7 years of age and 16 years of age, including 16 year old); and adult MLD (with an onset later than 16 years of age). Late infantile MLD patients have a devastating disease course with rapid and predictable decline that is homogeneous in the presentation of both motor and cognitive impairment (Kehrer et al., 2011a; Sessa et al., 2016). The majority of these children die before 5 years of age with a mean survival in 98 patients of 4.2 years and a 5 year survival of 25% (Mahmood et al., 2010). The phenotype of children with early juvenile MLD (symptom onset between 30 months and 6 years of age) is very similar to that of children with late infantile MLD, although early juvenile MLD patients may have a less rapid initial disease evolution (Biffi et al., 2008; Chen et al., 2016; Sessa et al., 2016). However, once overt symptoms appear, in particular when early juvenile MLD patients lose the ability to walk independently, their disease course can deteriorate as rapidly as late infantile MLD patients. These children also have similar signs and symptoms as late infantile MLD patients with neuromuscular difficulties developing first, either in isolation or concurrent with behavioral and cognitive symptoms (Groeschel et al., 2011; Kehrer et al., 2014). The early juvenile and late infantile phenotypes are collectively referred to as early onset MLD (Sessa et al., 2016).

In certain embodiments, the rAAV, vector, composition and method described herein are useful in treating MLD, early onset MLD, infantile MLD, late infantile MLD, juvenile MLD, early juvenile MLD, late juvenile MLD, or adult MLD. In certain embodiments, the rAAV, vector, compositions and methods described herein may ameliorate disease symptom and/or delay disease progression in a subject. In certain embodiments, the rAAV, vector, compositions and methods described herein are useful in treating late infantile and early juvenile MLD.

In certain embodiments, the subject or patient of the rAAV, vector, method or composition described herein has MLD, or is diagnosed with MLD. In certain embodiments, the subject or patient of rAAV, vector, the method or composition described herein is diagnosed with late infantile MLD or early juvenile MLD. The diagnosis of MLD may be made through both genetic and biochemical testing. Genetic testing can identify mutations in the ARSA, while biochemical testing includes sulfatase enzyme activity and urinary sulfatide excretion. An magnetic resonance imaging (MRI) can confirm a diagnosis of MLD. An MRI shows imaging of a person's brain and can show the presence and absence of myelin. There is a classic pattern of myelin loss in the brains of individuals affected by MLD. As the disease progresses, imaging shows accumulating injury to the brain. In young children, the initial brain imaging can be normal.

In certain embodiments, the subject of the rAAV, vector, method or composition described herein is a human less than 18 years old (e.g., less than about 1, 2, 3, 4, 5, 6, 7, 8, 9, 10, 11 month(s) old, or less than about 1, 1.5, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18 year(s) old). Additionally or alternatively, the subject is a newborn or a human more than 1 month old (e.g., more than about 2, 3, 4, 5, 6, 7, 8, 9, 10, 11 month(s) old, or more than about 1, 1.5, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18 year(s) old). In certain embodiments, the patient is about 1,. 2, 3, 4, 5, 6, 7, 8, 9, 10, 11 month(s) old, or about 1, 1.5, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18 year(s) old. In certain embodiments, the patient is about 30 months to about 7 years of age. In certain embodiments, the patient is from about 30 months to 16 years of age, from 7 years to 16 years of age, or from 16 years to 40 years of age.

"Patient" or "subject", as used herein interchangeably, means a male or female mammalian animal, including a human, a veterinary or farm animal, a domestic animal or pet, and animals normally used for clinical research. In one embodiment, the subject of these rAAV, vector, methods and compositions is a human patient. In one embodiment, the subject of these rAAV, vector, methods and compositions is a male or female human. In certain embodiments, the subject of these rAAV, vector, methods and compositions is diagnosed with Metachromatic Leukodystrophy and/or with symptoms of Metachromatic Leukodystrophy.

Disease symptoms (e.g., MLD symptoms, compared to a healthy control without MLD) may include, but are not limited to the following: decreased concentration and/or level and/or biological activity of ARSA (for example, in serum or in CSF), increased urine sulfatides, CNS myelination (demyelination load and pattern), white matter atrophy as measured by MRI, an abnormal (decreased or increased) neuronal metabolite N-acetylaspartate (NAA), myo-inositol (ml), choline (Cho) and/or lactate (Lac) levels (for example, as measured by proton magnetic resonance spectroscopy (MRS)), increased CSF sulfatide and lysosulfatide levels, abnormal Visual evoked potentials (VEPs), abnormal Brainstem auditory evoked responses (BAERs), gall-bladder wall thickening (for example, via ultrasound evaluation); impaired motor function (for example, measured by the Gross Motor Function Classification for Metachromatic Leukodystrophy (GMFC-MLD) or Gross Motor Function Measure (GMFM)), delayed Motor milestones achievement (as defined by World Health Organization [WHO] criteria) assessed by age at achievement, age at loss, and percentage of children maintaining or acquiring motor milestones, impaired cognitive function (for example, Total Intelligence Quotient [IQ] and sub-domain IQ measured by the Bayley Scale of Infant Development [BSID-III], Wechsler Intelligence Scale for Children, Fifth Edition [WISC-V]), increased lifespan (compared to a patient), an abnormal result of neurological clinical exam (NCE), a reduced nerve conduction velocity (NCV) of the ulnar, deep peroneal, median, sural nerves, an earlier age-at-onset and higher frequency of seizures captured by a seizure diary, impaired behavior function (for example, measured by Vineland Adaptive Behavior Scales, Third Edition (Vineland-III)), a lower Lansky Performance Index, a decreased Pediatric Quality of Life Inventory (for example, PedsQL and PedsQL-IS), and/or a decreased caregiver/parent quality of life.

In certain embodiments, disease symptoms (e.g., MLD symptoms, compared to a healthy control without MLD) may include abnormal properties (for example biomarker activity, electrophysiological activity, and/or imaging parameters) and clinical observations (for example, impaired gross and fine motor function, impaired cognitive and language development, abnormal neurological exam findings, impaired behavioral and milestone development, and caregiver/parent-reported outcomes and decreased quality of life assessments).

The abnormal properties include but are not limited to functional impairment of myelin-producing oligodendrocytes and Schwann cells, peripheral nerve conduction abnormalities, peripheral neuropathy with slow nerve conduction velocities (NCVs), brain magnetic resonance imaging (MRI) showing a typical white matter (for example, the splenium of the corpus callosum and parieto-occipital white matter, projection fibers, cerebellar white matter, basal ganglia, and the thalamus) pattern (for example, a "tigroid pattern" of radiating stripes with bands of normal signal intensity within the abnormal white matter, see, e.g., Gieselmann and Krageloh-Mann, 2010; Martin et al., 2012; van Rappard et al., 2015); U-fiber involvement and cerebellar changes, white matter demyelination, bilateral areas of white matter hypodensity, especially in the frontal lobes, and cerebral atrophy reflecting loss of myelin), abnormal levels of the brain biomarkers N-acetylaspartate and myo-inositol.

The clinical observations include but are not limited to gross motor disturbances that manifest as clumsiness, toe walking, and frequent falls; fine motor skills; gait abnormalities; spastic paraparesis or ataxic movement; neuromuscular difficulties; neurologic symptoms (signs of weakness, loss of coordination progressing to spasticity and incontinence); hypotonia, and depressed deep tendon reflexes; seizures; dementia; epilepsy; difficulty urinating spasticity; feeding difficulties; pain in the extremities; impaired language function; impaired cognitive skills; impaired vision and hearing; losing previously acquired motor and cognitive milestones; decline in school or job performance, inattention, abnormal behaviors, psychiatric symptoms, intellectual impairment, uncontrolled laughter, cortical disturbances (e.g., apraxia, aphasia, agnosia), alcohol or drug use, poor money management, emotional lability, inappropriate affect, and neuropsychiatric symptoms (including psychosis, schizophrenia, delusions, and hallucinations).

Disease progression refers to subject's age of onset, frequency of appearance, severity, or recurrence, of a disease symptom. A delay in disease progression normally means an elevated age of onset, a lower frequency of appearance, a decreased severity, or less recurrence, of a disease symptom.

As described above, the terms "increase" "decrease" "reduce" "ameliorate" "elevate" "lower" "higher" "less" "more" "improve" "delay" "impair" "abnormal" "thick" or any grammatical variation thereof, or any similar terms indication a change, means a variation of about 5 fold, about 2 fold, about 1 fold, about 90%, about 80%, about 70%, about 60%, about 50%, about 40%, about 30%, about 20%, about 10%, about 5% compared to the corresponding reference (e.g., untreated control or a subject in normal condition without MLD), unless otherwise specified.

The compositions and methods herein provide a fast-acting, disease-modifying treatment to symptomatic early onset patients for whom no standard of care exists (HSCT and HSC-GT are not efficacious); and/or provide a therapy that can preserve or correct both CNS pathologies and peripheral nerve function, the latter of which is not corrected by HSCT and causes progressive fine and gross motor function loss and respiratory failure; and/or provide an alternative treatment option to HSC-GT, which requires harsh myeloablative conditioning, is only efficacious when performed prior to onset of symptoms, and may not substantially address peripheral neuropathy in all patients.

In certain embodiments, the patient receives a co-therapy for which they would not have been eligible without the rAAV, vector, composition or method described herein. Such co-therapies may include enzyme replacement therapy (ERT) and hematopoietic stem cell transplantation (HSCT) via umbilical cord blood (UCB), allogeneic peripheral blood stem cells, or allogeneic bone marrow.

Optionally, an immunosuppressive co-therapy may be used in a subject in need. Immunosuppressants for such co-therapy include, but are not limited to, a glucocorticoid, steroids, antimetabolites, T-cell inhibitors, a macrolide (e.g., a rapamycin or rapalog), and cytostatic agents including an alkylating agent, an anti-metabolite, a cytotoxic antibiotic, an antibody, or an agent active on immunophilin. The immune suppressant may include a nitrogen mustard, nitrosourea, platinum compound, methotrexate, azathioprine, mercaptopurine, fluorouracil, dactinomycin, an anthracycline, mitomycin C, bleomycin, mithramycin, IL-2 receptor-(CD25-) or CD3-directed antibodies, anti-IL-2 antibodies, ciclosporin, tacrolimus, sirolimus, IFN-β, IFN-γ, an opioid, or TNF-α (tumor necrosis factor-alpha) binding agent. In certain embodiments, the immunosuppressive therapy may be started 0, 1, 2, 3, 4, 5, 6, 7, or more days prior to or after the gene therapy administration. Such immunosuppressive therapy may involve administration of one, two or more drugs (e.g., glucocorticoids, prednelisone, micophenolate mofetil (MMF) and/or sirolimus (i.e., rapamycin)). Such immunosuppressive drugs may be administered to a subject in need once, twice or for more times at the same dose or an adjusted dose. Such therapy may involve co-administration of two or more drugs, the (e.g., prednelisone, micophenolate mofetil (MMF) and/or sirolimus (i.e., rapamycin)) on the same day. One or more of these drugs may be continued after gene therapy administration, at the same dose or an adjusted dose. Such therapy may be for about 1 week (7 days), about 60 days, or longer, as needed. In certain embodiments, a tacrolimus-free regimen is selected.

III. Expression Cassette

Provided herein is a nucleic acid sequence comprising a hARSA coding sequence encoding a functional hARSA protein and regulatory sequences which directs the hARSA expression in a target cell, also termed as an expression cassette. As used herein, an "expression cassette" refers to a nucleic acid molecule which comprises a coding sequence (e.g., a hARSA coding sequence), promoter, and may include other regulatory sequences therefor. The regulatory sequences necessary are operably linked to the hARSA coding sequence in a manner which permits its transcription, translation and/or expression in target cell. As used herein, "operably linked" sequences include both expression control sequences that are contiguous with the hARSA coding sequence and expression control sequences that act in trans or at a distance to control the hARSA coding sequence. Such regulatory sequences typically include, e.g., one or more of a promoter, an enhancer, an intron, a Kozak sequence, a polyadenylation sequence, and a TATA signal. In certain embodiment, the promoter is a chicken beta actin promoter with a cytomegalovirus enhancer (CB7) promoter (e.g., nt 198 to nt 862 of SEQ ID NO: 5, also termed as hSyn or Syn herein). However, in certain embodiments, other promoters, or an additional promoter, may be selected.

In certain embodiments, the regulatory sequences direct hARSA expression in a target cell. In certain embodiment, a target cell is a nervous system cell, an oligodendrocyte, a microglia, a Central Nervous System (CNS) cell, a neuron in the CNS, a Peripheral Nervous System (PNS) cell, a Schwann cell, a macrophage in the PNS, or a cell in visceral organs (for example, a kidney cell, a liver cell and a gallbladder cell). In certain embodiment, the target cell may be a central nervous system cell. In certain embodiments, the target cell is one or more of an excitatory neuron, an inhibitory neuron, a glial cell, a cortex cell, a frontal cortex cell, a cerebral cortex cell, a spinal cord cell. In certain embodiments, the target cell is a peripheral nervous system (PNS) cell, for example a retina cell. Other cells other than those from nervous system may also be chosen as a target cell, such as a monocyte, a B lymphocyte, a T lymphocyte, a NK cell, a lymph node cell, a tonsil cell, a bone marrow mesenchymal cell, a stem cell, a bone marrow stem cell, a heart cell, an epithelium cell, a esophagus cell, a stomach cell, a fetal cut cell, a colon cell, a rectum cell, a liver cell, a kindly cell, a lung cell, a salivary gland cell, a thyroid cell, an adrenal cell, a breast cell, a pancreas cell, an islet of Langerhans cell, a gallbladder cell, a prostate cell, a urinary bladder cell, a skin cell, a uterus cell, a cervix cell, a testis cell, or any other cell which expresses a functional hARSA protein in a subject without MLD. See, genecards.org/cgi-bin/carddisp.pl?gene=ARSA&keywords=arsa #expression.

In certain embodiments, the regulatory sequences comprise a ubiquitous promoter, for example a CB7 promoter. In certain embodiments, the regulatory elements comprise one or more of a Kozak sequence, a polyadenylation sequence, an intron, an enhancer, and a TATA signal.

In certain embodiments, an additional or alternative promoter sequence may be included as part of the expression control sequences (regulatory sequences), e.g., located between the selected 5' ITR sequence and the coding sequence. Constitutive promoters, regulatable promoters [see, e.g., WO 2011/126808 and WO 2013/04943], tissue specific promoters, or a promoter responsive to physiologic cues may be utilized in the vectors described herein. The promoter(s) can be selected from different sources, e.g., human cytomegalovirus (CMV) immediate-early enhancer/promoter, the SV40 early enhancer/promoter, the JC polymovirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter.

In addition to a promoter, an expression cassette may contain one or more other appropriate transcription initiation sequences, transcription termination sequences, enhancer sequences, efficient RNA processing signals such as splicing and polyadenylation (polyA) signals; sequences that stabilize cytoplasmic mRNA for example WPRE; sequences that enhance translation efficiency (i.e., Kozak consensus sequence); sequences that enhance protein stability; and when desired, sequences that enhance secretion of the encoded product. An example of a suitable enhancer is the CMV enhancer. Other suitable enhancers include those that are appropriate for desired target tissue indications. In one embodiment, the regulatory sequences comprise one or more expression enhancers. In one embodiment, the regulatory sequences contain two or more expression enhancers. These enhancers may be the same or may differ from one another. For example, an enhancer may include a CMV immediate early enhancer (SEQ ID NO: 19). This enhancer may be present in two copies which are located adjacent to one another. Alternatively, the dual copies of the enhancer may be separated by one or more sequences. In still another embodiment, the expression cassette further contains an intron, e.g., the chicken beta-actin intron (SEQ ID NO: 17). In certain embodiments, the intron is a chimeric intron (CI)—a hybrid intron consisting of a human beta-globin splice donor and immunoglobulin G (IgG) splice acceptor elements. Other suitable introns include those known in the art, e.g., such as are described in WO 2011/126808. Examples of suitable polyA sequences include, e.g., Rabbit globin polyA, SV40, SV50, bovine growth hormone (bGH), human growth hormone, and synthetic polyAs. Optionally, one or more sequences may be selected to stabilize mRNA. An example of such a sequence is a modified WPRE sequence, which may be engineered upstream of the polyA sequence and downstream of the coding sequence (see, e.g., MA Zanta-Boussif, et al, Gene Therapy (2009) 16:605-619). In certain embodiments, no WPRE sequence is present.

Optionally, in certain embodiments, in addition to the hARSA coding sequence, another non-AAV coding sequence may be included, e.g., a peptide, polypeptide, protein, functional RNA molecule (e.g., miRNA, miRNA inhibitor) or other gene product, of interest. Useful gene products may include miRNAs. miRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

In certain embodiments, the expression cassette may further comprises a dorsal root ganglion (drg)-specific miRNA detargetting sequences to modulate expression levels in the CNS or peripheral dorsal root ganglia. In certain embodiments, the expression cassette or vector genome comprises one or more miRNA target sequences in the untranslated region (UTR) 3' to a gene product coding sequence. In certain embodiments, there are at least one target sequence specific for miR-183, miR-182, or miR-96. In certain embodiments, at least two drg-specific miRNA target sequences are located in both 5' and 3' to the hARSA coding sequence. In certain embodiments, the miRNA target sequence for the at least first and/or at least second miRNA target sequence for the expression cassette mRNA or DNA positive strand is selected from (i) AGTGAATTCTACCAGTGCCATA (miR183, SEQ ID NO: 20); (ii) AGCAAAAATGTGCTAGTGCCAAA (SEQ ID NO: 21); (iii) AGTGTGAGTTCTACCATTGCCAAA (SEQ ID NO: 22); and (iv) AGGGATTCCTGGGAAAACTGGAC (SEQ ID NO: 23). In certain embodiments, the construct further comprises at least two tandem repeats comprise at least a first miRNA target sequence and at least a second miRNA target sequence which may be the same or different. In certain embodiments, the tandem miRNA target sequences are continuous or are separated by a spacer of 1 to 10 nucleic acids, wherein said spacer is not an miRNA target sequence.

In certain embodiments, there are at least two drg-specific miRNA target sequences located at 3' to the hARSA coding sequence. In certain embodiments, the start of the first of the at least two drg-specific miRNA tandem repeats is within 20 nucleotides from the 3' end of the hARSA-coding sequence. In certain embodiments, the start of the first of the at least two drg-specific miRNA tandem repeats is at least 100 nucleotides from the 3' end of the hARSA-coding sequence. In certain embodiments, the miRNA tandem repeats comprise 200 to 1200 nucleotides in length. In certain embodiments, there are at least two drg-specific miRNA target sequences located at 5' to the hARSA coding sequence. In certain embodiments, two or more consecutive miRNA target sequences are continuous and not separated by a spacer. In certain embodiments, two or more of the miRNA target sequences are separated by a spacer and each spacer is independently selected from one or more of (A) GGAT; (B) CACGTG; or (C) GCATGC. In certain embodiments, the spacer located between the miRNA target sequences may be located 3' to the first miRNA target sequence and/or 5' to the last miRNA target sequence. In certain embodiments, the spacers between the miRNA target sequences are the same.

See, Provisional U.S. Patent Application No. 62/783,956, filed Dec. 21, 2018, and International Application No. PCT/US2019/067872, filed Dec. 20, 2019, which are hereby incorporated by reference. In certain embodiments, no miR sequences are included in an expression cassette or vector genome.

IV. AAVhu68

The AAVhu68 serotype, which was selected as the capsid for AAVhu68.CB7.CI.hARSAco.RBG, is 99% identical at the amino acid level to AAV9. AAVhu68 displays transduction characteristics in the nervous systems of NHPs and mice comparable to AAV9. This includes widespread transduction of cortical neurons (data not shown) and a small subset of myelin-producing oligodendrocytes. In addition, AAVhu68 transduces motor neurons with axons projecting into the PNS and DRG sensory neurons with axons projecting into the spinal cord and peripheral nerves (data not shown). Transduction was observed in lower motor neurons of the ventral horn and sensory neurons of the DRG. The transduced motor neurons have axons that contribute to the peripheral nerves. Thus, the AAVhu68 capsid targets cells in the CNS and PNS, which are both affected in MLD patients. Additionally, while newly synthesized ARSA can be transported directly from the trans-Golgi network to the lysosome, it can also be secreted and taken up by other cells via mannose-6-phosphate receptors where it is subsequently trafficked to the lysosomes. Thus, the underlying defect can be cross-corrected by rAAVhu68.hARSA expressing ARSA enzyme supplied to neighboring cells of the CNS that lack functional enzyme. AAVhu68 (previously termed AAV3G2) varies from another Clade F virus AAV9 by two encoded amino acids at positions 67 and 157 of vp1, based on the numbering of SEQ ID NO: 7. In contrast, the other Clade F AAV (AAV9, hu31, hu31) have an Ala at position 67 and an Ala at position 157. Provided are novel AAVhu68 capsids and/or engineered AAV capsids having valine (Val or V) at position 157 based on the numbering of SEQ ID NO: 7 and optionally, a glutamic acid (Glu or E) at position 67 based on the numbering of SEQ ID NO: 7. In certain embodiments, the AAV capsid stereotype may be selected from AAVhu31 vp1 (SEQ ID NOs: 11 and 12) or AAVhu32 vp1 (SEQ ID NOs: 13 and 14).

As used herein, the term "clade" as it relates to groups of AAV refers to a group of AAV which are phylogenetically related to one another as determined using a Neighbor- Joining algorithm by a bootstrap value of at least 75% (of at least 1000 replicates) and a Poisson correction distance measurement of no more than 0.05, based on alignment of the AAV vp1 amino acid sequence. The Neighbor-Joining algorithm has been described in the literature. See, e.g., M. Nei and S. Kumar, Molecular Evolution and Phylogenetics (Oxford University Press, New York (2000). Computer programs are available that can be used to implement this algorithm. For example, the MEGA v2.1 program implements the modified Nei-Gojobori method. Using these techniques and computer programs, and the sequence of an AAV vp1 capsid protein, one of skill in the art can readily determine whether a selected AAV is contained in one of the clades identified herein, in another clade, or is outside these clades. See, e.g., G Gao, et al, J Virol, 2004 June; 78 (10): 6381-6388, which identifies Clades A, B, C, D, E and F, and provides nucleic acid sequences of novel AAV, GenBank Accession Numbers AY530553 to AY530629. See, also, WO 2005/033321.

In certain embodiments, an AAVhu68 capsid is further characterized by one or more of the following. AAVhu68 capsid proteins comprise: AAVhu68 vp1 proteins produced by expression from a nucleic acid sequence which encodes the predicted amino acid sequence of 1 to 736 of SEQ ID NO: 7, vp1 proteins produced from SEQ ID NO: 6, or vp1 proteins produced from a nucleic acid sequence at least 70% identical to SEQ ID NO: 6 which encodes the predicted amino acid sequence of 1 to 736 of SEQ ID NO: 7; AAVhu68 vp2 proteins produced by expression from a nucleic acid sequence which encodes the predicted amino acid sequence of at least about amino acids 138 to 736 of SEQ ID NO: 7, vp2 proteins produced from a sequence comprising at least nucleotides 412 to 2211 of SEQ ID NO: 6, or vp2 proteins produced from a nucleic acid sequence at least 70% identical to at least nucleotides 412 to 2211 of SEQ ID NO: 6 which encodes the predicted amino acid sequence of at least about amino acids 138 to 736 of SEQ ID NO: 7; and/or AAVhu68 vp3 proteins produced by expression from a nucleic acid sequence which encodes the predicted amino acid sequence of at least about amino acids 203 to 736 of SEQ ID NO: 7, vp3 proteins produced from a sequence comprising at least nucleotides 607 to 2211 of SEQ ID NO: 6, or vp3 proteins produced from a nucleic acid sequence at least 70% identical to at least nucleotides 607 to 2211 of SEQ ID NO: 6 which encodes the predicted amino acid sequence of at least about amino acids 203 to 736 of SEQ ID NO: 7.

The AAVhu68 vp1, vp2 and vp3 proteins are typically expressed as alternative splice variants encoded by the same nucleic acid sequence which encodes the full-length vp1 amino acid sequence (amino acid 1 to 736). Optionally the vp1-encoding sequence is used alone to express the vp1, vp2 and vp3 proteins. Alternatively, this sequence may be co-expressed with one or more of a nucleic acid sequence which encodes the AAVhu68 vp3 amino acid sequence (about aa 203 to 736) without the vp1-unique region (about aa 1 to about aa 137) and/or vp2-unique regions (about aa 1 to about aa 202), or a strand complementary thereto, the corresponding mRNA or tRNA (for example, the mRNA transcribed from about nucleotide (nt) 607 to about nt 2211 of SEQ ID NO: 6), or a sequence at least 70% to at least 99% (e.g., at least 85%, at least 90%, at least 95%, at least 97%, at least 98% or at least 99%) identical to SEQ ID NO: 6 which encodes aa 203 to 736 of SEQ ID NO: 7. Additionally, or alternatively, the vp1-encoding and/or the vp2-encoding sequence may be co-expressed with the nucleic acid sequence which encodes the AAVhu68 vp2 amino acid sequence of SEQ ID NO: 7 (about aa 138 to 736) without the vp1-unique region (about aa 1 to about 137), or a strand complementary thereto, the corresponding mRNA or tRNA (for example, the mRNA transcribed from nt 412 to 2211 of SEQ ID NO: 6), or a sequence at least 70% to at least 99% (e.g., at least 85%, at least 90%, at least 95%, at least 97%, at least 98% or at least 99%) identical to SEQ ID NO: 6 which encodes about aa 138 to 736 of SEQ ID NO: 7.

As described herein, a rAAVhu68 has a rAAVhu68 capsid produced in a production system expressing capsids from an AAVhu68 nucleic acid sequence which encodes the vp1 amino acid sequence of SEQ ID NO: 7, and optionally additional nucleic acid sequences, e.g., encoding a vp 3 protein free of the vp1 and/or vp2-unique regions. The rAAVhu68 resulting from production using a single nucleic acid sequence vp1 produces the heterogenous populations of vp1 proteins, vp2 proteins and vp3 proteins. More particularly, the AAVhu68 capsid contains subpopulations within the vp1 proteins, within the vp2 proteins and within the vp3 proteins which have modifications from the predicted amino acid residues in SEQ ID NO: 7. These subpopulations include, at a minimum, deamidated asparagine (N or Asn) residues. For example, asparagines in asparagine-glycine pairs are highly deamidated.

In one embodiment, the AAVhu68 vp1 nucleic acid sequence has the sequence of SEQ ID NO: 6, or a strand complementary thereto, e.g., the corresponding mRNA or tRNA. In certain embodiments, the vp2 and/or vp3 proteins may be expressed additionally or alternatively from different nucleic acid sequences than the vp1, e.g., to alter the ratio of the vp proteins in a selected expression system. In certain embodiments, also provided is a nucleic acid sequence which encodes the AAVhu68 vp3 amino acid sequence of SEQ ID NO: 7 (about aa 203 to 736) without the vp1-unique region (about aa 1 to about aa 137) and/or vp2-unique regions (about aa 1 to about aa 202), or a strand complementary thereto, the corresponding mRNA or tRNA (about nt 607 to about nt 2211 of SEQ ID NO: 6). In certain embodiments, also provided is a nucleic acid sequence which encodes the AAVhu68 vp2 amino acid sequence of SEQ ID NO: 7 (about aa 138 to 736) without the vp1-unique region (about aa 1 to about 137), or a strand complementary thereto, the corresponding mRNA or tRNA (nt 412 to 2211 of SEQ ID NO: 6).

However, other nucleic acid sequences which encode the amino acid sequence of SEQ ID NO: 7 may be selected for use in producing rAAVhu68 capsids. In certain embodiments, the nucleic acid sequence has the nucleic acid sequence of SEQ ID NO: 6 or a sequence at least 70% to 99% identical, at least 75%, at least 80%, at least 85%, at least 90%, at least 95%, at least 97%, at least 99%, identical to SEQ ID NO: 6 which encodes SEQ ID NO: 7. In certain embodiments, the nucleic acid sequence has the nucleic acid sequence of SEQ ID NO: 6 or a sequence at least 70% to 99%, at least 75%, at least 80%, at least 85%, at least 90%, at least 95%, at least 97%, at least 99%, identical to about nt 412 to about nt 2211 of SEQ ID NO: 6 which encodes the vp2 capsid protein (about aa 138 to 736) of SEQ ID NO: 7. In certain embodiments, the nucleic acid sequence has the nucleic acid sequence of about nt 607 to about nt 2211 of SEQ ID NO: 6 or a sequence at least 70% to 99%, at least 75%, at least 80%, at least 85%, at least 90%, at least 95%, at least 97%, at least 99%, identical to nt 607 to about nt 2211 of SEQ ID NO: 6 which encodes the vp3 capsid protein (about aa 203 to 736) of SEQ ID NO: 7.

It is within the skill in the art to design nucleic acid sequences encoding this AAVhu68 capsid, including DNA (genomic or cDNA), or RNA (e.g., mRNA). In certain embodiments, the nucleic acid sequence encoding the AAVhu68 vp1 capsid protein is provided in SEQ ID NO: 6. See, WO 2018/160582 which is incorporated herein by reference in its entirety. In certain embodiments, the AAVhu68 capsid is produced using a nucleic acid sequence of SEQ ID NO: 6 or a sequence at least 70%, at least 75%, at least 80%, at least 85%, at least 90%, at least 95%, at least 97%, at least 99%, which encodes the vp1 amino acid sequence of SEQ ID NO: 7 with a modification (e.g., deamidated amino acid) as described herein. In certain embodiments, the vp1 amino acid sequence is reproduced in SEQ ID NO: 7.

As used herein when used to refer to vp capsid proteins, the term "heterogenous" or any grammatical variation thereof, refers to a population consisting of elements that are not the same, for example, having vp1, vp2 or vp3 monomers (proteins) with different modified amino acid sequences. SEQ ID NO: 7 provides the encoded amino acid sequence of the AAVhu68 vp1 protein. The term "heterogenous" as used in connection with vp1, vp2 and vp3 proteins (alternatively termed isoforms), refers to differences in the amino acid sequence of the vp1, vp2 and vp3 proteins within a capsid. The AAV capsid contains subpopulations within the vp1 proteins, within the vp2 proteins and within the vp3 proteins which have modifications from the predicted amino acid residues. These subpopulations include, at a minimum, certain deamidated asparagine (N or Asn) residues. For example, certain subpopulations comprise at least one, two, three or four highly deamidated asparagines (N) positions in asparagine-glycine pairs and optionally further comprising other deamidated amino acids, wherein the deamidation results in an amino acid change and other optional modifications.

As used herein, a "subpopulation" of vp proteins refers to a group of vp proteins which has at least one defined characteristic in common and which consists of at least one group member to less than all members of the reference group, unless otherwise specified.

For example, a "subpopulation" of vp1 proteins is at least one (1) vp1 protein and less than all vp1 proteins in an assembled AAV capsid, unless otherwise specified. A "subpopulation" of vp3 proteins may be one (1) vp3 protein to less than all vp3 proteins in an assembled AAV capsid, unless otherwise specified. For example, vp1 proteins may be a subpopulation of vp proteins; vp2 proteins may be a separate subpopulation of vp proteins, and vp3 are yet a further subpopulation of vp proteins in an assembled AAV capsid. In another example, vp1, vp2 and vp3 proteins may contain subpopulations having different modifications, e.g., at least one, two, three or four highly deamidated asparagines, e.g., at asparagine-glycine pairs.

Unless otherwise specified, highly deamidated refers to at least 45% deamidated, at least 50% deamidated, at least 60% deamidated, at least 65% deamidated, at least 70%, at least 75%, at least 80%, at least 85%, at least 90%, at least 95%, at least 97%, at least 99%, or up to about 100% deamidated at a referenced amino acid position, as compared to the predicted amino acid sequence at the reference amino acid position (e.g., at least 80% of the asparagines at amino acid 57 based on the numbering of SEQ ID NO: 7 (AAVhu68) may be deamidated based on the total vp1 proteins may be deamidated based on the total vp1, vp2 and vp3 proteins). Such percentages may be determined using 2D-gel, mass spectrometry techniques, or other suitable techniques.

Without wishing to be bound by theory, the deamidation of at least highly deamidated residues in the vp proteins in the AAV capsid is believed to be primarily non-enzymatic in nature, being caused by functional groups within the capsid protein which deamidate selected asparagines, and to a lesser extent, glutamine residues. Efficient capsid assembly of the majority of deamidation vp1 proteins indicates that either these events occur following capsid assembly or that deamidation in individual monomers (vp1, vp2 or vp3) is well-tolerated structurally and largely does not affect assembly dynamics. Extensive deamidation in the VP1-unique (VP1-u) region (~aa 1-137), generally considered to be located internally prior to cellular entry, suggests that VP deamidation may occur prior to capsid assembly. The deamidation of N may occur through its C-terminus residue's backbone nitrogen atom conducts a nucleophilic attack to the Asn's side chain amide group carbon atom. An intermediate ring-closed succinimide residue is believed to form. The succinimide residue then conducts fast hydrolysis to lead to the final product aspartic acid (Asp) or iso aspartic acid (IsoAsp). Therefore, in certain embodiments, the deamidation of asparagine (N or Asn) leads to an Asp or IsoAsp, which may interconvert through the succinimide intermediate e.g., as illustrated below.

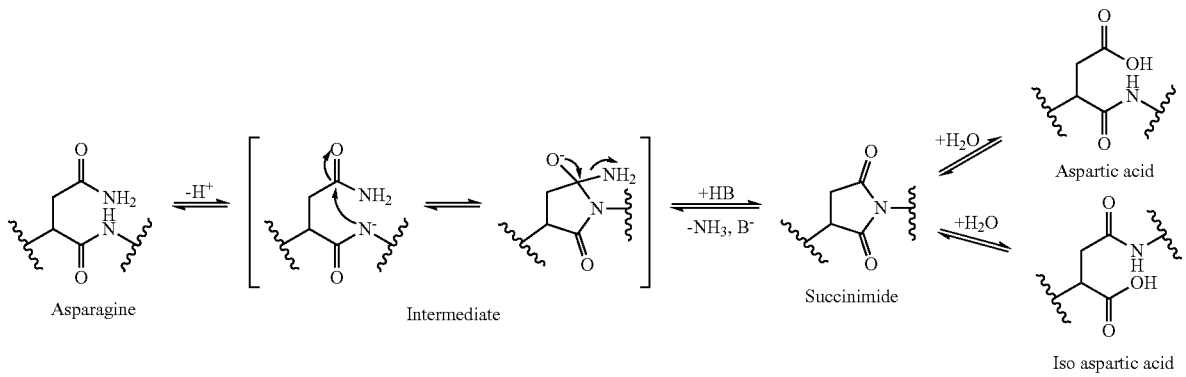

As provided herein, each deamidated N in the VP1, VP2 or VP3 may independently be aspartic acid (Asp), isoaspartic acid (isoAsp), aspartate, and/or an interconverting blend of Asp and isoAsp, or combinations thereof. Any suitable ratio of α- and isoaspartic acid may be present. For example, in certain embodiments, the ratio may be from 10:1 to 1:10 aspartic to isoaspartic, about 50:50 aspartic: isoaspartic, or about 1:3 aspartic: isoaspartic, or another selected ratio.

In certain embodiments, one or more glutamine (Q) may deamidates to glutamic acid (Glu), i.e., α-glutamic acid, γ-glutamic acid (Glu), or a blend of α- and γ-glutamic acid, which may interconvert through a common glutarinimide intermediate. Any suitable ratio of α- and γ-glutamic acid may be present. For example, in certain embodiments, the ratio may be from 10:1 to 1:10 a to γ, about 50:50 α: γ, or about 1:3 α: γ, or another selected ratio.

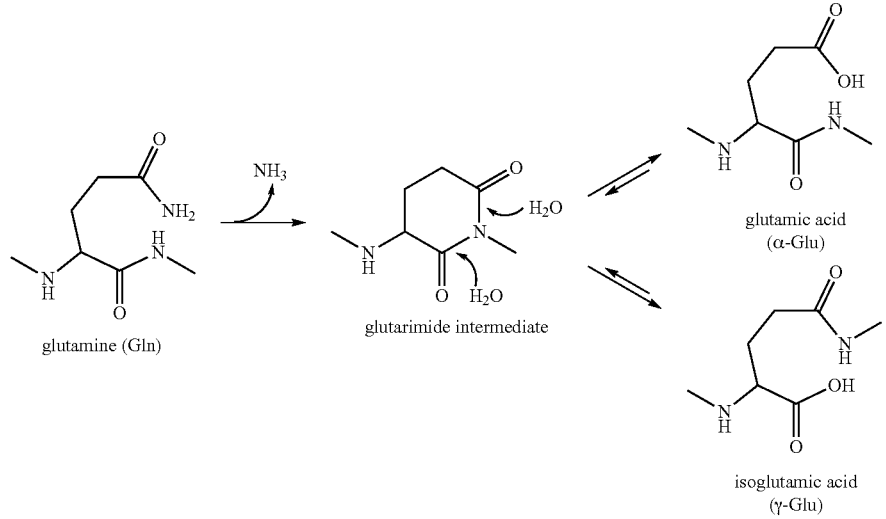

Thus, an rAAV includes subpopulations within the rAAV capsid of vp1, vp2 and/or vp3 proteins with deamidated amino acids, including at a minimum, at least one subpopulation comprising at least one highly deamidated asparagine. In addition, other modifications may include isomerization, particularly at selected aspartic acid (D or Asp) residue positions. In still other embodiments, modifications may include an amidation at an Asp position.

In certain embodiments, an AAV capsid contains subpopulations of vp1, vp2 and vp3 having at least 4 to at least about 25 deamidated amino acid residue positions, of which at least 1% to 10% are deamidated as compared to the encoded amino acid sequence of the vp proteins. The majority of these may be N residues. However, Q residues may also be deamidated.

In certain embodiments, a rAAV has an AAV capsid having vp1, vp2 and vp3 proteins having subpopulations comprising combinations of two, three, four or more deamidated residues at the positions set forth in the table provided in Example 11 and incorporated herein by reference. Deamidation in the rAAV may be determined using 2D gel electrophoresis, and/or mass spectrometry (MS), and/or protein modelling techniques. Online chromatography may be performed with an Acclaim PepMap column and a Thermo UltiMate 3000 RSLC system (Thermo Fisher Scientific) coupled to a Q Exactive HF with a NanoFlex source (Thermo Fisher Scientific). MS data is acquired using a data-dependent top-20 method for the Q Exactive HF, dynamically choosing the most abundant not-yet-sequenced precursor ions from the survey scans (200-2000 m/z). Sequencing is performed via higher energy collisional dissociation fragmentation with a target value of 1e5 ions determined with predictive automatic gain control and an isolation of precursors was performed with a window of 4 m/z. Survey scans were acquired at a resolution of 120,000 at m/z 200. Resolution for HCD spectra may be set to 30,000 at m/z200 with a maximum ion injection time of 50 ms and a normalized collision energy of 30. The S-lens RF level may be set at 50, to give optimal transmission of the m/z region occupied by the peptides from the digest. Precursor ions may be excluded with single, unassigned, or six and higher charge states from fragmentation selection. BioPharma Finder 1.0 software (Thermo Fischer Scientific) may be used for analysis of the data acquired. For peptide mapping, searches are performed using a single-entry protein FASTA database with carbamidomethylation set as a fixed modification; and oxidation, deamidation, and phosphorylation set as variable modifications, a 10-ppm mass accuracy, a high protease specificity, and a confidence level of 0.8 for MS/MS spectra. Examples of suitable proteases may include, e.g., trypsin or chymotrypsin. Mass spectrometric identification of deamidated peptides is relatively straightforward, as deamidation adds to the mass of intact molecule +0.984 Da (the mass difference between-OH and —NH₂ groups). The percent deamidation of a particular peptide is determined by the mass area of the deamidated peptide divided by the sum of the area of the deamidated and native peptides. Considering the number of possible deamidation sites, isobaric species which are deamidated at different sites may co-migrate in a single peak. Consequently, fragment ions originating from peptides with multiple potential deamidation sites can be used to locate or differentiate multiple sites of deamidation. In these cases, the relative intensities within the observed isotope patterns can be used to specifically determine the relative abundance of the different deamidated peptide isomers. This method assumes that the fragmentation efficiency for all isomeric species is the same and independent on the site of deamidation. It is understood by one of skill in the art that a number of variations on these illustrative methods can be used. For example, suitable mass spectrometers may include, e.g, a quadrupole time of flight mass spectrometer (QTOF), such as a Waters Xevo or Agilent 6530 or an orbitrap instrument, such as the Orbitrap Fusion or Orbitrap Velos (Thermo Fisher). Suitably liquid chromatography systems include, e.g., Acquity UPLC system from Waters or Agilent systems (1100 or 1200 series). Suitable data analysis software may include, e.g., MassLynx (Waters), Pinpoint and Pepfinder (Thermo Fischer Scientific), Mascot (Matrix Science), Peaks DB (Bioinformatics Solutions). Still other techniques may be described, e.g., in X. Jin et al, Hu Gene Therapy Methods, Vol. 28, No. 5, pp. 255-267, published online Jun. 16, 2017.

In addition to deamidations, other modifications may occur that do not result in conversion of one amino acid to a different amino acid residue. Such modifications may include acetylated residues, isomerizations, phosphorylations, or oxidations.

Modulation of Deamidation: In certain embodiments, the AAV is modified to change the glycine in an asparagine-glycine pair, to reduce deamidation. In other embodiments, the asparagine is altered to a different amino acid, e.g., a glutamine which deamidates at a slower rate; or to an amino acid which lacks amide groups (e.g., glutamine and asparagine contain amide groups); and/or to an amino acid which lacks amine groups (e.g., lysine, arginine and histidine contain amine groups). As used herein, amino acids lacking amide or amine side groups refer to, e.g., glycine, alanine, valine, leucine, isoleucine, serine, threonine, cystine, phenylalanine, tyrosine, or tryptophan, and/or proline. Modifications such as described may be in one, two, or three of the asparagine-glycine pairs found in the encoded AAV amino acid sequence. In certain embodiments, such modifications are not made in all four of the asparagine-glycine pairs. Thus, a method for reducing deamidation of AAV and/or engineered AAV variants having lower deamidation rates. Additionally, or alternative one or more other amide amino acids may be changed to a non-amide amino acid to reduce deamidation of the AAV. In certain embodiments, a mutant AAV capsid as described herein contains a mutation in an arginine-glycine pair, such that the glycine is changed to an alanine or a serine. A mutant AAV capsid may contain one, two or three mutants where the reference AAV natively contains four NG pairs. In certain embodiments, an AAV capsid may contain one, two, three or four such mutants where the reference AAV natively contains five NG pairs. In certain embodiments, a mutant AAV capsid contains only a single mutation in an NG pair. In certain embodiments, a mutant AAV capsid contains mutations in two different NG pairs. In certain embodiments, a mutant AAV capsid contains mutation is two different NG pairs which are located in structurally separate location in the AAV capsid. In certain embodiments, the mutation is not in the VP1-unique region. In certain embodiments, one of the mutations is in the VP1-unique region. Optionally, a mutant AAV capsid contains no modifications in the NG pairs, but contains mutations to minimize or eliminate deamidation in one or more asparagines, or a glutamine, located outside of an NG pair. In the AAVhu68 capsid protein, 4 residues (N57, N329, N452, N512) routinely display levels of deamidation >70% and it most cases >90% across various lots. Additional asparagine residues (N94, N253, N270, N304, N409, N477, and Q599) also display deamidation levels up to ~20% across various lots. The deamidation levels were initially identified using a trypsin digest and verified with a chymotrypsin digestion.

The AAVhu68 capsid contains subpopulations within the vp1 proteins, within the vp2 proteins and within the vp3 proteins which have modifications from the predicted amino acid residues in SEQ ID NO: 7. These subpopulations include, at a minimum, certain deamidated asparagine (N or Asn) residues. For example, certain subpopulations comprise at least one, two, three or four highly deamidated asparagines (N) positions in asparagine-glycine pairs in SEQ ID NO: 7 and optionally further comprising other deamidated amino acids, wherein the deamidation results in an amino acid change and other optional modifications. SEQ ID NO: 8 provide an amino acid sequence of a modified AAVhu68 capsid, illustrating positions which may have some percentage of deamidated or otherwise modified amino acids. The various combinations of these and other modifications are described herein.

As used herein, an "AAV9 capsid" is a self-assembled AAV capsid composed of multiple AAV9 vp proteins. The AAV9 vp proteins are typically expressed as alternative splice variants encoded by a nucleic acid sequence of SEQ ID NO: 9 or a sequence at least 70%, at least 75%, at least 80%, at least 85%, at least 90%, at least 95%, at least 97%, at least 99% thereto, which encodes the vp1 amino acid sequence of GenBank accession: AAS99264. In certain embodiments, "AAV9 capsid" includes an AAV having an amino acid sequence which is 99% identical to AAS99264 or 99% identical to SEQ ID NO: 10. See, also U.S. Pat. No. 7,906,111 and WO 2005/033321. As used herein "AAV9 variants" include those described in, e.g., WO2016/049230, U.S. Pat. No. 8,927,514, US 2015/0344911, and U.S. Pat. No. 8,734,809.

Methods of generating the capsid, coding sequences therefore, and methods for production of rAAV viral vectors have been described. See, e.g., Gao, et al, Proc. Natl. Acad. Sci. U.S.A. 100 (10), 6081-6086 (2003) and US 2013/0045186A1.

The term "substantial homology" or "substantial similarity," when referring to a nucleic acid, or fragment thereof, indicates that, when optimally aligned with appropriate nucleotide insertions or deletions with another nucleic acid (or its complementary strand), there is nucleotide sequence identity in at least about 95 to 99% of the aligned sequences. Preferably, the homology is over full-length sequence, or an open reading frame thereof, or another suitable fragment which is at least 15 nucleotides in length. Examples of suitable fragments are described herein.

The terms "sequence identity" "percent sequence identity" or "percent identical" in the context of nucleic acid sequences refers to the residues in the two sequences which are the same when aligned for maximum correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length and may be up to about 700 amino acids. Examples of suitable fragments are described herein.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, e.g., a cap protein, a rep protein, or a fragment thereof which is at least 8 amino acids, or more desirably, at least 15 amino acids in length. Examples of suitable fragments are described herein.

By the term "highly conserved" is meant at least 80% identity, preferably at least 90% identity, and more preferably, over 97% identity. Identity is readily determined by one of skill in the art by resort to algorithms and computer programs known by those of skill in the art.

Generally, when referring to "identity", "homology", or "similarity" between two different adeno-associated viruses, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. In the examples, AAV alignments are performed using the published AAV9 sequences as a reference point. Alignments are performed using any of a variety of publicly or commercially available Multiple Sequence Alignment Programs. Examples of such programs include, "Clustal Omega", "Clustal W", "CAP Sequence Assembly", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference. Multiple sequence alignment programs are also available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27 (13): 2682-2690 (1999).

V. rAAV

Provided herein is a therapeutic, recombinant, and replication-defective adeno-associated virus (rAAV) which is useful for treating a disease associated with an Arylsulfatase A gene (ARSA) mutation or caused by deficiencies in normal levels of functional Arylsulfatase A (for example, Metachromatic Leukodystrophy (MLD)) in a subject in need thereof. The rAAV is desirably replication-defective and carries a vector genome comprising inverted terminal repeats (ITR) and a nucleic acid sequence encoding a functional human Arylsulfatase A (hARSA) under the control of regulatory sequences which direct the hARSA expression in a target cell. In certain embodiments, the hARSA coding sequence comprises a sequence of nucleotide (nt) 55 to nt 1521 of SEQ ID NO: 1, or a sequence at least 95% to 99.9% identical thereto which encodes a functional hARSA. In certain embodiments, the vector genome comprises inverted terminal repeats (ITR) and an expression cassette as described in Part III. In a further embodiment, the rAAV comprises an AAV capsid.

The AAV capsid may be selected based on the target cell. In certain embodiment, the AAV capsid is suitable for delivery of the vector genome in nervous system (for example, CNS or PNS). In certain embodiments, the AAV capsid is suitable for delivery of the vector genome in a neuron, a nervous system cell, an oligodendrocyte, a microglia, a Central Nervous System (CNS) cell, a neuron in the CNS, a Peripheral Nervous System (PNS) cell, a Schwann cell, a macrophage in the PNS, or a cell in visceral organs (for example, a kidney cell, a liver cell and a gallbladder cell). In certain embodiments, the AAV capsid is suitable for delivery of the vector genome in another target cell as described herein.

In certain embodiments, the AAV capsid is selected from a cy02 capsid, a rh43 capsid, an AAV8 capsid, a rh01 capsid, an AAV9 capsid, an rh8 capsid, a rh10 capsid, a bb01 capsid, a hu37 capsid, a rh02 capsid, a rh20 capsid, a rh39 capsid, a rh64 capsid, an AAV6 capsid, an AAVl capsid, a hu44 capsid, a hu48 capsid, a cy05 capsid a hu11 capsid, a hu32 capsid, a pi2 capsid, or a variation thereof. In certain embodiments, the AAV capsid is a Clade F capsid, such as AAV9 capsid, AAVhu68 capsid, AAV-PHP.B capsid, hu31 capsid, hu32 capsid, or a variation thereof. See, e.g., WO 2005/033321 published Apr. 14, 2015, WO 2018/160582, and US 2015/0079038, each of which is incorporated herein by reference in its entirety. In certain embodiments, the AAV capsid is a non-clade F capsid, for example a Clade A, B, C, D, or E capsid. In certain embodiment, the non-Clade F capsid is an AAVI or a variation thereof. In certain embodiment, the AAV capsid transduces a target cell other than the nervous system cells. In certain embodiments, the AAV capsid is a Clade A capsid (e.g., AAVI, AAV6), a Clade B capsid (e.g., AAV 2), a Clade C capsid (e.g., hu53), a Clade D capsid (e.g., AAV7), or a Clade E capsid (e.g., rh10). Still, other AAV capsid may be chosen.

In certain embodiment, the rAAV comprises an AAVhu68 capsid in which the vector genome is packaged. In certain embodiments, the AAVhu68 capsid is produced from a sequence encoding the predicted amino acid sequence of SEQ ID NO: 7.

See, Part V for more details. In certain embodiments, the vector genome is entirely exogenous to the AAVhu68 capsid, as it contains no AAVhu68 genomic sequences.

The functional hARSA is described in Part I. In certain embodiments, the functional hARSA has a signal peptide and a sequence of amino acid (aa) 19 to aa 507 of SEQ ID NO: 2. In certain embodiments, the native hARSA signal peptide is used, e.g., aa 1 to aa 18 of SEQ ID NO: 2. In certain embodiments, the signal peptide has an amino acid sequence of aa 1 to aa 20 of SEQ ID NO: 4. In certain embodiment the functional hARSA has an amino acid sequence of SEQ ID NO: 2 or SEQ ID NO: 4.

In certain embodiments, the hARSA coding sequence is about 95% to 100% identical to nucleotide (nt) 55 to nt 1521 of SEQ ID NO: 1. In certain embodiments, the hARSA-coding sequence is SEQ ID NO: 1 or SEQ ID NO: 3. In a further embodiment, the hARSA coding sequence encodes a sequence of amino acid (aa) 19 to aa 507 of SEQ ID NO: 2. In yet a further embodiment, the hARSA coding sequence encodes a sequence of SEQ ID NO: 2 or SEQ ID NO: 4. See, Part I for more details about hARSA coding sequence.

In certain embodiments, the regulatory sequences direct hARSA expression in nervous system cells. In certain embodiments, the regulatory sequences comprise a ubiquitous promoter, for example, a CB7 promoter. In a further embodiment, the regulatory elements comprise one or more of a Kozak sequence, a polyadenylation sequence, an intron, an enhancer, and a TATA signal. In certain embodiments, the regulatory sequences comprise one or more of the following: a regulatory element derived from the chicken β-actin (BA)

promoter and human cytomegalovirus immediate-early enhancer (CMV IE) (for example, CB7 promoter, nt 198 to nt 862 of SEQ ID NO: 5), a chimeric intron consisting of a chicken BA splice donor and a rabbit β-globin (rBG) splice acceptor element (for example, CI, nt 956 to nt 1928 of SEQ ID NO: 5), and polyadenylation (PolyA) signal derived from the rBG gene (for example, rBG, nt 3539 to nt 3665 of SEQ ID NO: 5). In certain embodiments, the vector genome has a sequence of nucleotide (nt) 1 to nt 3883 of SEQ ID NO: 5. Sec, Part III for more details.

In certain embodiments, the rAAV or a composition comprising the rAAV is administrable to a subject in need thereof to ameliorate symptoms of a disease associated with an ARSA mutation or caused by deficiencies in normal levels of functional Arylsulfatase A (for example, MLD), and/or to delay progression of a disease associated with an ARSA mutation or caused by deficiencies in normal levels of functional Arylsulfatase A (for example, MLD). See, part II for more details.

In certain embodiments, the rAAV as described herein is suitable for administration to a patient via an intra-cisterna *magna* injection (ICM), including via a CT-guided sub-occipital injection into the cisterna *magna*. In certain embodiments, the rAAV as described herein is suitable for administration to a subject who is 7 years of age or younger. In certain embodiments, the rAAV as described herein is suitable for administration to a subject in need thereof to ameliorate symptoms of Metachromatic Leukodystrophy or a disease associated with Arylsulfatase A (ARSA) gene mutation, and/or to delay progression of Metachromatic Leukodystrophy or a disease associated with Arylsulfatase A (ARSA) gene mutation. See, Part II and Part VIII for more details. In certain embodiments, the rAAV as described herein is administered in a single dose.

In certain embodiment, the vector genome is a single-stranded AAV vector genome. In certain embodiments, a rAAV vector may be utilized in the invention which contains self-complementary (sc) AAV vector genome.

The regulatory control elements necessary are operably linked to the gene (e.g., hARSA coding sequence) in a manner which permits its transcription, translation and/or expression in a cell which takes up the rAAV. As used herein, "operably linked" sequences include both expression control sequences that are contiguous with the gene of interest and expression control sequences that act in trans or at a distance to control the gene of interest. Such regulatory sequences typically include, e.g., one or more of a promoter, an enhancer, an intron, a polyA, a self-cleaving linker (e.g., furin, furin-F2A, an IRES). The examples below utilize CB7 promoter for expression of hARSA. However, in certain embodiments, other promoters, or an additional promoter, may be selected. In certain embodiments, an additional or alternative promoter sequence may be included as part of the expression control sequences (regulatory sequences), e.g., located between the selected 5' ITR sequence and the coding sequence. Constitutive promoters, regulatable promoters [see, e.g., WO 2011/126808 and WO 2013/04943], tissue specific promoters, or a promoter responsive to physiologic cues may be utilized in the vectors described herein. The promoter(s) can be selected from different sources, e.g., human cytomegalovirus (CMV) immediate-early enhancer/promoter, the SV40 early enhancer/promoter, the JC polymovirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter. In addition to a promoter, a vector may contain one or more other appropriate transcription initiation sequences, transcription termination sequences, enhancer sequences, efficient RNA processing signals such as splicing and polyadenylation (polyA) signals; sequences that stabilize cytoplasmic mRNA for example WPRE; sequences that enhance translation efficiency (i.e., Kozak consensus sequence); sequences that enhance protein stability; and when desired, sequences that enhance secretion of the encoded product. An example of a suitable enhancer is the CMV enhancer. Other suitable enhancers include those that are appropriate for desired target tissue indications. In one embodiment, the regulatory sequences comprise one or more expression enhancers. In one embodiment, the regulatory sequences contain two or more expression enhancers. These enhancers may be the same or may differ from one another. For example, an enhancer may include a CMV immediate early enhancer (SEQ ID NO: 19). This enhancer may be present in two copies which are located adjacent to one another. Alternatively, the dual copies of the enhancer may be separated by one or more sequences. In still another embodiment, the expression cassette further contains an intron, e.g., the chicken beta-actin intron (SEQ ID NO: 17). In certain embodiments, the intron is a chimeric intron (CI)—a hybrid intron consisting of a human beta-globin splice donor and immunoglobulin G (IgG) splice acceptor elements. Other suitable introns include those known in the art, e.g., such as are described in WO 2011/126808. Examples of suitable polyA sequences include, e.g., SV40, SV50, bovine growth hormone (bGH), human growth hormone, and synthetic polyAs. Optionally, one or more sequences may be selected to stabilize mRNA. An example of such a sequence is a modified WPRE sequence, which may be engineered upstream of the polyA sequence and downstream of the coding sequence (see, e.g., MA Zanta-Boussif, et al, Gene Therapy (2009) 16:605-619). In certain embodiments, no WPRE sequence is present.

In certain embodiments, in addition to the hARSA coding sequence, another non-AAV coding sequence may be included, e.g., a peptide, polypeptide, protein, functional RNA molecule (e.g., miRNA, miRNA inhibitor) or other gene product, of interest. Useful gene products may include miRNAs. miRNAs and other small interfering nucleic acids regulate gene expression via target RNA transcript cleavage/degradation or translational repression of the target messenger RNA (mRNA). miRNAs are natively expressed, typically as final 19-25 non-translated RNA products. miRNAs exhibit their activity through sequence-specific interactions with the 3' untranslated regions (UTR) of target mRNAs. These endogenously expressed miRNAs form hairpin precursors which are subsequently processed into a miRNA duplex, and further into a "mature" single stranded miRNA molecule. This mature miRNA guides a multiprotein complex, miRISC, which identifies target site, e.g., in the 3' UTR regions, of target mRNAs based upon their complementarity to the mature miRNA.

The AAV sequences of the vector typically comprise the cis-acting 5' and 3' inverted terminal repeat (ITR) sequences (Sec, e.g., B. J. Carter, in "Handbook of Parvoviruses", ed., P. Tijsser, CRC Press, pp. 155 168 (1990)). The ITR sequences are about 145 base pairs (bp) in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J. Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. In one embodiment, the ITRs are from an AAV different than that supplying a capsid. In one embodiment, the ITR sequences are from AAV2. A shortened version of the 5' ITR, termed AITR, has been described in which the D-sequence and terminal resolution site (trs) are deleted. In other embodiments, the full-length AAV 5' and 3' ITRs are used. However, ITRs from other AAV sources may be selected. Where the source of the ITRs is from AAV2 and the AAV capsid is from another AAV source, the resulting vector may be termed pseudotyped. However, other configurations of these elements may be suitable.

In certain embodiments, vector genomes are constructed which comprise a 5' AAV ITR-promoter-optional enhancer-optional intron-hARSA coding sequence-polyA-3' ITR, termed as AAV.promoter.optional enhancer.optional intron.hARSA or hARSAco.polyA. In certain embodiments, the ITRs are from AAV2. In certain embodiments, more than one promoter is present. In certain embodiments, the enhancer is present in the vector genome. In certain embodiments, more than one enhancer is present. In certain embodiments, an intron is present in the vector genome. In certain embodiments, the enhancer and intron are present. In certain embodiments, the intron is a chimeric intron (CI)—a hybrid intron consisting of a human beta-globin splice donor and immunoglobulin G (IgG) splice acceptor elements. In certain embodiments, the polyA is an SV40 poly A (i.e., a polyadenylation (PolyA) signal derived from Simian Virus 40 (SV40) late genes). In certain embodiments, the polyA is a rabbit beta-globin (RBG) poly A. In certain embodiments, the vector genome comprises a 5' AAV ITR-CB7 promoter-hARSA coding sequence-poly A-3' ITR.

As used herein, a vector genome or a rAAV comprising the vector genome is illustrated herein as AAV.promoter (optional).Kozak (optional).intron (optional).hARSA coding sequence (e.g., hARSA, hARSAco). miRNA (optional) .polyA (optionl).Stuffer (optional). In certain embodiments, a rAAV is illustrated herein as AAVcapsid.promoter (optional).Kozak (optional).intron (optional).hARSA coding sequence. miRNA (optional).polyA (optionl).Stuffer (optional).

In another aspect, a production system useful for producing the rAAV is provided. In this system, cells were cultured which comprises a nucleic acid sequence encoding an AAVhu68 capsid protein, a vector genome as described herein and sufficient AAV rep functions and helper functions to permit packaging of the vector genome into the AAV capsid. In certain embodiments, the vector genome has a sequence of nt 1 to nt 3883 of SEQ ID NO: 5. In certain embodiments, the cell culture is a human embryonic kidney 293 cell culture. In certain embodiments, the AAV rep is from an AAV different from AAVhu68, for example, from AAV2. In certain embodiments, the AAV rep coding sequence and cap genes are on the same nucleic acid molecule, wherein there is optionally a spacer between the rep sequence and cap gene. In a further embodiment, the spacer is atgacttaaaccaggt (SEQ ID NO: 24).

For use in producing an AAV viral vector (e.g., a recombinant (r) AAV), the vector genomes can be carried on any suitable vector, e.g., a plasmid, which is delivered to a packaging host cell. The plasmids useful in this invention may be engineered such that they are suitable for replication and packaging in vitro in prokaryotic cells, insect cells, mammalian cells, among others. Suitable transfection techniques and packaging host cells are known and/or can be readily designed by one of skill in the art. An illustrative production process is provided in FIGS. 6-7. In certain embodiments, the plasmid has a sequence of SEQ ID NO: 5.

Methods for generating and isolating AAVs suitable for use as vectors are known in the art. See generally, e.g., Grieger & Samulski, 2005, Adeno-associated virus as a gene therapy vector: Vector development, production and clinical applications, Adv. Biochem. Engin/Biotechnol. 99:119-145; Buning et al., 2008, Recent developments in adeno-associated virus vector technology, J. Gene Med. 10:717-733; and the references cited below, each of which is incorporated herein by reference in its entirety. For packaging a gene into virions, the ITRs are the only AAV components required in cis in the same construct as the nucleic acid molecule containing the gene. The cap and rep genes can be supplied in trans.

In one embodiment, the selected genetic element may be delivered to an AAV packaging cell by any suitable method, including transfection, electroporation, liposome delivery, membrane fusion techniques, high velocity DNA-coated pellets, viral infection and protoplast fusion. Stable AAV packaging cells can also be made. The methods used to make such constructs are known to those with skill in nucleic acid manipulation and include genetic engineering, recombinant engineering, and synthetic techniques. See, e.g., Molecular Cloning: A Laboratory Manual, ed. Green and Sambrook, Cold Spring Harbor Press, Cold Spring Harbor, NY (2012).

The term "AAV intermediate" or "AAV vector intermediate" refers to an assembled rAAV capsid which lacks the desired genomic sequences packaged therein. These may also be termed an "empty" capsid. Such a capsid may contain no detectable genomic sequences of an expression cassette, or only partially packaged genomic sequences which are insufficient to achieve expression of the gene product. These empty capsids are non-functional to transfer the gene of interest to a host cell.

The recombinant adeno-associated virus (AAV) described herein may be generated using techniques which are known. See, e.g., WO 2003/042397; WO 2005/033321, WO 2006/110689; U.S. Pat. No. 7,588,772 B2. Such a method involves culturing a host cell which contains a nucleic acid sequence encoding an AAV capsid protein; a functional rep gene; an expression cassette composed of, at a minimum, AAV inverted terminal repeats (ITRs) and a transgene; and sufficient helper functions to permit packaging of the expression cassette into the AAV capsid protein. Methods of generating the capsid, coding sequences therefor, and methods for production of rAAV viral vectors have been described. See, e.g., Gao, et al, Proc. Natl. Acad. Sci. U.S.A. 100 (10), 6081-6086 (2003) and US 2013/0045186A1.

In one embodiment, a production cell culture useful for producing a recombinant AAVhu68 is provided. Such a cell culture contains a nucleic acid which expresses the AAVhu68 capsid protein in the host cell; a nucleic acid molecule suitable for packaging into the AAVhu68 capsid, e.g., a vector genome which contains AAV ITRs and a non-AAV nucleic acid sequence encoding a gene operably linked to regulatory sequences which direct expression of the gene in a host cell; and sufficient AAV rep functions and adenovirus helper functions to permit packaging of the vector genome into the recombinant AAVhu68 capsid. In one embodiment, the cell culture is composed of mammalian cells (e.g., human embryonic kidney 293 cells, among others) or insect cells (e.g., *Spodoptera frugiperda* (Sf9) cells). In certain embodiments, baculovirus provides the helper functions necessary for packaging the vector genome into the recombinant AAVhu68 capsid.

Optionally the rep functions are provided by an AAV other than AAVhu68. In certain embodiments, at least parts of the rep functions are from AAVhu68. In another embodiment, the rep protein is a heterologous rep protein other than AAVhu68rep, for example but not limited to, AAV1 rep protein, AAV2 rep protein, AAV3 rep protein, AAV4 rep protein, AAV5 rep protein, AAV6 rep protein, AAV7 rep protein, AAV8 rep protein; or rep 78, rep 68, rep 52, rep 40, rep68/78 and rep40/52; or a fragment thereof; or another source. Any of these AAVhu68 or mutant AAV capsid sequences may be under the control of exogenous regulatory control sequences which direct expression thereof in a host cell.

In one embodiment, cells are manufactured in a suitable cell culture (e.g., HEK 293 or Sf9) or suspension. Methods for manufacturing the gene therapy vectors described herein include methods well known in the art such as generation of plasmid DNA used for production of the gene therapy vectors, generation of the vectors, and purification of the vectors. In some embodiments, the gene therapy vector is an AAV vector and the plasmids generated are an AAV cis-plasmid encoding the AAV vector genome and the gene of interest, an AAV trans-plasmid containing AAV rep and cap genes, and an adenovirus helper plasmid. The vector generation process can include method steps such as initiation of cell culture, passage of cells, seeding of cells, transfection of cells with the plasmid DNA, post-transfection medium exchange to serum free medium, and the harvest of vector-containing cells and culture media. The harvested vector-containing cells and culture media are referred to herein as crude cell harvest. In yet another system, the gene therapy vectors are introduced into insect cells by infection with baculovirus-based vectors. For reviews on these production systems, see generally, e.g., Zhang et al., 2009, Adenovirus-adeno-associated virus hybrid for large-scale recombinant adeno-associated virus production, Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

The crude cell harvest may thereafter be subject method steps such as concentration of the vector harvest, diafiltration of the vector harvest, microfluidization of the vector harvest, nuclease digestion of the vector harvest, filtration of microfluidized intermediate, crude purification by chromatography, crude purification by ultracentrifugation, buffer exchange by tangential flow filtration, and/or formulation and filtration to prepare bulk vector.

A two-step affinity chromatography purification at high salt concentration followed anion exchange resin chromatography are used to purify the vector drug product and to remove empty capsids. These methods are described in more detail in WO 2017/160360, International Patent Application No. PCT/US2016/065970, filed Dec. 9, 2016 and its priority documents, U.S. Patent Application Nos. 62/322,071, filed Apr. 13, 2016 and 62/226,357, filed Dec. 11, 2015 and entitled "Scalable Purification Method for AAV9", which is incorporated by reference herein.

To calculate empty and full particle content, VP3 band volumes for a selected sample (e.g., in examples herein an iodixanol gradient-purified preparation where # of genome copies (GC)=# of particles) are plotted against GC particles loaded. The resulting linear equation (y=mx+c) is used to calculate the number of particles in the band volumes of the test article peaks. The number of particles (pt) per 20 μL loaded is then multiplied by 50 to give particles (pt)/mL. Pt/mL divided by GC/mL gives the ratio of particles to genome copies (pt/GC). Pt/mL.-GC/mL gives empty pt/mL. Empty pt/mL divided by pt/mL and x 100 gives the percentage of empty particles.

Generally, methods for assaying for empty capsids and AAV vector particles with packaged genomes have been known in the art. See, e.g., Grimm et al., Gene Therapy (1999) 6:1322-1330; Sommer et al., Molec. Ther. (2003) 7:122-128. To test for denatured capsid, the methods include subjecting the treated AAV stock to SDS-polyacrylamide gel electrophoresis, consisting of any gel capable of separating the three capsid proteins, for example, a gradient gel containing 3-8% Tris-acetate in the buffer, then running the gel until sample material is separated, and blotting the gel onto nylon or nitrocellulose membranes, preferably nylon. Anti-AAV capsid antibodies are then used as the primary antibodies that bind to denatured capsid proteins, preferably an anti-AAV capsid monoclonal antibody, most preferably the B1 anti-AAV-2 monoclonal antibody (Wobus et al., J. Virol. (2000) 74:9281-9293). A secondary antibody is then used, one that binds to the primary antibody and contains a means for detecting binding with the primary antibody, more preferably an anti-IgG antibody containing a detection molecule covalently bound to it, most preferably a sheep anti-mouse IgG antibody covalently linked to horseradish peroxidase. A method for detecting binding is used to semi-quantitatively determine binding between the primary and secondary antibodies, preferably a detection method capable of detecting radioactive isotope emissions, electromagnetic radiation, or colorimetric changes, most preferably a chemiluminescence detection kit. For example, for SDS-PAGE, samples from column fractions can be taken and heated in SDS-PAGE loading buffer containing reducing agent (e.g., DTT), and capsid proteins were resolved on pre-cast gradient polyacrylamide gels (e.g., Novex). Silver staining may be performed using SilverXpress (Invitrogen, CA) according to the manufacturer's instructions or other suitable staining method, i.e. SYPRO ruby or coomassie stains. In one embodiment, the concentration of AAV vector genomes (vg) in column fractions can be measured by quantitative real time PCR (Q-PCR). Samples are diluted and digested with DNase I (or another suitable nuclease) to remove exogenous DNA. After inactivation of the nuclease, the samples are further diluted and amplified using primers and a TaqMan™ fluorogenic probe specific for the DNA sequence between the primers. The number of cycles required to reach a defined level of fluorescence (threshold cycle, Ct) is measured for each sample on an Applied Biosystems Prism 7700 Sequence Detection System. Plasmid DNA containing identical sequences to that contained in the AAV vector is employed to generate a standard curve in the Q-PCR reaction. The cycle threshold (Ct) values obtained from the samples are used to determine vector genome titer by normalizing it to the Ct value of the plasmid standard curve. End-point assays based on the digital PCR can also be used.

In one aspect, an optimized q-PCR method is used which utilizes a broad spectrum serine protease, e.g., proteinase K (such as is commercially available from Qiagen). More particularly, the optimized qPCR genome titer assay is similar to a standard assay, except that after the DNase I digestion, samples are diluted with proteinase K buffer and treated with proteinase K followed by heat inactivation. Suitably samples are diluted with proteinase K buffer in an amount equal to the sample size. The proteinase K buffer may be concentrated to 2 fold or higher. Typically, proteinase K treatment is about 0.2 mg/mL, but may be varied from 0.1 mg/mL to about 1 mg/mL. The treatment step is generally conducted at about 55° C. for about 15 minutes, but may be performed at a lower temperature (e.g., about 37° C. to about 50° C.) over a longer time period (e.g., about 20 minutes to about 30 minutes), or a higher temperature (e.g., up to about 60° C.) for a shorter time period (e.g., about 5 to 10 minutes). Similarly, heat inactivation is generally at about 95° C. for about 15 minutes, but the temperature may be lowered (e.g., about 70 to about 90° C.) and the time extended (e.g., about 20 minutes to about 30 minutes). Samples are then diluted (e.g., 1000 fold) and subjected to TaqMan analysis as described in the standard assay.

Additionally, or alternatively, droplet digital PCR (ddPCR) may be used. For example, methods for determining single-stranded and self-complementary AAV vector genome titers by ddPCR have been described. See, e.g., M. Lock et al, Hu Gene Therapy Methods, Hum Gene Ther Methods. 2014 April;25 (2): 115-25. doi: 10.1089/hgtb.2013.131. Epub 2014 Feb. 14.

In brief, the method for separating rAAVhu68 particles having packaged genomic sequences from genome-deficient AAVhu68 intermediates involves subjecting a suspension comprising recombinant AAVhu68 viral particles and AAVhu68 capsid intermediates to fast performance liquid chromatography, wherein the AAVhu68 viral particles and AAVhu68 intermediates are bound to a strong anion exchange resin equilibrated at a pH of about 10.2, and subjected to a salt gradient while monitoring eluate for ultraviolet absorbance at about 260 nanometers (nm) and about 280 nm. Although less optimal for rAAVhu68, the pH may be in the range of about 10.0 to 10.4. In this method, the AAVhu68 full capsids are collected from a fraction which is eluted when the ratio of A260/A280 reaches an inflection point. In one example, for the Affinity Chromatography step, the diafiltered product may be applied to a Capture Select™ Poros-AAV2/9 affinity resin (Life Technologies) that efficiently captures the AAV2/hu68 serotype. Under these ionic conditions, a significant percentage of residual cellular DNA and proteins flow through the column, while AAV particles are efficiently captured.

The rAAV.hARSA is suspended in a suitable physiologically compatible composition (e.g., a buffered saline). This composition may be frozen for storage, later thawed and optionally diluted with a suitable diluent. Alternatively, the vector may be prepared as a composition which is suitable for delivery to a patient without proceeding through the freezing and thawing steps.

As used herein, the term "NAb titer" a measurement of how much neutralizing antibody (e.g., anti-AAV Nab) is produced which neutralizes the physiologic effect of its targeted epitope (e.g., an AAV). Anti-AAV NAb titers may be measured as described in, e.g., Calcedo, R., et al., Worldwide Epidemiology of Neutralizing Antibodies to Adeno-Associated Viruses. Journal of Infectious Diseases, 2009. 199 (3): p. 381-390, which is incorporated by reference herein.

The abbreviation "sc" refers to self-complementary. "Self-complementary AAV" refers a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"-containing only the gene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

In many instances, rAAV particles are referred to as DNase resistant. However, in addition to this endonuclease (DNase), other endo- and exo-nucleases may also be used in the purification steps described herein, to remove contaminating nucleic acids. Such nucleases may be selected to degrade single stranded DNA and/or double-stranded DNA, and RNA. Such steps may contain a single nuclease, or mixtures of nucleases directed to different targets, and may be endonucleases or exonucleases.

The term "nuclease-resistant" indicates that the AAV capsid has fully assembled around the expression cassette which is designed to deliver a gene to a host cell and protects these packaged genomic sequences from degradation (digestion) during nuclease incubation steps designed to remove contaminating nucleic acids which may be present from the production process.

VI. Other Vector

In one aspect, provided herein is a vector which is useful for treating a disease associated with an ARSA mutation or caused by deficiencies in normal levels of functional Arylsulfatase A (for example, MLD) in a subject in need thereof. The vector carries a nucleic acid sequence encoding a functional human Arylsulfatase A (hARSA) under the control of regulatory sequences which direct the hARSA expression in a target cell. In certain embodiments, the hARSA coding sequence is about 95% to 100% identical to SEQ ID NO: 1. Additionally or alternatively, the function hARSA protein has an amino acid sequence of SEQ ID NO: 2. In certain embodiments, the hARSA-coding sequence is SEQ ID NO: 1. In certain embodiments, the vector or a composition comprising the vector is administrable to a subject in need thereof to ameliorate symptoms of a disease associated with an ARSA mutation or caused by deficiencies in normal levels of functional Arylsulfatase A (for example, MLD), and/or to delay progression of a disease associated with an ARSA mutation or caused by deficiencies in normal levels of functional Arylsulfatase A (for example, MLD).

In certain embodiments, the vector comprises an expression cassette. In certain embodiments, the expression cassette comprises a nucleic acid sequence encoding a functional human Arylsulfatase A (hARSA) under control of regulatory sequences which direct the hARSA expression. In certain embodiments, the functional hARSA protein comprises a signal peptide and an amino acid sequence of amino acid (aa) 19 to aa 507 of SEQ ID NO: 2. In certain embodiments, the signal peptide has an amino acid sequence of aa 1 to aa 18 of SEQ ID NO: 2 or an amino acid sequence of aa 1 to aa 20 of SEQ ID NO: 4. In certain embodiments, the hARSA coding sequence has a sequence of nucleotide (nt) 55 to nt 1521 of SEQ ID NO: 1, or a sequence at least 95% to 99.9% identical thereto which encodes a functional hARSA. In certain embodiments, the hARSA coding sequence is SEQ ID NO: 1 or SEQ ID NO: 3. See, Parts I, and III for more details.

In certain embodiments, the vector is a viral vector selected from a recombinant parvovirus, a recombinant lentivirus, a recombinant retrovirus, or a recombinant adenovirus; or a non-viral vector selected from naked DNA, naked RNA, an inorganic particle, a lipid particle, a polymer-based vector, or a chitosan-based formulation. The selected vector may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, NY.

In certain embodiments, the vector is suitable for administration to a patient via an intra-cisterna *magna* injection (ICM), including via a CT-guided sub-occipital injection into the cisterna *magna*. In certain embodiments, the vector is suitable for administration to a subject who is 7 years of age or younger. In certain embodiments, the vector is suitable for administration to a subject in need thereof to ameliorate symptoms of Metachromatic Leukodystrophy or a disease associated with Arylsulfatase A (ARSA) gene mutation, and/or to delay progression of Metachromatic Leukodystrophy or a disease associated with Arylsulfatase A (ARSA) gene mutation. In certain embodiments, the vector is administered in a single dose. See, Part II and Part VIII for more details.

A "replication-defective virus" or "viral vector" refers to a synthetic or artificial viral particle in which an expression cassette containing a gene of interest (e.g., hARSA coding sequence) is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"-containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication. Such replication-defective viruses may be adeno-associated viruses (AAV), adenoviruses, lentiviruses (integrating or non-integrating), or another suitable virus source.

VII. Compositions

In a further aspect, provided herein is a composition comprising a rAAV or a vector as described herein and an aqueous suspension media. In certain embodiments, the aqueous composition is provided which comprises a formulation buffer and the rAAV or vector as described. In certain embodiments, the formulation buffer comprises: an artificial cerebrospinal fluid comprising buffered saline and one or more of sodium, calcium, magnesium, potassium, or mixtures thereof; and a surfactant. In certain embodiments, the formulation buffer comprises about 0.0005% to about 0.001% surfactant. In certain embodiments, the composition is at a pH of 7.2 to 7.8. In certain embodiments, AAV.CB7.CI.hARSAco.rBG drug product consists of a non-replicating recombinant adeno-associated viral (rAAV) vector as described herein and a formulation buffer.

In certain embodiments, an aqueous pharmaceutical composition comprising a rAAV according to any one of claims 1 to 10 and a formulation buffer is provided. In certain embodiments, the formulation buffer comprises: an artificial cerebrospinal fluid comprising buffered saline and one or more of sodium, calcium, magnesium, potassium, or mixtures thereof; and a surfactant. In certain embodiments, the surfactant is present at 0.0005% to about 0.001% of the pharmaceutical composition. In certain embodiments, the composition is at a pH in the range of 7.5 to 7.8. In certain embodiments, the formulation buffer is suitable for intravenous delivery, intrathecal administration, or intracerebroventricular administration.

In certain embodiments, provided is a pharmaceutical composition comprising a vector as described and a formulation buffer. In certain embodiments, the formulation buffer is suitable for intravenous delivery, intrathecal administration, or intracerebroventricular administration.

In certain embodiments, the composition is suitable for administration to a patient via an intra-cisterna *magna* injection (ICM), including via a CT-guided sub-occipital injection into the cisterna *magna*. In certain embodiments, the composition is suitable for administration to a subject who is 7 years of age or younger. In certain embodiments, the composition is suitable for administration to a subject in need thereof to ameliorate symptoms of Metachromatic Leukodystrophy or a disease associated with Arylsulfatase A (ARSA) gene mutation, and/or to delay progression of Metachromatic Leukodystrophy or a disease associated with Arylsulfatase A (ARSA) gene mutation. In certain embodiments, the composition is administered in a single dose. In certain embodiments, the composition has an at least $2.50 \times 10^{13}$ GC rAAV per mL.

Provided herein are compositions containing at least one rAAV stock (e.g., an rAAVhu68 stock or a mutant rAAVhu68 stock) and an optional carrier, excipient and/or preservative. An TAAV stock refers to a plurality of rAAV vectors which are the same, e.g., such as in the amounts described below in the discussion of concentrations and dosage units.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host. Delivery vehicles such as liposomes, nanocapsules, microparticles, microspheres, lipid particles, vesicles, and the like, may be used for the introduction of the compositions of the present invention into suitable host cells. In particular, the rAAV vector delivered vector genomes may be formulated for delivery either encapsulated in a lipid particle, a liposome, a vesicle, a nanosphere, or a nanoparticle or the like.

In one embodiment, a composition includes a final formulation suitable for delivery to a subject, e.g., is an aqueous liquid suspension buffered to a physiologically compatible pH and salt concentration. Optionally, one or more surfactants are present in the formulation. In another embodiment, the composition may be transported as a concentrate which is diluted for administration to a subject. In other embodiments, the composition may be lyophilized and reconstituted at the time of administration.

A suitable surfactant, or combination of surfactants, may be selected from among non-ionic surfactants that are non-toxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits x 100 give the approximate molecular mass of the polyoxypropylene core, and the last digit x 10 gives the percentage polyoxyethylene content. In one embodiment Poloxamer 188 is selected. In one embodiment, the surfactant may be present in an amount up to about 0.0005% to about 0.001% (based on weight ratio, w/w %) of the suspension. In another embodiment, the surfactant may be present in an amount up to about 0.0005% to about 0.001% (based on volume ratio, v/v %) of the suspension. In yet another embodiment, the surfactant may be present in an amount up to about 0.0005% to about 0.001% of the suspension, wherein n % indicates n gram per 100 mL of the suspension. In yet another embodiment, the surfactant may be present in an amount up to about 0.0005% to about 0.001% (based on weight over volume ratio, v/w %) of the suspension.

As used herein, in certain embodiments, "%" upon referring to a concentration, is a weight ratio, for example, percentage of the substance (to be dissolved via a solvent into a solution) weight over the solvent's weight, or percentage of the substance (to be dissolved via a solvent into a solution) weight over the solution's weight. In certain embodiments, "%" upon referring to a concentration, is a volume ratio, for example, percentage of the substance (to be dissolved via a solvent into a solution) volume over the solvent's volume, or percentage of the substance (to be dissolved via a solvent into a solution) volume over the solution's volume. In certain embodiments, "%" upon referring to a concentration, indicates gram of the substance (to be dissolved via a solvent into a solution) per 100 mL of the solvent or solution. In certain embodiments, "%" upon referring to a concentration, is a weight over volume ratio, for example, percentage of the substance (to be dissolved via a solvent into a solution) weight over the solvent's volume, or percentage of the substance (to be dissolved via a solvent into a solution) weight over the solution's volume.

The vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., brain, CSF, the liver (optionally via the hepatic artery), lung, heart, eye, kidney,), oral, inhalation, intranasal, intrathecal, intratracheal, intraarterial, intraocular, intravenous, intramuscular, subcutaneous, intradermal, intraparenchymal, intracerebroventricular, intrathecal, ICM, lumbar puncture and other parenteral routes of administration. Routes of administration may be combined, if desired.

Dosages of the viral vector depend primarily on factors such as the condition being treated, the age, weight and health of the patient, and can thus vary among patients. For example, a therapeutically effective human dosage of the viral vector is generally in the range of from about 25 to about 1000 microliters to about 100 mL of solution containing concentrations of from about $1 \times 10^9$ to $1 \times 10^{16}$ vector genome copies. In certain embodiments, a volume of about 1 mL to about 15 mL, or about 2.5 mL to about 10 mL, or about 5 mL suspension is delivered. In certain embodiments, a volume of about 1, about 2, about 3, about 4, about 5, about 6, about 7, about 8, about 9, about 10, about 11, about 12, about 13, about 14, or about 15 mL suspension is delivered. In certain embodiments, a dose of about $8.9 \times 10^{12}$ to $2.7 \times 10^{14}$ GC total is administered in this volume. In certain embodiments, a dose of about $1.1 \times 10^{10}$ GC/g brain mass to about $3.3 \times 10^{11}$ GC/g brain mass is administered in this volume. In certain embodiments, a dose of about $3.0 \times 10^9$, about $4.0 \times 10^9$, about $5.0 \times 10^9$, about $6.0 \times 10^9$, about $7.0 \times 10^9$, about $8.0 \times 10^9$, about $9.0 \times 10^9$, about $1.0 \times 10^{10}$, about $1.1 \times 10^{10}$, about $1.5 \times 10^{10}$, about $2.0 \times 10^{10}$, about $2.5 \times 10^{10}$, about $3.0 \times 10^{10}$, about $3.3 \times 10^{10}$, about $3.5 \times 10^{10}$, about $4.0 \times 10^{10}$, about $4.5 \times 10^{10}$, about $5.0 \times 10^{10}$, about $5.5 \times 10^{10}$, about $6.0 \times 10^{10}$, about $6.5 \times 10^{10}$, about $7.0 \times 10^{10}$, about $7.5 \times 10^{10}$, about $8.0 \times 10^{10}$, about $8.5 \times 10^{10}$, about $9.0 \times 10^{10}$, about $9.5 \times 10^{10}$, about $1.0 \times 10^{11}$, about $1.1 \times 10^{11}$, about $1.5 \times 10^{11}$, about $2.0 \times 10^{11}$, about $2.5 \times 10^{11}$, about $3.0 \times 10^{11}$, about $3.3 \times 10^{11}$, about $3.5 \times 10^{11}$, about $4.0 \times 10^{11}$, about $4.5 \times 10^{11}$, about $5.0 \times 10^{11}$, about $5.5 \times 10^{11}$, about $6.0 \times 10^{11}$, about $6.5 \times 10^{11}$, about $7.0 \times 10^{11}$, about $7.5 \times 10^{11}$, about $8.0 \times 10^{11}$, about $8.5 \times 10^{11}$, about $9.0 \times 10^{11}$ GC per gram brain mass is administered in this volume.

| Subject Age | Assumed brain mass (g) |
| --- | --- |
| ≥4 to <9 months | 600 |
| ≥9 to <18 months | 1000 |
| ≥18 months to <3 years | 1100 |
| ≥3 years | 1300 |

The dosage is adjusted to balance the therapeutic benefit against any side effects and such dosages may vary depending upon the therapeutic application for which the recombinant vector is employed. The levels of expression of the transgene product can be monitored to determine the frequency of dosage resulting in viral vectors, preferably AAV vectors containing the minigene. Optionally, dosage regimens similar to those described for therapeutic purposes may be utilized for immunization using the compositions of the invention.

The replication-defective virus compositions can be formulated in dosage units to contain an amount of replication-defective virus that is in the range of about $1.0 \times 10^9$ GC to about $1.0 \times 10^{16}$ GC (to treat an subject) including all integers or fractional amounts within the range, and preferably $1.0 \times 10^{12}$ GC to $1.0 \times 10^{14}$ GC for a human patient. In one embodiment, the compositions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range.

In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, or $9 \times 10^{11}$ GC per dose including all integers or fractional amounts within the range. In another embodiment, the compositions are formulated to contain at least $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per dose including all integers or fractional amounts within the range. In another embodiment, the compositions are formulated to contain at least $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $1 \times 10^{10}$ to about $1 \times 10^{12}$ GC per dose including all integers or fractional amounts within the range.

These above doses may be administered in a variety of volumes of carrier, excipient or buffer formulation, ranging from about 25 to about 1000 microliters, or higher volumes, including all numbers within the range, depending on the size of the area to be treated, the viral titer used, the route of administration, and the desired effect of the method. In one embodiment, the volume of carrier, excipient or buffer is at least about 25 μL. In one embodiment, the volume is about 50 μL. In another embodiment, the volume is about 75 μL. In another embodiment, the volume is about 100 μL. In another embodiment, the volume is about 125 μL. In another embodiment, the volume is about 150 μL. In another embodiment, the volume is about 175 μL. In yet another embodiment, the volume is about 200 μL. In another embodiment, the volume is about 225 μL. In yet another embodiment, the volume is about 250 μL. In yet another embodiment, the volume is about 275 μL. In yet another embodiment, the volume is about 300 μL. In yet another embodiment, the volume is about 325 μL. In another embodiment, the volume is about 350 μL. In another embodiment, the volume is about 375 μL. In another embodiment, the volume is about 400 μL. In another embodiment, the volume is about 450 μL. In another embodiment, the volume is about 500 μL. In another embodiment, the volume is about 550 μL. In another embodiment, the volume is about 600 μL. In another embodiment, the volume is about 650 μL. In another embodiment, the volume is about 700 μL. In another embodiment, the volume is between about 700 and 1000 μL.

In certain embodiments, the dose may be in the range of about $1 \times 10^9$ GC/g brain mass to about $1 \times 10^{12}$ GC/g brain mass. In certain embodiments, the dose may be in the range of about $1 \times 10^{10}$ GC/g brain mass to about $1 \times 10^{12}$ GC/g brain mass. In certain embodiments, the dose may be in the range of about $3 \times 10^{10}$ GC/g brain mass to about $5 \times 10^{11}$ GC/g brain mass.

In one embodiment, the viral constructs may be delivered in doses of from at least about least $1 \times 10^9$ GC to about $1 \times 10^{15}$, or about $1 \times 10^{11}$ to $5 \times 10^{13}$ GC. Suitable volumes for delivery of these doses and concentrations may be determined by one of skill in the art. For example, volumes of about 1 μL to 150 mL may be selected, with the higher volumes being selected for adults. Typically, for newborn infants a suitable volume is about 0.5 mL to about 10 mL, for older infants, about 0.5 mL to about 15 mL may be selected. For toddlers, a volume of about 0.5 mL to about 20 mL. may be selected. For children, volumes of up to about 30 mL may be selected. For pre-teens and teens, volumes up to about 50 mL may be selected. In still other embodiments, a patient may receive an intrathecal administration in a volume of about 5 mL to about 15 mL are selected, or about 7.5 mL to about 10 mL. Other suitable volumes and dosages may be determined. The dosage may be adjusted to balance the therapeutic benefit against any side effects and such dosages may vary depending upon the therapeutic application for which the recombinant vector is employed.

The above-described recombinant vectors may be delivered to host cells according to published methods. The rAAV, preferably suspended in a physiologically compatible carrier, may be administered to a human or non-human mammalian patient. In certain embodiments, for administration to a human patient, the rAAV is suitably suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.5 to 7.5, pH 7.0 to 7.7, or pH 7.2 to 7.8. As the pH of the cerebrospinal fluid is about 7.28 to about 7.32, for intrathecal delivery, a pH within this range may be desired; whereas for intravenous delivery, a pH of about 6.8 to about 7.2 may be desired. However, other pHs within the broadest ranges and these subranges may be selected for other route of delivery.

In another embodiment, the composition includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV, from sticking to the infusion tubing but does not interfere with the rAAV binding activity in vivo. A suitable surfactant, or combination of surfactants, may be selected from among non-ionic surfactants that are nontoxic. In one embodiment, a difunctional block copolymer surfactant terminating in primary hydroxyl groups is selected, e.g., such as Poloxamer 188 (also known under the commercial names Pluronic® F68 [BASF], Lutrol® F68, Synpcronic® F68, Kolliphor® P188) which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy-oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits x 100 give the approximate molecular mass of the polyoxypropylene core, and the last digit x 10 gives the percentage polyoxyethylene content. In one embodiment Poloxamer 188 is selected. The surfactant may be present in an amount up to about 0.0005% to about 0.001% of the suspension.

In one example, the formulation may contain, e.g., buffered saline solution comprising one or more of sodium chloride, sodium bicarbonate, dextrose, magnesium sulfate (e.g., magnesium sulfate ·7H$_2$O), potassium chloride, calcium chloride (e.g., calcium chloride ·2H$_2$O), dibasic sodium phosphate, and mixtures thereof, in water. Suitably, for intrathecal delivery, the osmolarity is within a range compatible with cerebrospinal fluid (e.g., about 275 to about 290); see, e.g., emedicine.medscape.com/-article/2093316-overview. Optionally, for intrathecal delivery, a commercially available diluent may be used as a suspending agent, or in combination with another suspending agent and other optional excipients.

See, e.g., Elliotts B® solution [Lukare Medical]. Each 10 mL of Elliotts B Solution contains: Sodium Chloride, USP-73 mg; Sodium Bicarbonate, USP-19 mg; Dextrose, USP8 mg; Magnesium Sulfate ·7H2O, USP 3 mg; Potassium Chloride, USP-3 mg; Calcium Chloride ·2H2O, USP-2 mg; Sodium Phosphate, dibasic ·7H2O, USP-2 mg; Water for Injection, USP qs 10 mL.

Concentration of Electrolytes: Sodium 149 mEq/liter; Bicarbonate 22.6 mEq/liter; Potassium 4.0 mEq/liter; Chloride 132 mEq/liter; Calcium 2.7 mEq/liter; Sulfate 2.4 mEq/liter; Magnesium 2.4 mEq/liter; Phosphate 1.5 mEq/liter.

The formulae and molecular weights of the ingredients are:

| INGREDIENT | MOLECULAR FORMULA | MOLECULAR WEIGHT |
|---|---|---|
| Sodium Chloride | NaCl | 58.44 |
| Sodium Bicarbonate | NaHCO$_3$ | 84.01 |
| Dextrose | C$_6$H$_{12}$O$_6$ | 180.16 |
| Magnesium Sulfate•7H2O | Mg$_2$SO$_4$•7H$_2$O | 246.48 |
| Potassium Chloride | KCl | 74.55 |
| Calcium Chloride•2H2O | CaCl$_2$•2H$_2$O | 147.01 |
| Sodium Phosphate, dibasic•7H2O | Na$_2$HPO$_4$•7H$_2$O | 268.07 |

The pH of Elliotts B Solution is 6 to 7.5, and the osmolarity is 288 mOsmol per liter (calculated). In certain embodiments, the composition containing the rAAVhu68.hARSA is delivered at a pH in the range of 6.8 to 8, or 7.2 to 7.8, or 7.5 to 8. For intrathecal delivery, a pH above 7.5 may be desired, e.g., 7.5 to 8, or 7.8.

In certain embodiments, the formulation may contain a buffered saline aqueous solution not comprising sodium bicarbonate. Such a formulation may contain a buffered saline aqueous solution comprising one or more of sodium phosphate, sodium chloride, potassium chloride, calcium chloride, magnesium chloride and mixtures thereof, in water, such as a Harvard's buffer. The aqueous solution may further contain Kolliphor® P188, a poloxamer which is commercially available from BASF which was formerly sold under the trade name Lutrol® F68. The aqueous solution may have a pH of 7.2.

In another embodiment, the formulation may contain a buffered saline aqueous solution comprising 1 mM Sodium Phosphate (Na$_3$PO$_4$), 150 mM sodium chloride (NaCl), 3 mM potassium chloride (KCl), 1.4 mM calcium chloride (CaCl$_2$)), 0.8 mM magnesium chloride (MgCl$_2$), and 0.001% poloxamer (e.g., Kolliphor®) 188, pH 7.2. See, e.g., harvardapparatus.com/harvard-apparatus-perfusion-fluid.html. In certain embodiments, Harvard's buffer is preferred due to better pH stability observed with Harvard's buffer. The table below provides a comparison of Harvard's buffer and Elliot's B buffer.

| Component | Units | CSF | Elliot's B | Harvard's |
|---|---|---|---|---|
| Na$^+$ | mEq/L | 117-137 | 149 | 150 |
| K$^+$ | mEq/L | 2.3-4.6 | 4.0 | 3.0 |
| Mg$^+$ | mEq/L | 2.2 | 2.4 | 0.8 |
| Ca$^{2+}$ | mEq/L | 2.2 | 2.7 | 1.4 |
| Cl$^-$ | mEq/L | 113-127 | 132 | 155 |
| HCO$_3^-$ | mEq/L | 22.9 | 22.6 | 0 |
| Phos | mg/dL | 1.2-2.1 | 1.5 | 1.0 |
| Glucose | mg/dL | 45-80 | 80 | — |
| Pluronic | % | — | 0.001% (added) | 0.001% (added) |
| Osmolarity | mOsm/L | 295 | 288 | 290 |
| pH | | 7.31 | 6.0-7.5* Drift to 9+ (8.2+ w/o titratn) | 7.2 (titrated to) |

In certain embodiments, the formulation buffer is artificial CSF with Pluronic F68. In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The compositions according to the present invention may comprise a pharmaceutically acceptable carrier, such as defined above. Suitably, the compositions described herein comprise an effective amount of one or more AAV suspended in a pharmaceutically suitable carrier and/or admixed with suitable excipients designed for delivery to the subject via injection, osmotic pump, intrathecal catheter, or for delivery by another device or route. In one example, the composition is formulated for intrathecal delivery.

As used herein, the terms "intrathecal delivery" or "intrathecal administration" refer to a route of administration for drugs via an injection into the spinal canal, more specifically into the subarachnoid space so that it reaches the cerebrospinal fluid (CSF). Intrathecal delivery may include lumbar puncture, intraventricular (including intracerebroventricular (ICV)), suboccipital/intracisternal, and/or C1-2 puncture. For example, material may be introduced for diffusion throughout the subarachnoid space by means of lumbar puncture. In another example, injection may be into the cisterna *magna*.

As used herein, the terms "intracisternal delivery" or "intracisternal administration" refer to a route of administration for drugs directly into the cerebrospinal fluid of the cisterna *magna* cerebellomedularis, more specifically via a suboccipital puncture or by direct injection into the cisterna *magna* or via permanently positioned tube.

In certain embodiments, the final formulation buffer comprises an artificial cerebrospinal fluid comprising buffered saline and one or more of sodium, calcium, magnesium, potassium, or mixtures thereof; and a surfactant. In certain embodiments, the surfactant is about 0.0005% w/w to about 0.001% w/w of the suspension. In certain embodiments, the surfactant is Pluronic F68. In certain embodiments, the Pluronic F68 is present in an amount of about 0.0001% of the suspension. In certain embodiments, the composition is at a pH in the of 7.5 to 7.8 for intrathecal delivery.

In certain embodiments, treatment of the composition described herein has minimal to mild asymptomatic degeneration of DRG sensory neurons in animals and/or in human patients, well-tolerated with respect to sensory nerve toxicity and subclinical sensory neuron lesions.

In certain embodiment, the composition described herein is useful in improving functional and clinical outcomes in the subject treated. Such outcomes may be measured at about 30 days, about 60 days, about 90 days, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, about 24 months, about 2.5 years, about 3 years, about 3.5 years, about 4 years, about 4.5 years and then yearly up to the about 5 years after administration of the composition. Measurement frequency may be about every 1 month, about every 2 months, about every 3 months, about every 4 months, about every 5 months, about every 6 months, about every 7 months, about every 8 months, about every 9 months, about every 10 months, about every 11 months, or about every 12 months.

In certain embodiments, the composition described herein shows pharmacodynamics and clinical efficacy measured in treated subjects compared to untreated controls.

In certain embodiments, the pharmacodynamics efficacy, clinical efficacy, functional outcomes, clinical outcomes, disease amelioration, or disease progression may be assessed via one or more of the following: concentration and/or level and/or biological activity of ARSA (for example, in serum or in CSF), urine sulfatides, CNS myelination (demyelination load and pattern), white matter atrophy as measured by MRI, neuronal metabolite N-acetylaspartate (NAA), myo-inositol (ml), choline (Cho) and/or lactate (Lac) levels (for example, as measured by proton magnetic resonance spectroscopy (MRS)), CSF sulfatide and lyso-sulfatide levels, Visual evoked potentials (VEPs), Brainstem auditory evoked responses (BAERs), gall-bladder wall thickening (for example, via ultrasound evaluation); motor function (for example, measured by the Gross Motor Function Classification for Metachromatic Leukodystrophy (GMFC-MLD) or Gross Motor Function Measure (GMFM)), Motor milestones achievement (as defined by World Health Organization [WHO] criteria) assessed by age at achievement, age at loss, and percentage of children maintaining or acquiring motor milestones, cognitive function (for example, Total Intelligence Quotient [IQ] and sub-domain IQ measured by the Bayley Scale of Infant Development [BSID-III], Wechsler Intelligence Scale for Children, Fifth Edition [WISC-V]), lifespan (compared to a patient), neurological clinical exam (NCE), nerve conduction velocity (NCV) of the ulnar, deep peroneal, median, sural nerves, age-at-onset and frequency of seizures captured by a seizure diary, behavior function (for example, measured by Vineland Adaptive Behavior Scales, Third Edition (Vineland-III)), Lansky Performance Index, Pediatric Quality of Life Inventory (for example, PedsQL and PedsQL-IS), and caregiver/parent quality of life.

In certain embodiments, the pharmacodynamics efficacy, clinical efficacy, functional outcomes, clinical outcomes, disease amelioration, or disease progression may be assessed abnormal properties (for example biomarker activity, electrophysiological activity, and/or imaging parameters) and clinical observations (for example, gross and fine motor function, cognitive and language development, neurological exam findings, behavioral and milestone development, and caregiver/parent-reported outcomes and decreased quality of life assessments). Other disease amelioration or disease progression may be assessed, see, Parts II and VIII, relative section thereof is incorporated herein by reference in their entireties.

Alternatively or additionally, the pharmacodynamics efficacy, clinical efficacy, functional outcomes, or clinical outcomes may include biomarkers, for example, pharmacodynamics and biological activity of rAAVhu68.hARSAco . . .

IIX. Methods

In another aspect, a method of treating a subject having a disease associated with an ARSA mutation or caused by deficiencies in normal levels of functional Arylsulfatase A (for example, MLD), or ameliorating symptoms of a disease associated with an ARSA mutation or caused by deficiencies in normal levels of functional Arylsulfatase A (for example, MLD), or delaying progression of a disease associated with an ARSA mutation or caused by deficiencies in normal levels of functional Arylsulfatase A (for example, MLD) is provided. The method comprises administrating an effective amount of a rAAV or a vector as described herein to a subject in need thereof. In certain embodiments, the vector or rAAV is administrable to a patient via an intra-cisterna *magna* injection (ICM), for example, CT-guided sub-occipital injection into the cisterna *magna*. In certain embodiments, a vector or a composition is provided which is administrable to a patient having Metachromatic Leukodystrophy who is 7 years of age or younger. In certain embodiments, the method involves delivering the rAAV or the vector to a human patient in a single dose. In certain embodiments, the rAAV is administered at a dose between $3.00 \times 10^{10}$ genome copies (GC) per gram (GC/g) of brain mass and $1.00 \times 10^{12}$ GC/g of brain mass. In certain embodiments, following the administration, disease symptom of the subject is ameliorated and/or the disease progression is delayed.

Although nervous system-directed AAV gene therapy targets primarily neurons in vivo, the cross-correction potential opens the possibility to correct ARSA-deficient myelinating cells, which cannot be transduced in vivo by most gene therapy vectors (Cearley et al., 2008; Lawlor et al., 2009).

In certain embodiments, an "effective amount" herein is the amount which achieves amelioration of MLD symptoms and/or delayed MLD progression.

The vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to a desired organ (e.g., brain, CSF, the liver (optionally via the hepatic artery), lung, heart, eye, kidney,), oral, inhalation, intranasal, intrathecal, intratracheal, intraarterial, intraocular, intravenous, intramuscular, subcutaneous, intradermal, intraparenchymal, intracerebroventricular, intrathecal, ICM, lumbar puncture and other parenteral routes of administration. Routes of administration may be combined, if desired.

Dosages of the viral vector (for example, rAAV) depend primarily on factors such as the condition being treated, the age, weight and health of the patient, and can thus vary among patients. For example, a therapeutically effective human dosage of the viral vector is generally in the range of from about 25 to about 1000 microliters to about 100 mL of solution containing concentrations of from about $1\times10^9$ to $1\times10^{16}$ vector genome copies. In certain embodiments, a volume of about 1 mL to about 15 mL, or about 2.5 mL to about 10 mL, or about 5 mL suspension is delivered. In certain embodiments, a volume of about 1, about 2, about 3, about 4, about 5, about 6, about 7, about 8, about 9, about 10, about 11, about 12, about 13, about 14, or about 15 mL suspension is delivered. In certain embodiments, a dose of about $8.9\times10^{12}$ to $2.7\times10^{14}$ GC total is administered in this volume. In certain embodiments, a dose of about $1.1\times10^{10}$ GC/g brain mass to about $3.3\times10^{11}$ GC/g brain mass is administered in this volume. In certain embodiments, a dose of about $3.0\times10^9$, about $4.0\times10^9$, about $5.0\times10^9$, about $6.0\times10^9$, about $7.0\times10^9$, about $8.0\times10^9$, about $9.0\times10^9$, about $1.0\times10^{10}$, about $1.1\times10^{10}$, about $1.5\times10^{10}$, about $2.0\times10^{10}$, about $2.5\times10^{10}$, about $3.0\times10^{10}$, about $3.3\times10^{10}$, about $3.5\times10^{10}$, about $4.0\times10^{10}$, about $4.5\times10^{10}$, about $5.0\times10^{10}$, about $5.5\times10^{10}$, about $6.0\times10^{10}$, about $6.5\times10^{10}$, about $7.0\times10^{10}$, about $7.5\times10^{10}$, about $8.0\times10^{10}$, about $8.5\times10^{10}$, about $9.0\times10^{10}$, about $9.5\times10^{10}$, about $1.0\times10^{11}$, about $1.1\times10^{11}$, about $1.5\times10^{11}$, about $2.0\times10^{11}$, about $2.5\times10^{11}$, about $3.0\times10^{11}$, about $3.3\times10^{11}$, about $3.5\times10^{11}$, about $4.0\times10^{11}$, about $4.5\times10^{11}$, about $5.0\times10^{11}$, about $5.5\times10^{11}$, about $6.0\times10^{11}$, about $6.5\times10^{11}$, about $7.0\times10^{11}$, about $7.5\times10^{11}$, about $8.0\times10^{11}$, about $8.5\times10^{11}$, about $9.0\times10^{11}$ GC per gram brain mass is administered in this volume.

The dosage is adjusted to balance the therapeutic benefit against any side effects and such dosages may vary depending upon the therapeutic application for which the recombinant vector is employed. The levels of expression of the transgene product can be monitored to determine the frequency of dosage resulting in viral vectors, preferably AAV vectors containing the minigene. Optionally, dosage regimens similar to those described for therapeutic purposes may be utilized for immunization using the compositions of the invention.

The replication-defective virus compositions can be formulated in dosage units to contain an amount of replication-defective virus that is in the range of about $1.0\times10^9$ GC to about $1.0\times10^{16}$ GC (to treat an subject) including all integers or fractional amounts within the range, and preferably $1.0\times10^{12}$ GC to $1.0\times10^{14}$ GC for a human patient. In one embodiment, the compositions are formulated to contain at least $1\times10^9$, $2\times10^9$, $3\times10^9$, $4\times10^9$, $5\times10^9$, $6\times10^9$, $7\times10^9$, $8\times10^9$, or $9\times10^9$ GC per dose including all integers or fractional amounts within the range. In another embodiment, the compositions are formulated to contain at least $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ GC per dose including all integers or fractional amounts within the range. In another embodiment, the compositions are formulated to contain at least $1\times10^{11}$, $2\times10^{11}$, $3\times10^{11}$, $4\times10^{11}$, $5\times10^{11}$, $6\times10^{11}$, $7\times10^{11}$, $8\times10^{11}$, or $9\times10^{11}$ GC per dose including all integers or fractional amounts within the range. In another embodiment, the compositions are formulated to contain at least $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ GC per dose including all integers or fractional amounts within the range. In another embodiment, the compositions are formulated to contain at least $1\times10^{13}$, $2\times10^{13}$, $3\times10^{13}$, $4\times10^{13}$, $5\times10^{13}$, $6\times10^{13}$, $7\times10^{13}$, $8\times10^{13}$, or $9\times10^{13}$ GC per dose including all integers or fractional amounts within the range. In another embodiment, the compositions are formulated to contain at least $1\times10^{14}$, $2\times10^{14}$, $3\times10^{14}$, $4\times10^{14}$, $5\times10^{14}$, $6\times10^{14}$, $7\times10^{14}$, $8\times10^{14}$, or $9\times10^{14}$ GC per dose including all integers or fractional amounts within the range. In another embodiment, the compositions are formulated to contain at least $1\times10^{15}$, $2\times10^{15}$, $3\times10^{15}$, $4\times10^{15}$, $5\times10^{15}$, $6\times10^{15}$, $7\times10^{15}$, $8\times10^{15}$, or $9\times10^{15}$ GC per dose including all integers or fractional amounts within the range.

In one embodiment, for human application the dose can range from $1\times10^{10}$ to about $1\times10^{15}$ GC per kg body weight including all integers or fractional amounts within the range.

In one embodiment, the effective amount of the vector is about $1\times10^9$, $2\times10^9$, $3\times10^9$, $4\times10^9$, $5\times10^9$, $6\times10^9$, $7\times10^9$, $8\times10^9$, or $9\times10^9$ GC per kg body weight including all integers or fractional amounts within the range. In another embodiment, the effective amount of the vector is about $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ GC per kg body weight including all integers or fractional amounts within the range. In another embodiment, the effective amount of the vector is about $1\times10^{11}$, $2\times10^{11}$, $3\times10^{11}$, $4\times10^{11}$, $5\times10^{11}$, $6\times10^{11}$, $7\times10^{11}$, $8\times10^{11}$, or $9\times10^{11}$ GC per kg body weight including all integers or fractional amounts within the range. In another embodiment, the effective amount of the vector is about $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ GC per kg body weight including all integers or fractional amounts within the range. In another embodiment, the effective amount of the vector is about $1\times10^{13}$, $2\times10^{13}$, $3\times10^{13}$, $4\times10^{13}$, $5\times10^{13}$, $6\times10^{13}$, $7\times10^{13}$, $8\times10^{13}$, or $9\times10^{13}$ GC per kg body weight including all integers or fractional amounts within the range. In another embodiment, the effective amount of the vector is about $1\times10^{14}$, $2\times10^{14}$, $3\times10^{14}$, $4\times10^{14}$, $5\times10^{14}$, $6\times10^{14}$, $7\times10^{14}$, $8\times10^{14}$, or $9\times10^{14}$ GC per kg body weight including all integers or fractional amounts within the range. In another embodiment, the effective amount of the vector is about $1\times10^{15}$, $2\times10^{15}$, $3\times10^{15}$, $4\times10^{15}$, $5\times10^{15}$, $6\times10^{15}$, $7\times10^{15}$, $8\times10^{15}$, or $9\times10^{15}$ GC per kg body weight including all integers or fractional amounts within the range.

In one embodiment, for human application the dose can range from $1\times10^{10}$ to about $1\times10^{15}$ GC per gram (g) brain mass including all integers or fractional amounts within the range. In one embodiment, the effective amount of the vector is about $1\times10^9$, $2\times10^9$, $3\times10^9$, $4\times10^9$, $5\times10^9$, $6\times10^9$, $7\times10^9$, $8\times10^9$, or $9\times10^9$ GC per gram (g) brain mass including all integers or fractional amounts within the range. In another embodiment, the effective amount of the vector is about $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ GC per gram (g) brain mass including all integers or fractional amounts within the range. In another embodiment, the effective amount of the vector is about $1\times10^{11}$, $2\times10^{11}$, $3\times10^{11}$, $4\times10^{11}$, $5\times10^{11}$, $6\times10^{11}$, $7\times10^{11}$, $8\times10^{11}$, or $9\times10^{11}$ GC per gram (g) brain mass including all integers or fractional amounts within the range. In another embodiment, the effective amount of the vector is about $1\times10^{12}$, $2\times10^{12}$, $3\times10^{12}$, $4\times10^{12}$, $5\times10^{12}$, $6\times10^{12}$, $7\times10^{12}$, $8 \times 10^{12}$, or $9 \times 10^{12}$ GC per gram (g) brain mass including all integers or fractional amounts within the range. In another embodiment, the effective amount of the vector is about $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per gram (g) brain mass including all integers or fractional amounts within the range. In another embodiment, the effective amount of the vector is about $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per gram (g) brain mass including all integers or fractional amounts within the range. In another embodiment, the effective amount of the vector is about $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per gram (g) brain mass including all integers or fractional amounts within the range.

These above doses may be administered in a variety of volumes of carrier, excipient or buffer formulation, ranging from about 25 to about 1000 microliters, or higher volumes, including all numbers within the range, depending on the size of the area to be treated, the viral titer used, the route of administration, and the desired effect of the method. In one embodiment, the volume of carrier, excipient or buffer is at least about 25 µL. In one embodiment, the volume is about 50 µL. In another embodiment, the volume is about 75 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 225 µL. In yet another embodiment, the volume is about 250 µL. In yet another embodiment, the volume is about 275 µL. In yet another embodiment, the volume is about 300 µL. In yet another embodiment, the volume is about 325 µL. In another embodiment, the volume is about 350 µL. In another embodiment, the volume is about 375 µL. In another embodiment, the volume is about 400 µL. In another embodiment, the volume is about 450 µL. In another embodiment, the volume is about 500 µL. In another embodiment, the volume is about 550 µL. In another embodiment, the volume is about 600 µL. In another embodiment, the volume is about 650 µL. In another embodiment, the volume is about 700 µL. In another embodiment, the volume is between about 700 and 1000 µL.

In certain embodiments, the dose may be in the range of about $1 \times 10^{9}$ GC/g brain mass to about $1 \times 10^{12}$ GC/g brain mass. In certain embodiments, the dose may be in the range of about $1 \times 10^{10}$ GC/g brain mass to about $3 \times 10^{11}$ GC/g brain mass. In certain embodiments, the dose may be in the range of about $1 \times 10^{10}$ GC/g brain mass to about $2.5 \times 10^{11}$ GC/g brain mass. In certain embodiments, the dose may be in the range of about $5 \times 10^{10}$ GC/g brain mass.

In one embodiment, the viral constructs may be delivered in doses of from at least about least $1 \times 10^{9}$ GC to about $1 \times 10^{15}$, or about $1 \times 10^{11}$ to $5 \times 10^{13}$ GC. Suitable volumes for delivery of these doses and concentrations may be determined by one of skill in the art. For example, volumes of about 1 µL to 150 mL may be selected, with the higher volumes being selected for adults. Typically, for newborn infants a suitable volume is about 0.5 mL to about 10 mL, for older infants, about 0.5 mL to about 15 mL may be selected. For toddlers, a volume of about 0.5 mL to about 20 mL may be selected. For children, volumes of up to about 30 mL may be selected. For pre-teens and teens, volumes up to about 50 mL may be selected. In still other embodiments, a patient may receive an intrathecal administration in a volume of about 5 mL to about 15 mL are selected, or about 7.5 mL to about 10 mL. Other suitable volumes and dosages may be determined. The dosage may be adjusted to balance the therapeutic benefit against any side effects and such dosages may vary depending upon the therapeutic application for which the recombinant vector is employed.

The above-described recombinant vectors may be delivered to host cells according to published methods. The rAAV, preferably suspended in a physiologically compatible carrier, may be administered to a human or non-human mammalian patient. In certain embodiments, for administration to a human patient, the rAAV is suitably suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.5 to 7.5, pH 7.0 to 7.7, or pH 7.2 to 7.8. As the pH of the cerebrospinal fluid is about 7.28 to about 7.32, for intrathecal delivery, a pH within this range may be desired; whereas for intravenous delivery, a pH of about 6.8 to about 7.2 may be desired. However, other pHs within the broadest ranges and these subranges may be selected for other route of delivery.

In certain embodiments, treatment of the composition described herein has minimal to mild asymptomatic degeneration of DRG sensory neurons in animals and/or in human patients, well-tolerated with respect to sensory nerve toxicity and subclinical sensory neuron lesions.

In certain embodiments, the proposed population for the rAAV, vector, composition, and method consist of subjects with early onset late infantile and early juvenile MLD who have symptom onset <7 years of age and whose predictable and rapid decline supports a robust study design and evaluation of functional outcomes within a reasonable follow-up period.

Treatment via the rAAV, vector, composition or method is for disease symptom amelioration and delayed disease progression, including stabilizing the underlying pathology, thereby preventing disease onset and enabling normal or near-normal motor and cognitive development, or substantially preventing or delaying loss of skills (such as acquired developmental and motor milestones) and disease progression. Pre-symptomatic patients arc eligible for this treatment.

The AAVhu68 capsid of AAV.hARSAco and the ICM ROA effectively transduces cortical neurons, a small subset of myelin-producing oligodendrocytes, motor neurons with axons projecting into the PNS, and DRG sensory neurons with axons projecting into both the spinal cord and peripheral nerves. Given the broad transduction profile in both the CNS and PNS, ARSA enzyme cross-correction may treat both the CNS manifestations and the peripheral neuropathy observed in many MLD patients, which is not addressed by HSC-GT or HSCT.

Given the nature of MLD, with CNS injury thought to be largely irreversible and the rapid disease progression in the early onset population, the rAAV, vector, composition or method as described herein confers the greatest potential for benefit in patients with no or mild to moderate disease. ICM-delivered AAV gene therapies, such as AAV. hARSAco, show rapid kinetic onset compared to that of HSC-based therapies, with peak ARSA expression in the CSF by 3 weeks after administration (See, Examples). As a result, AAVhARSAco may halt disease progression even in patients who already have some clinical signs of disease. Therefore, patients with early onset MLD who have mild to moderate signs and symptoms would be eligible for the treatment by the rAAV, vector, composition or method as described herein (termed as "treatment"), including those with mild gait abnormalities in patients who are ambulatory and are able to walk at least 10 steps independently, apparent delays in motor milestones acquisition (defined as >95th percentile for age in achieving a given milestone based on WHO criteria (Wijnhoven et al., 2004)), and mild signs on neurological exam.

Indicators of disease progression that are not commonly found in patients with mild to moderate symptoms, include, such as feeding difficulties requiring gastrostomy, development of seizures, low cognitive function, severe abnormalities found on neurological exam (such as very brisk reflexes, severe hypotonus or spasticity of the limbs, severe dysphagia, dyspraxia, or ataxia), and vision or hearing loss would result in exclusion from the trial. A delay in this disease progression, in certain embodiments, is shown as stabilization of disease at a low level of clinical function.

In certain embodiments, pharmacodynamic and efficacy outcomes of the methods is measured at 1, 3, and 6 months, and then every 6 months during the 2 year short-term follow-up period, except for those that require sedation and/or LP. During the long term follow up phase, evaluation frequency decreases to once every 12 months. The early time points and 6 month intervals for the first 2 years were also selected in consideration of the rapid rate of disease progression in untreated early onset MLD patients.

In certain embodiments, amelioration of a disease symptom or delay in disease progression is shown via assessing gross motor function. The GMFC-MLD is a validated, reliable, and simple tool for standardized assessment of gross motor function and decline over time in MLD patients (Kehrer et al., 2011b). It was modeled on a similar tool that assesses motor function in children with cerebral palsy and classifies children's motor function into one of five levels based on differences in self-initiated movements (Palisano et al., 2006). Kehrer et al. adapted the classification system to be relevant to patients with MLD and to provide a classification system in which distinctions between the levels would be considered meaningful in the daily life of children with MLD (the table below) (Kehrer et al., 2011a; Kehrer et al., 2011b). The GMFC-MLD has been used to both describe the natural history of MLD (Kehrer et al., 2011a) and evaluate motor function after therapeutic intervention (Sessa et al., 2016). One potential limitation of the GMFC-MLD is that the tool was validated for children from 18 months of age onwards, as this represents the upper age limit when children normally learn to walk (Largo et al., 1985; WHO, 2006). However, the tool would still apply for children who achieve the walking milestone before this age.

TABLE

Gross Motor Function Classification System
in Metachromatic Leukodystrophy

| Level 0 | Walking without support with quality of performance normal for age |
| Level 1 | Walking without support but with reduced quality of performance, i.e., instability when standing or walking |
| Level 2 | Walking with support. Walking without support not possible (fewer than five steps) |
| Level 3 | Sitting without support and locomotion such as crawling or rolling. Walking with or without support not possible |
| Level 4 | (a) Sitting without support but no locomotion or (b) Sitting without support not possible, but locomotion such as crawling or rolling |

TABLE-continued

Gross Motor Function Classification System
in Metachromatic Leukodystrophy

| Level 5 | No locomotion nor sitting without support, but head control is possible |
| Level 6 | Loss of any locomotion as well as loss of any head and trunk control |

The GMFM is included as a measurement for evaluating amelioration of a disease symptom or delay in disease progression. It is a standardized observational instrument designed and validated to measure change in gross motor function over time and after intervention in children with cerebral palsy (Russell et al., 1989; Lundkvist Josenby et al., 2009; Alotaibi et al., 2014). The GMFM is an 88-item tool that assesses motor function grouped across five functional domains: lying and rolling, sitting, crawling and kneeling, standing, and walking, running and jumping. Reference curves have also been developed for healthy children, who typically attain the most difficult skills on the scale (walking, running, jumping) by 5 years of age (Palisano et al., 2006). Although the tool is not validated for children with MLD, it has been proven useful for early onset MLD patients who received HSC-GT in demonstrating (near) normal gross motor development in subjects treated in the pre-symptomatic stage (Sessa et al., 2016; Fumagalli et al., 2017). One of the advantages of the 88-item instrument is that it contains a large amount of information about various aspects of motor function and the sub-domains can be summarized and reported separately. Due to a plateau effect, the tool may not be as informative in older early juvenile patients who may already have reached the maximum GMFM score prior to study enrolment (i.e., cannot measure acquisition of new skills), although it would still be able to show maintenance or loss of gross motor function over time.

Peripheral neuropathy is a common, painful, and progressively debilitating manifestation of MLD that can aggravate the fine and gross motor dysfunction in these patients (Gieselmann and Krageloh-Mann, 2010; van Rappard et al., 2015). HSC-based treatments do not appear to substantially ameliorate peripheral neuropathy (Boucher et al., 2015; van Rappard et al., 2016). The ability of AAV.hARSAco to transduce neurons, DRG, and peripheral nerve axons cells allow for expression of the ARSA enzyme within the brain and peripheral nerve dysfunction. Neurological examinations may be performed to assess clinical manifestations of peripheral neuropathy, and nerve conduction studies may be performed on representative motor and sensory nerves (deep peroneal nerve, median nerve, ulnar nerve, and sural nerve). As MLD is primarily a demyelinating disease, nerve conduction velocity is considered a relevant neurophysiologic parameter of the disease (Biffi et al., 2008) and may be measured.

Motor milestone development depends on the age and stage of disease at the time of subject enrollment. Depending on the age of the subject at enrollment, subjects may have . . . achieved certain motor skills or not yet shown signs of motor milestone development. Assessments will track age-at-achievement and age-at-loss for all milestones. Motor milestone achievement will be defined for six gross milestones based on the WHO criteria outlined in the table below.

TABLE

World Health Organization Performance Criteria for Gross Motor Milestones

| Gross Motor Milestone | Multicenter Growth Reference Study Performance Criteria |
| --- | --- |
| Sitting without support | Child sits up straight with the head erect for at least 10 seconds. Child does not use arms or hands to balance body or support position. |
| Hands-and-knees crawling | Child alternately moves forward or backward on hands and knees. The stomach does not touch the supporting surface. There are continuous and consecutive movements, at least three in a row. |
| Standing with assistance | Child stands in upright position on both feet, holding onto a stable object (e.g., furniture) with both hands without leaning on it. The body does not ouch the stable object, and the legs support most of the body weight. Child thus stands with assistance for at least 10 seconds. |
| Walking with assistance | Child is in upright position with the back straight. Child makes sideways or forward steps by holding on a stable objects (e.g., furniture) with one of both hands. One leg moves forward while the other supports part of the body weight. Child takes at least five steps in this manner. |
| Standing alone | Childs stands in upright position on both feed (not on the toes) with the back straight. The legs support 100% of the child's weigh. There is no contact with a person or objects. Child stands alone for at least 10 seconds. |
| Walking alone | Child takes at least five steps independently in upright position with the back straight. One leg moves forward while the other supports most of the body weight. There is no contact with a person or object. |
| Gross Motor Milestone | Multicenter Growth Reference Study Performance Criteria |

Adapted from (Wijnhoven et al., 2004).

Neurocognitive and behavioral manifestations may be assessed to show amelioration of a disease symptom or delay in disease progression. Assessing these manifestations is especially important in children with early juvenile MLD, in whom behavioral and cognitive symptoms are an important manifestation of the disease that may develop simultaneously with motor dysfunction. Clinical scales may be used to quantify the effects of AAV.hARSAco on development of and changes in cognition, language, and motor function, which may be assessed using the BSID-III and the WISC-V with transition to age-appropriate assessment tools done according to the patient's estimated developmental age. Outcomes may be compared to the norms of typically developing children and untreated children. Each proposed measure has been previously used in the MLD population (Clarke et al., 1989; Boucher et al., 2015; Sessa et al., 2016).

BSID-III: This scale used primarily to assess the development of infants and toddlers, ages 1-42 months (Albers and Grieve, 2007). It consists of a standardized series of developmental play tasks. It derives a developmental quotient by converting raw scores of successfully completed items to scale scores and composite scores followed by a comparison of the scores with norms taken from typically developing children of the same age. The BSID-III has three main subtests. A Cognitive Scale includes such items as attention to familiar and unfamiliar objects, looking for a fallen object, and pretend play. A Language Scale assesses understanding and expression of language (e.g., the ability to follow directions and naming objects). A Motor Scale measures gross and fine motor skills (e.g., grasping, sitting, stacking blocks, and climbing stairs). Thus, the BSID-III can provide additional motor function information to complement the GMFC-MLD and GMFM.

WISC-V: This scale is an individually administered intelligence test or children between the ages of 6 and 16 years of age. It generates a Full Scale IQ that represents a child's general intellectual ability and provides five primary index scores: Verbal Comprehension Index, Visual Spatial Index, Fluid Reasoning Index, Working Memory Index, and Processing Speed Index. These indices represent a child's abilities in discrete cognitive domains.

Survival is included as a measurement for amelioration of a disease symptom or delay in disease progression. Death is expected in the first 5 years of life for the majority of patients diagnosed with late infantile MLD, with 5 year survival of 25% (Mahmood et al., 2010), although survival can extend into the second decade of life with current levels of supportive care (Gomez-Ospina, 2017). Thus, the 5 year follow-up may be sufficient to demonstrate a survival benefit in the late infantile population, although it may not be sufficiently long to assess survival in the early juvenile cohort. Importantly, with improved levels of supportive care, children with early onset MLD can now remain alive beyond 10 years of age, albeit it at a very low level of function.

While seizures are not usually a presenting symptom for the early onset population, it is a feature of later stages of the disease (Gieselmann and Krageloh-Mann, 2010; Mahmood et al., 2010). Parents may be asked to maintain a diary to record seizure activity (onset, frequency, length, and type of seizure), which enables assessing whether AAV.hARSAco can either prevent or delay onset of seizures or decrease the frequency of seizure events.

Measures of adaptive behavior along with parent and patient quality of life may be evaluated to show amelioration of a disease symptom or delay in disease progression using the tools that have been previously utilized in MLD patients (Martin et al., 2013; Boucher et al., 2015; Sessa et al., 2016):

Vineland-III: Assesses adaptive behavior from birth through adulthood (0-90 years) across five domains: communication, daily living skills, socialization, motor skills, and maladaptive behavior. Improvements from the Vineland-II to the Vineland-III incorporate questions to enable better understanding of developmental disabilities.

PedsQOL and PedsQL-IS: As is the case with severe pediatric diseases, the burden of the disease on the family is significant. The Pediatric Quality of Life Inventory™ is a validated a tool that assesses quality of life in children and their parents (by parent proxy reports). It has been validated in healthy children and adolescents and has been used in various pediatric diseases (Iannaccone et al., 2009; Absoud et al., 2011; Consolaro and Ravelli, 2016). Therefore, the PedsQL is included to evaluate the impact of AAV.hARSAco on the quality of life of the patient and their family. It can be applied to parents of children 2 years old and above and may therefore be informative as the children age over the 5 year follow-up period. The Pediatric Quality of Life Inventory™ Infant Scale (Varni et al., 2011) is a validated modular instrument completed by parents designed to measure health-related quality of life specifically for healthy and ill infants aged 1-24 months. It also provides the possibility for self-reporting by children aged 5 years and up.

Lansky Performance Index: A scale that measures the functional status of an individual and provides a score that represents the person's ability to carry out normal daily activities.

Effect of rAAV (e.g., AAV . . . hARSAco), vector, composition or method as described herein on disease pathology may be measured to show amelioration of a disease symptom or delay in disease progression, including changes in myelination, functional outcomes related to myelination, and potential disease biomarkers.

The primary hallmark of MLD, central and peripheral demyelination, may be examined to show amelioration of a disease symptom or delay in disease progression following rAAV administration. Central demyelination may be tracked by MRI measurements of white matter regions, changes in which are indicators of disease state and progression (Gieselmann and Krageloh-Mann, 2010; Martin et al., 2012; van Rappard et al., 2015). Central demyelination detected by MRI positively correlates with the degree of gross motor dysfunction (Groeschel et al., 2011). Peripheral demyelination may be measured indirectly via NCV studies on the motor nerves (deep peroneal, tibial, and ulnar nerves) and sensory nerves (sural and median nerves), which also provides a readout of peripheral neuropathy. NCV studies monitor for fluctuations indicative of a change in biologically active myelin (i.e., F-wave and distal latencies, amplitude, or presence or absence of a response).

In addition to measuring total demyelination scores and brain white matter atrophy, various brain neuronal metabolites, including NAA, ml, Cho, and Lac, may be measured over time using proton MRS. There is evidence that NAA levels strongly correlate with gross motor function, with the NAA signal intensity decreasing as the disease process advances (Kruse et al., 1993; Dali et al., 2010). Additionally, proton MRS studies have shown a decrease in the NAA/creatinine ratio and an increase in the Cho/creatinine ratio and ml and Lac levels during MLD disease evolution (Martin et al., 2012). Thus, neuronal metabolites may be evaluated as biomarkers showing amelioration of a disease symptom or delay in disease progression.

There is evidence that peripheral nerve and CSF sulfatide and lysosulfatide accumulation correlates with abnormalities in electrophysiological parameters and large myelinated fiber loss in the sural nerve (Dali et al., 2015). CSF (lyso)-sulfatide levels may therefore reflect disease severity in the PNS and could provide a marker to assess the impact of a therapy on the peripheral nervous system. CSF sulfatide and lyso-sulfatide levels may be included to show amelioration of a disease symptom or delay in disease progression.

Similar to seizures, vision loss is not a common presenting symptom in early onset MLD, but it does appear in the later stages of disease (Gieselmann and Krageloh-Mann, 2010; van Rappard et al., 2015). Tracking vision loss through the use of VEPs offers the opportunity to assess the ability of the rAAV as described herein to delay or prevent vision loss. VEPs may be used to objectively measure responses to visual stimuli as an indicator of central visual impairment or loss. Hearing loss is also common during disease progression, and early indications of auditory abnormalities may be measured via BAER testing.

One of the sequelae of MLD in visceral tissues involves sulfatide deposition in the gallbladder wall, resulting in gallbladder wall thickening and polyps that may require surgical intervention and can be visualized on ultrasound (Rodriguez-Waitkus et al., 2011; Kim et al., 2017). Gallbladder abnormalities are a common finding in MLD and predispose the patient to gallbladder carcinoma (van Rappard et al., 2016) and occur in all subtypes of MLD.

In certain embodiment, the assays listed below may be performed to show amelioration of a disease symptom and/or a delay in disease progression:

Hematology, Serum Chemistry, Coagulation, LFTs; Urinalysis; HepB/HepC/HIV Serology; Serum Biomarkers (ARSA); Vector DNA in serum and urine;Serum anti-AAVhu68 nAbs; ELISpot (capsid and ARSA); CSF Collection and Assessments; LP (to collect CSF); CSF Cytology and Chemistry; CSF Disease Biomarkers (ARSA, sulfatide, lyso-sulfatide); CSF anti-AAVhu68 nAbs; Vector DNA in CSF; Physical Exam (including length and weight); Neurological Exam; Vital Signsd; ECGd; Sensory Nerve Conduction Studies; GMFC-MLD; GMFM; BSID-IIIe; WISC-V; Vineland-IIIe; Lansky Performance Index; PedsQL; PedsQL-IS; Caregiver/Parent QOL Assessment; Motor Milestone Assessment; Training on Seizure Diary Completion; Review of Seizure Diary; Imaging Assessments; MRI; MRS; NCV Measurements; and VEP.

Related abbreviations are listed below:

AAVhu68, adeno-associated virus serotype hu68; AE, adverse event; ARSA, Arylsulfatase A; BAER, brainstem auditory evoked response; BSID-III, Bayley Scales of Infant and Toddler Development, Third Edition; CSF, cerebrospinal fluid; DNA, deoxyribonucleic acid; ECG, electrocardiogram; ELISpot, enzyme-linked immunospot; GMFC-MLD, Gross Motor Function Classification in Metachromatic Leukodystrophy; GMFM, Gross Motor Function Measure; HepB, hepatitis B; HepC, hepatitis C; HIV, human immunodeficiency virus; ICM, intra-cisterna *magna*; LFTs, liver function tests; LP, lumbar puncture; MRI, magnetic resonance imaging; MRS, magnetic resonance spectroscopy; nAbs, neutralizing antibodies; NCV, nerve conduction velocity; PedsQL/PedQL-IS, Pediatric Quality of Life Inventory; QOL, Quality of Life; VEP, visual evoked potentials; Vineland-III, Vineland Adaptive Behavior Scales, Third Edition; WISC-V, Wechsler Intelligence Scale for Children, Fifth Edition.

The rAAV, vector, composition and methods provides supra-physiologic levels of the ARSA enzyme within days of administration to both the CNS and PNS, both of which are affected in MLD patients. The AAVhu68 capsid and ICM route were selected based upon the observation of superior transduction of neurons, DRG, and peripheral nerve axons cells. Although vector transduction of myelinating cells is limited, the cross-correction potential would allow for enzyme uptake by oligodendrocytes. Furthermore, AAV vector and ARSA enzyme can be transported along axons, expanding the expression of the therapeutic enzyme within the brain and to the periphery.

X. Apparatus and Method For Delivery of a Pharmaceutical Composition into Cerebrospinal Fluid In certain embodiments, the AAV.CB7.CI.hARSAco.rBG is administered as a single dose via a computed tomography-(CT-) guided sub-occipital injection into the cisterna *magna* (intra-cisterna *magna* [ICM]).

Many animal models of monogenic CNS diseases have been successfully treated using AAV-mediated gene transfer, and several early human studies using a first-generation AAV vector demonstrated the safety of vector delivery to the brain (Janson et al., 2002; Mandel and Burger, 2004; Kaplitt et al., 2007; Mittermeyer et al., 2012; Bartus et al., 2014). However, the low efficiency of these vectors prevented the translation of efficacy in animal models into clinical benefits. With the advent of second-generation AAV vectors, the potential for gene transfer to the brain has been greatly enhanced. In particular, some clade F isolates, such as AAV9, have demonstrated extremely efficient brain transduction (Gray et al., 2013; Haurigot et al., 2013; Hinderer et al., 2014; Bell et al., 2015). Using these more efficient vectors, gene therapy has shown greatly enhanced potential to treat a variety of neurological disorders, and several programs utilizing second-generation vectors have progressed into the clinic (Haurigot et al., 2013; Hinderer et al., 2014; Bell et al., 2015; Gurda et al., 2016; Hinderer et al., 2016).

Early studies of CNS gene transfer were challenged not only by the low gene transfer efficiency of first-generation AAV vectors, but also limitations in the available delivery methods. Most early non-clinical and clinical studies utilized direct vector injection into the parenchyma of the brain or spinal cord (Vite et al., 2005; Worgall et al., 2008; Colle et al., 2010; Ellinwood et al., 2011; Tardieu et al., 2014). While this method yields robust transduction near the injection site, translating this approach to diseases affecting cells throughout the CNS was difficult because large numbers of vector injections were required to achieve widespread transgene delivery. An additional obstacle to CNS gene transfer was the finding that intraparenchymal vector injection could trigger inflammation at the injection site, which could promote adaptive immune responses against the transgene product (Worgall et al., 2008; Colle et al., 2010; Ellinwood et al., 2011; Ciesielska et al., 2013). Two alternative vector delivery methods have been developed to more safely and effectively target large regions of the CNS.

The first was based on the discovery that some AAV vectors, including AAV9, can transduce cells within the CNS after IV delivery (Foust et al., 2009). However, IV vector delivery has two critical limitations. First, the low efficiency of vector penetration into the CNS necessitates extremely large vector doses to achieve therapeutic levels of transgene expression, increasing the risk of systemic toxicity and potentially requiring quantities of vector that may not be feasible to manufacture for many patient populations (Gray et al., 2011; Hinderer et al., 2014; Gurda et al., 2016). Second, gene transfer to the CNS after IV vector delivery is profoundly limited by pre existing NAbs to the vector capsid (Gray et al., 2011). Given the high prevalence of AAV NAbs in humans, this leaves a significant population of patients who would not be candidates for IV AAV treatment. In order to circumvent the limitations of IV AAV for targeting the CNS, IT vector delivery has been developed as an alternative approach. Using the CSF as a vehicle for vector dispersal, the IT ROA has the potential to achieve transgene delivery throughout the CNS and PNS with a single minimally invasive injection. Animal studies have demonstrated that by obviating the need to cross the blood-brain barrier, IT delivery results in substantially more efficient CNS gene transfer with much lower vector doses than those required for the IV approach (Gray et al., 2011; Hinderer et al., 2014). Since antibodies are present at very low levels in CSF, IT vector delivery is not affected by pre-existing NAbs to the AAV capsid, making this approach applicable to a broader patient population (Haurigot et al., 2013). IT AAV delivery can be performed using a variety of routes for CSF access. Lumbar puncture (LP) is the most common method for accessing CSF, and was therefore evaluated as a route for AAV administration in NHPs. Delivery of an AAV9 vector into the CSF via an LP was found to be at least 10-fold less efficient at transducing cells of the brain and spinal cord compared to injection. of the vector more superiorly at the level of the cisterna *magna* (Hinderer et al., 2014).

The superior brain transduction achieved with a single ICM injection in NHPs resulted in the selection of this ROA for the clinical studies of AAV.CB7.CI.hARSAco.rBG. Once a common procedure, ICM injection (also known as suboccipital puncture) was ultimately supplanted by LPs in the pre-imaging era due to rare cases of injury to the brainstem or nearby blood vessels (Saunders and Riordan, 1929). Today, the procedure can be performed under real-time CT guidance, allowing for visualization of critical structures, such as the medulla, vertebral arteries, and posterior inferior cerebellar arteries during needle insertion (Pomerantz et al., 2005; Hinderer et al., 2014).

In one aspect, the vectors provided herein may be administered intrathecally via the method and/or the device provided in this section and described in WO 2018/160582, which is incorporated by reference herein. Alternatively, other devices and methods may be selected.

In certain embodiments, the method comprises the steps of CT-guided sub-occipital injection via spinal needle into the cisterna *magna* of a patient. As used herein, the term Computed Tomography (CT) refers to radiography in which a three-dimensional image of a body structure is constructed by computer from a series of plane cross-sectional images made along an axis.

On the day of treatment, the appropriate concentration of rAAVhu68.hARSAco is be prepared. A syringe containing 5.6 mL of rAAVhu68.hARSAco at the appropriate concentration is delivered to the procedure room. The following personnel are present for study drug administration: interventionalist performing the procedure; anesthesiologist and respiratory technician(s); nurses and physician assistants; CT (or operating room) technicians; site research coordinator. Prior to drug administration, a lumbar puncture is performed to remove a predetermined volume of CSF and then to inject iodinated contrast intrathecally (IT) to aid in visualization of relevant anatomy of the cisterna *magna*. Intravenous (IV) contrast may be administered prior to or during needle insertion as an alternative to the intrathecal contrast. The decision to used IV or IT contrast is at the discretion of the interventionalist. The subject is anesthetized, intubated, and positioned on the procedure table. The injection site is prepped and draped using sterile technique. A spinal needle (22-25 G) are advanced into the cisterna *magna* under fluoroscopic guidance. A larger introducer needle may be used to assist with needle placement. After confirmation of needle placement, the extension set are attached to the spinal needle and allowed to fill with CSF. At the discretion of the interventionalist, a syringe containing contrast material may be connected to the extension set and a small amount injected to confirm needle placement in the cisterna *magna*. After the needle placement is confirmed by CT guidance +/−contrast injection, a syringe containing 5.6 mL of rAAVhu68.hARSAco is connected to the extension set. The syringe contents are slowly injected over 1-2 minutes, delivering a volume of 5.0 mL. The needle are slowly removed from the subject.

In one embodiment, doses may be scaled by brain mass, which provides an approximation of the size of the CSF compartment. In a further embodiment, dose conversions are based on a brain mass of 0.4 g for an adult mouse, 90 g for a juvenile rhesus macaque, and 800 g for children 4-18 months of age. The following table provides illustrative doses for a murine MED study, NHP toxicology study, and equivalent human doses.

| Dose (GC/g brain mass) | Mouse (GC) | NHP (GC) | Human (GC) |
| --- | --- | --- | --- |
| $3.33 \times 10^{11}$ | $1.30 \times 10^{11}$ | $3.00 \times 10^{13}$ | $2.70 \times 10^{14}$ |
| $1.11 \times 10^{11}$ | $4.40 \times 10^{10}$ | $1.00 \times 10^{13}$ | $8.90 \times 10^{13}$ |
| $3.33 \times 10^{10}$ | $1.30 \times 10^{10}$ | $3.00 \times 10^{12}$ | $2.70 \times 10^{13}$ |
| $1.11 \times 10^{10}$ | $4.40 \times 10^{9}$ | — | $8.90 \times 10^{12}$ |

In certain embodiments, a rAAVhu68.hARSAco vector is administered to a subject in a single dose. In certain embodiments, multiple doses (for example 2 doses) may be desired. For example, for infants under 6 months, multiple doses delivered days, weeks, or months, apart may be desired.

In certain embodiments, a single dose of rAAVhu68.hARSAco vector is about $1 \times 10^9$ GC to about $3 \times 10^{11}$ GC. In certain embodiments, the dose of rAAVhu68.HARSA is $1 \times 10^{10}$ GC/brain mass to $3.33 \times 10^{11}$ GC/brain mass. In other embodiments, different doses may be selected.

The compositions can be formulated in dosage units to contain an amount of AAV that is in the range of about $1 \times 10^9$ genome copies (GC) to about $5 \times 10^{13}$ GC (to treat an average subject of 70 kg in body weight). In one embodiment, a spinal tap is performed in which from about 15 mL (or less) to about 40 mL CSF is removed and in which vector is admixed with the CSF and/or suspended in a compatible carrier and delivered to the subject. In one example, the vector concentration is about $3 \times 10^{13}$ GC, but other amounts such as about $1 \times 10^9$ GC, about $5 \times 10^9$ GC, about $1 \times 10^{10}$ GC, about $5 \times 10^{10}$ GC, about $1 \times 10^{11}$ GC, about $5 \times 10^{11}$ GC, about $1 \times 10^{12}$ GC, about $5 \times 10^{12}$ GC, or about $1.0 \times 10^{13}$ GC. A co-therapy may be delivered with the rAAVhu68.hARSAco compositions provided herein. Co-therapies such as described earlier in this application are incorporated herein by reference.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

The term "expression" is used herein in its broadest meaning and comprises the production of RNA or of RNA and protein. With respect to RNA, the term "expression" or "translation" relates in particular to the production of peptides or proteins. Expression may be transient or may be stable.

As used herein, an "expression cassette" refers to a nucleic acid molecule which comprises a coding sequence, promoter, and may include other regulatory sequences therefor. In certain embodiments, a vector genome may contain two or more expression cassettes. In other embodiments, the term "transgene" may be used interchangeably with "expression cassette". Typically, such an expression cassette for generating a viral vector contains the coding sequence for the gene product described herein flanked by packaging signals of the viral genome and other expression control sequences such as those described herein.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous.

As used herein, an "effective amount" refers to the amount of the rAAV composition which delivers and expresses in the target cells an amount of the gene product from the vector genome. An effective amount may be determined based on an animal model, rather than a human patient. Examples of a suitable murine or NHP model are described herein.

The term "translation" in the context of the present invention relates to a process at the ribosome, wherein an mRNA strand controls the assembly of an amino acid sequence to generate a protein or a peptide.

It is to be noted that the term "a" or "an", refers to one or more, for example, "an enhancer", is understood to represent one or more enhancer(s). As such, the terms "a" (or "an"), "one or more," and "at least one" is used interchangeably herein.

As described above, the term "about" when used to modify a numerical value means a variation of +10%, unless otherwise specified.

Unless defined otherwise in this specification, technical and scientific terms used herein have the same meaning as commonly understood by one of ordinary skill in the art and by reference to published texts, which provide one skilled in the art with a general guide to many of the terms used in the present application.

EXAMPLES

The following examples are illustrative only and are not intended to limit the present invention.

The vector AAVhu68.CB7.CI.hARSAco.rBG (also termed as AAV.CB7.CI.hARSAco.rBG or AAVhu68.hARSAco or AAV.hARSAco) was delivered into the CSF to achieve therapeutic ARSA expression levels and rescue several biomarkers of MLD.

Several proof-of-concept pharmacology studies of AAV.CB7.CI.hARSAco.rBG were performed in healthy wild type mice. Non-clinical studies in healthy mice and nonhuman primates (NHPs) have demonstrated that CSF delivery of AAV.CB7.CI.hARSAco.rBG results in overexpression of ARSA in the CNS, PNS, and CSF (Examples 1 to 4). Example 2 demonstrated that intracerebroventricular (ICV) administration of AAV.CB7.CI.hARSAco.rBG leads to expression of enzymatically active ARSA in the brain of healthy wild type mice. Example 3 demonstrated that the observed-expression of ARSA results in part from the transduction and/or cross-correction of both cortical neurons and oligodendrocytes, which are the two main cell types affected by ARSA deficiency in MLD patients. Potentially therapeutic levels of ARSA have also been obtained in a size-relevant animal, the cynomolgus macaque (Example 4), and efficacy studies are conducted in an in vivo and/or in vitro MLD disease model. Additional experiment testing a dose range was also performed in healthy adult cynomolgus macaques, which demonstrated that despite the induction of anti-human ARSA (hARSA) antibodies, neurons of the brain, spinal cord, and DRG showed robust expression of ARSA for at least 6 weeks after ICM administration of AAV.CB7.CI.hARSAco.rBG (Example 4). A doubling of baseline CSF ARSA activity levels was also observed 2 weeks after treatment (Example 4), suggesting the possibility of achieving therapeutic expression levels of ARSA in early onset MLD patients.

Experiments are also performed in order to assess the pharmacology and toxicology of AAV.CB7.CI.hARSAco.rBG in a new mouse model of MLD (Experiment 5) for subsequent use in a MED study (Example 6). An in vitro model is under investigation to test the efficacy of AAV.CB7.CI.hARSAco.rBG for reducing disease biomarkers in MLD patient-derived cell lines (Example 7). Further, Example 8 provides a pharmacology and toxicology study of AAV.CB7.CI.hARSAco.rBG in juvenile rhesus macaques. Example 10 shows a trial of AAV.CB7.CI.hARSAco.rBG in a pediatric MLD population.

Example 1—AAV.hARSAco Vector

Components of an AAV.hARSAco are illustrated in the following table.

| | |
|---|---|
| Name: | AAV.CB7.CI.hARSAco.rBG (AAVhu68.CB7.CI.hARSAco.rBG) |
| Gene Inserts: | Engineered human arylsulfatase A (ARSA) gene |
| Control Element: | Regulatory element derived from the chicken β-actin (BA) promoter<br>Human cytomegalovirus immediate-early enhancer (CMV IE) |
| Other Elements: | Chimeric intron consisting of a chicken BA splice donor and a rabbit β-globin (rBG) splice acceptor element<br>Polyadenylation (PolyA) signal derived from the rBG gene<br>Two inverted terminal repeat sequences (ITRs) |
| AAV Serotype: | AAVhu68 |

Vectors are constructed from cis-plasmids containing a coding sequence for human ARSA (SEQ ID NO: 1 and SEQ ID NO: 3) expressed from the chicken beta actin promoter with a cytomegalovirus enhancer (CB7; SEQ ID NO: 16) flanked by AAV2 inverted terminal repeats.

The vectors are packaged in an AAV serotype hu68 capsid (WO 2018/160582) by triple transfection of adherent HEK 293 cells and purified by iodixanol gradient centrifugation as previously described in Lock, M., et al. Rapid, Simple, and Versatile Manufacturing of Recombinant Adeno-Associated Viral Vectors at Scale. Human Gene Therapy 21, 1259-1271 (2010).

More particularly, AAV.CB7.CI.hARSAco.rBG is produced by triple plasmid transfection of HEK293 working cell bank (WCB) cells with the AAV cis plasmid (pENN.AAV.CB7.CI.hARSAco.rBG.KanR), the AAV trans plasmid encoding the AAV2 rep and AAVhu68 cap genes (pAAV2/hu68.KanR), and the helper adenovirus plasmid (pAdAF6.KanR). The size of the AAV.CB7.CI.hARSAco.rBG packaged vector genome is 3883 bases (nt 1 to nt 3883 of SEQ ID NO: 5).

The cis plasmid (FIG. 2) contains the following vector genome sequence elements:

Inverted Terminal Repeat (ITR): The ITRs are identical, reverse complementary sequences derived from AAV2 (130 base pairs [bp], GenBank: NC_001401) that flank all components of the vector genome. The ITRs function as both the origin of vector DNA replication and the packaging signal for the vector genome when AAV and adenovirus helper functions are provided in trans. As such, the ITR sequences represent the only cis sequences required for vector genome replication and packaging.

Human Cytomegalovirus Immediate-Early Enhancer (CMV IE): This enhancer sequence obtained from human-derived cytomegalovirus (382 bp, GenBank: K03104.1) increases expression of downstream transgenes.

Chicken β-Actin (BA) Promoter (SEQ ID NO: 18): This ubiquitous promoter (281 bp, GenBank: X00182.1) was selected to drive transgene expression in any cell type.

Chimeric Intron (CI): The hybrid intron consists of a chicken BA splice donor (973 bp, GenBank: X00182.1) and rabbit β-globin splice acceptor element. The intron is transcribed, but removed from the mature messenger ribonucleic acid (mRNA) by splicing, bringing together the sequences on either side of it. The presence of an intron in an expression cassette has been shown to facilitate the transport of mRNA from the nucleus to the cytoplasm, thus enhancing the accumulation of the steady level of mRNA for translation. This is a common feature in gene vectors intended for increased levels of gene expression.

Coding Sequence: The engineered complementary deoxyribonucleic acid (cDNA) of the human ARSA gene (SEQ ID NO: 1 or SEQ ID NO: 3) encodes arylsulfatase A, which is a lysosomal enzyme responsible for the desulfation of the sulfated galactosphingolipids, galactosylceramide-3-O-sulfate and galactosylsphingosine-3-O-sulfate (1527 bp; 509 amino acids [aa], GenBank: NP_000478.3).

Rabbit β-Globin Polyadenylation Signal (rBG PolyA): The rBG PolyA signal (127 bp, GenBank: V00882.1) facilitates efficient polyadenylation of the transgene mRNA in cis. This element functions as a signal for transcriptional termination, a specific cleavage event at the 3' end of the nascent transcript and the addition of a long polyadenyl tail.

All component parts of the plasmid have been verified by direct sequencing.

Figure 3:
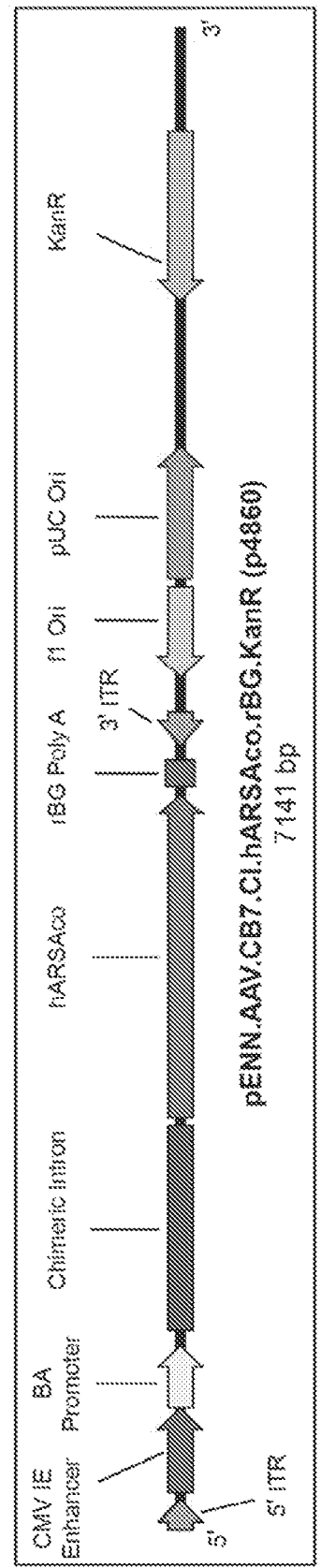
FIG. 3 provides a linear map of the cis plasmid, termed PENN.AAV.CB7.CI.hARSAco.rBG.KanR. BA, β actin; bp, base pairs; CMV IE, cytomegalovirus immediate-early; hARSAco, human arylsulfatase A (engineered); ITR, inverted terminal repeat; KanR, kanamycin resistance; Ori, origin of replication; PolyA, polyadenylation; rBG, rabbit β-globin.

The AAV2/hu68 trans plasmid (FIG. 3) is pAAV2/hu68.KanR. It is 8030 bp in length and encodes four wild type AAV2 replicase (Rep) proteins required for the replication and packaging of the AAV vector genome. The pAAV2/hu68.KanR plasmid also encodes three wild type AAVhu68 virion protein capsid (Cap) proteins, which assemble into a virion shell of the AAV serotype hu68 to house the AAV vector genome. The novel AAVhu68 sequence was obtained from human heart tissue DNA.

To create the pAAV2/hu68.KanR trans plasmid, the AAV9 cap gene from plasmid pAAV2/9n (which encodes the wild type AAV2 rep and AAV9 cap genes on a plasmid backbone derived from the pBluescript KS vector) was removed and replaced with the AAVhu68 cap gene. The ampicillin resistance (AmpR) gene was also replaced with the kanamycin resistance (KanR) gene, yielding pAAV2/hu68.KanR. This cloning strategy relocated the AAV p5 promoter sequence (which normally drives rep expression) from the 5' end of rep to the 3' end of cap, leaving behind a truncated p5 promoter upstream of rep. This truncated promoter serves to down-regulate expression of rep and, consequently, maximize vector production. All component parts of the plasmid have been verified by direct sequencing.

Plasmid pAdDeltaF6 (KanR) (FIG. 4) was constructed and is 15,770 bp in size. The plasmid contains the regions of adenovirus genome that are important for AAV replication; namely, E2A, E4, and VA RNA (the adenovirus E1 functions are provided by the HEK293 cells). However, the plasmid does not contain other adenovirus replication or structural genes. The plasmid does not contain the cis elements critical for replication, such as the adenoviral ITRs; therefore, no infectious adenovirus is expected to be generated. The plasmid was derived from an E1, E3-deleted molecular clone of Ad5 (pBHG10, a pBR322-based plasmid). Deletions were introduced into Ad5 to eliminate expression of unnecessary adenovirus genes and reduce the amount of adenovirus DNA from 32 kb to 12 kb (FIG. 5A). Finally, the ampicillin resistance gene was replaced by the kanamycin resistance gene to create pAdeltaF6 (KanR) (FIG. 5B). The E2, E4, and VA adenoviral genes that remain in this plasmid, along with E1, which is present in HEK293 cells, are necessary for AAV vector production.

AAV.CB7.CI.hARSAco.rBG is manufactured by transient transfection of HEK293 cells followed by downstream purification. A manufacturing process flow diagram is shown FIGS. 6 and 7. The major reagents entering into the preparation of the product are indicated on the left side of the diagram and in-process quality assessments are depicted on the right side of the diagram. A description of each production and purification step is also provided. Product manufacturing follows a linear flow of unit operations and utilizes disposable, closed bioprocessing systems unless otherwise specified. All steps of the production process involving cell culture, from cell seeding to harvest collection, are performed aseptically using sterile, single-use disposable tubing and bag assemblies. Cells are expanded using Corning flatware (T-Flasks, CellSTACKs [CS-10] and/or HYPERStacks [HS-36]). Cells are transfected in a bioreactor(s), and all open manipulations are performed in class II biological safety cabinets (BSCs) in an ISO Class 5 environment. The purification process are performed in a closed system where possible.

The manufacturing process for AAV.CB7.CI.hARSAco.rBG was developed and involves transient transfection of human embryonic kidney 293 (HEK293) cells with plasmid DNA. The HEK293 working cell bank (WCB) used in the production was tested and qualified as detailed in FDA and International Council for Harmonisation (ICH) guidelines. To support clinical development, a single batch or multiple batches of the bulk drug substance (BDS) is/are produced by polyethylenimine- (PEI-) mediated triple transfection of HEK293 cells in bioreactors. Harvested AAV material is purified sequentially by clarification, tangential flow filtration (TFF), affinity chromatography, and anion exchange chromatography in disposable, closed bioprocessing systems where possible. The product is formulated in intrathecal final formulation buffer (ITFFB; artificial CSF with 0.001% Pluronic F-68). The BDS batch or batches are frozen, subsequently thawed, pooled if necessary, adjusted to the target concentration, and sterile-filtered through a 0.22 µm filter, and vials are filled.

Two different bioreactors are used: a small or pilot-scale bioreactor and a large-scale bioreactor. The small-scale bioreactor is a linearly scaled bioreactor with equal bed height for cell growth with respect to the large-scale bioreactor. The use of the small-scale bioreactor and the large-scale bioreactor allows for scalable manufacturing with minimal process and material impact. The large-scale bioreactor and/or the small-scale bioreactor is utilized for the production of the toxicology lot(s). The large-scale bioreactor is used for the production of the good manufacturing practice (GMP) drug substance (DS) lot(s) to be utilized in clinical trials and for licensure. Large-scale GMP production batch sizes are generated with multiple batches planned and pooled if necessary to satisfy the needed vector amount for drug product (DP) supply. The manufacturing process for AAV.CB7.CI.hARSAco.rBG remains largely unchanged as the product moves from IND-enabling non-clinical studies to clinical development and through licensure. Process parameters hypothesized to affect product quality are not be modified. Most critical source materials remain the same, including the HEK293 WCB, although the PEI and plasmid DNA utilized for GMP manufacturing is GMP-Source™ or INDReady™ grade materials.

As the scale-up manufacturing process with the large-scale bioreactor is implemented, and based on the combined manufacturing experience in the current bioreactor platform, any potential impact is addressed related to changes in the process through comparability testing to ensure there is no change to identity, purity, potency, and safety of the product. The comparability testing that is conducted to compare a new lot manufactured with an updated procedure or with new material to a previous lot consists of a subset of tests included in the certificate of analysis (COA). The new lot meets the specifications that were previously established, and any tests included in the comparability assessment (the table below) are completed using similar methodologies and, if possible, the same testing sites.

TABLE

Comparability Assessment

| Comparability | Test | Method | Specification/Acceptance Criteria |
|---|---|---|---|
| Potency | In Vitro Potency | Enzyme Activity Assay | Conforms to Reference |
|  | GC:IU Ratio | $TCID_{50}$ | 500-3000 GC:IU |
| Purity | Purity | SDS-PAGE | ≥90% Virion Proteins |
|  | Particle Content Analysis | AUC | TBD$^a$ |

TABLE-continued

Comparability Assessment

| Comparability | Test | Method | Specification/Acceptance Criteria |
|---|---|---|---|
| Identity | Serotype Identity | MS | Confirmed as AAVhu68 serotype |
| | Molecular Identity | Sanger Sequencing or NGS | Conforms to reference sequence, excluding ITRs |
| Safety | Sterility | USP <71> | No microbial growth |
| | rcAAV | Triple passage, qPCR | Not detected |

[a]Particle content analysis by AUC is determined upon competion of toxicology lot manufacturing and product establishment manufacturing runs.
AUC, analytical ultracentrifugation; GC, genome copies; ITR, inverted terminal repeat; IU, infectious units; MS, mass spectrometry; NGS, next-generation sequencing; qPCR, quantitative polymerase chain reaction; rcAAV, replication-competent adeno-associated virus; SDS-PAGE, sodium dodecyl sulfate polyacrylamide gel electrophoresis; TBD, to be determined; $TCID_{50}$, 50% tissue culture infective dose; USP, United States Pharmacopeia.

Figure 6:
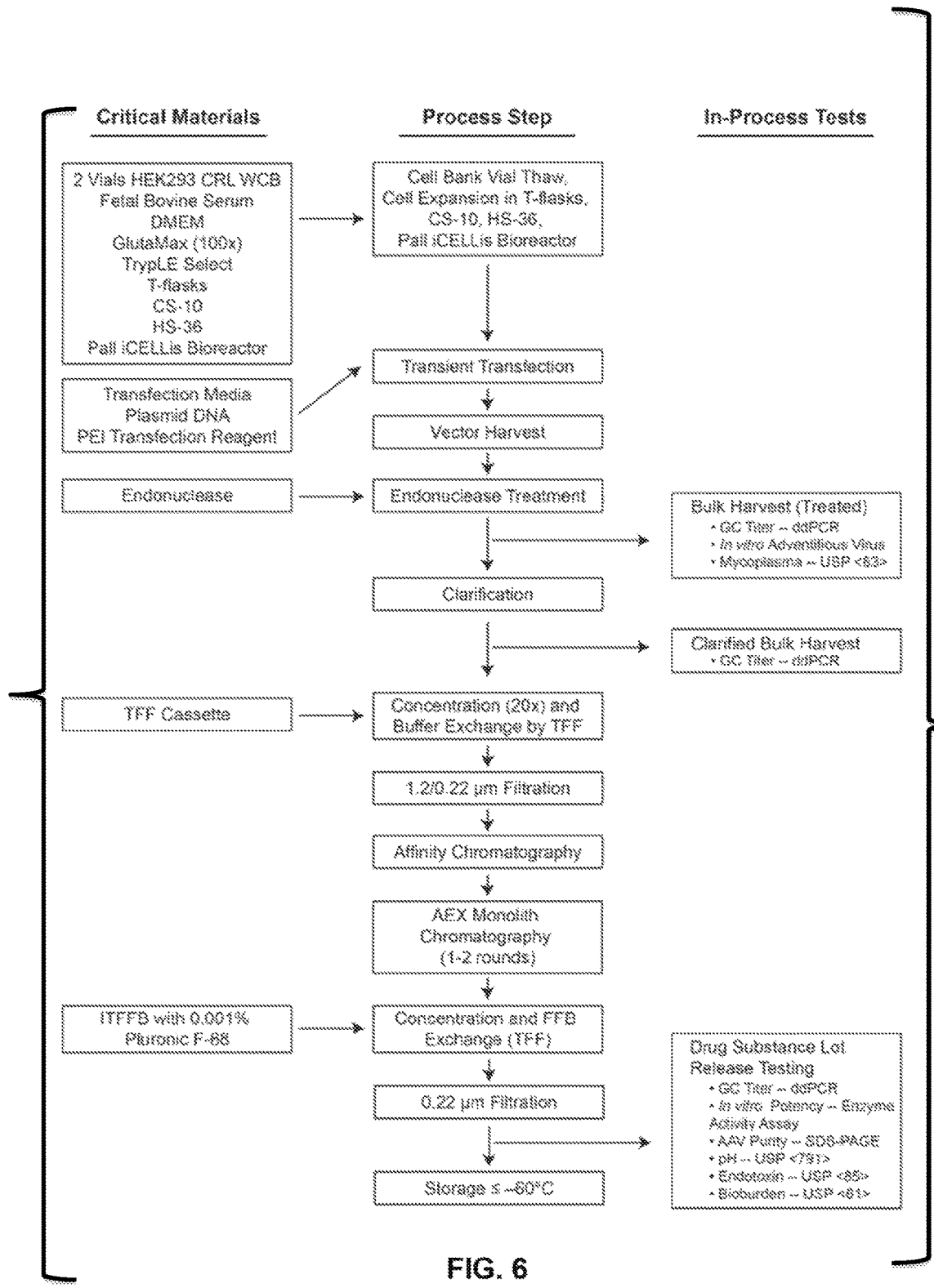
FIG. 6 provides a manufacturing process flow diagram for producing AAVhu68.hARSAco vector. AAV, adeno-associated virus; AEX, anion exchange; CRL, Charles River Laboratories; ddPCR, droplet digital polymerase chain reaction; DMEM, Dulbecco's modified Eagle medium; DNA, deoxyribonucleic acid; FFB, final formulation buffer; GC, genome copies; HEK293, human embryonic kidney 293 cells; ITFFB, intrathecal final formulation buffer; PEI, polyethylenimine; SDS-PAGE, sodium dodecyl sulfate polyacrylamide gel electrophoresis; TFF, tangential flow filtration; USP, United States Pharmacopeia; WCB, working cell bank.

The cell culture and harvest manufacturing process comprise four main manufacturing steps: (a) cell seeding and expansion, (b) transient transfection, (c) vector harvest, and (d) vector clarification. These process setups are depicted in the overview process diagram (FIG. 6). General descriptions of each of these processes are provided below.

(a) Cell Seeding and Expansion

A fully characterized HEK293 cell line is used for the production process. A WCB has been produced. Cell culture used for vector production is initiated from one or two thawed WCB vials and expanded as per a Master Batch Record (MBR) document. Cells are expanded using tissue culture plastic to allow sufficient cell mass to be generated for seeding in a large-scale bioreactor vessel surface area for vector production per DS batch. Cells are cultivated in medium composed of Dulbecco's Modified Eagle Medium (DMEM) supplemented with 10% gamma irradiated New Zealand-sourced fetal bovine serum (FBS). The cells are anchorage-dependent, and cell disassociation is accomplished using TrypI.ETM Select, an animal product-free cell dissociation reagent. Cell seeding is accomplished using sterile, single-use disposable bioprocess bags and tubing sets. The reactor is temperature-, pH-, and dissolved oxygen- (DO-) controlled.

(b) Transient Transfection

Following approximately 4 days of growth (DMEM media+10% FBS), cell culture media is replaced with fresh, serum-free DMEM media and the cells are transfected with the three production plasmids using a PEI-based transfection method. All plasmids used in the production process are produced in the context of a CMO quality system as described above with infrastructure-utilizing controls to ensure traceability, document control, and materials segregation. Sufficient plasmid DNA transfection complexes are prepared in the BSC to transfect up to 500 m² (per BDS batch). Initially, a DNA/PEI mixture is prepared containing cis (vector genome) plasmid, trans (rep and cap genes) plasmid, and helper plasmid in an optimal ratio with GMP-grade PEI (PEIPro HQ, PolyPlus Transfection SA). This plasmid ratio was determined to be optimal for AAV production in small-scale optimization studies. After mixing well, the solution is allowed to sit at room temperature for up to 25 minutes, then added to serum-free media to quench the reaction, and finally added to the bioreactor. The reactor is temperature- and DO-controlled, and cells are incubated for 5 days.

(c) Vector Harvesting

Transfected cells and media are harvested from the bioreactor using disposable bioprocess bags by aseptically pumping the medium out of the bioreactor. Following the harvest, detergent, endonuclease, and $MgCl_2$ (a co-factor for the endonuclease) are added to release vector and digest unpackaged DNA. The product (in a disposable bioprocess bag) is incubated at 37° C. for 2 hours in a temperature-controlled single-use mixer to provide sufficient time for enzymatic digestion of residual cellular and plasmid DNA present in the harvest as a result of the transfection procedure. This step is performed to minimize the amount of residual DNA in the final vector DP. Following incubation, NaCl is added to a final concentration of 500 mM to aid in the recovery of the product during filtration and downstream TFF.

(d) Vector Clarification

Cells and cellular debris are removed from the product using a pre-filter and depth filter capsule (1.2/0.22 µm) connected in series as a sterile, closed tubing and bag set that is driven by a peristaltic pump. Clarification assures that downstream filters and chromatography columns are protected from fouling, and bioburden reduction filtration ensures that at the end of the filter train, any bioburden potentially introduced during the upstream production process is removed before downstream purification.

The purification process comprises four main manufacturing steps: (a) concentration and buffer exchange by TFF, (b) affinity chromatography, (c) anion exchange chromatography, and (d) concentration and buffer exchange by TFF. These process steps are depicted in the overview process diagram (FIG. 6). General descriptions of each of these processes are provided below.

(a) Large-Scale Tangential Flow Filtration

Volume reduction (20-fold) of the clarified product is achieved by TFF using a custom sterile, closed bioprocessing tubing, bag, and membrane set. The principle of TFF is to flow a solution under pressure parallel to a membrane of suitable porosity (100 kDa). The pressure differential drives molecules of smaller size through the membrane and effectively into the waste stream while retaining molecules larger than the membrane pores. By recirculating the solution, the parallel flow sweeps the membrane surface, preventing membrane pore fouling and product loss through binding to the membrane. By choosing an appropriate membrane pore size and surface area, a liquid sample may be rapidly reduced in volume while retaining and concentrating the desired molecule. Diafiltration in TFF applications involves addition of a fresh buffer to the recirculating sample at the same rate that liquid is passing through the membrane and to the waste stream. With increasing volumes of diafiltration, increasing amounts of the small molecules are removed from the recirculating sample. This diafiltration results in a modest purification of the clarified product, but also achieves buffer exchange compatible with the subsequent affinity column chromatography step. Accordingly, a 100 kDa, PES (polyethersulfone) membrane for concentration is utilized, which is then diafiltered with a minimum of four diavolumes of a buffer composed of 20 mM Tris pH 7.5 and 400 mM NaCl. The diafiltered product is then further clarified with a 1.2/0.22 μm depth filter capsule to remove any precipitated material.

(b) Affinity Chromatography

The diafiltered product is applied to a Poros™ CaptureSelect™ AAV affinity resin (Life Technologies) that efficiently captures the AAVhu68 serotype. Under these ionic conditions, a significant percentage of residual cellular DNA and proteins flow through the column, while AAV particles are efficiently captured. Following application, the column is treated with 5 volumes of a low-salt endonuclease solution (250 U/mL endonuclease, 20 mM Tris pH 7.5, 40 mM NaCl, and 1.5 mM $MgCl_2$) to remove any remaining host cells and plasmid nucleic acids. The column is washed to remove additional feed impurities followed by a low pH step elution (400 mM NaCl, 20 mM sodium citrate, pH 2.5) that is immediately neutralized by collection into a ¹⁄₁₀th volume of neutralization buffer (200 mM Bis-Tris propane, pH 10.2).

(c) Anion Exchange Chromatography

To achieve further reduction of in-process impurities, including empty AAV particles, the Poros-AAV elution pool is diluted 50-fold (20 mM Bis-Tris propane, 0.001% Pluronic F-68, pH 10.2) to reduce ionic strength and enable binding to a CIMultus™ QA monolith matrix (BIA Separations). Following a low-salt wash, vector product is eluted using a 60 column volume NaCl linear salt gradient (10-180 mM NaCl). This shallow salt gradient effectively separates capsid particles without a vector genome (empty particles) from particles containing vector genome (full particles) and results in a preparation enriched for full particles. The full particle peak eluate is collected and neutralized. The peak area is assessed and compared to previous data for determination of the approximate vector yield.

(d) Concentration and Buffer Exchange by Hollow Fiber Tangential Flow Filtration The pooled anion exchange intermediate is concentrated and buffer-exchanged using TFF. In this step, a 100 kDa membrane hollow fiber TFF membrane is used. During this step, the product is brought to a target concentration and then buffer-exchanged into the ITFFB (artificial CSF with 0.001% Pluronic F-68).

Figure 7:
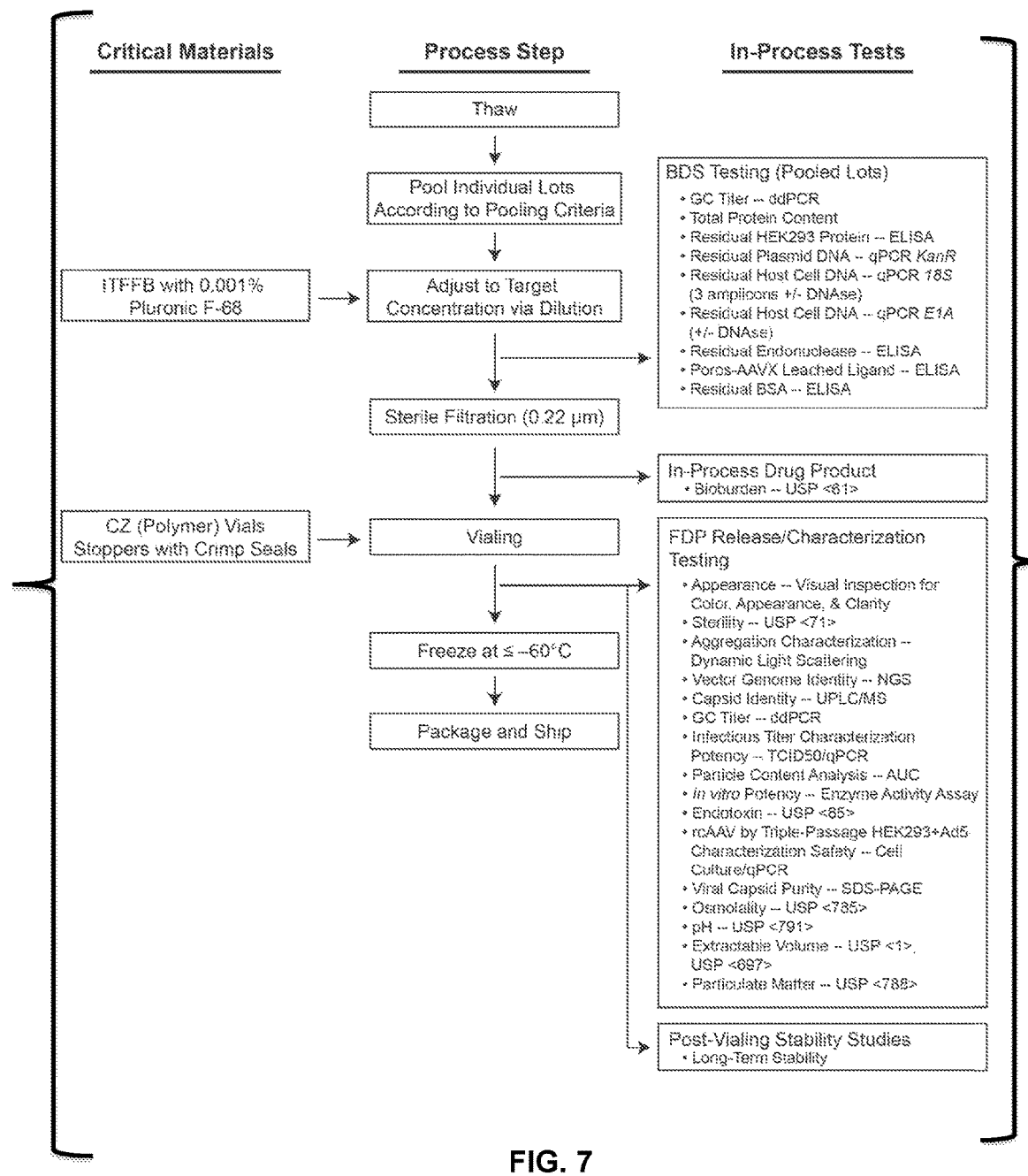
FIG. 7 provides a manufacturing process Flow Diagram for AAVhu68.hARSAco vector. Ad5, adenovirus serotype 5; AUC, analytical ultracentrifugation; BDS, bulk drug substance; BSA, bovine serum albumin; C7., Crystal Zenith; ddPCR, droplet digital polymerase chain reaction; E1A, early region 1A (gene); ELISA, enzyme-linked immunosorbent assay; FDP, filled drug product; GC, genome copies; HEK293, human embryonic kidney 293 cells; ITFFB, intrathecal final formulation buffer; KanR, kanamycin resistance (gene); MS, mass spectrometry; NGS, next-generation sequencing; qPCR, quantitative polymerase chain reaction; SDS-PAGE, sodium dodecyl sulfate polyacrylamide gel electrophoresis; TCID50, 50% tissue culture infective dose; UPLC, ultra-performance liquid chromatography; USP, United States Pharmacopeia.

Samples are removed for testing (FIG. 7). The bulk drug substance (BDS) is sterile filtered (0.22 μm), stored in sterile containers, and frozen at ≤-60° C. in a quarantine location until release for final fill.

The frozen bulk drug substance are thawed, pooled, and adjusted to the target concentration (dilution or concentrating step via TFF) using the final formulation buffer (FFB). The product is terminally filtered through a 0.22 μm filter and filled into sterile West Pharmaceutical's Crystal Zenith (cyclic olefin polymer) vials with crimp seal stoppers. Labeled vials are stored at ≤-60° C.

Bacterial master cell bank (BMCB) glycerol stocks of the cis, trans and helper plasmids were made by mixing 1 mL from a 1 L overnight culture of transformed Stbl2TM *E. coli* cells with an equal volume of sterile 50% glycerol. Two 0.5 mL. aliquots of the BMCB glycerol stocks per construct are prepared from the mixture and stored in Nalgene cryogenic vials at -80° C. To verify BMCB glycerol stocks, amplified plasmid DNA is subjected to in-house structure analysis involving restriction enzyme digestion followed by gel electrophoresis, and full-plasmid sequence analysis by Sanger sequencing at Qiagen. To prepare bacterial working cell bank (BWCB) glycerol stock aliquots for shipping to the plasmid DNA manufacturer, a 3 mL culture is inoculated from a BMCB glycerol stock and grown overnight. Next, 1 mL of the overnight culture is used to prepare BWCB glycerol stock aliquots as described above. New BWCB glycerol stock aliquots are verified by the aforementioned structure analysis on DNA extracted from the remaining 2 mL of overnight bacterial culture. Once received at the plasmid DNA manufacturer, the BWCB glycerol stock is stored in a project-specific location at -80° C. Production cultures are inoculated by scraping the frozen BWCB glycerol stock.

Plasmids used as source material for Good Manufacturing Practice (GMP) vector manufacturing are produced at a facility that is not qualified as a GMP facility; however, plasmids are produced in a manner that is designed to meet the requirements for Current Good Manufacturing Practice (cGMP) intermediates. Plasmid production is conducted on dedicated components and in a dedicated suite. The production procedures and oversight are conducted to ensure a consistent quality product with highly pure DNA, which meets stringent release criteria as captured in the following table. Components used in the production of plasmids are "animal-free" (based on the COAs from each vendor for component products), and all components used in the process (fermentation flasks, containers, membranes, resin, columns, tubing and any component that comes into contact with the plasmid) are dedicated to a single plasmid and are certified TSE/BSE-free. The PolyFlo® resin, columns and components utilized are procured for the exclusive use in the manufacturing of a single plasmid. The fermentation, lysis and purification of the plasmid occurs in dedicated rooms marked with the designated plasmid name. No other plasmids are processed in those rooms at the same time. The rooms and equipment are cleaned between each plasmid production campaign. Prior to use in the production of recombinant vectors, each manufactured plasmid is fully sequenced using next-generation sequencing (NGS) to rule out contamination by other plasmids, in addition to testing for sterility and the presence of *mycoplasma*.

All plasmid DNA used in the production of vectors for pharmacology/toxicology are made through Puresyn's Premium-Research Ready Program. Puresyn's Premium-Research Ready Program are produced using cleaning and segregation procedures and single-use components however they are not produced in a dedicated room.

TABLE

Release Specifications for Plasmid Production

| Parameter | Specifications |
|---|---|
| Appearance | Clear, colorless, and no visible particulates |
| A260:280 | 1.7-2.0 |
| Concentration | 1.0-1.1 mg/mL |
| DNA Homogeneity | ≥90% supercoiled |
| Residual RNA | None detected at 1.0 μg load |
| ssDNA, Linear DNA, Chromosomal DNA | None detected at 1.0 μg load |
| Endotoxin | <30 EU/mg |
| Identity | Consistent with provided sequence and structure information |

TABLE-continued

Release Specifications for Plasmid Production

| Parameter | Specifications |
|---|---|
| Protein | For information only |
| Bioburden | No growth after 5 days |
| pH | 7.5-8.5 |
| Formulation | TE (10 mM Tris, 1.0 mM EDTA pH 7.9-8.1) |

HEK293 cells were originally generated by transforming HEK cells with sheared adenovirus type 5 (Ad5) DNA (Graham et al., 1977). The cells express the E1A and E1B gene products required for rAAV production. HEK293 cells are highly transfectable, yielding high levels of rAAV upon plasmid DNA transfection.

Vector Genome Identity: DNA Sequencing

AAV vector ($2.00 \times 10^{11}$ GC) is treated with Baseline Zero endonuclease and Plasmid Safe DNAse to eliminate non-encapsulated DNA in the environment and then incubated for 10 min at 95° C. in 1× phosphate-buffered saline (PBS) and 0.5% sodium dodecyl sulfate (SDS) to denature the vector genome. Denatured vector genome is subsequently annealed by slowly cooling the reaction mix to 24° C. at a rate of 0.6° C./minute in a thermocycler, cleaned up using the QIAquick PCR Purification Kit (QIAGEN), and sheared to an average size of 500 bp on a Covaris Ultrasonicator. DNA shearing is evaluated on a 2100 Bioanalyzer with High Sensitivity DNA reagent kit (Agilent). Sheared DNA is prepared into NGS libraries using the NEBNextUltraII library kit according to the manufacturer's protocol, size-selected, and cleaned up by Agencourt AMPure XP beads (Beckman Coulter). Individual NGS libraries are then analyzed on a Bioanalyzer again for fragment size distribution and quantified by a Qubit® 3.0 Fluorometer prior to pooling at equal molarity. The concentration of final pooled library is measured by a Qubit® 3.0 Fluorometer, denatured, and diluted to 8 pM according to Illumina's Miseq System Denature and Dilute Libraries Guide. PhiX control is spiked in the final library at 10%. Sequencing is performed using an Illumina MiSeq Nano Reagent Kit V2 (250 bp paired-end) on a MiSeq sequencer. Data analysis is performed as described above using the NGS alignment approach.

Sequencing reads are automatically de-multiplexed and adapter-trimmed by the MiSeq computer. The trimmed reads for each plasmid are aligned to the corresponding reference sequence, and sequence variants are called using BBTools bioinformatics software suite (sourceforge.net/projects/bb-map). Additionally, BBMap (jgi.doc.gov/data-and-tools/bbtools/) is used to generate VCF and BAM files. VCF files are further parsed by a custom UNIX script to generate simplified tab-delimited tables (retaining only CHROM, REF, ALT, QUAL, TYPE, DEPTH, AF, RAF, SB, DP4 fields). BAM files are visually inspected in IGV Integrated Genomic Viewer software (software.broadinstitute.org/software/igv/) to ensure proper NGS alignments. In parallel with the NGS alignment approach, de novo assembly is conducted to build a long, circularized sequence using NOVO-Plasty (github.com/ndierckx/NOVOPlasty). The de novo sequence is aligned against the original vector genome reference sequence to characterize large sequence arrangements that can be overlooked in the alignment approach.

Vector Capsid Identity: AAV Capsid Mass Spectrometry of VP1

Confirmation of the AAVhu68 scrotype of the DP is achieved using a new assay developed at the University of Pennsylvania and Bioproximity, LLC based upon the analysis of peptides of a AAV capsid protein. The method involves trypsin digestion of the VP followed by tandem mass spectrometry (MS) characterization on a Q-Exactive Orbitrap mass spectrometer to sequence the capsid protein peptides. A spectral library from the tandem mass spectra sequenced and a targeted MS method is used to assay for signature peptides that can uniquely identify specific AAV viral particles serotypes. A bank of signature peptides specific for eight serotypes (AAVhu68, AAV1, AAV2, AAV6, AAV8, AAV9, AAVrh10, and AAVhu37) are screened against the tandem mass spectra produced by digestion of the test article. For a positive identification, signature peptide(s) from a single serotype only are detected.

Genomic Copy Titer

A ddPCR-based technique for determining the GC titer for AAV vectors has been developed (Lock et al., 2014). The reference standard is generated during the pilot runs and is used to qualify the assay. The method is practical, reports equivalent or better titers than qPCR, and does not require a plasmid standard curve. The assay utilized involves digestion with DNase I, followed by ddPCR analysis to measure encapsulated vector GC. DNA detection is accomplished using sequence-specific primers targeting the polyA region in combination with a fluorescently tagged probe hybridizing to this same region. A number of standards, validation samples, and controls (for background and DNA contamination) have been introduced into the assay. This assay is qualified using pilot reference standard. The assay is qualified by establishing and defining assay parameters, including sensitivity, limit of detection (LOD), range of qualification, and intra- and inter-assay precision. An internal AAVhu68 reference lot is established and used to perform the qualification studies.

Infectious Unit Titer

The infectious unit (IU) assay is used to determine the productive uptake and replication of rAAV vector in RC32 cells (rep2 expressing Hela cells). A 96-well endpoint format has been employed similar to that previously published. Briefly, RC32 cells are co-infected by serial dilutions of rAAV BDS and a uniform dilution of Ad5 with 12 replicates at each dilution of rAAV. Seventy-two hours after infection, the cells are lysed, and qPCR is performed to detect rAAV vector amplification over input. An endpoint dilution 50% tissue culture infectious dose (TCID50) calculation (Spearman-Karber) is performed to determine a replicative titer expressed as IU/mL. Since "infectivity" values are dependent on each particle's contact with cells, receptor binding, internalization, transport to the nucleus, and genome replication, they are influenced by assay geometry and the presence of appropriate receptors and post-binding pathways in the cell line used. Receptors and post-binding pathways are not usually maintained in immortalized cell lines, and thus infectivity assay titers are not an absolute measure of the number of "infectious" particles present. However, the ratio of encapsidated GC to "infectious units" (described as GC/IU ratio) can be used as a measure of product consistency from lot to lot.

Particle Content Analysis

Sedimentation velocity, as measured in an analytical ultracentrifuge (AUC), can detect aggregates, other minor components, as well as provide good quantitation of relative amounts of different particle species based upon their different sedimentation coefficients. This is an absolute method based on fundamental units of length and time, requiring no standard molecules as references. Vector samples are loaded into cells with two-channel charcoal-epon centerpieces with 12 mM optical path length. The supplied dilution buffer is loaded into the reference channel of each cell. The loaded cells are then placed into an AN-60Ti analytical rotor and loaded into a Beckman-Coulter ProteomeLab XL-I analytical ultracentrifuge equipped with both absorbance and RI detectors. After full temperature equilibration at 20° C., the rotor is brought to the final run speed of 12,000 revolutions per minute (RPM). Absorbance at 280 nm scans are recorded approximately every 3 minutes for approximately 5.5 hours (110 total scans for each sample). The raw data is analyzed using the c(s) method and implemented in the analysis program SEDFIT. The resultant size distributions are graphed and the peaks integrated. The percentage values associated with each peak represent the peak area fraction of the total area under all peaks and are based upon the raw data generated at 280 nm. Many labs use these values to calculate full: empty ratios. However, because empty and full particles have different extinction coefficients at this wavelength, the raw data can be adjusted accordingly. The ratio of the empty particle and full monomer peak values both before and after extinction coefficient adjustment is used to determine the full: empty ratio, and both ratios are recorded.

Host Cell DNA

A qPCR assay is used to detect residual HEK293 DNA. After spiking with a "non-relevant DNA," total DNA (non-relevant, vector, and residual genomic DNA) is extracted from approximately 1 mL of product. The HCDNA is quantified using qPCR targeting 18S rDNA. The quantities of DNA detected are normalized based on the recovery of the spiked non-relevant DNA. Three different amplicon sizes are tested to establish the size spectrum of residual HCDNA.

Host Cell Protein

An ELISA is performed to measure levels of contaminating host HEK293 cell proteins. The *Cygnus* Technologies HEK293 Host Cell Proteins 2nd Generation ELISA kit is used according to the instructions provided by the vendor.

Replication-Competent AAV Assay

A sample is analyzed for the presence of replication-competent AAV2/hu68 (rcAAV) that could potentially arise during the production process. A three-passage assay has been developed consisting of cell-based amplification and passage followed by detection of rcAAV DNA by real-time qPCR (caphu68 target). The cell-based component consists of inoculating monolayers of HEK293 cells (P1) with dilutions of the test sample and wild type human Ad5. The maximal amount of the product tested is $1.00 \times 10^{10}$ GC of the vector product. Due to the presence of adenovirus, rcAAV amplifies in the cell culture. After 2 days, a cell lysate is generated, and Ad5 is heat-inactivated. The clarified lysate is then passed onto a second round of cells (P2) to enhance sensitivity (again in the presence of Ad5). After 2 days, a cell lysate is generated, and Ad5 is heat-inactivated. The clarified lysate is then passed onto a third round of cells (P3) to maximize sensitivity (again in the presence of Ad5). After 2 days, cells are lysed to release DNA, which is then subjected to qPCR to detect AAVhu68 cap sequences. Amplification of AAVhu68 cap sequences in an Ad5-dependent manner indicates the presence of rcAAV. The use of a AAV2/hu68 surrogate positive control containing AAV2 rep and AAVhu68 cap genes enables the LOD of the assay to be determined (0.1 IU, 1 IU, 10 IU, and 100 IU). Using a serial dilution of rAAV ($1.00 \times 10^{10}$ GC, $1.00 \times 10^{9}$ GC, $1.00 \times 10^{8}$ GC, and $1.00 \times 10^{7}$ GC), the approximate quantity of rcAAV present in the test sample can be quantitated. The test method is performed.

In Vitro Potency

To relate the ddPCR GC titer to gene expression, an in vitro relative potency bioassay is performed. Briefly, cells are plated in a 96-well plate and incubated at 37° C./5% $CO_2$ overnight. The next day, cells are infected with serially diluted AAV vector and are incubated at 37° C./5% $CO_2$ for up to 3 days. At the end of the culture period, cell culture media are collected and assayed for ARSA activity based on cleavage of a colorimetric substrate. Optimization of the assay is ongoing.

Total Protein, Capsid Protein, Protein Purity, and Capsid Protein Ratio

Vector samples are first quantified for total protein against a bovine serum albumin (BSA) protein standard curve using a bicinchoninic acid (BCA) assay. The determination is made by mixing equal parts of sample with a Micro-BCA reagent provided in the kit. The same procedure is applied to dilutions of a BSA standard. The mixtures are incubated at 60° C. and absorbance measured at 562 nm. A standard curve is generated from the standard absorbance of the known concentrations using a 4-parameter fit. Unknown samples are quantified according to the 4-parameter regression.

To provide a semi-quantitative determination of rAAV purity, the samples are normalized for genome titer, and $5.00 \times 10^{9}$ GC is separated by sodium dodecyl sulfate polyacrylamide gel electrophoresis (SDS-PAGE) under reducing conditions. The SDS-PAGE gel is then stained with SYPRO Ruby dye. Any impurity bands are quantified by densitometry. Stained bands that appear in addition to the three AAV-specific proteins (VP1, VP2, and VP3) are considered protein impurities. The impurity mass percent as well as approximate molecular weight of contaminant bands are reported. The SDS-PAGE gel is also used to quantify the VP1, VP2, and VP3 proteins and determine their ratio.

Ratio of Genome Copy to Infectious Unit

The GC/IU ratio is a measure of product consistency. The ddPCR titer (GC/mL) is divided by the "infectious unit" (IU/mL) to give the calculated GC/IU ratio.

Example 2—Proof-of-Concept Pharmacology and Dose Range Study in Mice

Experiment was performed to establish the potency of the AAVhu68.hARSAco vector after ICV injection in mice. Healthy 6-8-week-old C57BL6/J mice were selected for this Proof-of-Concept (POC) experiments. The ICV route was selected because the small size of mice makes it difficult to reliably inject AAV vector via ICM. The age was selected based on historical data and our previous experience performing ICV injections in this age of mice (Hinderer et al., 2016). A 21 day necropsy time point was chosen to capture stable transgene expression based upon previous experience with other ICV-administered AAV vectors in mice (Hinderer et al., 2016).

C57BL6/J wild type mice were administered the AAVhu68.CB7.CI.hARSAco.rBG vector into the CSF via a single ICV injection into the right cerebral ventricle at either a low dose of $1.00 \times 10^{10}$ GC or a high dose of $1.00 \times 10^{11}$ GC. The doses were selected based upon previous dose ranging studies of an ICV-administered AAV vector in a different LSD mouse model (Hinderer et al., 2016). As a control, age-matched C57BL6/J mice were injected with a single ICV injection into the right cerebral ventricle with vehicle (PBS) to obtain baseline ARSA activity levels. Twenty-one days after the administration, mice were necropsied, and ARSA activity levels quantified in dialyzed protein extracts from samples of brain, liver, and serum using a colorimetric assay based on the cleavage of an artificial substrate, 4-Nitrocatechol Sulfate.

Figure 8:
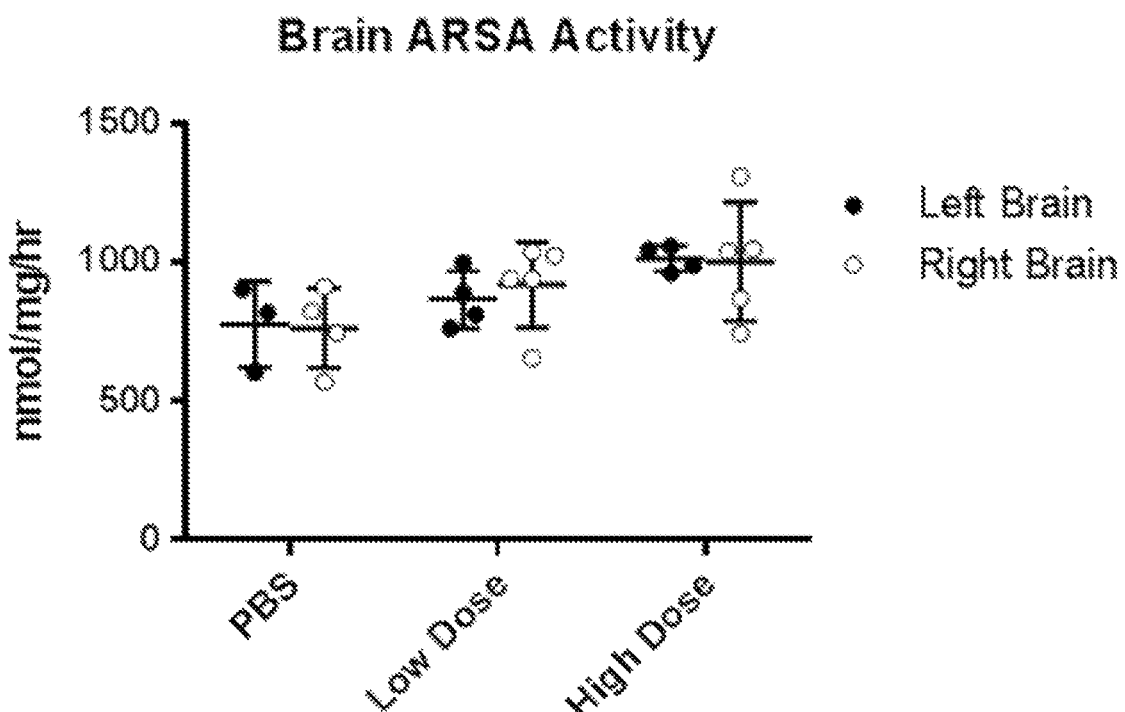
FIG. 8 shows ARSA enzyme activity in the left and right cerebral hemispheres of mice following intracerebroventricular administration of the AAVhu68.CB7.CI.hARSAco.rBG vector. Six-week-old C57BL6/J wild type mice received a single ICV injection of the AAVhu68.CB7.CI.hARSAco.rBG vector into the right ventricle at a dose of either $1.00 \times 10^{10}$ GC (low dose) or $1.00 \times 10^{11}$ GC (high dose) (N=5/group). Age-matched C57BL6/J wild type mice were ICV-administered PBS into the right ventricle as a control (N=4). Mice were necropsied 21 days later, and ARSA enzyme activity in the left and right cerebral hemispheres was measured based upon the rate of hydrolysis of the chromogenic substrate, 4-nitrocatechol sulfate (nmol/mg/hr). ARSA, arylsulfatase A (protein); GC, genome copies; ICV, intracerebroventricular; N, number of animals; PBS, phosphate-buffered saline. See, Example 2 for more details.

Since the brain is a key target tissue for the treatment of MLD, ARSA activity levels were measured in the left versus right cerebral hemispheres 21 days after the AAVhu68.CB7.CI.hARSAco.rBG vector administration. ARSA activity was 12% and 31% higher in the brains of mice administered the low dose ($1.00 \times 10^{10}$ GC) or high dose ($1.00 \times 10^{11}$ GC) of the AAVhu68.CB7.CI.hARSAco.rBG vector, respectively, compared to PBS-treated controls. Moreover, no obvious difference in ARSA activity levels between the right and left hemispheres was observed for AAVhu68.CB7.CI.hARSAco.rBG-treated animals (FIG. 8). These results suggest that delivery of the AAVhu68.CB7.CI.hARSAco.rBG vector into the CSF via a single unilateral ICV injection was sufficient to transduce cells of both cerebral hemispheres and/or facilitate cross-correction through circulating ARSA enzyme released into the CSF. Both doses of AAV.CB7.CI.HARSACO.RBG result in overexpression of an enzymatically active ARSA enzyme in the brain following ICV administration to wild type mice.

Figure 9A:
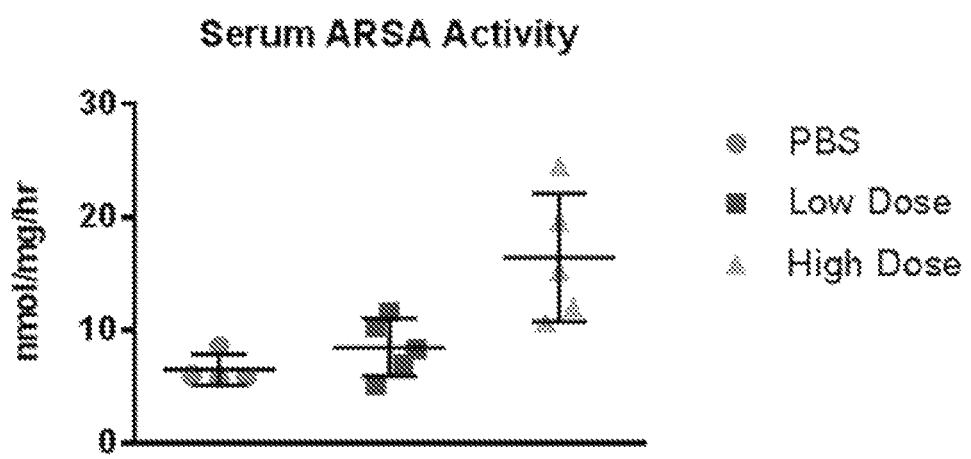

To quantify functional ARSA enzyme activity in tissues outside the nervous system, samples of serum and liver were obtained 21 days after the AAVhu68.CB7.CI.hARSAco.rBG vector administration. Compared to baseline levels in PBS-treated controls, ARSA activity levels in the serum were 30% and 151% higher in mice administered the low dose ($1.00 \times 10^{10}$ GC) or high dose ($1.00 \times 10^{11}$ GC) of the AAVhu68.CB7.CI.hARSAco.rBG vector, respectively (FIG. 9A). In the liver, ARSA activity levels were 11-fold and 28-fold higher in mice administered the low dose ($1.00 \times 10^{10}$ GC) or high dose ($1.00 \times 10^{11}$ GC) of the AAVhu68.CB7.CI.hARSAco.rBG vector, respectively (FIG. 9B). These results suggest that, in addition to the brain, CSF-delivered AAVhu68.CB7.CI.hARSAco.rBG vector may have transduced and/or cross-corrected cells of peripheral organ systems, particularly in the liver. Overexpression of enzymatically active ARSA is also detected in liver and serum at both doses of AAV.CB7.CI.hARSAco.rBG.

In summary, this experiment confirmed that a single unilateral ICV injection of the AAVhu68.CB7.CI.hARSAco.rBG vector in mice resulted in dose-dependent expression of an enzymatically active ARSA enzyme in both hemispheres of the brain within 21 days. Functional ARSA enzyme was also present in the serum and liver, suggesting that the AAVhu68.CB7.CI.hARSAco.rBG vector was transduced in peripheral organ systems. However, because we were measuring ARSA activity as overexpression above wild type baseline levels, this overexpression precluded the translation of these results to a potentially effective therapeutic dose. An MED study is therefore performed in Arsa$^{-/-}$ mice to confirm the dose range (Example 4).

Example 3—Cell Tropism Study in Mice

The CNS expression profile of ARSA enzyme was assessed following ICV administration of vector in wild-type mice. It was shown that AAVhu68 predominantly transduces neurons and experiments were performed to determine whether ARSA localized to myelin-producing oligodendrocytes. Oligodendrocyte-specific expression of ARSA supports the possibly of cross-correction of a key cell type affected in MLD patients. For this study, AAVhu68.CB7.CI.hARSAcoHA.rBG was utilized which is an AAVhu68 vector similar to AAVhu68.CB7.CI.hARSAco.rBG that encodes human engineered ARSA enzyme tagged with a C-terminal HA peptide. Because anti-ARSA antibodies can, in theory, cross-react with endogenous murine ARSA in wild type animals, an anti-hemagglutinin (HA) antibody was used to assess ARSA expression following ICV administration. The observed ARSA expression profile following the administration of this similar AAVhu68 vector is expected to be representative of ARSA expression following AAVhu68.CB7.CI.hARSAco.rBG administration.

Adult C57BL6/J wild type mice (6-8 weeks old) were ICV-administered AAVhu68.CB7.CI.hARSAcoHA.rBG into the CSF at either a low dose of $1.00 \times 10^{10}$ GC or a high dose of $1.00 \times 10^{11}$ GC. Twenty-one days after vector administration, mice were necropsied, and brain samples containing cortex and subcortical white matter were obtained to assess expression of ARSA in oligodendrocytes (which are identified by expression of oligodendrocyte transcription factor 2 (OLIG2)). The vector dose, mouse strain, age, and necropsy time point were selected to mirror Example 2, and the cortex and subcortical white matter were examined because these regions are consistently transduced after ICV administration and are key tissues to target for treating MLD.

Administration of the low dose ($1.00 \times 10^{10}$ GC) resulted in a minimal number of ARSA-expressing cells in the cortex and subcortical white matter. In contrast, animals administered the high dose ($1.00 \times 10^{11}$ GC) displayed a greater number of cells expressing ARSA in the cortex and subcortical white matter. Moreover, an enrichment of ARSA-expressing oligodendrocytes was observed in brain regions containing a large number of ARSA-positive OLIG2-negative cells (presumptive neurons) (FIG. 10). Because oligodendrocytes are typically minimally transduced by AAVhu68, this cellular distribution pattern of ARSA expression suggests that cross-correction of oligodendrocytes by neighboring neurons had occurred. These data support the possibility that AAVhu68.CB7.CI.hARSAco.rBG can provide a long-lasting source of secreted ARSA enzyme to both the neurons and myelinating cells of the CNS and PNS that are affected in MLD patients.

In summary, this experiment demonstrated that by 21 days after ICV administration of a vector similar to AAVhu68.CB7.CI.hARSAco.rBG in wild type mice, ARSA enzyme was successfully delivered to both neurons and oligodendrocytes in the brain, which are key target cell types for the treatment of MLD. Transduced cells expressing HA-tagged ARSA were observed in both sides of the brain after a unilateral ICV administration. Neurons and oligodendrocytes, the two main target cells, both expressed ARSA.

Example 4—Pilot Dose Range Study in Cynomolgus Macaques

This study was a pilot study to determine the dose range required to increase ARSA activity levels in the CSF above baseline levels in Non-human Primates (NHPs) following ICM administration of the AAVhu68.CB7.CI.hARSAco.rBG vector. Results from a Phase 1/2 trial of a ex vivo lentiviral HSC-GT have shown that the achievement of normal levels of ARSA activity in the CSF correlates with good outcomes for early onset MLD patients (Sessa et al., 2016). Because HSC-GT is similar to the therapeutic approach described in these Examples in that it relies on cross-correction from CNS-resident cells secreting ARSA, it was reasoned that CSF levels of ARSA in NHPs would be predictive of the potential efficacy of the AAVhu68.CB7.CI.hARSAco.rBG vector.

The AAVhu68.CB7.CI.hARSAco.rBG vector was administered ICM at a dose of $3.00 \times 10^{12}$ GC (low dose), $1.00 \times 10^{13}$ GC (mid-dose), or $3.00 \times 10^{13}$ GC (high dose) to adult cynomolgus macaques. CSF and serum were collected weekly during the 42 days following AAVhu68.CB7.CI.hARSAco.rBG administration (with the exception of Day 30 for CSF collection) to assess the dynamics of ARSA activity levels and the presence of inhibitory anti-ARSA antibodies. The doses of AAVhu68.CB7.CI.hARSAco.rBG were selected based upon previous experience with ICM-administered vectors expressing secretable proteins in NHPs (Hordeaux et al., 2018). Sample collection time points during the 42 days following AAVhu68.CB7.CI.hARSAco.rBG treatment were expected to capture a stable plateau for ARSA activity levels based upon our previous experience that transgene expression is detectable by 14 days after IT AAV administration (Hinderer et al., 2014; Hinderer et al., 2018).

Figure 11:
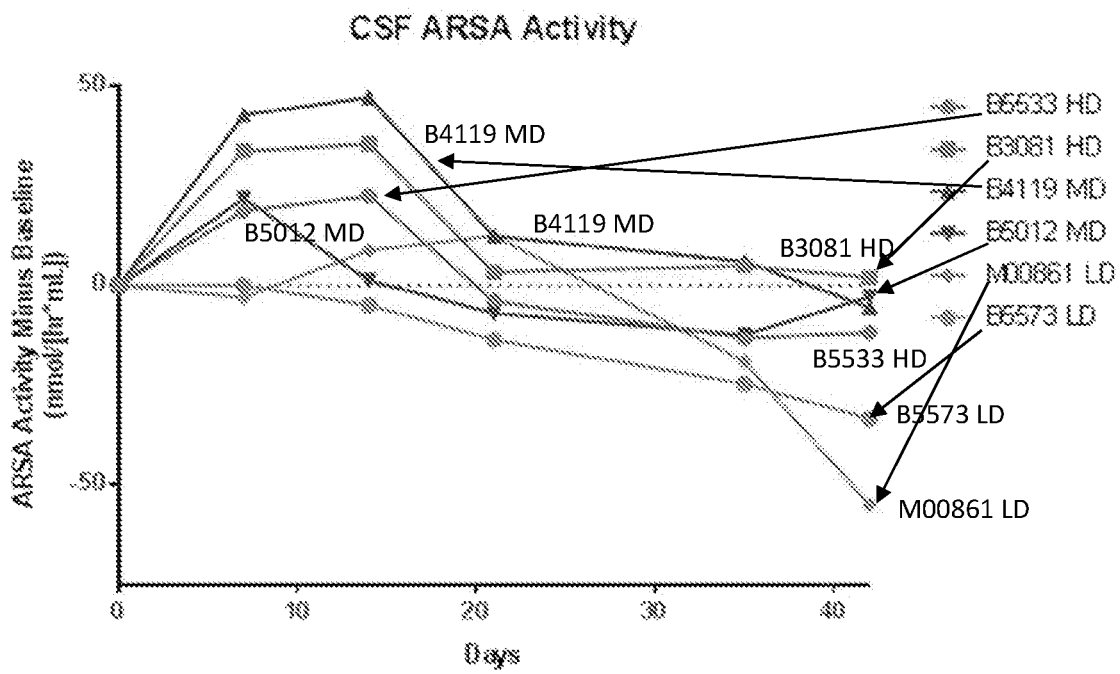
FIG. 11 shows ARSA activity levels in cerebrospinal fluid of nonhuman primates following intra-cisterna magna administration of AAVhu68.CB7.CI.hARSAco.rBG. Adult cynomolgus macaques received a single ICM administration of AAVhu68.CB7.CI.hARSAco.rBG at a dose of $3.00 \times 10^{12}$ GC (LD), $1.00 \times 10^{13}$ GC (MD), or $3.00 \times 10^{13}$ GC (HD) (N=2/group). After AAVhu68.CB7.CI.hARSAco.rBG administration (Day 0), CSF was collected on Days 7, 14±1, 21±1, 35±1, and 42±2. ARSA activity was measured by the rate of hydrolysis of the chromogenic substrate, 4-nitrocatechol sulfate (nmol/[hr*mL]). Endogenous macaque ARSA activity, which was defined as each individual's baseline ARSA activity levels prior to ICM administration, was subtracted to obtain ARSA activity resulting from AAVhu68.CB7.CI.hARSAco.rBG administration. The dotted line represents baseline ARSA activity levels for each individual. ARSA, arylsulfatase A (protein); CSF, cerebrospinal fluid; GC, genome copies; HD, high dose; ICM, intra-cisterna magna; LD, low dose; MD, mid-dose; N, number of animals. Arrows from the legend are used to indicate each trial.

Administration of either the mid-dose ($1.00 \times 10^{13}$ GC) or high dose ($3.00 \times 10^{13}$ GC) of AAVhu68.CB7.CI.hARSAco.rBG increased CSF ARSA activity above baseline levels. ARSA activity peaked 7-14 days post treatment and subsequently returned to baseline levels by 35-42 days post treatment. At its peak, ARSA activity was at least double that of baseline for each NHP receiving the mid-dose or high dose, suggesting that AAVhu68.CB7.CI.hARSAco.rBG might be capable of restoring normal ARSA levels when administered to an ARSA-deficient MLD patient. In contrast, the low dose ($3.00 \times 10^{12}$ GC) of AAVhu68.CB7.CI.hARSAco.rBG was not effective at increasing ARSA activity levels (FIG. 11).

Figure 12A:
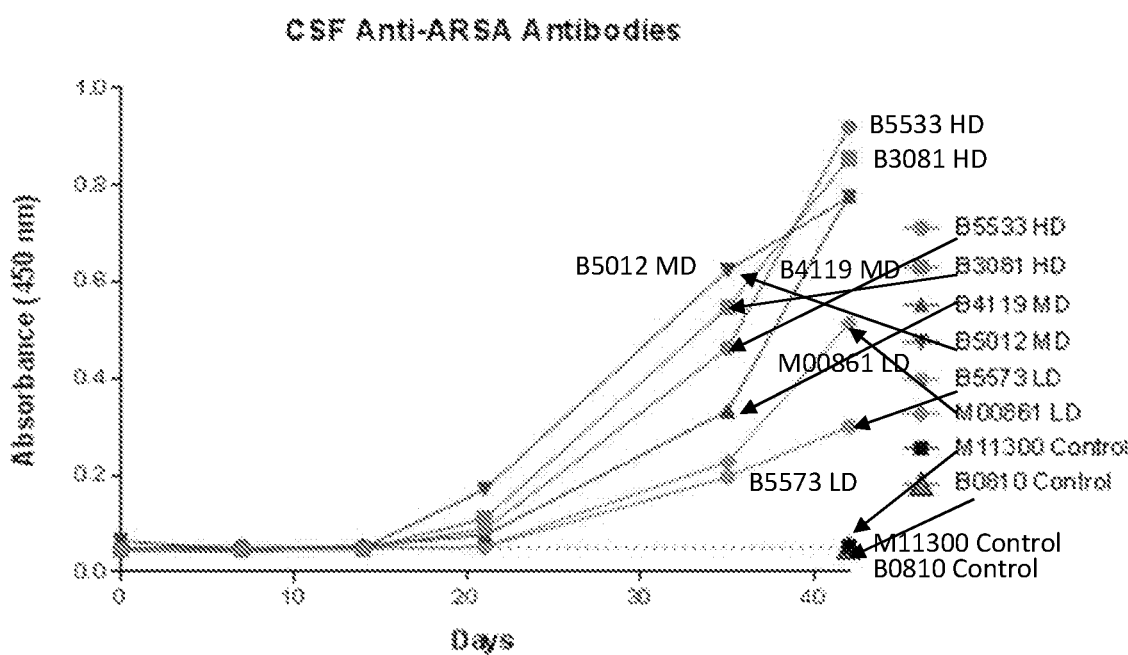
FIGS. 12A and 12B provide anti-ARSA antibody levels in cerebrospinal fluid and serum of nonhuman primates following intra-cisterna magna administration of AAVhu68.CB7.CI.hARSAco.rBG. Adult cynomolgus macaques received a single ICM administration of AAVhu68.CB7.CI.hARSAco.rBG on Day 0 at a dose of $3.00 \times 10^{12}$ GC (LD), $1.00 \times 10^{13}$ GC (MD), or $3.00 \times 10^{13}$ GC (HD) (N=2/group). Untreated age-matched cynomolgus macaques served as a control (N=2). After AAVhu68.CB7.CI.hARSAco.rBG administration (Day 0), CSF was collected on Days 7, 14+1, 21+1, 35+1, and 42+2. Serum was collected on Days 7, 14+1, 21+1, 28+1, 35+1, and 42+2. An indirect ELISA was performed on the CSF (dilution 1:20, FIG. 12A) and serum (dilution 1:1000, FIG. 12B) using plates pre-coated with recombinant human ARSA to measure anti-hARSA antibody levels (absorbance at 450 nm). The dotted line represents the absorbance average in untreated controls. ARSA, arylsulfatase A (protein); CSF, cerebrospinal fluid; ELISA, enzyme-linked immunosorbent assay; GC, genome copies; hARSA, human arylsulfatase A; HD, high dose; ICM, intra-cisterna magna; LD, low dose; MD, mid dose; N, number of animals. Arrows from the legend are used to indicate each trial.
Figure 12B:
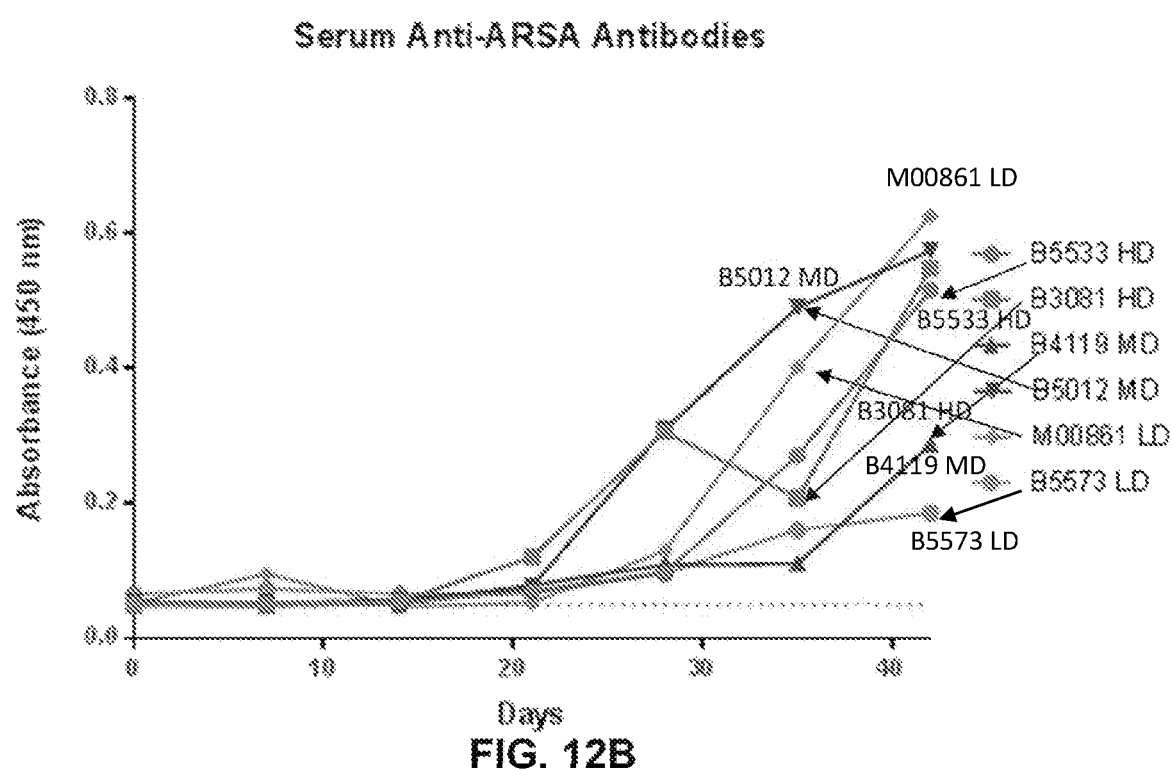

The observed drop in ARSA activity levels after 14 days post AAVhu68.CB7.CI.hARSAco.rBG administration may have resulted from the production of inhibitory anti-hARSA antibodies. Analysis revealed that in the CSF, an increase in anti-hARSA antibodies was observed in some animals by 3 weeks post treatment. By 42 days, all animals displayed elevated anti-hARSA antibodies, and higher antibody levels appeared to correlate with higher doses of AAVhu68.CB7.CI.hARSAco.rBG (FIG. 12A). In the serum, an increase in circulating anti-hARSA antibodies was apparent in some animals by 21-28 days after AAVhu68.CB7.CI.hARSAco.rBG administration. By 42 days, most animals displayed elevated anti-hARSA antibodies, but unlike CSF, serum levels did not appear to correlate with the dose of AAVhu68.CB7.CI.hARSAco.rBG (FIG. 12B). These results suggest that the observed drop in ARSA activity 14 days after AAVhu68.CB7.CI.hARSAco.rBG administration was due to the induction of CSF- and serum-circulating anti-hARSA antibodies.

In addition to a humoral response to the AAVhu68.CB7.CI.hARSAco.rBG transgene product (i.e., the production of anti hARSA antibodies), it was also possible that the elimination of transduced cells via a cytotoxic T-cell response may have contributed to loss of ARSA activity in the CSF. To address this possibility, CNS, PNS, and peripheral tissues were harvested from NHPs necropsied 42 days after treatment for a comprehensive evaluation of ARSA expression.

In NHPs administered the high dose of AAVhu68.CB7.CI.hARSAco.rBG ($3.00 \times 10^{13}$ GC), transduced cells expressing human ARSA enzyme were detected throughout the brain, including the cortex (FIG. 13E, FIG. 13F, FIG. 13G, FIG. 13I, and FIG. 13J), hippocampus (FIG. 13H), thalamus (FIG. 13K), and cerebellum (FIG. 13L). Cells of the cervical (FIG. 14D), thoracic (FIG. 14E), and lumbar (FIG. 14F) spinal cord along with cervical (FIG. 14G), thoracic (FIG. 14H), and lumbar (FIG. 14I) DRG also expressed human ARSA enzyme. These findings suggest that despite the humoral immune response to the transgene product, transduced cells still persisted within the target tissues for at least 42 days after AAVhu68.CB7.CI.hARSAco.rBG administration, producing ARSA where it would be needed to correct neurons and myelin-producing cells. These data support the possibility that AAVhu68.CB7.CI.hARSAco.rBG could provide therapeutic levels of ARSA to both the CNS and PNS of MLD patients.

It was observed that a minimal to moderate dorsal sensory axonopathy at the high dose of AAVhu68.CB7.CI.hARSAco.rBG ($3.00 \times 10^{13}$ GC) consistent with what is usually seen after successful ICM gene transfer. No clinical signs of peripheral neuropathy were observed in the animals during the study. Histopathology slides for NHPs administered the low dose ($3.00 \times 10^{12}$ GC) or mid-dose ($1.00 \times 10^{13}$ GC) of AAVhu68.CB7.CI.hARSAco.rBG were generated, and analysis is performed.

Cumulatively, this study showed that by 14 days after ICM administration of AAVhu68.CB7.CI.hARSAco.rBG, total ARSA activity levels in the CSF of NHPs more than doubled. CSF ARSA activity levels returned to approximately baseline levels over the subsequent 28 days due to the production of antibodies against the human ARSA transgene. However, transduced cells throughout the brain and spinal cord still persisted for the duration of the 42 day study, including cells that have projections into the PNS (e.g., DRGs and motor neurons). Axonopathy at the high dose ($3.00 \times 10^{13}$ GC) without clinical signs were observed and were consistent with previous findings following ICM AAV administration. These data support use of AAVhu68.CB7.CI.hARSAco.rBG for delivering ARSA to deficient neurons and myelin-producing cells in the CNS and PNS of MLD patients.

Overexpression of ARSA was achieved at the MD and HD in CSF and target tissues (CNS, PNS). The LD was suboptimal.

Example 5—Arsa$^{-/-}$ Mouse Model

No naturally occurring animal model of MLD has been reported in the literature. There are two laboratory-generated mouse models of MLD, both of which were created by Volkmar Gieselmann's group in Germany (Hess et al., 1996; Ramakrishnan et al., 2007). Due to difficulties obtaining these published lines for studies, an MLD mouse model was generated using clustered regularly interspaced short palindromic repeats-CRISPR-associated protein 9 (CRISPR-Cas9) gene editing technology. A comparison of the three different laboratory-generated mouse models is provided in table below.

TABLE

Mouse Models of Metachromatic Leukodystrophy

| Genotype | Description | Sulfatide Accumulation | Demyelination | Neurological Symptoms | Lifespan |
|---|---|---|---|---|---|
| Arsa$^{-/-}$ (Single Mutant) | Arsa knockout (homologous recombination) | By 6 months (lipid analysis) By 10-12 months (histology) | None | Gait pattern abnormalities and reduced rotarod performance by 6-10 months | Normal |
| tg/Arsa$^{-/-}$ (Double Mutant) | Arsa knockout (homologous recombination) Gal3st1 transgene under the control of the Plp1 promoter (driving overexpression in myelinating cells) | By 6 months (lipid analysis) By 17 months (histology) | By 17-18 months (PNS > CNS) | Hind limb grasping upon tail suspension in mice >16 months old leading to progressive hind limb paralysis and inability to stay on rotarod by 21-24 months Reduced nerve conduction velocity by 22-24 months | Normal |
| Arsa−/− (+/−AAV-PH.B-GAL3ST1) | Arsa knockout (CRISPR/Cas9) With and without AAV-mediated overexpression of GAL3ST1 | Analysis ongoing | | | |

Arsa, arylsulfatase A (gene, mouse); CNS, central nervous system; CRISPR/Cas9, clustered regularly interspaced short palindromic repeats/CRISPR-associated protein 9; Gal3st1, galactose-3-O-sulfotransferase-1 (gene, mouse); GAL3ST1, galactose-3-O-sulfotransferase-1 (protein); PNS, peripheral nervous system; tg, transgene.

A. Non-Demyelinating MLD Mouse (Arsa$^{-/-}$)

The classic MLD mouse model (referred to in the literature as "non-demyelinating MLD mice") was developed through homologous recombination via insertion of a 1.3 kb neomycin cassette into exon 4 of the Arsa gene. This insertion resulted in a complete knock out of the gene with homozygous Arsa$^{-/-}$ mice lacking detectable Arsa mRNA and functional protein. These mice develop progressive sulfatide storage in the CNS, PNS, kidneys, and liver similar to what has been described in MLD patients. However, the storage and associated phenotypes are slower to progress when compared to human patients, manifesting around middle age in the mouse (6-12 months). Increased sulfatide levels can be detected by 6 months using a biochemical analysis (Ramakrishnan et al., 2007), but significant histological sulfatide staining is only observable by 10-12 months of age (Gieselmann et al., 1998). The most consistent neurological symptoms measurable in Arsa$^{-/-}$ mice are abnormalities in gait pattern (based upon footprint analysis) and reduced motor coordination (measured by rotarod performance) (Gieselmann et al., 1998; Matzner et al., 2009; Stroobants et al., 2011), which usually appear after 6-10 months of age. In contrast to human MLD patients, no demyelination is found in the CNS or PNS of Arsa$^{-/-}$ mice, which explains the surprisingly mild phenotype and normal lifespan observed for these animals.

B. Demyelinating (Aggravated) MLD Mouse (tg/Arsa$^{-/-}$)

It was hypothesized that slow sulfatide storage accounted for the delayed disease onset and lack of demyelination observed in Arsa$^{-/-}$ mice (Ramakrishnan et al., 2007). To address this hypothesis, a genetically aggravated mouse model of MLD was developed that displays demyelination (referred to in the literature as "demyelinating MLD mice"). This line was created by crossing Arsa$^{-/-}$ mice with mice carrying a transgene (tg) overexpressing GAL3ST1 enzyme in myelin-producing cells. GAL3ST1 is involved in the biosynthesis of sulfatides, and the double mutant mice (tg/Arsa$^{-/-}$) accumulate about two times more sulfatides in their tissues when compared to Arsa$^{-/-}$ mice. The tg/Arsa$^{-/-}$ mice exhibit increased storage of sulfolipids in the CNS and PNS detected by alcianophilic histological staining, impaired nerve conduction, and decreased myelination in the PNS and, to a lesser extent, the CNS (Ramakrishnan et al., 2007), all of which are key features of MLD in human patients. However, the appearance of these findings was delayed when compared to disease progression in human patients, with features manifesting in adult mice beginning around 6 months of age. Specifically, the researchers described sulfatide accumulation by 6 months using a biochemical assay, and all other phenotypes arose by 17-22 months. The delay in sulfatide storage and subsequent demyelination is likely the reason for the normal lifespan observed in tg/Arsa$^{-/-}$ mice, which is in contrast to the shortened lifespan of MLD patients.

C. Novel MLD Mouse Models

The pharmacological activity of AAVhu68.CB7.CI.hARSAco.rBG is assessed in both in vivo and in vitro models of MLD. For the in vivo model, a novel Arsa$^{-/-}$(+/−AAV-PH.β-GAL3ST1) mouse model was generated and is characterized as the availability of published in vivo models (Arsa$^{-/-}$[single mutation] and tg/Arsa$^{-/-}$[double mutation]) is limited. It is under evaluation that the new mouse model displays a natural history comparable to that of the classic Arsa$^{-/-}$ mouse, including phenotypes similar to those observed in MLD patients, specifically sulfatide storage in cells of the central nervous system (CNS), peripheral nervous system (PNS), kidneys, and liver along with gait abnormalities and reduced motor coordination. The new Arsa$^{-/-}$ mouse line was generated using CRISPR/Cas9 embryonic microinjection. Four founders were produced that have deletions of exons 2-4 that ranged from 1105 bp to 1133 bp in length. All four founders were bred once with C57BL/6J wild type mice and successfully transmitted the deleted allele to the F1 generation. F1 generation carriers were crossbred once more into a C57BL6/J background to further dilute any unwanted off-target editing. All four lines produced F2 generation carriers that are being bred to generate and characterize the four Arsa$^{-/-}$ mouse lines. The first Arsa$^{-/-}$ mice were born.

The utilized genetic engineering strategy targets the mouse Arsa gene located on chromosome 15 using several guide RNAs to facilitate the targeted deletion of exon 2 through exon 4. While the classic Arsa$^{-/-}$ model employed homologous recombination of a neomycin cassette to produce a null allele, CRISPR/Cas9 gene editing is anticipated to produce a complete knock out with a comparable phenotype in less time than previous gene targeting methods.

Unlike the published Arsa$^{-/-}$ mouse models, demyelination is not expected to be observed in the new Arsa$^{-/-}$ mouse lines. Therefore another model in Arsa$^{-/-}$ mice is developed where the sulfatide-synthesizing enzyme, galactose-3-O-sulfotransferase-1 (GAL3ST1) is overexpressed which increases sulfatide storage. The increase in sulfatide storage should lead to demyelination in the PNS, impaired nerve conduction, and paralysis similar to the classic Arsa$^{-/-}$ mouse model. These features are observed in MLD patients. Mice that overexpress GAL3ST1 similar to tg/Arsa$^{-/-}$ mice is also generated to determine whether demyelination can be observed under aggravated conditions. However, instead of generating double mutants, an AAV-PHP.B vector is employed to overexpress GAL3ST (AAV-PHP.B.CB7.GAL3STIco.rBG [AAV-PH.B.GAL3ST1]). The AAV.PHP.B capsid was selected because it displays robust CNS tropism after systemic (IV) injection in C57BL6/J mice (Deverman et al., 2016; Hordeaux et al., 2019).

This approach avoids the problem of breeding double transgenic mice with different genetic backgrounds, since mixed genetic backgrounds frequently result in confounding neurobehavioral abnormalities in the F2 generation that are not subsequently reproducible in a purer genetic background. Thus, these mice are expected to overexpress GAL3ST1 at high levels in the CNS with the added experimental benefits of an isogenic background.

A natural history study was performed according to the following phenotypic criteria (listed in increasing order of disease severity):

1. Demonstration of reduced or absent residual ARSA activity in the CNS and peripheral tissues;
2. Demonstration of sulfatide storage in the CNS, PNS, kidney, and liver;
3. Demonstration of demyelination on histopathology;
4. Demonstration of a behavioral phenotype consistent with demyelination.

Either the Arsa-mouse or the AAV-PH.B.GAL3ST1-mediated aggravated Arsa$^{-/-}$ mouse or both are selected for pharmacology and MED studies. The decision is based on which mouse line displays the best breeding performance and percentage of Arsa$^{-/-}$ mice from crosses of Arsa$^{+/-}$ carriers, in addition to meeting the greatest number of phenotypic criteria above.

Mice with approximately 8 weeks of age are enrolled in the natural history study after 1 week of acclimation to the mouse vivarium. A minimum of six Arsa$^{-/-}$ males (M) and six Arsa$^{-/-}$ females (F) per line is assessed and compared to wild type littermates. Mice are monitered weekly for development of ataxia using a scoring system adapted from (Guyenet et al., 2010). Animals are weighed and evaluated monthly for motor coordination (rotarod assay), grip strength, and signs of sensory deficits (hot plate assay). Gait analysis is completed every 2 months using the CatWalk™ gait analysis system. At 6 months of age, a subset of each cohort (Arsa$^{-/-}$: N 3 M, 3 F; Wild type: N=1 M, 1 F) is necropsied and evaluated for ARSA enzyme activity, demyelination, and sulfatide storage in the brain, kidneys, liver, sciatic nerve, and spinal cord. The remaining mice are followed for a longer period of time to fully characterize the natural history of these lines and to monitor for the possibility of delayed-onset demyelination.

A delayed or absent demyelination phenotype may be observed. A subset of mice in each line is treated with an IV bolus of an AAV-PHP.B vector encoding the sulfatide-synthesizing enzyme GAL3ST1 (AAV-PHP.B.CB7.GAL3STIco.rBG) to increase sulfatide synthesis rates. As in the tg/Arsa$^{-/-}$ mice, overexpression of GAL3ST1 may create a more rapid storage overload and an aggravated disease model that demonstrates demyelination along a time course more similar to the disease progression observed in humans. All mice are subjected to weekly clinical observations to monitor general health and ataxia in parallel with Arsa$^{-/-}$ mice in the natural history study. A subset of mice from each cohort (Arsa$^{-/-}$: N=3 M, 3 F; Arsa$^{+/+}$: N=1 M, 1 F) are necropsied at 6 months of age to assess sulfatide storage and demyelination.

Example 6—Identification of the Minimum Effective Dose (MED) of AAVhu68.CB7.Cl.hARSAco.rBG in Arsa$^{-/-}$ Mice The Arsa$^{-/-}$ mouse line identified Example 5 is selected to conduct the MED study of ICV-administered AAV.CB7.CI.hARSAco.rBG. The age at injection, in-life parameters, and age at necropsy are based on the most relevant disease biomarkers defined in other examples.

The MED study is performed using the toxicological vector lot that is manufactured for the GLP NHP toxicology study. The study evaluates four dose levels to determine the MED, pharmacology, and histopathology (efficacy and safety). The dose levels were selected based on the pilot dose range in wild type mice Examples 2 and 3 and the maximal feasible dose when scaled to humans. The age of ICV injection is determined based on the natural history study results. Animals are sacrificed at an appropriate time point post-injection to obtain pharmacological and efficacy readouts and compared to age-matched controls administered ITFFB. The necropsy time points are determined based upon Example 5, and may be performed when mice are approximately 5-12 months of age based upon the natural history of the published Arsa$^{-/-}$ models. However, the necropsy time point may be extended based on the results of the natural history study and the endpoints that are measured. Efficacy endpoints are defined based on results from Example 5 and may include assays such as ataxia scoring, body weight, motor coordination on a rotarod, and sensory function on a hotplate. In the absence of a satisfying neurobehavioral endpoint, ARSA activity levels, sulfatide storage, and histopathology may be the criteria used to define the MED.

Example 5 identifies a reliable aggravated model using AAV-PHP.β-mediated GAL3ST1 overexpression (sulfatide overload), one study arm for aggravated mice is performed at each dose level. Those mice concurrently receive an IV-administered dose of AAV.PHP.B.GAL3ST1 and an ICV-administered dose of AAV.CB7.CI.hARSAco.rBG on Study Day 0 to avoid the production of cross-reactive NAbs, which might occur with staggered dosing.

The study design is presented in table below:

| Treatment (ICV) (Dose) | Arsa$^{-/-}$ | Arsa$^{-/-}$ + GAL3ST1 | Wild Type | Wild Type + GAL3ST1 | In-Life Evaluations | Pharmacology[a] |
|---|---|---|---|---|---|---|
| Genotype/Treatment AAV-PH.B.GAL3ST1 (IV) (N) | | | | | | |
| Vehicle (Artificial CSF) | 8 | 8 | 8 | 8 | Body weight | Brain ARSA activity |
| AAV.CB7.CI.hARSAco.RBG ($1.30 \times 10^{11}$ GC) | 8 | 8 | — | — | Ataxia score Rotarod (coordination) | Thoracic and lumbar |
| AAV.CB7.CI.hARSAco.RBG ($4.50 \times 10^{11}$ GC) | 8 | 8 | — | — | Grip strength Catwalk (gait) | spinal cord ARSA activity |
| AAV.CB7.CI.hARSAco.RBG ($1.30 \times 10^{10}$ GC) | 8 | 8 | — | — | Hotplate (sensory nerves) | Peripheral nerve |
| AAV.CB7.CI.hARSAco.RBG ($4.50 \times 10^{9}$ GC) | 8 | 8 | — | — | | histology to assess myelination ARSA activity Histopathology of major organs[b] CNS, PNS, liver, and kidney sulfatide storage |

[a]All mice are necropsied 5-12 months after vector administration for the indicated assessments.
[b]Initial histopathology analysis focuses on the brain, cervical spinal cord, cervical DRG, peripheral nerves, liver, spleen, kidney, lungs, heart, diaphragm, and muscle. Additional tissues are also collected for optional histopathology, including gastrointestinal tract, reproductive organs, adrenal glands, and lymph nodes. Organs are weighed as appropriate.
AAV-PH.B.GAL3ST1, AAV-PHP.B.CB7.CI.GAL3ST1co.rBG; Arsa, arylsulfatase A (gene, mouse); ARSA, arylsulfatase A (protein); CNS, central nervous system; CSF, cerebrospinal fluid; GAL3ST1, galactose-3-O-sulfotransferase-1 (protein); GC, genome copies; ICV, intracerebroventricular; IV, intravenous; MED, minimum effective dose; N, number of animals; PNS, peripheral nervous system; TBD, to be determined.

Example 7—Characterization of In Vitro Disease Model Using Patient-Derived Cells for Proof-of-Concept Pharmacology Studies To complement in vivo studies of AAV.CB7.CI.hARSAco.rBG, efficacy of AAV-mediated ARSA gene delivery is assessed using an in vitro disease model. Recently, an MLD patient-derived iPSC-based model recapitulating defective glial and neuronal differentiation as well as several features of MLD, such as lysosomal compartment expansion, sulfatide storage, oxidative stress, and apoptosis was characterized (Frati et al., 2018). One patient-derived cell line (RIKEN cell bank reference HPS0240), as well as two CRISPR-Cas9 ARSA knockout iPSC clones, is characterized. An appropriate cell line is identified. The extent of disease biomarker rescue following AAV vector administration is assessed. Because the AAVhu68 capsid is known to poorly transduce cells in culture, a different AAV serotype may be used to deliver an ARSA-encoding vector genome which is or similar to AAV.CB7.CI.hARSAco.rBG for these studies.

The neural progenitor cell stage did not show any conclusive phenotype in terms of oxidative stress or morphological changes described by Frati et al. (2018), Differentiated cells (neurons and oligodendrocytes) are under investigation because they demonstrated a more prominent sulfatide storage phenotype in the published work. With reliable sulfatide storage, phenotype rescue is tested using AAV-mediated ARSA transduction. Because the AAVhu68 capsid is known to poorly transduce cells in culture, a capsid of a different serotype may be used to deliver an ARSA-encoding vector genome which is or similar to AAV.CB7.CI.hARSAco.rBG.

Data from both the in vivo mouse model(s) (Example 6) and one or more of the aforementioned in vitro models of MID are used to support the pharmacological activity of AAV.CB7.CI.hARSAco.rBG.

Example 8—Toxicology Study in Nonhuman Primates

Adult cynomolgus macaques, 6-8 years of age, were used in a non-GLP pilot dose ranging study of AAV.CB7.CI.hARSAco.rBG. Juvenile rhesus macaques (1.-2 years old) are selected for the toxicology study of AAV.CB7.CI.hARSAco.rBG. For convenience purposes (availability of animals), two different species of NHPs are used. There is no difference in transduction profile after AAV ICM administration between rhesus and cynomolgus macaques. Both adult cynomolgus macaques and juvenile Rhesus macaques have similar anatomical and physiological features and replicate the CNS anatomy of the intended infantile clinical population and can be treated using the clinical ROA (ICM). The similarity in anatomy and ROA may result in representative vector distribution and transduction profiles, which allow for more accurate assessment of toxicity than is possible in mice. In addition, more rigorous neurological assessments are performed in NHPs than in a rodent model, allowing for more sensitive detection of CNS toxicity.

Completed non-clinical pharmacology studies demonstrated the potential for AAV-mediated delivery of ARSA enzyme via transduction and/or cross-correction of both neurons and myelin-producing oligodendrocytes in the brain of healthy mice following ICV administration of AAV.CB7.CI.hARSAco.rBG. A pharmacology study in cynomolgus macaques administered AAV.CB7.CI.hARSAco.rBG via the clinical route (ICM) showed increased ARSA activity in the CSF by at least double endogenous levels during the first 14 days after treatment. Since the achievement of normal levels of ARSA activity in the cerebrospinal fluid (CSF) correlates with good outcomes for our intended patient population (early onset MLD patients) (Sessa et al., 2016), AAV.CB7.CI.hARSAco.rBG has the potential to deliver therapeutic levels of ARSA to the CSF of MLD patients. Furthermore, it is demonstrated that for at least 42 days after AAV.CB7.CI.hARSAco.rBG administration, transduced and/or cross-corrected cells expressing ARSA persist broadly throughout the brain and spinal cord, including cells with projections into the PNS (spinal motor neurons and dorsal root ganglia [DRG]). AAV.CB7.CI.hARSAco.rBG therefore has the potential to provide a long-lasting source of secreted ARSA enzyme to both the neurons and myelinating cells of the CNS and PNS that are affected in MLD patients.

To extend this pharmacology study and collect safety data, a 180 day GLP-compliant toxicology study of AAV.CB7.CI.hARSAco.rBG is performed in juvenile Rhesus macaques using the intended clinical route of administration (ROA). Intrathecal (IT) delivery of other AAV vectors into the CSF of Rhesus macaques has resulted in peak transgene expression 2-3 weeks after injection followed by a stable plateau in transgene expression by 90 days. We have demonstrated that a peak in ARSA expression is observed 14 days after ICM administration in cynomolgus macaques. Therefore, a 180 day time point is sufficient to evaluate any toxicity occurring during the period of maximum exposure to the transgene product. Evaluations through 180 days are also adequate to detect immediate toxicity due to the injection procedure or an innate inflammatory response to the test article, as well as adaptive immune responses to the vector capsid or transgene product.

A 180 day GLP-compliant safety study are conducted in juvenile Rhesus macaques (approximately 1-2 years of age) to investigate the toxicology of AAV.CB7.CI.hARSAco.rBG following ICM administration. The 180 day evaluation period was selected because this allows sufficient time for a secreted transgene product to reach stable plateau levels following ICM AAV administration. The age of administration was selected to be representative of our intended infantile population in terms of CNS anatomy. The study design is outlined in the table below.

nile macaques (N=2) are administered vehicle (ITFFB) as a control. AAV.CB7.CI.hARSAco.rBG dose levels are selected to be equivalent to those that is evaluated in the MED study when scaled by brain mass (assuming 0.4 g for the mouse and 90 g for the Rhesus macaque). NHPs are dosed using the same vector delivery device as described.

Baseline neurologic examinations, clinical pathology (cell counts with differentials, clinical chemistries, and a coagulation panel), CSF chemistry, and CSF cytology are performed. After AAV.CB7.CI.hARSAco.rBG or vehicle administration, the animals are monitored daily for signs of distress and abnormal behavior. Blood and CSF clinical pathology assessments and neurologic examinations are performed on a weekly basis for 30 days following: AAV.CB7.CI.hARSAco.rBG or vehicle administration, and every 30 days thereafter. At baseline and at each 30 day time point thereafter, anti-AAVhu68 NAbs and cytotoxic T lymphocyte responses to AAVhu68 and the AAV.CB7.CI.hARSAco.rBG transgene product are assessed by an interferon gamma (IFN-γ) enzyme-linked immunospot (ELISpot) assay.

Ninety days after AAV.CB7.CI.hARSAco.rBG or vehicle administration, 50% of the animals (Groups 1-4) are euthanized, and a histopathological analysis is performed on a comprehensive list of tissues, including, but not limited to, brain, spinal cord, DRG, peripheral nerves, heart, liver, spleen, kidney, lungs, reproductive organs, adrenal glands, and lymph nodes. Organs are weighed as appropriate. Lymphocytes are harvested from the circulating compartment (peripheral blood mononuclear cells) and CNS-draining lymph nodes are evaluated for the presence of T cells reactive to both the capsid and transgene product in these organs at the time of necropsy. Ninety days after Groups 1-4 are euthanized (One hundred and eighty days after AAV.CB7.CI.hARSAco.rBG or vehicle administration) the remaining animals (Groups 5-8) are euthanized, and a histopathological analysis is performed as above.

| | | | | |
|---|---|---|---|---|
| Species | | | Macaca mulatta | |
| Synonym | | | Rhesus Macaques | |
| Age of animals at initiation of study | | | 1-2 years | |
| Weight of animals at initiation of study | | | 1.0-3.5 kg | |
| Number of animals used | | | 20 Total | |
| | | | 8 Males | |
| | | | 12 Females | |
| Group Designation | 1 | 2 | 3 | 4 |
| Number of Macaques | 1 | 3 | 3 | 3 |
| Sex | M or F | M + F | M + F | M + F |
| Age | | | Juvenile (1-2 years) | |
| Test Article | Vehicle$^a$ | AAV.CB7.CI.hARSAco.rBG | AAV.CB7.CI.hARSAco.rBG | AAV.CB7.CI.hARSAco.rBG |
| Vector Dose (Total Dose) | NA | $3.0 \times 10^{12}$ GC | $1.0 \times 10^{13}$ GC | $3.0 \times 10^{13}$ GC |
| ROA | | | ICM | |
| Necropsy Day | | | 90 ± 5 | |
| Group Designation | 5 | 6 | 7 | 8 |
| Number of Macaques | 1 | 3 | 3 | 3 |
| Sex | M or F | M + F | M + F | M + F |
| Age | | | Juvenile (1-2 years) | |
| Test Article | Vehicle$^a$ | AAV.CB7.CI.hARSAco.rBG | AAV.CB7.CI.hARSAco.rBG | AAV.CB7.CI.hARSAco.rBG |
| Vector Dose (Total Dose) | NA | $3.0 \times 10^{12}$ GC | $1.0 \times 10^{13}$ GC | $3.0 \times 10^{13}$ GC |
| ROA | | | ICM | |
| Necropsy Day | | | 180 ± 5 | |

F, female; GLP, good laboratory practice; ICM, intra-cisterna magna; ITFFB, intrathecal final formulation buffer; M, male; NA, not applicable; ROA, route of administration.

Juvenile Rhesus macaques receive one of three dose levels of AAV.CB7.CI.hARSAco.rBG: $3.0 \times 10^{12}$ GC, $1.0 \times 10^{13}$ GC, or $3.0 \times 10^{13}$ GC (N=3 per dose). Additional juve- Tissues, CSF, and serum for vector biodistribution are harvested and archived, in addition to urine and feces to assess vector excretion. qPCR in tissue samples was assessed using the same capsid and ROA in juvenile macaques.

ICM vector administration results in immediate vector distribution within the CSF compartment, and both efficacy and toxicity are related to CNS vector exposure. Doses are therefore scaled by brain mass, which provides an approximation of the size of the CSF compartment. Dose conversions are based on a brain mass 0.4 g for an adult mouse (Gu et al., 2012), 90 g for juvenile rhesus macaques (Herndon et al., 1998), and 800 g for 4-12-month-old human infants (Dekaban, 1978). Equivalent human doses are shown in the table below.

TABLE

Doses for the Murine MED Study, NHP Dose Range and Toxicology Studies, and Equivalent Human Doses

| Dose (GC/g brain mass) | Mouse MED Study (GC) | Adult Cynomolgus Macaque Dose Range Study (GC) | Juvenile Rhesus Macaque Toxicology Study (GC) | Human Infant (GC) |
|---|---|---|---|---|
| $3.30 \times 10^{11}$ | $1.30 \times 10^{11}$ | $3.00 \times 10^{13}$ | $3.00 \times 10^{13}$ | $2.70 \times 10^{14}$ |
| $1.10 \times 10^{11}$ | $4.50 \times 10^{10}$ | $1.00 \times 10^{13}$ | $1.00 \times 10^{13}$ | $9.30 \times 10^{13}$ |
| $3.30 \times 10^{10}$ | $1.30 \times 10^{10}$ | $3.00 \times 10^{12}$ | $3.00 \times 10^{12}$ | $2.70 \times 10^{13}$ |
| $1.10 \times 10^{10}$ | $4.50 \times 10^{9}$ | — | — | $9.30 \times 10^{12}$ |

Abbreviations: GC, genome copies; MED, minimum effective dose; NHP, nonhuman primate.

Example 9—Sensory Neuron Toxicity in Non-Clinical Adeno-Associated Virus Studies In order to reduce minimal to mild asymptomatic degeneration of DRG sensory neurons which appear in the AAV.CB7.CI.hARSAco.rBG toxicology study, vector genomes are constructed which include drg-detargetting miRNA sequences. A rAAV vector genome is constructed as, from 5' to 3', CB7 promoter, engineered hARSA coding sequence, four consecutive miRNA183 (with sequence of AGTGAATTCTACCAGTGCCATA, SEQ ID NO: 20) which are separated by a spacer and each spacer is independently selected from one or more of (A) GGAT; (B) CACGTG; or (C) GCATGC, and a rBG poly A. This vector genome is termed as AAV.CB7.CI.hARSAco.miRNA183.rBG while a rAAV comprising this vector genome and an AAVhu68 capsid is termed as AAVhu68.CB7.CI.hARSAco.miRNA183.rBG. Production of the rAAV vector comprising this vector genome is performed similar to the method described in Example 1. Efficacy and toxicity of the AAVhu68.CB7.CI.hARSAco.miRNA183.rBG are tested using methods and models described in Examples 2-8 and 10.

Example 10—First-In-Human Trial

A Phase 1/2, multi-center, open-label, single-arm, dose escalation study of AAV.CB7.CI.hARSAco.rBG administered by a single ICM injection in pediatric patients (≥4 months of age) with early onset (late infantile or early juvenile) MLD caused by ARSA enzyme deficiency is performed. Safety and tolerability, pharmacodynamics, and clinical efficacy are assessed over 2 years, and all subjects are followed through 5 years post-administration of AAV.CB7.CI.hARSAco.rBG for the long-term evaluation of safety and tolerability, pharmacodynamics, disease progression, and clinical outcomes.

The study consists of a screening phase to determine eligibility of each potential subject from approximately Day-35 to Day-1. After confirmation of subject eligibility and parent's/guardian's willingness to have their child participate in the study, the subject undergoes baseline assessments, which include brain MRI, LP for CSF collection, blood draw, urine collection, vitals, ECG, a physical exam, a neurological exam, and clinical assessments. Baseline assessments occur on Days-1 and Day 0, and eligibility is reconfirmed at baseline prior to administration of AAV.CB7.CI.hARSAco.rBG.

During the treatment phase, subjects are admitted to the hospital on the morning of Day 0. Subjects receive a single ICM dose of AAV.CB7.CI.hARSAco.rBG on Day 0 and remain in the hospital for at least 24 hours after dosing for observation. Subsequent study visits occur at Day 7, Day 14, Day 30, 3 months, and 6 months after dosing, followed by every 6 months for the first 2 years after dosing. Long-term follow-up (LTFU) visits occur for an additional 3 years at a frequency of every 12 months through 5 years post-dosing.

A single dose of AAV.CB7.CI.hARSAco.rBG is administered at one of dose levels as indicated below.

Cohort 1 (Low Dose): Three eligible subjects (Subjects #1-3) are sequentially enrolled and administered the low dose of AAV.CB7.CI.hARSAco.rBG with a 4 week safety observation period between the first and second subject. If no SRTs are observed, all available safety data is evaluated by a safety board 4 weeks after the third subject in Cohort 1 is administered AAV.CB7.CI.hARSAco.rBG.

Cohort 2 (High Dose): Three eligible subjects (Subjects #4-6) are sequentially enrolled and administered the high dose of AAV.CB7.CI.hARSAco.rBG with a 4 week safety observation period between the fourth and fifth subject. If no SRTs are observed, the safety board evaluates all available safety data 4 weeks after Subject #6 is administered AAV.CB7.CI.hARSAco.rBG, including safety data from subjects in Cohort 1.

Cohort 3 (MTD, Maximum Tolerated Dose): With a positive recommendation by the safety board, 6 additional subjects (Subjects #7-12) are enrolled and administered a single ICM dose AAV.CB7.CI.hARSAco.rBG at the MTD. Dosing for subjects in this cohort are not staggered with a 4 week safety observation period between each subject.

A total enrollment of 9 subjects are enrolled in either the high dose or low dose cohort, and 12 subjects in total (across all doses). A safety margin is applied so that the high dose selected for human subjects is 30-50% of the equivalent MTD in NHPs. The low dose is typically 2-3-fold less than the selected high dose provided it is a dose that exceeds the equivalent scaled MED in the animal studies. With the understanding that if tolerated, the higher dose would be expected to be advantageous.

Since early onset MLD, is marked by a very rapid disease course once symptoms emerge, a study is performed to allow for concurrent enrollment of subjects 30 days after dosing of the first patient in Cohort 1 (low dose) and Cohort 2 (high dose) based on the Investigator's benefit-risk assessment for that subject. In this case, the dosing window between the second and third patient in the cohort would be at least 24 hours to observe the patient for acute toxicity, allergic reactions, and procedure-related events. Given the rarity of the disease, the probability that two subjects would present simultaneously for treatment is considered low. The rationale for the proposed approach is that the risk of missing the treatment window because the patient experienced rapid disease progression would outweigh the potential benefit of prolonged safety follow-up before dosing the next patient in the cohort. Such a scenario where patients experience substantial disease progression between enrollment and treatment was cited as a possible cause of the poor outcomes observed in some early onset MLD patients treated with HSC-GT (Sessa et al., 2016), highlighting the need for prompt identification and treatment of patients at risk of rapid disease progression.

The pediatric patients (>4 months of age) with early onset (late infantile or early juvenile) MLD caused by ARSA enzyme deficiency represent the population with the highest unmet need. Those MLD patients enrolled in our proposed FIH trial may have a 0/0 (two null ARSA alleles with no detectable functional enzyme produced) or 0/R (Heterozygosity for one null ARSA allele and one "residual" ARSA allele (R) encoding enzyme with residual functional activity that can still degrade small amounts of sulfatide) genotype. They display a devastating disease course with rapid and predictable decline in both motor and cognitive impairment leading to death within a few years of disease onset. Disease-modifying treatments are unavailable for most early onset patients. Hematopoietic stem cell transplant (HSCT) does not provide benefit in this population, while hematopoietic stem cell with gene therapy (HSC-GT) is an investigational treatment that is only effective in pre-symptomatic patients, who constitute a small minority of the early onset population.

Primary endpoints assess the safety and tolerability of AAV.CB7.CI.hARSAco.rBG. Secondary or exploratory endpoints include pharmacokinetic and pharmacodynamic properties (transgene expression, biomarker activity, and imaging parameters) and clinical efficacy outcomes (gross and fine motor function, cognitive and language development, neurological exam findings, behavioral and milestone development, and parent-reported outcomes and quality of life assessments). Efficacy endpoints and timing of follow-up were selected to measure prevention or stabilization of disease progression.

Gallbladder pathologies are therefore monitored in our proposed FIH trial as both a safety signal and an exploratory endpoint.

To assess the safety and tolerability of AAV.CB7.CI.hARSAco.rBG through 24 months following administration of a single ICM dose through evaluation of: AEs and SAEs, Vital signs and physical examinations, Neurological examinations, Electrocardiograms (ECGs), Sensory nerve conduction studies (for evaluation of DRG toxicity), Laboratory assessments (serum chemistry, hematology, coagulation studies, liver function tests [LFTs], urinalysis, and CSF chemistry and cytology), and/or immunogenicity of the vector and transgene product.

To assess the effect of AAV.CB7.CI.hARSAco.rBG on gross motor function through 2 years post-treatment as measured by the Gross Motor Function Classification for Metachromatic Leukodystrophy (GMFC-MLD).

Additional measurements for efficacy of AAV.CB7.CI.hARSAco.rBG includes the following:

To assess the pharmacodynamics and biological activity of AAV.CB7.CI.hARSACO.RBG over 2 years following administration of a single ICM dose based on the following endpoints: Levels of ARSA in CSF and serum;

To assess the efficacy of AAV.CB7.CI.hARSAco.rBG through 2 years following administration of a single ICM dose as measured by: Gross Motor Function Measure (GMFM), Neuro-cognitive (Total Intelligence Quotient [IQ] and sub-domain IQ measured by the Bayley Scale of Infant Development [BSID-III], Wechsler Intelligence Scale for Children, Fifth Edition [WISC-V]), Survival, Neurological clinical exam (NCE), NCV of the ulnar, deep peroneal, median, sural nerves, Motor milestones achievement (as defined by World Health Organization [WHO] criteria) assessed by age at achievement, age at loss, and percentage of children maintaining or acquiring motor milestones;

To further assess the efficacy of AAV.CB7.CI.hARSAco.rBG through 2 years following administration of a single ICM dose as measured by: Age-at-onset and frequency of seizures captured by a seizure diary, Vineland Adaptive Behavior Scales, Third Edition (Vineland-III), Lansky Performance Index, Pediatric Quality of Life Inventory (PedsQL and PedsQL-IS), Caregiver/parent quality of life;

To further assess the pharmacodynamic effects of AAV.CB7.CI.hARSAco.rBG through 2 years following administration of a single ICM dose as measured by: CNS myelination (demyelination load and pattern) and white matter atrophy as measured by MRI, Neuronal metabolite N-acetylaspartate (NAA), myo-inositol (ml), choline (Cho) and lactate (Lac) levels as measured by proton magnetic resonance spectroscopy (MRS), CSF sulfatide and lyso-sulfatide levels, Visual evoked potentials (VEPs), Brainstem auditory evoked responses (BAERs), Ultrasound evaluation of gall-bladder wall thickening.

Inclusion Criteria comprises the following:
  (i) Documented biochemical and molecular diagnosis of MLD based on ARSA activity below the normal range and identification of two disease-causing ARSA alleles, either known or novel mutations. In the case of a novel mutation(s), a 24 hour urine collection must show elevated sulfatide levels;
  (ii) ≥4 months of age;
  (iii) Pre-Symptomatic Subjects must have either
    An older sibling affected by MLD (index case) whose age of symptom onset was <7 years of age. Subjects are classified as late infantile, early juvenile, or intermediate late infantile/early juvenile based on age of symptom onset in the index case and their ARSA genotype as follows: Late infantile: symptom onset in index case≤30 months of age and genotype typically 0/0; Early juvenile: symptom onset in index case >30 months and <7 years of age with genotype typically 0/R; Intermediate late infantile/early juvenile: symptom onset in index case <7 years of age, but unable to unambiguously characterize index case as late infantile or early juvenile
    or
    If MLD is diagnosed in a pre-symptomatic child without an older affected sibling (e.g., incidentally or via newborn screening when available), the totality of available data strongly suggest that the subject has an early onset variant of MLD likely to benefit from gene therapy, and the subject is <7 years of age, then the subject may be considered eligible after discussion and approval by the Sponsor Medical Monitor;

(iv) Symptomatic Late Infantile Subjects are eligible provided they have mild clinical or neurological manifestations of MLD manifested by:

A delay in expected achievement of motor milestones such as a delay in achieving independent standing or walking (>95th percentile on WHO milestone ranges)

And/or

Mild abnormalities on NCE including, but not limited to, increased tone, spasticity, or hyperreflexia. If the subject has achieved independent walking, then signs of mild ataxia are acceptable provided the subject can walk at least 10 steps independently;

(v) Symptomatic Early Juvenile Subjects are eligible if they have mild/moderate abnormalities on NCE including, but not limited to, increased tone, spasticity, hyperreflexia, or mild gait abnormalities not requiring aids for walking;

(vi) Parent/guardian signed and dated informed consent.

Exclusion Criteria comprises the following:

Evidence of regression of achieved motor milestones;

Ambulatory subjects requiring aids for walking;

EJ MLD subjects with cognitive deficit based on Total IQ<70;

Any clinically significant neurocognitive deficit not attributable to MLD that may, in the opinion of the Investigator, confound interpretation of study results;

Patients with a positive test result for human immunodeficiency virus (HIV) or Hepatitis C (HepC);

Any current or previous condition or physical exam or laboratory test finding that, in the opinion of the Investigator, would put the subject at undue risk or would interfere with evaluation and interpretation of the investigational product safety or efficacy results;

Any contraindication to the ICM administration procedure, including contraindications to fluoroscopic imaging;

Any contraindication to MRI or LP;

Enrollment in any other clinical study with an investigational product within 4 weeks prior to screening or within 5 half-lives of the investigational product used in that clinical study, whichever is longer;

Has previously undergone allogeneic HSCT and has evidence of residual cells of donor origin;

Previous gene therapy.

Route of Administration and Procedure are described in detail below.

AAV.CB7.CI.hARSAco.rBG is administered as a single dose to hospitalized subjects on Day 0 via real-time CT-guided sub-occipital injection into the cisterna *magna*.

On Day 0, a syringe containing 5.6 mL of AAV.CB7.CI.hARSAco.rBG at the appropriate titer is prepared by the Investigational Pharmacy associated with the study and delivered to the procedure room.

Prior to study drug administration, the subject is anesthetized, intubated, and the injection site is prepped and draped using sterile technique. An LP is performed to remove a predetermined volume of CSF, after which iodinated contrast is IT injected to aid in visualization of relevant anatomy of the cisterna *magna*. IV contrast may be administered prior to or during needle insertion as an alternative to the IT contrast. The decision to use IV or IT contrast is at the discretion of the interventionalist performing the procedure. A spinal needle (22-25 G) is advanced into the cisterna *magna* under CT-fluoroscopic guidance. A larger introducer needle may be used to assist with needle placement. After confirmation of needle placement, the extension set is attached to the spinal needle and allowed to fill with CSF. At the discretion of the interventionalist, a syringe containing contrast material may be connected to the extension set and a small amount injected to confirm needle placement in the cisterna *magna*. After the needle placement is confirmed, the syringe containing AAV.CB7.CI.hARSAco.rBG is connected to the extension set. The syringe contents are slowly injected over 1-2 minutes, delivering a volume of 5.0 mL.

Safety assessments, including collection of Adverse Events (AEs) and Serious Adverse Events (SAEs), physical and neurologic examinations, vital signs, clinical laboratory tests (serum chemistry, hematology, coagulation, LFTs, urinalysis), ECGs, nerve conduction studies, and CSF cytology and chemistry (cell counts, protein, glucose) are performed. Safety evaluations after the first three subjects in Cohort 1 and after the first three subjects in Cohort 2 are conducted.

Statistical comparisons are performed for secondary and exploratory endpoints. Measurements at each time point are compared to baseline values for each subject, as well as data from age-matched healthy controls and natural history data from MLD patients with comparable cohort characteristics where available for each endpoint.

All data is presented in subject data listings. Categorical variables are summarized using frequencies and percentages, and continuous variables are summarized using descriptive statistics (number of non-missing observations, mean, standard deviation, median, minimum, and maximum). Graphical displays are presented as appropriate.

Example 11—AAVhu68+Deamidation

AAVhu68 was analyzed for modifications. Briefly, AAVhu68 vectors were produced using vector genomes which are not relevant to this study, each produced using conventional triple transfection methods in 293 cells. For a general description of these techniques, see, e.g., Bell CL, et al., The AAV9 receptor and its modification to improve in vivo lung gene transfer in mice. J Clin Invest. 2011; 121: 2427-2435. Briefly, a plasmid encoding the sequence to be packaged (a transgene expressed from a chicken β-actin promoter, an intron and a poly A derived from Simian Virus 40 (SV40) late gene) flanked by AAV2 inverted terminal repeats, was packaged by triple transfection of HEK293 cells with plasmids encoding the AAV2 rep gene and the AAVhu68 cap gene and an adenovirus helper plasmid (pAdAF6). The resulting AAV viral particles can be purified using CsCl gradient centrifugation, concentrated, and frozen for later use.

Denaturation and alkylation: To 100 μg of the thawed viral preparation (protein solution), add 2 μl of 1M Dithiothreitol (DTT) and 2 μl of 8M guanidine hydrochloride (GndHCl) and incubate at 90° C. for 10 minutes. Allow the solution to cool to room temperature then add 5 μl of freshly prepared 1M iodoacetamide (IAM) and incubate for 30 minutes at room temperature in the dark. After 30 minutes, quench alkylation reaction by adding 1 μl of 1 M DTT.

Digestion: To the denatured protein solution add 20 mM Ammonium Bicarbonate, pH 7.5-8 at a volume that dilutes the final GndHCl concentration to 800 mM. Add trypsin solution for a 1:20 trypsin to protein ratio and incubate at 37° C. overnight. After digestion, add TFA to a final of 0.5% to quench digestion reaction.

Mass Spectrometry: Approximately 1 microgram of the combined digestion mixture is analyzed by UHPLC-MS/

MS. LC is performed on an UltiMate 3000 RSLCnano System (Thermo Scientific). Mobile phase A is MilliQ water with 0.1% formic acid. Mobile phase B is acetonitrile with 0.1% formic acid. The LC gradient is run from 4% B to 6% B over 15 min, then to 10% B for 25 min (40 minutes total), then to 30% B for 46 min (86 minutes total). Samples are loaded directly to the column. The column size is 75 cm×15 μm I.D. and is packed with 2 micron C18 media (Acclaim PepMap). The LC is interfaced to a quadrupole-Orbitrap mass spectrometer (Q-Exactive HF, Thermo Scientific) via nanoflex electrospray ionization using a source. The column is heated to 350C and an electrospray voltage of 2.2 kV is applied. The mass spectrometer is programmed to acquire tandem mass spectra from top 20 ions. Full MS resolution to 120,000 and MS/MS resolution to 30,000. Normalized collision energy is set to 30, automatic gain control to 1e5, max fill MS to 100 ms, max fill MS/MS to 50 ms.

Data Processing: Mass spectrometer RAW data files were analyzed by BioPharma Finder 1.0 (Thermo Scientific). Briefly, all searches required 10 ppm precursor mass tolerance, 5 ppm fragment mass tolerance, tryptic cleavage, up to 1 missed cleavages, fixed modification of cysteine alkylation, variable modification of methionine/tryptophan oxidation, asparagine/glutamine deamidation, phosphorylation, methylation, and amidation.

In the following table, T refers to the trypsin and C refers to chymotrypsin.

| | Modification AAVhu68 | | | | | | | | | | |
|---|---|---|---|---|---|---|---|---|---|---|---|
| Enzyme | T | T | T | T | C | C | C | C | T | T | T |
| % Coverage | 93.6 | 92 | 93.1 | 92.5 | 90.2 | 89.7 | 91.1 | 88.9 | 98.9 | 97 | 94.6 | 92.4 |
| +Deamidation (Deamid) | | | | | | | | | | | |
| ~N35 | | | | | | | | | | | |
| N57 + Deamid | 87.6 | 95.5 | 89.3 | 88.2 | 90.5 | 96.3 | 86.4 | 84.8 | 100.0 | 100.0 | 99.0 | 92.7 |
| N66 + Deamid | 4.7 | | | | | | | | | | |
| N94 + Deamid | 11.3 | 10.9 | 11.0 | 5.3 | 11.6 | 10.4 | 10.8 | 5.6 | 5.0 | 11.1 | 5.4 | 16.0 |
| N113 + Deamid | | | 1.8 | | | | | | | | |
| ~N253 + Deamid | 17.7 | 22.0 | 21.1 | 15.0 | 17.0 | 22.6 | 20.5 | 15.6 | 4.2 | 5.5 | |
| Q259 + Deamid | 35.2 | 25.6 | 21.0 | | 35.4 | 26.3 | 20.9 | 9.2 | | | |
| ~N270 + Deamid | 16.4 | 25.1 | 23.2 | 16.6 | 15.9 | 24.9 | 23.5 | 16.1 | 0.2 | | |
| ~N304 + Deamid | 2.6 | 2.9 | 2.8 | 1.3 | 2.5 | 2.8 | 2.9 | 1.3 | 16.6 | 10.3 | |
| ~N314 + Deamid | | | | | | | | | 6.5 | | |
| N319 + Deamid | 0.3 | 2.8 | 2.8 | 0.2 | | 2.9 | 2.8 | 0.2 | | | |
| N329 + Deamid | 72.7 | 85.6 | 89.1 | 86.8 | 71.0 | 87.2 | 88.7 | 84.7 | 85.5 | 79.4 | 78.9 | 91.8 |
| N336 + Deamid | | 30.8 | 9.3 | 100.0 | | 31.0 | 9.2 | 95.7 | | | |
| ~N409 + Deamid | 21.3 | 22.9 | 23.9 | 24.0 | 22.0 | 23.4 | 24.7 | 24.2 | | | |
| N452 + Deamid | 98.8 | 99.7 | 99.2 | 100.0 | 98.9 | 97.3 | 98.1 | 95.2 | 98.2 | 68.7 | 67.4 | 49.4 |
| N477 + Deamid | 4.4 | 4.3 | 4.3 | 2.6 | 4.5 | 4.4 | 4.3 | 2.6 | | | 0.8 | |
| N512 + Deamid | 97.5 | 97.9 | 95.3 | 95.7 | 92.2 | 91.8 | 99.2 | 96.1 | 99.7 | 98.2 | 87.9 | 75.7 |
| ~N515 + Deamid | 8.2 | 21.0 | 16.0 | | 8.3 | 21.0 | 16.5 | 0.0 | 2.5 | 3.0 | | 15.1 |
| ~Q599 + Deamid | 4.0 | 15.4 | 10.1 | 13.6 | 4.0 | 15.5 | 10.0 | 13.8 | 15.8 | | |
| N628 + Deamid | 5.3 | | 5.6 | | 5.4 | 0.0 | 5.4 | 0.0 | | | |
| N651 + Deamid | 0.9 | 1.6 | 1.6 | | | | | | 0.5 | | |
| N663 + Deamid | 3.4 | | 3.5 | | 3.7 | 3.4 | 0.0 | 3.4 | 3.6 | | |
| N709 + Deamid | 0.6 | 0.8 | 20.2 | 0.6 | 0.6 | 0.8 | 19.8 | 0.6 | 0.3 | 1.3 | 0.1 | 0.2 |
| N735 | | | | | | | | | 25.0 | 42.7 | | 21.7 |
| +Acetylation (Ac): | | | | | | | | | | | |
| K332 + Ac | | | | 100.0 | | | | | | | |
| ~K693 + Ac | 13.0 | | 13.5 | | | | | | | | |
| ~K666 + Ac | | | | 93.8 | | | | | | | |
| ~K68 + Ac | | 59.2 | | | | | | | | | |
| +Isomerization (Iso): | | | | | | | | | | | |
| D97 + Iso | 0.5 | 0.4 | 0.4 | 0.2 | 0.5 | | 0.4 | 0.2 | | | |
| D107 + Iso | | 0.3 | | 0.3 | | 0.3 | | | | | |
| D384 + Iso | 0.8 | | | | | 0.9 | | | | | |
| +Phosphorylation (Phos) | | | | | | | | | | | |
| S149 + Phos | 5.8 | 5.7 | 5.2 | 9.8 | 5.7 | 5.9 | 5.2 | 9.9 | | | |
| ~S499 + Phos | | | | 30.6 | | | | | | | |
| ~T569 + Phos | 0.9 | | | | | | | | | | |
| ~S586 + Phos | | 3.6 | | | | | | | | | |
| +Oxidation | | | | | | | | | | | |
| ~W23 + Oxi | | 4.7 | 5.5 | | | 4.8 | 5.5 | | | | |
| W247 + Oxi | 1.5 | 0.4 | 0.7 | | 1.4 | | | | | | |
| W247 + Oxi to kynurenine | | 0.1 | | | | 0.1 | | | | | |
| W306 + Oxi | 0.7 | 0.9 | 1.6 | 1.8 | 0.7 | 1.0 | 1.6 | 1.8 | | | |
| W306 + Oxidation to kynurenine | | | 0.3 | | | | 0.3 | | | | |
| M404 + Oxi | 0.1 | | 0.2 | | 0.1 | | 0.2 | | | | |
| M436 + Oxi | 4.9 | | 10.2 | 23.0 | 4.8 | | 10.2 | 22.6 | | | |
| ~M518 + Oxi | 29.9 | | 1.5 | 10.6 | 29.9 | | 1.5 | 10.5 | | | |
| ~M524 + Oxi | 18.8 | 31.6 | 52.7 | | 18.4 | 31.1 | 52.5 | 14.2 | | | |
| M559 + Oxi | 19.0 | 21.6 | 19.6 | 20.9 | 19.6 | 21.3 | 20.1 | 20.9 | | | |
| ~M605 + Oxi | 12.2 | 15.2 | | | 12.8 | 14.8 | | | | | |
| W619 + Oxi | 1.0 | | 0.6 | 1.5 | 1.0 | | 0.6 | 1.5 | | | |

-continued

| | | | | | | | | |
|---|---|---|---|---|---|---|---|---|
| W619 + Oxidation | | | 20.3 | | | | | |
| ~M640 + Oxi | 23.5 | 64.2 | 24.6 | | 22.4 | 21.1 | 25.6 | |
| W695 + Oxi | 0.3 | | | 0.4 | 0.4 | 0.3 | 0.4 | 0.4 |
| +Amidation | | | | | | | | |
| ~D297 + Amidation | | 72.9 | | 73.3 | | | | |

In the case of the AAVhu68 capsid protein, 4 residues (N57, N329, N452, N512) routinely display levels of deamidation >70% and it most cases >90% across various lots. Additional asparagine residues (N94, N253, N270, N304, N409, N477, and Q599) also display deamidation levels up to ~20% across various lots. The deamidation levels were initially identified using a trypsin digest and verified with a chymotrypsin digestion.

Adult Rhesus macaques were ICM-administered AAVhu68.CB7.CI.eGFP.WPRE.rBG ($3.00 \times 10^{13}$ GC) and necropsied 28 days later to assess vector transduction. Transduction of AAVhu68 was observed in widespread areas of the brain. Thus, the AAVhu68 capsid provides the possibility of cross-correction in the CNS.

REFERENCES

Abbott N.J. (2013). "Blood-brain barrier structure and function and the challenges for CNS drug delivery." J Inherit Metab Dis. 36 (3): 437-49.

Absoud M., Cummins C., Chong W.K., De Goede C., Foster K., Gunny R., Hemingway C., Jardine P., Kneen R., Likeman M., Lim M.J., Pike M., Sibtain N., Whitehouse W.P., & Wassmer E. (2011). "Paediatric UK demyelinating disease longitudinal study (PUDDLS)." BMC Pediatrics. 11 (1): 68.

Albers C.A. & Grieve A.J. (2007). "Test Review: Bayley, N. (2006). Bayley Scales of Infant and Toddler Development-Third Edition. San Antonio, TX: Harcourt Assessment." J of Psychoed Assess. 25 (2): 180-190.

Alotaibi M., Long T., Kennedy E., & Bavishi S. (2014). "The efficacy of GMFM-88 and GMFM-66 to detect changes in gross motor function in children with cerebral palsy (CP): a literature review." Disabil Rehabil. 36 (8): 617-27.

Arbour L.T., Silver K., Hechtman P., Treacy E.P., & Coulter-Mackie M.B. (2000). "Variable onset of metachromatic leukodystrophy in a Vietnamese family." Pediatr Neurol. 23 (2): 173-6.

Aubourg P. (2016). "Gene therapy for leukodystrophy: progress, challenges and opportunities." Exp Opin Orph Drugs. 4 (4): 359-367.

Audentes (2018). Audentes announces continuing positive data from first dose cohort of ASPIRO, a Phase 1/2 clinical trial of AT132 in patients with X-linked myotubular myopathy.

Bartus R.T., Weinberg M.S., & Samulski R.J. (2014). "Parkinson's disease gene therapy: Success by design meets failure by efficacy." Mol Ther. 22 (3): 487-497.

Batzios S.P. & Zafeiriou D.I. (2012). "Developing treatment options for metachromatic leukodystrophy." Mol Genet Metab. 105 (1): 56-63.

Baumann N., Turpin J.C., Lefevre M., & Colsch B. (2002). "Motor and psycho-cognitive clinical types in adult metachromatic leukodystrophy: genotype/phenotype relationships?" J Physiol Paris. 96 (3-4): 301-6.

Bell P., Hinderer C., Louboutin J.P., Yu H., Grant R., Bote E., & Wilson J.M. (2015). "Motor neuron transduction after intracisternal delivery of AAV9 in a cynomolgus macaque." Hum Gene Ther Methods. 26 (2): 43-4.

Bell P., Moscioni A.D., McCarter R.J., Wu D., Gao G., Hoang A., Sanmiguel J.C., Sun X., Wivel N.A., Raper S.E., Furth E.E., Batshaw M.L., & Wilson J.M. (2006). "Analysis of tumors arising in male B6C3F1 mice with and without AAV vector delivery to liver." Mol Ther. 14 (1): 34-44.

Bell P., Wang L., Lebherz C., Flieder D.B., Bove M.S., Wu D., Gao G.P., Wilson J.M., & Wivel N.A. (2005). "No evidence for tumorigenesis of AAV vectors in a large-scale study in mice." Mol Ther. 12 (2): 299-306.

Bevan A.K., Duque S., Foust K.D., Morales P.R., Braun L., Schmelzer L., Chan C.M., McCrate M., Chicoine L.G., Coley B.D., Porensky P.N., Kolb S., Mendell J.R., Burghes A.H., & Kaspar B.K. (2011). "Systemic gene delivery in large species for targeting spinal cord, brain, and peripheral tissues for pediatric disorders." Mol Ther. 19 (11): 1971-80.

Biffi A. (2017). "Hematopoietic stem cell gene therapy for storage disease: Current and new indications." Mol Ther. 25 (5): 1155-1162.

Biffi A., Cesani M., Fumagalli F., Del Carro U., Baldoli C., Canale S., Gerevini S., Amadio S., Falautano M., Rovelli A., Comi G., Roncarolo M.G., & Sessa M. (2008). "Metachromatic leukodystrophy-mutation analysis provides further evidence of genotype-phenotype correlation." Clin Genet. 74 (4): 349-57.

Biffi A., De Palma M., Quattrini A., Del Carro U., Amadio S., Visigalli I., Sessa M., Fasano S., Brambilla R., Marchesini S., Bordignon C., & Naldini L. (2004). "Correction of metachromatic leukodystrophy in the mouse model by transplantation of genetically modified hematopoietic stem cells." J Clin Invest. 113 (8): 1118-29.

Biffi A., Montini E., Lorioli L., Cesani M., Fumagalli F., Plati T., Baldoli C., Martino S., Calabria A., Canale S., Benedicenti F., Vallanti G., Biasco L., Leo S., Kabbara N., Zanetti G., Rizzo W.B., Mehta N.A., Cicalese M.P., Casiraghi M., Boelens J.J., Del Carro U., Dow D.J., Schmidt M., Assanelli A., Neduva V., Di Serio C., Stupka E., Gardner J., von Kalle C., Bordignon C., Ciceri F., Rovelli A., Roncarolo M.G., Aiuti A., Sessa M., & Naldini L. (2013). "Lentiviral hematopoietic stem cell gene therapy benefits metachromatic leukodystrophy." Science. 341 (6148): 1233158.

Bisgaard A.M., Kirchhoff M., Nielsen J.E., Kibaek M., Lund A., Schwartz M., & Christensen E. (2009). "Chromosomal deletion unmasking a recessive disease: 22q13 deletion syndrome and metachromatic leukodystrophy." Clin Genet. 75 (2): 175-9.

Boucher A.A., Miller W., Shanley R., Ziegler R., Lund T., Raymond G., & Orchard P.J. (2015). "Long-term outcomes after allogeneic hematopoietic stem cell transplantation for metachromatic leukodystrophy: the largest single-institution cohort report." Orphanet J Rare Dis. 10:94.

Bredius R.G., Laan L.A., Lankester A.C., Poorthuis B.J., van Tol M.J., Egeler R.M., & Arts W.F. (2007). "Early marrow transplantation in a pre-symptomatic neonate with late infantile metachromatic leukodystrophy does not halt disease progression." Bone Marrow Transplant. 39 (5): 309-10.

Bryant L.M., Christopher D.M., Giles A.R., Hinderer C., Rodriguez. J.L., Smith J.B., Traxler E.A., Tycko J., Wojno A.P., & Wilson J.M. (2013). "Lessons learned from the clinical development and market authorization of Glybera." Hum Gene Ther Clin Dev. 24 (2): 55-64.

Calcedo R., Vandenberghe L.H., Gao G., Lin J., & Wilson J.M. (2009). "Worldwide epidemiology of neutralizing antibodies to adeno-associated viruses." J Infect Dis. 199 (3): 381-90.

Cameron C.L., Kang P.B., Burns T.M., Darras B.T., & Jones H.R., Jr. (2004). "Multifocal slowing of nerve conduction in metachromatic leukodystrophy." Muscle Nerve. 29 (4): 531-6.

Castle M.J., Perlson E., Holzbaur E.L., & Wolfe J.H. (2014). "Long-distance axonal transport of AAV9 is driven by dynein and kinesin-2 and is trafficked in a highly motile Rab7-positive compartment." Mol Ther. 22 (3): 554-566.

Cearley C.N., Vandenberghe L.H., Parente M.K., Carnish E.R., Wilson J.M., & Wolfe J.H. (2008). "Expanded repertoire of AAV vector serotypes mediate unique patterns of transduction in mouse brain." Mol Ther. 16 (10): 1710-8.

Cesani M., Capotondo A., Plati T., Sergi L.S., Fumagalli F., Roncarolo M.G., Naldini L., Comi G., Sessa M., & Biffi A. (2009). "Characterization of new arylsulfatase A gene mutations reinforces genotype-phenotype correlation in metachromatic leukodystrophy." Hum Mutat. 30 (10): E936-45.

Cesani M., Lorioli L., Grossi S., Amico G., Fumagalli F., Spiga I., Filocamo M., & Biffi A. (2016). "Mutation Update of ARSA and PSAP Genes Causing Metachromatic Leukodystrophy." Hum Mutat. 37 (1): 16-27.

Chandler R.J., LaFave M.C., Varshney G.K., Trivedi N.S., Carrillo-Carrasco N., Senac J.S., Wu W., Hoffmann V., Elkahloun A.G., Burgess S.M., & Venditti C.P. (2015). "Vector design influences hepatic genotoxicity after adeno-associated virus gene therapy." J Clin Invest. 125 (2): 870-80.

Chen X., Gill D., Shaw P., Ouvrier R., & Troedson C. (2016). "Outcome of Early Juvenile Onset Metachromatic Leukodystrophy After Unrelated Cord Blood Transplantation: A Case Series and Review of the Literature." J Child Neurol. 31 (3): 338-44.

Ciesielska A., Hadaczek P., Mittermeyer G., Zhou S., Wright J.F., Bankiewicz K.S., & Forsayeth J. (2013). "Cerebral infusion of AAV9 vector-encoding non-self proteins can elicit cell-mediated immune responses." Mol Ther. 21 (1): 158-66.

Clarke J.T., Skomorowski M.A., & Chang P.L. (1989). "Marked clinical difference between two sibs affected with juvenile metachromatic leukodystrophy." Am J Med Genet. 33 (1): 10-3.

Colle M.A., Piguet F., Bertrand L., Raoul S., Bieche I., Dubreil L., Sloothaak D., Bouquet C., Moullier P., Aubourg P., Cherel Y., Cartier N., & Sevin C. (2010). "Efficient intracerebral delivery of AAV5 vector encoding human ARSA in non-human primate." Hum Mol Genet. 19 (1): 147-58.

Consolaro A. & Ravelli A. (2016). "Chapter 5-Assessment Tools in Juvenile Idiopathic Arthritis." Handbook of Systemic Autoimmune Diseases. R. Cimaz and T. Lehman: Elsevier. 11:107-127.

Couto L., Parker A., & Gordon J.W. (2004). "Direct exposure of mouse spermatozoa to very high concentrations of a serotype-2 adeno-associated virus gene therapy vector fails to lead to germ cell transduction." Hum Gene Ther. 15 (3): 287-91.

Dali C.I., Barton N.W., Farah M.H., Moldovan M., Mansson J.E., Nair N., Duno M., Risom L., Cao H., Pan L., Sellos-Moura M., Corse A.M., & Krarup C. (2015). "Sulfatide levels correlate with severity of neuropathy in metachromatic leukodystrophy." Ann Clin Transl Neurol. 2 (5): 518-33.

Dali C.I., Hanson L.G., Barton N.W., Fogh J., Nair N., & Lund A.M. (2010). "Brain N-acetylaspartate levels correlate with motor function in metachromatic leukodystrophy." Neurology. 75 (21): 1896-903.

de Hosson L.D., van de Warrenburg B.P., Preijers F.W., Blijlevens N.M., van der Reijden B.A., Kremer H.P., Lefeber D.J., Allebes W.A., Al-Ali H., Niederwieser D.W., Schaap N.P., & Schattenberg A.V. (2011). "Adult metachromatic leukodystrophy treated by allo-SCT and a review of the literature." Bone Marrow Transplant. 46 (8): 1071-6.

Dekaban A.S. (1978). "Changes in brain weights during the span of human life: relation of brain weights to body heights and body weights." Ann Neurol. 4 (4): 345-56.

Deverman B.E., Pravdo P.L., Simpson B.P., Kumar S.R., Chan K.Y., Banerjee A., Wu W.L., Yang B., Huber N., Pasca S.P., & Gradinaru V. (2016). "Cre-dependent selection yields AAV variants for widespread gene transfer to the adult brain." Nat Biotechnol. 34 (2): 204-9.

Ding X.Q., Bley A., Kohlschutter A., Fiehler J., & Lanfermann H. (2012). "Long-term neuroimaging follow-up on an asymptomatic juvenile metachromatic leukodystrophy patient after hematopoietic stem cell transplantation: evidence of myelin recovery and ongoing brain maturation." Am J Med Genet A. 158a (1): 257-60.

Donsante A., Vogler C., Muzyczka N., Crawford J.M., Barker J., Flotte T., Campbell-Thompson M., Daly T., & Sands M.S. (2001). "Observed incidence of tumorigenesis in long-term rodent studies of rAAV vectors." Gene Ther. 8 (17): 1343-6.

Duyff R.F. & Weinstein H.C. (1996). "Late-presenting metachromatic leukodystrophy." Lancet. 348 (9038): 1382-3.

Ellinwood N.M., Ausseil J., Desmaris N., Bigou S., Liu S., Jens J.K., Snella E.M., Mohammed E.E., Thomson C.B., Raoul S., Joussemet B., Roux F., Cherel Y., Lajat Y., Piraud M., Benchaouir R., Hermening S., Petry H., Froissart R., Tardieu M., Ciron C., Moullier P., Parkes J., Kline K.L., Maire I., Vanier M.T., Heard J.M., & Colle M.A. (2011). "Safe, efficient, and reproducible gene therapy of the brain in the dog models of Sanfilippo and Hurler syndromes." Mol Ther. 19 (2): 251-9.

Ferla R., Alliegro M., Marteau J.B., Dell'Anno M., Nusco E., Pouillot S., Galimberti S., Valsecchi M.G., Zuliani V., & Auricchio A. (2017). "Non-clinical safety and efficacy of an AAV2/8 vector administered intravenously for treatment of Mucopolysaccharidosis Type VI." Mol Ther Methods Clin Dev. 6:143-158.

Flanigan K. (2018). Voyager Therapeutics Corpoate Presentation. ASGCT Annual Meeting.

Foust K.D., Nurre E., Montgomery C.L., Hernandez A., Chan C.M., & Kaspar B.K. (2009). "Intravascular AAV9 preferentially targets neonatal neurons and adult astrocytes." Nat Biotechnol. 27 (1): 59-65.

Frati G., Luciani M., Meneghini V., De Cicco S., Stahlman M., Blomqvist M., Grossi S., Filocamo M., Morena F., Menegon A., Martino S., & Gritti A. (2018). "Human iPSC-based models highlight defective glial and neuronal differentiation from neural progenitor cells in metachromatic leukodystrophy." Cell Death Dis. 9 (6): 698.

Fumagalli F., Calbi V., Zambon A., Ciotti F., Lorioli L., Sessa M., Sarzana M., Canale S., Antonioli G., Medaglini S., Del Carro U., Quattrini A., Baldoli C., Martino S., Di Serio C., Ciceri F., Naldini L., Natali Sora M.G., Biffi A., & Aiuti A. (2017). "Update on safety and efficacy of lentiviral hematopoietic stem cell gene therapy (HSC-GT) for metachromatic leukodystrophy (MLD)." Eur J of Paed Neurol. 21: e20.

Gallo S., Randi D., Bertelli M., Salviati A., & Pandolfo M. (2004). "Late onset MLD with normal nerve conduction associated with two novel missense mutations in the ASA gene." J Neurol Neurosurg Psychiatry. 75 (4): 655-7.

Gao G., Vandenberghe L.H., Alvira M.R., Lu Y., Calcedo R., Zhou X., & Wilson J.M. (2004). "Clades of adeno-associated viruses are widely disseminated in human tissues." J Virol. 78 (12): 6381-8.

Garavelli L., Rosato S., Mele A., Wischmeijer A., Rivieri F., Gelmini C., Sandona F., Sassatelli R., Carlinfante G., Giovanardi F., Gemmi M., Della Giustina E., Amarri S., Banchini G., & Bedogni G. (2009). "Massive hemobilia and papillomatosis of the gallbladder in metachromatic leukodystrophy: a life-threatening condition." Neuropediatrics. 40 (6): 284-6.

Ghosh P., Dahms N.M., & Kornfeld S. (2003). "Mannose 6-phosphate receptors: new twists in the tale." Nat Rev Mol Cell Biol. 4 (3): 202-12.

Gieselmann V. & Krageloh-Mann I. (2010). "Metachromatic leukodystrophy—an update." Neuropediatrics. 41 (1): 1-6.

Gieselmann V., Matzner U., Hess B., Lullmann-Rauch R., Coenen R., Hartmann D., D'Hooge R., DeDeyn P., & Nagels G. (1998). "Metachromatic leukodystrophy: Molecular genetics and an animal model." J Inherit Metab Dis. 21 (5): 564-74.

Gieselmann V., Polten A., Kreysing J., & von Figura K. (1989). "Arylsulfatase A pseudodeficiency: loss of a polyadenylylation signal and N-glycosylation site." Proc Natl Acad Sci USA. 86 (23): 9436-40.

Gieselmann V. & von Figura K. (1990). "Advances in the molecular genetics of metachromatic leukodystrophy." J Inherit Metab Dis. 13 (4): 560-71.

Gil-Farina I., Fronza R., Kaeppel C., Lopez-Franco E., Ferreira V., D'Avola D., Benito A., Prieto J., Petry H., Gonzalez-Aseguinolaza G., & Schmidt M. (2016). "Recombinant AAV integration is not associated with hepatic genotoxicity in nonhuman primates and patients." Mol Ther. 24 (6): 1100-1105.

Giugliani R., Dali C., Sevin C., Krägeloh-Mann I., Troedson C., Sakai N., Wu J., & Wasilewski M. (2018). "Intrathecal delivery of recombinant human arylsulfatase A in children with late-infantile metachromatic leukodystrophy: A post hoc analysis of responders and non-responders." Molec Genet Metab. 123 (2): S54.

Godel T., Pham M., Heiland S., Bendszus M., & Baumer P. (2016). "Human dorsal-root-ganglion perfusion measured in-vivo by MRI." Neuroimage. 141:81-87.

Gombash S.E., Cowley C.J., Fitzgerald J.A., Lepak C.A., Neides M.G., Hook K., Todd L.J., Wang G.D., Mueller C., Kaspar B.K., Bielefeld E.C., Fischer A.J., Wood J.D., & Foust K.D. (2017). "Systemic gene delivery transduces the enteric nervous system of guinea pigs and cynomolgus macaques." Gene Ther. 24 (10): 640-648.

Gomez-Ospina N. (2017). "Arylsulfatase A Deficiency." GeneReviews. M. P. Adam, H. H. Ardinger, R. A. Pagon et al. (eds). Seattle, WA: University of Washington, Seattle.

Graham F.L., Smiley J., Russell W.C., & Nairn R. (1977). "Characteristics of a human cell line transformed by DNA from human adenovirus type 5." J Gen Virol. 36 (1): 59-74.

Gray S., Matagne V., Bachaboina L., Yadav S., Ojeda S.R., & Samulski R.J. (2011). "Preclinical differences of intravascular AAV9 delivery to neurons and glia: a comparative study of adult mice and nonhuman primates." Mol Ther. 19 (6): 1058-69.

Gray S., Nagabhushan Kalburgi S., McCown T.J., & Jude Samulski R. (2013). "Global CNS gene delivery and evasion of anti-AAV-neutralizing antibodies by intrathecal AAV administration in non-human primates." Gene Ther. 20 (4): 450-9.

Greig J.A., Limberis M.P., Bell P., Chen S., Calcedo R., Rader D.J., & Wilson J.M. (2017). "Non-clinical study examining AAV8.TBG.hLDLR vector-associated toxicity in chow-fed wild-type and LDLR (+/−) Rhesus macaques." Hum Gene Ther Clin Dev. 28 (1): 39-50.

Groeschel S., Kehrer C., Engel C., C I.D., Bley A., Steinfeld R., Grodd W., & Krageloh-Mann I. (2011). "Metachromatic leukodystrophy: natural course of cerebral MRI changes in relation to clinical course." J Inherit Metab Dis. 34 (5): 1095-102.

Gu Z., Liu Y., Zhang Y., Jin S., Chen Q., Goltzman D., Karaplis A., & Miao D. (2012). "Absence of PTHrP nuclear localization and carboxyl terminus sequences leads to abnormal brain development and function." PLOS One. 7 (7): e41542.

Gurda B.L., De Guilhem De Lataillade A., Bell P., Zhu Y., Yu H., Wang P., Bagel J., Vite C.H., Sikora T., Hinderer C., Calcedo R., Yox A.D., Steet R.A., Ruane T., O'Donnell P., Gao G., Wilson J.M., Casal M., Ponder K.P., & Haskins M.E. (2016). "Evaluation of AAV-mediated gene therapy for central nervous system disease in canine Mucopolysaccharidosis VII." Mol Ther. 24 (2): 206-216.

Guyenet S., Furrer S.A., Damian V.M., Baughan T.D., La Spada A.R., & Garden G.A. (2010). "A simple composite phenotype scoring system for evaluating mouse models of cerebellar ataxia." J Vis Exp (39).

Hageman A.T., Gabreels F.J., de Jong J.G., Gabreels-Festen A.A., van den Berg C.J., van Oost B.A., & Wevers R.A. (1995). "Clinical symptoms of adult metachromatic leukodystrophy and arylsulfatase A pseudodeficiency." Arch Neurol. 52 (4): 408-13.

Haurigot V., Marco S., Ribera A., Garcia M., Ruzo A., Villacampa P., Ayuso E., Anor S., Andaluz A., Pineda M., Garcia-Fructuoso G., Molas M., Maggioni L., Munoz S., Motas S., Ruberte J., Mingozzi F., Pumarola M., & Bosch F. (2013). "Whole body correction of mucopolysaccharidosis IIIA by intracerebrospinal fluid gene therapy." J Clin Invest.

Heim P., Claussen M., Hoffmann B., Conzelmann E., Gartner J., Harzer K., Hunneman D.H., Kohler W., Kurlemann G., & Kohlschutter A. (1997). "Leukodystrophy incidence in Germany." Am J Med Genet. 71 (4): 475-8.

Herndon J.G., Tigges J., Klumpp S.A., & Anderson D.C. (1998). "Brain weight does not decrease with age in adult rhesus monkeys." Neurobiol Aging. 19 (3): 267-72.

Hess B., Saftig P., Hartmann D., Coenen R., Lullmann-Rauch R., Goebel H.H., Evers M., von Figura K., D'Hooge R., Nagels G., De Deyn P., Peters C., & Gieselmann V. (1996). "Phenotype of arylsulfatase A-deficient mice: relationship to human metachromatic leukodystrophy." Proc Natl Acad Sci USA. 93 (25): 14821-6.

Hinderer C., Bell P., Katz N., Vite C.H., Louboutin J.P., Bote E., Yu H., Zhu Y., Casal M.L., Bagel J., O'Donnell P., Wang P., Haskins M.E., Goode T., & Wilson J.M. (2018). "Evaluation of intrathecal routes of administration for adeno-associated viral vectors in large animals." Hum Gene Ther. 29 (1): 15-24.

Hinderer C., Bell P., Vite C.H., Louboutin J.P., Grant R., Bote E., Yu H., Pukenas B., Hurst R., & Wilson J.M. (2014). "Widespread gene transfer in the central nervous system of cynomolgus macaques following delivery of AAV9 into the cisterna *magna*." Mol Ther Methods Clin Dev. 1:14051.

Hinderer C., Katz N., Louboutin J.P., Bell P., Yu H., Nayal M., Kozarsky K., O'Brien W.T., Goode T., & Wilson J.M. (2016). "Delivery of an adeno-associated virus vector into cerebrospinal fluid attenuates central nervous system disease in Mucopolysaccharidosis Type II mice." Hum Gene Ther. 27 (11): 906-915.

Hordeaux J., Hinderer C., Goode T., Katz N., Buza E.L., Bell P., Calcedo R., Richman L.K., & Wilson J.M. (2018). "Toxicology study of intra-cisterna *magna* adeno-associated virus 9 expressing human alpha-L-iduronidase in Rhesus macaques." Mol Ther Methods Clin Dev. 10:79-88.

Hordeaux J., Yuan Y., Clark P.M., Wang Q., Martino R.A., Sims J.J., Bell P., Raymond A., Stanford W.L., & Wilson J.M. (2019). "The GPI-Linked Protein LY6A Drives AAV-PHP.B Transport across the Blood-Brain Barrier." Molec Ther.

Hyde T.M., Ziegler J.C., & Weinberger D.R. (1992). "Psychiatric disturbances in metachromatic leukodystrophy. Insights into the neurobiology of psychosis." Arch Neurol. 49 (4): 401-6.

Iannaccone S.T., Hynan L.S., Morton A., Buchanan R., Limbers C.A., Varni J.W., & Am S.G. (2009). "The PedsQL in pediatric patients with Spinal Muscular Atrophy: feasibility, reliability, and validity of the Pediatric Quality of Life Inventory Generic Core Scales and Neuromuscular Module." Neuromuscular disorders: NMD. 19 (12): 805-812.

Jabbehdari S., Rahimian E., Jafari N., Sanii S., Khayatzadehkakhki S., & Nejad Biglari H. (2015). "The clinical features and diagnosis of Metachromatic leukodystrophy: A case series of Iranian Pediatric Patients." Iran J Child Neurol. 9 (3): 57-61.

Jakob M., Muhle C., Park J., Weiss S., Waddington S., & Schneider H. (2005). "No evidence for germ-line transmission following prenatal and early postnatal AAV-mediated gene delivery." J Gene Med. 7 (5): 630-7.

Janson C., McPhee S., Bilaniuk L., Haselgrove J., Testaiuti M., Freese A., Wang D.J., Shera D., Hurh P., Rupin J., Saslow E., Goldfarb O., Goldberg M., Larijani G., Sharrar W., Liouterman L., Camp A., Kolodny E., Samulski J., & Leone P. (2002). "Clinical protocol. Gene therapy of Canavan disease: AAV-2 vector for neurosurgical delivery of aspartoacylase gene (ASPA) to the human brain." Hum Gene Ther. 13 (11): 1391-412.

Kapaun P., Dittmann R.W., Granitzny B., Eickhoff W., Wulbrand H., Neumaier-Probst E., Zander A., & Kohlschuetter A. (1999). "Slow progression of juvenile metachromatic leukodystrophy 6 years after bone marrow transplantation." J Child Neurol. 14 (4): 222-8.

Kaplitt M.G., Feigin A., Tang C., Fitzsimons H.L., Mattis P., Lawlor P.A., Bland R.J., Young D., Strybing K., Eidelberg D., & During M.J. (2007). "Safety and tolerability of gene therapy with an adeno-associated virus (AAV) borne GAD gene for Parkinson's disease: an open label, phase I trial." Lancet. 369 (9579): 2097-105.

Kay M.A., Manno C.S., Ragni M.V., Larson P.J., Couto L.B., McClelland A., Glader B., Chew A.J., Tai S., Herzog R.W., Arruda V., Johnson F., Scallan C., Skarsgard E., Flake A.W., & High K.A. (2000). "Evidence for gene transfer and expression of factor IX in haemophilia B patients treated with an AAV vector." Nat Genet. 24 (3): 257-61.

Kehrer C., Blumenstock G., Gieselmann V., & Krageloh-Mann I. (2011a). "The natural course of gross motor deterioration in metachromatic leukodystrophy." Dev Med Child Neurol. 53 (9): 850-855.

Kehrer C., Blumenstock G., Raabe C., & Krageloh-Mann I. (2011b). "Development and reliability of a classification system for gross motor function in children with metachromatic leucodystrophy." Dev Med Child Neurol. 53 (2): 156-60.

Kehrer C., Groeschel S., Kustermann-Kuhn B., Burger F., Kohler W., Kohlschutter A., Bley A., Steinfeld R., Gieselmann V., & Krageloh-Mann I. (2014). "Language and cognition in children with metachromatic leukodystrophy: onset and natural course in a nationwide cohort." Orphanet J Rare Dis. 9:18.

Kim J., Sun Z., Ezekian B., Schooler G.R., Prasad V.K., Kurtzberg J., Rice H.E., & Tracy E.T. (2017). "Gallbladder abnormalities in children with metachromatic leukodystrophy." J Surg Res. 208:187-191.

Krageloh-Mann I., Groeschel S., Kehrer C., Opherk K., Nagele T., Handgretinger R., & Muller I. (2013). "Juvenile metachromatic leukodystrophy 10 years post transplant compared with a non-transplanted cohort." Bone Marrow Transplant. 48 (3): 369-75.

Krivit W., Shapiro E., Kennedy W., Lipton M., Lockman L., Smith S., Summers C.G., Wenger D.A., Tsai M.Y., Ramsay N.K., & et al. (1990). "Treatment of late infantile metachromatic leukodystrophy by bone marrow transplantation." N Engl J Med. 322 (1): 28-32.

Kruse B., Hanefeld F., Christen H.J., Bruhn H., Michaelis T., Hanicke W., & Frahm J. (1993). "Alterations of brain metabolites in metachromatic leukodystrophy as detected by localized proton magnetic resonance spectroscopy in vivo." J Neurol. 241 (2): 68-74.

Kumperscak H.G., Paschke E., Gradisnik P., Vidmar J., & Bradac S.U. (2005). "Adult metachromatic leukodystrophy: disorganized schizophrenia-like symptoms and postpartum depression in 2 sisters." J Psychiatry Neurosci. 30 (1): 33-6.

Largo R.H., Molinari L., Weber M., Comenale Pinto L., & Duc G. (1985). "Early development of locomotion: Significance of prematurity, cerebral palsy and sex." Dev Med Child Neurol. 27 (2): 183-91.

Lawlor P.A., Bland R.J., Mouravlev A., Young D., & During M.J. (2009). "Efficient gene delivery and selective transduction of glial cells in the mammalian brain by AAV serotypes isolated from nonhuman primates." Mol Ther. 17 (10): 1692-702.

Li C., He Y., Nicolson S., Hirsch M., Weinberg M.S., Zhang P., Kafri T., & Samulski R.J. (2013). "Adeno-associated virus capsid antigen presentation is dependent on endosomal escape." J Clin Invest. 123 (3): 1390-401.

Li H., Malani N., Hamilton S.R., Schlachterman A., Bussadori G., Edmonson S.E., Shah R., Arruda V.R., Mingozzi F., Wright J.F., Bushman F.D., & High K.A. (2011). "Assessing the potential for AAV vector genotoxicity in a murine model." Blood. 117 (12): 3311-9.

Lock M., Alvira M.R., Chen S., & Wilson J.M. (2014). "Absolute determination of single-stranded and self-complementary adeno-associated viral vector genome titers by droplet digital PCR." Hum Gene Ther Methods. 25 (2): 115-25.

Lugowska A., Poninska J., Krajewski P., Broda G., & Ploski R. (2011). "Population carrier rates of pathogenic ARSA gene mutations: is metachromatic leukodystrophy underdiagnosed?" PLOS One. 6 (6): e20218.

Lundkvist Josenby A., Jarnlo G.B., Gummesson C., & Nordmark E. (2009). "Longitudinal construct validity of the GMFM-88 total score and goal total score and the GMFM-66 score in a 5-year follow-up study." Phys Ther. 89 (4): 342-50.

Mahmood A., Berry J., Wenger D.A., Escolar M., Sobeih M., Raymond G., & Eichler F.S. (2010). "Metachromatic leukodystrophy: a case of triplets with the late infantile variant and a systematic review of the literature." J Child Neurol. 25 (5): 572-80.

Mandel R.J. & Burger C. (2004). "Clinical trials in neurological disorders using AAV vectors: promises and challenges." Curr Opin Mol Ther. 6 (5): 482-90.

Marcao A.M., Wiest R., Schindler K., Wiesmann U., Weis J., Schroth G., Miranda M.C., Sturzenegger M., & Gieselmann V. (2005). "Adult onset metachromatic leukodystrophy without electroclinical peripheral nervous system involvement: a new mutation in the ARSA gene." Arch Neurol. 62 (2): 309-13.

Martin A., Sevin C., Lazarus C., Bellesme C., Aubourg P., & Adamsbaum C. (2012). "Toward a better understanding of brain lesions during metachromatic leukodystrophy evolution." AJNR Am J Neuroradiol. 33 (9): 1731-9.

Martin H.R., Poe M.D., Provenzale J.M., Kurtzberg J., Mendizabal A., & Escolar M.L. (2013). "Neurodevelopmental outcomes of umbilical cord blood transplantation in metachromatic leukodystrophy." Biol Blood Marrow Transplant. 19 (4): 616-24.

Matthes F., Stroobants S., Gerlach D., Wohlenberg C., Wessig C., Fogh J., Gieselmann V., Eckhardt M., D'Hooge R., & Matzner U. (2012). "Efficacy of enzyme replacement therapy in an aggravated mouse model of metachromatic leukodystrophy declines with age." Hum Mol Genet. 21 (11): 2599-609.

Matzner U., Herbst E., Hedayati K.K., Lullmann-Rauch R., Wessig C., Schroder S., Eistrup C., Moller C., Fogh J., & Gieselmann V. (2005). "Enzyme replacement improves nervous system pathology and function in a mouse model for metachromatic leukodystrophy." Hum Mol Genet. 14 (9): 1139-52.

Matzner U., Lullmann-Rauch R., Stroobants S., Andersson C., Weigelt C., Eistrup C., Fogh J., D'Hooge R., & Gieselmann V. (2009). "Enzyme replacement improves ataxic gait and central nervous system histopathology in a mouse model of metachromatic leukodystrophy." Mol Ther. 17 (4): 600-6.

McCarty D.M., Young S.M., Jr., & Samulski R.J. (2004). "Integration of adeno-associated virus (AAV) and recombinant AAV vectors." Annu Rev Genet. 38:819-45.

McFadden K. & Ranganathan S. (2015). "Pathology of the gallbladder in a child with metachromatic leukodystrophy." Pediatr Dev Pathol. 18 (3): 228-30.

Melnick J.L., Mayor H.D., Smith K.O., & Rapp F. (1965). "Association of 20 milli-micron particles with adenoviruses." J Bacteriol. 90 (1): 271-4.

Mendell J.R., Al-Zaidy S., Shell R., Arnold W.D., Rodino-Klapac L.R., Prior T.W., Lowes L., Alfano L., Berry K., Church K., Kissel J.T., Nagendran S., L'Italien J., Sproule D.M., Wells C., Cardenas J.A., Heitzer M.D., Kaspar A., Corcoran S., Braun L., Likhite S., Miranda C., Meyer K., Foust K.D., Burghes A.H.M., & Kaspar B.K. (2017). "Single-dose gene-replacement therapy for spinal muscular atrophy." N Engl J Med. 377 (18): 1713-1722.

Miller N. (2012). "Glybera and the future of gene therapy in the European Union." Nat Rev Drug Discov. 11 (5): 419.

Mittermeyer G., Christine C.W., Rosenbluth K.H., Baker S.L., Starr P., Larson P., Kaplan P.L., Forsayeth J., Aminoff M.J., & Bankiewicz K.S. (2012). "Long-term evaluation of a Phase 1 study of AADC gene therapy for Parkinson's disease." Hum Gene Ther. 23 (4): 377-81.

Nathwani A.C., Tuddenham E.G., Rangarajan S., Rosales C., McIntosh J., Linch D.C., Chowdary P., Riddell A., Pie A.J., Harrington C., O'Beirne J., Smith K., Pasi J., Glader B., Rustagi P., Ng C.Y., Kay M.A., Zhou J., Spence Y., Morton C.L., Allay J., Coleman J., Sleep S., Cunningham J.M., Srivastava D., Basner-Tschakarjan E., Mingozzi F., High K.A., Gray J.T., Reiss U.M., Nienhuis A.W., & Davidoff A.M. (2011). "Adenovirus-associated virus vector-mediated gene transfer in hemophilia B." N Engl J Med. 365 (25): 2357-65.

Nault J.C., Mami I., La Bella T., Datta S., Imbeaud S., Franconi A., Mallet M., Couchy G., Letouze E., Pilati C., Verret B., Blanc J.F., Balabaud C., Calderaro J., Laurent A., Letexier M., Bioulac-Sage P., Calvo F., & Zucman-Rossi J. (2016). "Wild-type AAV Insertions in Hepatocellular Carcinoma Do Not Inform Debate Over Genotoxicity Risk of Vectorized AAV." Mol Ther. 24 (4): 660-1.

Navarro C., Fernandez J.M., Dominguez C., Fachal C., & Alvarez M. (1996). "Late juvenile metachromatic leukodystrophy treated with bone marrow transplantation; a 4-year follow-up study." Neurology. 46 (1): 254-6.

Palisano R.J., Cameron D., Rosenbaum P.L., Walter S.D., & Russell D. (2006). "Stability of the gross motor function classification system." Dev Med Child Neurol. 48 (6): 424-8.

Passini M.A., Dodge J.C., Bu J., Yang W., Zhao Q., Sondhi D., Hackett N.R., Kaminsky S.M., Mao Q., Shihabuddin L.S., Cheng S.H., Sleat D.E., Stewart G.R., Davidson B.L., Lobel P., & Crystal R.G. (2006). "Intracranial delivery of CLN2 reduces brain pathology in a mouse model of classical late infantile neuronal ceroid lipofuscinosis." J Neurosci. 26 (5): 1334-42.

Patil S.A. & Maegawa G.H. (2013). "Developing therapeutic approaches for metachromatic leukodystrophy." Drug Des Devel Ther. 7:729-45.

Penaud-Budloo M., Le Guiner C., Nowrouzi A., Toromanoff A., Cherel Y., Chenuaud P., Schmidt M., von Kalle C., Rolling F., Moullier P., & Snyder R.O. (2008). "Adeno-associated virus vector genomes persist as episomal chromatin in primate muscle." J Virol. 82 (16): 7875-85.

Peng L. & Suzuki K. (1987). "Ultrastructural study of neurons in metachromatic leukodystrophy." Clin Neuropathol. 6 (5): 224-30.

Perusi C., Lira M.G., Duyff R.F., Weinstein H.C., Pignatti P.F., Rizzuto N., & Salviati A. (1999). "Mutations associated with very late-onset metachromatic leukodystrophy." Clin Genet. 55 (2): 130.

Piguet F., Sondhi D., Piraud M., Fouquet F., Hackett N.R., Ahouansou O., Vanier M.T., Bieche I., Aubourg P., Crystal R.G., Cartier N., & Sevin C. (2012). "Correction of brain oligodendrocytes by AAVrh. 10 intracerebral gene therapy in metachromatic leukodystrophy mice." Hum Gene Ther. 23 (8): 903-14.

Pilz H., Duensing I., Heipertz R., Seidel D., Lowitzsch K., Hopf H.C., & Goebel H.H. (1977). "Adult metachromatic leukodystrophy. I. Clinical manifestation in a female aged 44 years, previously diagnosed in the preclinical state." Eur Neurol. 15 (6): 301-7.

Pinto R., Caseiro C., Lemos M., Lopes L., Fontes A., Ribeiro H., Pinto E., Silva E., Rocha S., Marcao A., Ribeiro I., Lacerda L., Ribeiro G., Amaral O., & Sa Miranda M.C. (2004). "Prevalence of lysosomal storage diseases in Portugal." Eur J Hum Genet. 12 (2): 87-92.

Polten A., Fluharty A.L., Fluharty C.B., Kappler J., von Figura K., & Gieselmann V. (1991). "Molecular basis of different forms of metachromatic leukodystrophy." N Engl J Med. 324 (1): 18-22.

Pomerantz S.R., Buchbinder B., & Hirsch J.A. (2005). Suboccipital puncture of the cisterna *magna* under CT-guidance with intravenous enhancement in order to circumvent anomalous course of posterior inferior cerebellar artery (PICA) American Society of Spine Radiology Symposium.

Poorthuis B.J., Wevers R.A., Kleijer W.J., Groener J.E., de Jong J.G., van Weely S., Niezen-Koning K.E., & van Diggelen O.P. (1999). "The frequency of lysosomal storage diseases in The Netherlands." Hum Genet. 105 (1-2): 151-6.

Rafi M.A., Rao H.Z., Luzi P., Curtis M.T., & Wenger D.A. (2012). "Extended normal life after AAVrh10-mediated gene therapy in the mouse model of Krabbe disease." Mol Ther. 20 (11): 2031-42.

Ramakrishnan H., Hedayati K.K., Lullmann-Rauch R., Wessig C., Fewou S.N., Maier H., Goebel H.H., Gieselmann V., & Eckhardt M. (2007). "Increasing sulfatide synthesis in myelin-forming cells of arylsulfatase A-deficient mice causes demyelination and neurological symptoms reminiscent of human metachromatic leukodystrophy." J Neurosci. 27 (35): 9482-90.

Rangarajan S., Walsh L., Lester W., Perry D., Madan B., Laffan M., Yu H., Vettermann C., Pierce G.F., Wong W.Y., & Pasi K.J. (2017). "AAVS-Factor VIII gene transfer in severe hemophilia A." N Engl J Med. 377 (26): 2519-2530.

Rauschka H., Colsch B., Baumann N., Wevers R., Schmidbauer M., Krammer M., Turpin J.C., Lefevre M., Olivier C., Tardieu S., Krivit W., Moser H., Moser A., Gieselmann V., Zalc B., Cox T., Reuner U., Tylki-Szymanska A., Aboul-Enein F., LeGuern E., Bernheimer H., & Berger J. (2006). "Late-onset metachromatic leukodystrophy: genotype strongly influences phenotype." Neurology. 67 (5): 859-63.

REGENXBIO (2019). REGENXBIO reports fourth quarter and full-year 2018 financial results and recent operational highlights.

Regis S., Corsolini F., Stroppiano M., Cusano R., & Filocamo M. (2002). "Contribution of arylsulfatase A mutations located on the same allele to enzyme activity reduction and metachromatic leukodystrophy severity." Hum Genet. 110 (4): 351-5.

Rodriguez-Waitkus P.M., Byrd R., & Hicks J. (2011). "Metachromatic leukodystrophy and its effects on the gallbladder: a case report." Ultrastruct Pathol. 35 (6): 271-6.

Rosas L.E., Grieves J.L., Zaraspe K., La Perle K.M.D., Fu H., & McCarty D.M. (2012). "Patterns of scAAV vector insertion associated with oncogenic events in a mouse model for genotoxicity." Mol Ther. 20 (11): 2098-2110.

Rosenberg J.B., Kaminsky S.M., Aubourg P., Crystal R.G., & Sondhi D. (2016). "Gene therapy for metachromatic leukodystrophy." J Neurosci Res. 94 (11): 1169-79.

Russell D.J., Rosenbaum P.L., Cadman D.T., Gowland C., Hardy S., & Jarvis S. (1989). "The gross motor function measure: a means to evaluate the effects of physical therapy." Dev Med Child Neurol. 31 (3): 341-52.

Samaranch L., Salegio E.A., San Sebastian W., Kells A.P., Bringas J.R., Forsayeth J., & Bankiewicz. K.S. (2013). "Strong cortical and spinal cord transduction after AAV7 and AAV9 delivery into the cerebrospinal fluid of non-human primates." Hum Gene Ther. 24 (5): 526-32.

Sands M.S. (2014). "A Hitchhiker's guide to the blood-brain barrier: in trans delivery of a therapeutic enzyme." Mol Ther. 22 (3): 483-484.

Saunders H.C. & Riordan T.J. (1929). "Cisternal or suboccipital puncture: A report of 2019 punctures." New England Journal of Medicine. 201:166-168.

Schuster D.J., Dykstra J.A., Riedl M.S., Kitto K.F., Belur L.R., McIvor R.S., Elde R.P., Fairbanks C.A., & Vulchanova L. (2014). "Biodistribution of adeno-associated virus serotype 9 (AAV9) vector after intrathecal and intravenous delivery in mouse." Front Neuroanat. 8:42.

Sessa M., Lorioli L., Fumagalli F., Acquati S., Redaelli D., Baldoli C., Canale S., Lopez I.D., Morena F., Calabria A., Fiori R., Silvani P., Rancoita P.M., Gabaldo M., Benedicenti F., Antonioli G., Assanelli A., Cicalese M.P., Del Carro U., Sora M.G., Martino S., Quattrini A., Montini E., Di Serio C., Ciceri F., Roncarolo M.G., Aiuti A., Naldini L., & Biffi A. (2016). "Lentiviral haemopoietic stem-cell gene therapy in early-onset metachromatic leukodystrophy: an ad-hoc analysis of a non-randomised, open-label, phase 1/2 trial." Lancet. 388 (10043): 476-87.

Sevin C., Aubourg P., & Cartier N. (2007). "Enzyme, cell and gene-based therapies for metachromatic leukodystrophy." J Inherit Metab Dis. 30 (2): 175-83.

Sevin C., Roujeau T., Cartier N., Baugnon T., Adamsbaum C., Piraud M., Martino S., Mouiller P., Couzinie C., Bellesme C., Lalande C.C., Cormary C., Souweidane M.M., Colle M.-A., Adjali O., Sondhi D., Crystal R.G., Aubourg P., & Zerah M. (2018). "Intracerebral gene therapy in children with metachromatic leukodystrophy: Results of a phase I/II trial." Molec Genet Metab. 123 (2): S129.

Skorupa A.F., Fisher K.J., Wilson J.M., Parente M.K., & Wolfe J.H. (1999). "Sustained production of beta-glucuronidase from localized sites after AAV vector gene transfer results in widespread distribution of enzyme and reversal of lysosomal storage lesions in a large volume of brain in mucopolysaccharidosis VII mice." Exp Neurol. 160 (1): 17-27.

Smith N.J., Marcus R.E., Sahakian B.J., Kapur N., & Cox T.M. (2010). "Haematopoietic stem cell transplantation does not retard disease progression in the psycho-cognitive variant of late-onset metachromatic leukodystrophy." J Inherit Metab Dis. 33 Suppl 3: S471-5.

Solders M., Martin D.A., Andersson C., Remberger M., Andersson T., Ringden O., & Solders G. (2014). "Hematopoietic SCT: a useful treatment for late metachromatic leukodystrophy." Bone Marrow Transplant. 49 (8): 1046-51.

Spark (2018). European Commission approves Spark Therapeutics' LUXTURNA® (voretigene neparvovec), a one-time gene therapy for inherited retinal disease caused by confirmed biallelic RPE65 mutations.

Strolin M., Krageloh-Mann I., Kehrer C., Wilke M., & Groeschel S. (2017). "Demyelination load as predictor for disease progression in juvenile metachromatic leukodystrophy." Ann Clin Transl Neurol. 4 (6): 403-410.

Stroobants S., Gerlach D., Matthes F., Hartmann D., Fogh J., Gieselmann V., D'Hooge R., & Matzner U. (2011). "Intracerebroventricular enzyme infusion corrects central nervous system pathology and dysfunction in a mouse model of metachromatic leukodystrophy." Hum Mol Genet. 20 (14): 2760-9.

Taber C. & Thomas C. (1997). Taber's Cyclopedic Medical Dictionary. Philadelphia, F.A. Davis.

Tardieu M., Zerah M., Husson B., de Bournonville S., Deiva K., Adamsbaum C., Vincent F., Hocquemiller M., Broissand C., Furlan V., Ballabio A., Fraldi A., Crystal R.G., Baugnon T., Roujeau T., Heard J.M., & Danos O. (2014). "Intracerebral administration of adeno-associated viral vector serotype rh. 10 carrying human SGSH and SUMF1 cDNAs in children with mucopolysaccharidosis type IIIA disease: results of a phase I/II trial." Hum Gene Ther. 25 (6): 506-16.

Toda K., Kobayashi T., Goto I., Ohno K., Eto Y., Inui K., & Okada S. (1990). "Lysosulfatide (sulfogalactosylsphingosine) accumulation in tissues from patients with metachromatic leukodystrophy." J Neurochem. 55 (5): 1585-91.

Tylki-Szymanska A., Berger J., Loschl B., Lugowska A., & Molzer B. (1996). "Late juvenile metachromatic leukodystrophy (MLD) in three patients with a similar clinical course and identical mutation on one allele." Clin Genet. 50 (5): 287-92.

van Egmond M.E., Pouwels P.J., Boelens J.J., Lindemans C.A., Barkhof F., Steenwijk M.D., van Hasselt P.M., van der Knaap M.S., & Wolf N.I. (2013). "Improvement of white matter changes on neuroimaging modalities after stem cell transplant in metachromatic leukodystrophy." JAMA Neurol. 70 (6): 779-82.

van Rappard D.F., Boelens J.J., & Wolf N.I. (2015). "Metachromatic leukodystrophy: Disease spectrum and approaches for treatment." Best Pract Res Clin Endocrinol Metab. 29 (2): 261-73.

van Rappard D.F., Bugiani M., Boelens J.J., van der Steeg A.F., Daams F., de Meij T.G., van Doorn M.M., van Hasselt P.M., Gouma D.J., Verbeke J.I., Hollak C.E., van Hecke W., Salomons G.S., van der Knaap M.S., & Wolf N.I. (2016). "Gallbladder and the risk of polyps and carcinoma in metachromatic leukodystrophy." Neurology. 87 (1): 103-11.

van Rappard D.F., de Vries A.L.C., Oostrom K.J., Boelens J.J., Hollak C.E.M., van der Knaap M.S., & Wolf N.I. (2018). "Slowly Progressive Psychiatric Symptoms: Think Metachromatic Leukodystrophy." J Am Acad Child Adolesc Psychiatry. 57 (2): 74-76.

Varni J.W., Limbers C.A., Neighbors K., Schulz K., Lieu J.E., Heffer R.W., Tuzinkiewicz K., Mangione-Smith R., Zimmerman J.J., & Alonso E.M. (2011). "The PedsQL Infant Scales: feasibility, internal consistency reliability, and validity in healthy and ill infants." Qual Life Res. 20 (1): 45-55.

Virgens M.Y., Siebert M., Bock H., Burin M., Giugliani R., & Saraiva-Pereira M.L. (2015). "Genotypic characterization of Brazilian patients with infantile and juvenile forms of metachromatic leukodystrophy." Gene. 568 (1): 69-75.

Vite C.H., McGowan J.C., Niogi S.N., Passini M.A., Drobatz K.J., Haskins M.E., & Wolfe J.H. (2005). "Effective gene therapy for an inherited CNS disease in a large animal model." Ann Neurol. 57 (3): 355-64.

Von Figura K., Gieselmann V., & Jacken J. (2001). "Metachromatic leukodystrophy." The Metabolic and Molecular Bases of Inherited Disease. S. C.R., B. A.L., S. W.S. and V. D. (eds). New York, NY: McGraw-Hill.

Wang R.Y., Bodamer O.A., Watson M.S., & Wilcox W.R. (2011). "Lysosomal storage diseases: diagnostic confirmation and management of presymptomatic individuals." Genet Med. 13 (5): 457-84.

WHO (2006). Reliability of motor development data in the WHO Multicentre Growth Reference Study. Acta Paediatr Suppl. 450:47-55.

Wijnhoven T.M., de Onis M., Onyango A.W., Wang T., Bjoerneboe G.E., Bhandari N., Lartey A., & al Rashidi B. (2004). "Assessment of gross motor development in the WHO Multicentre Growth Reference Study." Food Nutr Bull. 25 (1 Suppl): S37-45.

Worgall S., Sondhi D., Hackett N.R., Kosofsky B., Kekatpure M.V., Neyzi N., Dyke J.P., Ballon D., Heier L., Greenwald B.M., Christos P., Mazumdar M., Souweidane M.M., Kaplitt M.G., & Crystal R.G. (2008). "Treatment of late infantile neuronal ceroid lipofuscinosis by CNS administration of a serotype 2 adeno-associated virus expressing CLN2 cDNA." Hum Gene Ther. 19 (5): 463-74.

Zafeiriou D.I., Kontopoulos E.E., Michelakakis H.M., Anastasiou A.L., & Gombakis N.P. (1999). "Neurophysiology and MRI in late-infantile metachromatic leukodystrophy." Pediatr Neurol. 21 (5): 843-6.

Zerah M., Piguet F., Colle M.A., Raoul S., Deschamps J.Y., Deniaud J., Gautier B., Toulgoat F., Bieche I., Laurendeau I., Sondhi D., Souweidane M.M., Cartier-Lacave N., Moullier P., Crystal R.G., Roujeau T., Sevin C., & Aubourg P. (2015). "Intracerebral Gene Therapy Using AAVrh.10-hARSA Recombinant Vector to Treat Patients with Early-Onset Forms of Metachromatic Leukodystrophy: Preclinical Feasibility and Safety Assessments in Nonhuman Primates." Hum Gene Ther Clin Dev. 26 (2): 113-24.

(Sequence Listing Free Text)

The following information is provided for sequences containing free text under numeric identifier <223>.

| SEQ ID NO | Free Text under <223> |
|---|---|
| 1 | <223> Engineered hARSA coding sequence <br> <220> <br> <221> CDS <br> <222> (1) . . . (1521) |
| 2 | <223> Synthetic Construct |
| 3 | <223> Engineered hARSA coding sequence <br> <220> <br> <221> CDS <br> <222> (1) . . . (1527) |
| 4 | <223> Synthetic Construct |
| 5 | <223> Production plasmid for AAV.CB7, CI.hARSAco.RBG <br> <220> <br> <221> repeat_region <br> <222> (1) . . . (130) <br> <223> 5' ITR <br> <220> <br> <221> promoter <br> <222> (198) . . . (579) <br> <223> CMV IE promoter <br> <220> <br> <221> promoter <br> <222> (582) . . . (862) |

| SEQ ID NO | Free Text under <223> |
|---|---|
|  | <223> CB promoter |
|  | <220> |
|  | <221> TATA signal |
|  | <222> (836) . . . (839) |
|  | <223> TATA |
|  | <220> |
|  | <221> Intron |
|  | <222> (956) . . . (1928) |
|  | <223> chicken beta-actin intron |
|  | <220> |
|  | <221> misc_feature |
|  | <222> (1935) . . . (3506) |
|  | <223> Engineered ARSA coding sequence (hARSAco) |
|  | <220> |
|  | <221> polyA_signal |
|  | <222> (3539) . . . (3665) |
|  | <223> Rabbit globin poly A |
|  | <220> |
|  | <221> repeat_region |
|  | <222> (3754) . . . (3883) |
|  | <223> 3' ITR |
|  | <220> |
|  | <221> rep_origin |
|  | <222> (4060) . . . (4498) |
|  | <223> f1 ori |
|  | <220> |
|  | <221> rep_origin |
|  | <222> (4527) . . . (5169) |
|  | <223> pUC origin of replication |
|  | <220> |
|  | <221> misc_feature |
|  | <222> (5844) . . . (6649) |
| 6 | <223> AAVhu68 vp1 |
|  | <220> |
|  | <221> CDS |
|  | <222> (1) . . . (2211) |
| 7 | <223> Synthetic Construct |
| 8 | <223> modified hu68vp1 |
|  | <220> |
|  | <221> MISC_FEATURE |
|  | <222> (23) . . . (23) |
|  | <223> Xaa may be W (Trp, tryptophan), or oxidated W. |
|  | <220> |
|  | <221> MISC_FEATURE |
|  | <222> (35) . . . (35) |
|  | <223> Xaa may be Asn, or deamidated to Asp, isoAsp, or Asp/isoAsp |
|  | <220> |
|  | <221> MISC_FEATURE |
|  | <222> (57) . . . (57) |
|  | <223> Xaa may be Asn, or deamidated to Asp, isoAsp, or Asp/isoAsp |
|  | <220> |
|  | <221> MISC_FEATURE |
|  | <222> (66) . . . (66) |
|  | <223> Xaa may be Asn, or deamidated to Asp, isoAsp, or Asp/isoAsp |
|  | <220> |
|  | <221> MISC_FEATURE |
|  | <222> (94) . . . (94) |
|  | <223> Xaa may be Asn, or deamidated to Asp, isoAsp, or Asp/isoAsp |
|  | <220> |
|  | <221> MISC_FEATURE |
|  | <222> (97) . . . (97) |
|  | <223> Xaa may be D (asp, aspartic acid), or isomerized D. |
|  | <220> |
|  | <221> MISC_FEATURE |
|  | <222> (107) . . . (107) |
|  | <223> Xaa may be D (asp, aspartic acid), or isomerized D. |
|  | <220> |
|  | <221> misc_feature |
|  | <222> (113) . . . (113) |
|  | <223> Xaa can be any naturally occurring amino acid |
|  | <220> |
|  | <221> MISC_FEATURE |
|  | <222> (149) . . . (149) |
|  | <223> Xaa may be S (Ser, serine), or Phosphorilated S |
|  | <220> |
|  | <221> MISC_FEATURE |
|  | <222> (149) . . . (149) |
|  | <223> Xaa may be S (Ser, serine), or Phosphorylated S |
|  | <220> |
|  | <221> MISC_FEATURE |
|  | <222> (247) . . . (247) |
|  | <223> Xaa may be W (Trp, tryptophan), or oxidated W (e.g., kynurenine). |
|  | <220> |
|  | <221> MISC_FEATURE |
|  | <222> (253) . . . (253) |
|  | <223> Xaa may be Asn, or deamidated to Asp, isoAsp, or Asp/isoAsp |
|  | <220> |
|  | <221> MISC_FEATURE |
|  | <222> (259) . . . (259) |
|  | <223> Xaa represents Q, or Q deamidated to glutamic acid (alpha-glutamic acid), gamma-glutamic acid (Glu), or a blend of alpha- and gamma-glutamic acid |
|  | <220> |
|  | <221> MISC_FEATURE |
|  | <222> (270) . . . (270) |
|  | <223> Xaa may be Asn, or deamidated to Asp, isoAsp, or Asp/isoAsp |
|  | <220> |
|  | <221> MISC_FEATURE |
|  | <222> (297) . . . (297) |
|  | <223> Xaa represents D (Asp, aspartic acid) or amindated D to N (Asn, asparagine) |
|  | <220> |
|  | <221> MISC_FEATURE |
|  | <222> (304) . . . (304) |
|  | <223> Xaa may be Asn, or deamidated to Asp, isoAsp, or Asp/isoAsp |
|  | <220> |
|  | <221> MISC_FEATURE |
|  | <222> (306) . . . (306) |
|  | <223> Xaa may be W (Trp, tryptophan), or oxidated W (e.g., kynurenine). |
|  | <220> |
|  | <221> MISC_FEATURE |
|  | <222> (314) . . . (314) |
|  | <223> Xaa may be Asn, or deamidated to Asp, isoAsp, or Asp/isoAsp |
|  | <220> |
|  | <221> MISC_FEATURE |
|  | <222> (319) . . . (319) |
|  | <223> Xaa may be Asn, or deamidated to Asp, isoAsp, or Asp/isoAsp |
|  | <220> |
|  | <221> MISC_FEATURE |
|  | <222> (329) . . . (329) |
|  | <223> Xaa may be Asn, or deamidated to Asp, isoAsp, or Asp/isoAsp |
|  | <220> |
|  | <221> MISC_FEATURE |
|  | <222> (332) . . . (332) |
|  | <223> Xaa may be K (lys, lysine), or acetylated K |
|  | <220> |
|  | <221> MISC_FEATURE |
|  | <222> (336) . . . (336) |
|  | <223> Xaa may be Asn, or deamidated to Asp, isoAsp, or Asp/isoAsp |
|  | <220> |
|  | <221> MISC_FEATURE |
|  | <222> (384) . . . (384) |
|  | <223> Xaa may be D (asp, aspartic acid), or isomerized D. |
|  | <220> |
|  | <221> MISC_FEATURE |
|  | <222> (404) . . . (404) |
|  | <223> Xaa may be M (Met, Methionine), or oxidated M. |
|  | <220> |
|  | <221> MISC_FEATURE |

| SEQ ID NO | Free Text under <223> |
|---|---|
| | <221> MISC_FEATURE<br><222> (409) . . . (409)<br><223> Xaa may be Asn, or deamidated to Asp, isoAsp, or Asp/isoAsp<br><220><br><221> MISC_FEATURE<br><222> (436) . . . (436)<br><223> Xaa may be M (Met, Methionine), or oxidated M.<br><220><br><221> MISC_FEATURE<br><222> (452) . . . (452)<br><223> Xaa may be Asn, or deamidated to Asp, isoAsp, or Asp/isoAsp<br><220><br><221> MISC_FEATURE<br><222> (477) . . . (477)<br><223> Xaa may be Asn, or deamidated to Asp, isoAsp, or Asp/isoAsp<br><220><br><221> MISC_FEATURE<br><222> (499) . . . (499)<br><223> Xaa may be S (Ser, serine), or Phosphorylated S<br><220><br><221> MISC_FEATURE<br><222> (512) . . . (512)<br><223> Xaa may be Asn, or deamidated to Asp, isoAsp, or Asp/isoAsp<br><220><br><221> MISC_FEATURE<br><222> (515) . . . (515)<br><223> Xaa may be Asn, or deamidated to Asp, isoAsp, or Asp/isoAsp<br><220><br><221> MISC_FEATURE<br><222> (518) . . . (518)<br><223> Xaa may be M (Met, Methionine), or oxidated M.<br><220><br><221> MISC_FEATURE<br><222> (524) . . . (524)<br><223> Xaa may be M (Met, Methionine), or oxidated M.<br><220><br><221> MISC_FEATURE<br><222> (559) . . . (559)<br><223> Xaa may be M (Met, Methionine), or oxidated M.<br><220><br><221> MISC_FEATURE<br><222> (569) . . . (569)<br><223> Xaa may be T (Thr, threonine), or Phosphorylated T<br><220><br><221> MISC_FEATURE<br><222> (586) . . . (586)<br><223> Xaa may be S (Ser, serine), or Phosphorylated S<br><220><br><221> MISC_FEATURE<br><222> (599) . . . (599)<br><223> Xaa represents Q, or Q deamidated to glutamic acid (alpha-glutamic acid), gamma-glutamic acid (Glu), or a blend of alpha- and gamma-glutamic acid<br><220><br><221> MISC_FEATURE<br><222> (605) . . . (605)<br><223> Xaa may be M (Met, Methionine), or oxidated M.<br><220><br><221> MISC_FEATURE<br><222> (619) . . . (619)<br><223> Xaa may be W (Trp, tryptophan), or oxidated W (e.g., kynurenine).<br><220><br><221> MISC_FEATURE<br><222> (628) . . . (628)<br><223> Xaa may be Asn, or deamidated to Asp, isoAsp, or Asp/isoAsp<br><220><br><221> MISC_FEATURE<br><222> (640) . . . (640) |
| | <223> Xaa may be M (Met, Methionine), or oxidated M.<br><220><br><221> MISC_FEATURE<br><222> (651) . . . (651)<br><223> Xaa may be Asn, or deamidated to Asp, isoAsp, or Asp/isoAsp<br><220><br><221> MISC_FEATURE<br><222> (663) . . . (663)<br><223> Xaa may be Asn, or deamidated to Asp, isoAsp, or Asp/isoAsp<br><220><br><221> MISC_FEATURE<br><222> (666) . . . (666)<br><223> Xaa may be K (lys, lysine), or acetylated K<br><220><br><221> MISC_FEATURE<br><222> (689) . . . (689)<br><223> Xaa may be K (lys, lysine), or acetylated K<br><220><br><221> MISC_FEATURE<br><222> (693) . . . (693)<br><223> Xaa may be K (lys, lysine), or acetylated K<br><220><br><221> MISC_FEATURE<br><222> (695) . . . (695)<br><223> Xaa may be W (Trp, tryptophan), or oxidated W.<br><220><br><221> MISC_FEATURE<br><222> (709) . . . (709)<br><223> Xaa may be Asn, or deamidated to Asp, isoAsp, or Asp/isoAsp<br><220><br><221> MISC_FEATURE<br><222> (735) . . . (735)<br><223> Xaa may be Asn, or deamidated to Asp, isoAsp, or Asp/isoAsp |
| 9 | <223> AAV9 vp1 coding sequence |
| 10 | <223> Encoded AAV9 vp1 amino acid sequence |
| 11 | <223> AAVhu31 vp1 coding sequence |
| 12 | <223> Encoded AAVhu31 vp1 amino acid sequence |
| 13 | <223> AAVhu32 vp1 coding sequence |
| 14 | <223> Encoded AAVhu32 vp1 amino acid sequence |
| 16 | <223> chicken beta actin promoter with a cytomegalovirus enhancer (CB7) |
| 17 | <223> chicken beta-actin intron |
| 18 | <223> CB promoter |
| 19 | <223> CMV Immediate early Promoter |
| 20 | <223> miR183 |
| 21 | <223> miRNA target sequence |
| 22 | <223> miRNA target sequence |
| 23 | <223> miRNA target sequence |
| 24 | <223> Spacer |

All documents cited in this specification are incorporated herein by reference. U.S. Provisional Patent Application No. 62/843,091, filed May 3, 2019, is incorporated by reference in its entirety, together with its sequence listings. The Sequence Listing filed 5 herewith, labelled "UPN-18-8585PCT_SeqListing_ST25.txt", and the sequences and text therein are incorporated by reference. While the invention has been described with reference to particular embodiments, it will be appreciated that modifications can be made without departing from the spirit of the invention. Such modifications are intended to fall within the scope of the appended claims.

The invention claimed is:

1. A recombinant adeno-associated virus (rAAV), wherein the rAAV comprises:
   (a) an AAVhu68 capsid; and
   (b) a vector genome packaged in the AAV capsid of (a), wherein the vector genome comprises inverted terminal repeats (ITR) and a nucleic acid sequence encoding a functional human Arylsulfatase A (hARSA) operably linked to regulatory sequences which direct the hARSA expression, wherein the hARSA coding sequence comprises a nucleic acid sequence encoding a signal peptide and a sequence of nucleotide (nt) 55 to nt 1521 of SEQ ID NO: 1, or a sequence at least 95% to 99.9% identical thereto which encodes a functional hARSA.

2. The rAAV according to claim 1, wherein the functional hARSA protein comprises a signal peptide and an amino acid sequence of amino acid (aa) 19 to aa 507 of SEQ ID NO: 2.

3. The rAAV according to claim 1, wherein the signal peptide has an amino acid sequence of aa 1 to aa 18 of SEQ ID NO: 2 or an amino acid sequence of aa 1 to aa 20 of SEQ ID NO: 4.

4. The rAAV according to claim 1, wherein the regulatory sequences direct hARSA expression in nervous system cells.

5. The rAAV according to claim 1, wherein the regulatory sequences comprise an enhancer and a chicken beta actin promoter.

6. The rAAV according to claim 1, wherein the regulatory elements comprise one or more of a Kozak sequence, a polyadenylation sequence, an intron, an enhancer, and a TATA signal.

7. The rAAV according to claim 1, wherein the hARSA coding sequence is at least 95% to 99.9% identical to SEQ ID NO: 1 and encodes a functional hARSA.

8. The rAAV according to claim 1, wherein the hARSA coding sequence is SEQ ID NO: 1 or SEQ ID NO: 3.

9. The rAAV according to claim 1, wherein the vector genome has a sequence of nt 1 to nt 3883 of SEQ ID NO: 5.

10. The rAAV according to claim 1, wherein the AAVhu68 capsid is produced from a sequence encoding the predicted amino acid sequence of SEQ ID NO: 7.

11. An aqueous pharmaceutical composition comprising a rAAV according to claim 1 and a formulation buffer.

12. The pharmaceutical composition according to claim 11, wherein the formulation buffer comprises: an artificial cerebrospinal fluid comprising buffered saline and one or more of sodium, calcium, magnesium, potassium, or mixtures thereof; and a surfactant.

13. The pharmaceutical composition according to claim 11, wherein the surfactant is present at 0.0005% to about 0.001% of the pharmaceutical composition.

14. The pharmaceutical composition according to claim 11, wherein the composition is at a pH in the range of 7.5 to 7.8.

15. The pharmaceutical composition according to claim 11, wherein the formulation buffer is suitable for an intracisterna magna injection (ICM), intravenous delivery, intrathecal administration, or intracerebroventricular administration.

16. A vector comprising an expression cassette, wherein the expression cassette comprises a nucleic acid sequence encoding a functional human Arylsulfatase A (hARSA) under control of regulatory sequences which direct the hARSA expression, wherein the hARSA coding sequence is SEQ ID NO: 1 or SEQ ID NO: 3, or a sequence at least 95% to 99.9% identical thereto which encodes a functional hARSA.

17. The vector according to claim 16, wherein the vector is a viral vector or a non-viral vector which is a naked DNA, a naked RNA, an inorganic particle, a lipid particle, a polymer-based vector, or a chitosan-based formulation.

18. A method for delivering functional Arylsulfatase A (ARSA) to a subject in need thereof, comprising administering to the subject an rAAV which comprises:

(a) an AAVhu68 capsid; and (b) a vector genome packaged in the AAV capsid of (a), wherein the vector genome comprises inverted terminal repeats (ITR) and a nucleic acid sequence encoding a functional human Arylsulfatase A (hARSA) operably linked to regulatory sequences which direct the hARSA expression, wherein the hARSA coding sequence comprises a nucleic acid sequence encoding a signal peptide and a sequence of nucleotide (nt) 55 to nt 1521 of SEQ ID NO: 1, or a sequence at least 95% identical thereto which encodes a functional hARSA.

19. The vector according to claim 16 which is an rAAV vector comprising an AAV capsid and wherein the expression cassette comprises an hARSA coding sequence which is at least 99% identical to nt 1 to 1521 of SEQ ID NO: 1.

20. The vector according to claim 16 which comprises nucleotides 1935 to 3506 of SEQ ID NO: 5 or at least 99% identity to SEQ ID NO: 5.

21. An rAAV comprising:

(a) an AAVhu68 capsid and (b) a vector genome in the AAVhu68 capsid, the vector genome comprising:
an AAV inverted terminal (ITR),
an expression cassette comprising an enhancer, a promoter, an intron, an hARSA coding sequence which is at least 99% identical to nt 1935 to 3506 of SEQ ID NO: 5, a polyadenylation signal, and
an AAV ITR.

22. The rAAV of claim 21, wherein the chicken beta actin promoter has the sequence of nucleotide 582 to nucleotide 862 of SEQ ID NO: 5.

23. The rAAV of claim 22, wherein the enhancer is a human cytomegalovirus immediate early enhancer.

24. The rAAV of claim 23, wherein the cytomegalovirus immediate early enhancer has the sequence of nucleotide 198 to nucleotide 579 of SEQ ID NO: 5.

25. The rAAV of claim 21, wherein the intron has the sequence of nucleotides 956 to 1928 of SEQ ID NO: 5.

26. The rAAV of claim 21, wherein the polyadenylation signal is a rabbit globin poly A.

27. The rAAV of claim 26, wherein the polyA has the sequence of nucleotide 3539 to nucleotide 3665 of SEQ ID NO: 5.

28. A pharmaceutical composition comprising an aqueous suspending agent and the rAAV of claim 21.

* * * * *

SEQUENCE LISTING

<160> NUMBER OF SEQ ID NOS: 24

<210> SEQ ID NO 1
<211> LENGTH: 1521
<212> TYPE: DNA
<213> ORGANISM: Artificial Sequence
<220> FEATURE:
<223> OTHER INFORMATION: Engineered hARSA coding sequence
<220> FEATURE:
<221> NAME/KEY: CDS
<222> LOCATION: (1)..(1521)
<223> OTHER INFORMATION: Engineered hARSA coding sequence

<400> SEQUENCE: 1

```
atg gga gcc cct aga tct ctg ctg ctg gct ctg gct gct gga ctg gca      48
Met Gly Ala Pro Arg Ser Leu Leu Leu Ala Leu Ala Ala Gly Leu Ala
1               5                   10                  15 gtt gcc aga cct cct aac atc gtg ctg atc ttc gcc gac gat ctc ggc      96
Val Ala Arg Pro Pro Asn Ile Val Leu Ile Phe Ala Asp Asp Leu Gly
                20                  25                  30 tac ggc gat ctg ggc tgt tac gga cac ccc agc agc acc aca cct aac     144
Tyr Gly Asp Leu Gly Cys Tyr Gly His Pro Ser Ser Thr Thr Pro Asn
            35                  40                  45 ctg gat caa ctt gcc gct ggc ggc ctg aga ttc acc gat ttc tac gtg     192
Leu Asp Gln Leu Ala Ala Gly Gly Leu Arg Phe Thr Asp Phe Tyr Val
        50                  55                  60 ccc gtg tct ctg tgc acc cct tct aga gct gct ctg ctg aca ggc aga     240
Pro Val Ser Leu Cys Thr Pro Ser Arg Ala Ala Leu Leu Thr Gly Arg
65                  70                  75                  80 ctc cct gtg cgg atg gga atg tat cct ggc gtg ctg gtg cct agc tct     288
Leu Pro Val Arg Met Gly Met Tyr Pro Gly Val Leu Val Pro Ser Ser
                85                  90                  95 aga ggc gga ctg cct ctg gaa gaa gtg aca gtt gcc gaa gtg ctg gcc     336
Arg Gly Gly Leu Pro Leu Glu Glu Val Thr Val Ala Glu Val Leu Ala
                100                 105                 110 gcc aga gga tat ctg act ggc atg gcc gga aag tgg cac ctc gga gtt     384
Ala Arg Gly Tyr Leu Thr Gly Met Ala Gly Lys Trp His Leu Gly Val
            115                 120                 125 gga cca gaa ggc gct ttt ctg cct cct cac cag ggc ttc cac cgg ttt     432
Gly Pro Glu Gly Ala Phe Leu Pro Pro His Gln Gly Phe His Arg Phe
        130                 135                 140 ctg ggc atc cct tac tct cac gat cag ggc ccc tgc cag aac ctg acc     480
Leu Gly Ile Pro Tyr Ser His Asp Gln Gly Pro Cys Gln Asn Leu Thr
145                 150                 155                 160 tgt ttt cct cct gcc aca cct tgc gac ggc ggc tgt gat caa gga ctg     528
Cys Phe Pro Pro Ala Thr Pro Cys Asp Gly Gly Cys Asp Gln Gly Leu
                165                 170                 175 gtg cca att cct ctg ctg gcc aac ctg agc gtg gaa gct caa cct cct     576
Val Pro Ile Pro Leu Leu Ala Asn Leu Ser Val Glu Ala Gln Pro Pro
                180                 185                 190 tgg ctg cca gga ctg gaa gcc cgg tat atg gcc ttc gct cac gac ctg     624
Trp Leu Pro Gly Leu Glu Ala Arg Tyr Met Ala Phe Ala His Asp Leu
            195                 200                 205 atg gcc gac gct cag aga cag gac aga cca ttc ttc ctg tac tac gcc     672
Met Ala Asp Ala Gln Arg Gln Asp Arg Pro Phe Phe Leu Tyr Tyr Ala
        210                 215                 220 agc cac cac aca cac tac cct cag ttt agc ggc cag agc ttc gcc gag     720
Ser His His Thr His Tyr Pro Gln Phe Ser Gly Gln Ser Phe Ala Glu
225                 230                 235                 240 aga tct ggc aga gga cct ttc ggc gac agc ctg atg gaa ctg gat gcc     768
Arg Ser Gly Arg Gly Pro Phe Gly Asp Ser Leu Met Glu Leu Asp Ala
                245                 250                 255
```

```
gct gtg ggc aca ctg atg aca gcc atc gga gat ctg gga ctg ctg gaa      816
Ala Val Gly Thr Leu Met Thr Ala Ile Gly Asp Leu Gly Leu Leu Glu
        260                 265                 270 gag aca ctg gtc atc ttc acc gcc gac aac ggc ccc gag aca atg aga      864
Glu Thr Leu Val Ile Phe Thr Ala Asp Asn Gly Pro Glu Thr Met Arg
    275                 280                 285 atg agc aga ggc ggc tgt agc ggc ctg ctg aga tgt ggc aag ggc acc      912
Met Ser Arg Gly Gly Cys Ser Gly Leu Leu Arg Cys Gly Lys Gly Thr
290                 295                 300 aca tat gaa ggc ggc gtg aga gaa cct gct ctg gcc ttt tgg cct ggc      960
Thr Tyr Glu Gly Gly Val Arg Glu Pro Ala Leu Ala Phe Trp Pro Gly
305                 310                 315                 320 cat att gct cca ggc gtg aca cac gag ctg gcc tct tct ctg gat ctg     1008
His Ile Ala Pro Gly Val Thr His Glu Leu Ala Ser Ser Leu Asp Leu
            325                 330                 335 ctg cct aca ctg gca gct ctt gct ggt gct ccc ctg cct aat gtg acc     1056
Leu Pro Thr Leu Ala Ala Leu Ala Gly Ala Pro Leu Pro Asn Val Thr
        340                 345                 350 ctg gat ggc ttc gat ctg agc cca ctg ctc ggc aca ggc aag tct         1104
Leu Asp Gly Phe Asp Leu Ser Pro Leu Leu Leu Gly Thr Gly Lys Ser
    355                 360                 365 cca aga cag agc ctg ttc ttc tac cct agc tac ccc gac gaa gtg cgg     1152
Pro Arg Gln Ser Leu Phe Phe Tyr Pro Ser Tyr Pro Asp Glu Val Arg
370                 375                 380 gga gtg ttt gcc gtg cgg acc gga aag tat aag gcc cac ttc ttc acc     1200
Gly Val Phe Ala Val Arg Thr Gly Lys Tyr Lys Ala His Phe Phe Thr
385                 390                 395                 400 caa ggc agc gcc cac tct gac acc aca gct gat cct gct tgt cac gcc     1248
Gln Gly Ser Ala His Ser Asp Thr Thr Ala Asp Pro Ala Cys His Ala
            405                 410                 415 agc tct agc ctg aca gcc cat gaa cct cca ctg ctg tac gac ctg agc     1296
Ser Ser Ser Leu Thr Ala His Glu Pro Pro Leu Leu Tyr Asp Leu Ser
        420                 425                 430 aag gac ccc ggc gag aac tac aat ctg ctt ggc gga gtt gcc ggc gct     1344
Lys Asp Pro Gly Glu Asn Tyr Asn Leu Leu Gly Gly Val Ala Gly Ala
    435                 440                 445 aca cct gaa gtt ctg cag gcc ctg aaa cag ctc cag ctg ctg aaa gcc     1392
Thr Pro Glu Val Leu Gln Ala Leu Lys Gln Leu Gln Leu Leu Lys Ala
450                 455                 460 cag ctg gac gct gcc gtg aca ttt gga cct agt cag gtg gcc aga ggc     1440
Gln Leu Asp Ala Ala Val Thr Phe Gly Pro Ser Gln Val Ala Arg Gly
465                 470                 475                 480 gag gat cct gct ctg cag atc tgt tgt cac cct ggc tgc aca ccc aga     1488
Glu Asp Pro Ala Leu Gln Ile Cys Cys His Pro Gly Cys Thr Pro Arg
            485                 490                 495 cct gcc tgc tgt cat tgt cct gat cca cac gcc                        1521
Pro Ala Cys Cys His Cys Pro Asp Pro His Ala
        500                 505
```

<210> SEQ ID NO 2
<211> LENGTH: 507
<212> TYPE: PRT
<213> ORGANISM: Artificial Sequence
<220> FEATURE:
<223> OTHER INFORMATION: Synthetic Construct

<400> SEQUENCE: 2

```
Met Gly Ala Pro Arg Ser Leu Leu Leu Ala Leu Ala Ala Gly Leu Ala
1               5                   10                  15

Val Ala Arg Pro Pro Asn Ile Val Leu Ile Phe Ala Asp Asp Leu Gly
```

```
                    20                  25                  30
Tyr Gly Asp Leu Gly Cys Tyr Gly His Pro Ser Ser Thr Thr Pro Asn
                35                  40                  45
Leu Asp Gln Leu Ala Ala Gly Gly Leu Arg Phe Thr Asp Phe Tyr Val
        50                  55                  60
Pro Val Ser Leu Cys Thr Pro Ser Arg Ala Ala Leu Leu Thr Gly Arg
65                  70                  75                  80
Leu Pro Val Arg Met Gly Met Tyr Pro Gly Val Leu Val Pro Ser Ser
                85                  90                  95
Arg Gly Gly Leu Pro Leu Glu Glu Val Thr Val Ala Glu Val Leu Ala
                100                 105                 110
Ala Arg Gly Tyr Leu Thr Gly Met Ala Gly Lys Trp His Leu Gly Val
            115                 120                 125
Gly Pro Glu Gly Ala Phe Leu Pro Pro His Gln Gly Phe His Arg Phe
        130                 135                 140
Leu Gly Ile Pro Tyr Ser His Asp Gln Gly Pro Cys Gln Asn Leu Thr
145                 150                 155                 160
Cys Phe Pro Pro Ala Thr Pro Cys Asp Gly Cys Asp Gln Gly Leu
                165                 170                 175
Val Pro Ile Pro Leu Leu Ala Asn Leu Ser Val Glu Ala Gln Pro Pro
                180                 185                 190
Trp Leu Pro Gly Leu Glu Ala Arg Tyr Met Ala Phe Ala His Asp Leu
            195                 200                 205
Met Ala Asp Ala Gln Arg Gln Asp Arg Pro Phe Phe Leu Tyr Tyr Ala
        210                 215                 220
Ser His His Thr His Tyr Pro Gln Phe Ser Gly Gln Ser Phe Ala Glu
225                 230                 235                 240
Arg Ser Gly Arg Gly Pro Phe Gly Asp Ser Leu Met Glu Leu Asp Ala
                245                 250                 255
Ala Val Gly Thr Leu Met Thr Ala Ile Gly Asp Leu Gly Leu Leu Glu
                260                 265                 270
Glu Thr Leu Val Ile Phe Thr Ala Asp Asn Gly Pro Glu Thr Met Arg
            275                 280                 285
Met Ser Arg Gly Gly Cys Ser Gly Leu Leu Arg Cys Gly Lys Gly Thr
        290                 295                 300
Thr Tyr Glu Gly Gly Val Arg Glu Pro Ala Leu Ala Phe Trp Pro Gly
305                 310                 315                 320
His Ile Ala Pro Gly Val Thr His Glu Leu Ala Ser Ser Leu Asp Leu
                325                 330                 335
Leu Pro Thr Leu Ala Ala Leu Ala Gly Ala Pro Leu Pro Asn Val Thr
                340                 345                 350
Leu Asp Gly Phe Asp Leu Ser Pro Leu Leu Leu Gly Thr Gly Lys Ser
            355                 360                 365
Pro Arg Gln Ser Leu Phe Phe Tyr Pro Ser Tyr Pro Asp Glu Val Arg
        370                 375                 380
Gly Val Phe Ala Val Arg Thr Gly Lys Tyr Lys Ala His Phe Phe Thr
385                 390                 395                 400
Gln Gly Ser Ala His Ser Asp Thr Thr Ala Asp Pro Ala Cys His Ala
                405                 410                 415
Ser Ser Ser Leu Thr Ala His Glu Pro Pro Leu Leu Tyr Asp Leu Ser
                420                 425                 430
Lys Asp Pro Gly Glu Asn Tyr Asn Leu Leu Gly Gly Val Ala Gly Ala
            435                 440                 445
```

```
Thr Pro Glu Val Leu Gln Ala Leu Lys Gln Leu Gln Leu Leu Lys Ala
    450                 455                 460
Gln Leu Asp Ala Ala Val Thr Phe Gly Pro Ser Gln Val Ala Arg Gly
465                 470                 475                 480
Glu Asp Pro Ala Leu Gln Ile Cys Cys His Pro Gly Cys Thr Pro Arg
                485                 490                 495
Pro Ala Cys Cys His Cys Pro Asp Pro His Ala
            500                 505
```

<210> SEQ ID NO 3
<211> LENGTH: 1527
<212> TYPE: DNA
<213> ORGANISM: Artificial Sequence
<220> FEATURE:
<223> OTHER INFORMATION: Engineered hARSA coding sequence
<220> FEATURE:
<221> NAME/KEY: CDS
<222> LOCATION: (1)..(1527)
<223> OTHER INFORMATION: Engineered hARSA coding sequence

<400> SEQUENCE: 3

```
atg tct atg gga gcc cct aga tct ctg ctg ctg gct ctg gct gct gga    48
Met Ser Met Gly Ala Pro Arg Ser Leu Leu Leu Ala Leu Ala Ala Gly
1               5                   10                  15 ctg gca gtt gcc aga cct cct aac atc gtg ctg atc ttc gcc gac gat    96
Leu Ala Val Ala Arg Pro Pro Asn Ile Val Leu Ile Phe Ala Asp Asp
                20                  25                  30 ctc ggc tac ggc gat ctg ggc tgt tac gga cac ccc agc agc acc aca   144
Leu Gly Tyr Gly Asp Leu Gly Cys Tyr Gly His Pro Ser Ser Thr Thr
            35                  40                  45 cct aac ctg gat caa ctt gcc gct ggc ggc ctg aga ttc acc gat ttc   192
Pro Asn Leu Asp Gln Leu Ala Ala Gly Gly Leu Arg Phe Thr Asp Phe
        50                  55                  60 tac gtg ccc gtg tct ctg tgc acc cct tct aga gct gct ctg ctg aca   240
Tyr Val Pro Val Ser Leu Cys Thr Pro Ser Arg Ala Ala Leu Leu Thr
65                  70                  75                  80 ggc aga ctc cct gtg cgg atg gga atg tat cct ggc gtg ctg gtg cct   288
Gly Arg Leu Pro Val Arg Met Gly Met Tyr Pro Gly Val Leu Val Pro
                85                  90                  95 agc tct aga ggc gga ctg cct ctg gaa gaa gtg aca gtt gcc gaa gtg   336
Ser Ser Arg Gly Gly Leu Pro Leu Glu Glu Val Thr Val Ala Glu Val
                100                 105                 110 ctg gcc gcc aga gga tat ctg act ggc atg gcc gga aag tgg cac ctc   384
Leu Ala Ala Arg Gly Tyr Leu Thr Gly Met Ala Gly Lys Trp His Leu
            115                 120                 125 gga gtt gga cca gaa ggc gct ttt ctg cct cct cac cag ggc ttc cac   432
Gly Val Gly Pro Glu Gly Ala Phe Leu Pro Pro His Gln Gly Phe His
        130                 135                 140 cgg ttt ctg ggc atc cct tac tct cac gat cag ggc ccc tgc cag aac   480
Arg Phe Leu Gly Ile Pro Tyr Ser His Asp Gln Gly Pro Cys Gln Asn
145                 150                 155                 160 ctg acc tgt ttt cct cct gcc aca cct tgc gac ggc ggc tgt gat caa   528
Leu Thr Cys Phe Pro Pro Ala Thr Pro Cys Asp Gly Gly Cys Asp Gln
                165                 170                 175 gga ctg gtg cca att cct ctg ctg gcc aac ctg agc gtg gaa gct caa   576
Gly Leu Val Pro Ile Pro Leu Leu Ala Asn Leu Ser Val Glu Ala Gln
                180                 185                 190 cct cct tgg ctg cca gga ctg gaa gcc cgg tat atg gcc ttc gct cac   624
Pro Pro Trp Leu Pro Gly Leu Glu Ala Arg Tyr Met Ala Phe Ala His
            195                 200                 205
```

```
gac ctg atg gcc gac gct cag aga cag gac aga cca ttc ttc ctg tac    672
Asp Leu Met Ala Asp Ala Gln Arg Gln Asp Arg Pro Phe Phe Leu Tyr
    210             215                 220 tac gcc agc cac cac aca cac tac cct cag ttt agc ggc cag agc ttc    720
Tyr Ala Ser His His Thr His Tyr Pro Gln Phe Ser Gly Gln Ser Phe
225             230                 235                 240 gcc gag aga tct gga aga gga cct ttc ggc gac agc ctg atg gaa ctg    768
Ala Glu Arg Ser Gly Arg Gly Pro Phe Gly Asp Ser Leu Met Glu Leu
                245                 250                 255 gat gcc gct gtg gga aca ctg atg aca gcc atc gga gat ctg gga ctg    816
Asp Ala Ala Val Gly Thr Leu Met Thr Ala Ile Gly Asp Leu Gly Leu
            260                 265                 270 ctg gaa gag aca ctg gtc atc ttc acc gcc gac aac ggc ccc gag aca    864
Leu Glu Glu Thr Leu Val Ile Phe Thr Ala Asp Asn Gly Pro Glu Thr
        275                 280                 285 atg aga atg agc aga ggc ggc tgt agc ggc ctg ctg aga tgt ggc aag    912
Met Arg Met Ser Arg Gly Gly Cys Ser Gly Leu Leu Arg Cys Gly Lys
    290                 295                 300 ggc acc aca tat gaa ggc ggc gtg aga gaa cct gct ctg gcc ttt tgg    960
Gly Thr Thr Tyr Glu Gly Gly Val Arg Glu Pro Ala Leu Ala Phe Trp
305                 310                 315                 320 cct ggc cat att gct cca ggc gtg aca cac gag ctg gcc tct tct ctg   1008
Pro Gly His Ile Ala Pro Gly Val Thr His Glu Leu Ala Ser Ser Leu
                325                 330                 335 gat ctg ctg cct aca ctg gca gct ctt gct ggt gct ccc ctg cct aat   1056
Asp Leu Leu Pro Thr Leu Ala Ala Leu Ala Gly Ala Pro Leu Pro Asn
            340                 345                 350 gtg acc ctg gat ggc ttc gat ctg agc cca ctg ctc ggc aca ggc       1104
Val Thr Leu Asp Gly Phe Asp Leu Ser Pro Leu Leu Leu Gly Thr Gly
        355                 360                 365 aag tct cca aga cag agc ctg ttc ttc tac cct agc tac ccc gac gaa   1152
Lys Ser Pro Arg Gln Ser Leu Phe Phe Tyr Pro Ser Tyr Pro Asp Glu
    370                 375                 380 gtg cgg gga gtg ttt gcc gtg cgg acc gga aag tat aag gcc cac ttc   1200
Val Arg Gly Val Phe Ala Val Arg Thr Gly Lys Tyr Lys Ala His Phe
385                 390                 395                 400 ttc acc caa ggc agc gcc cac tct gac acc aca gct gat cct gct tgt   1248
Phe Thr Gln Gly Ser Ala His Ser Asp Thr Thr Ala Asp Pro Ala Cys
                405                 410                 415 cac gcc agc tct agc ctg aca gcc cat gaa cct cca ctg ctg tac gac   1296
His Ala Ser Ser Ser Leu Thr Ala His Glu Pro Pro Leu Leu Tyr Asp
            420                 425                 430 ctg agc aag gac ccc ggc gag aac tac aat ctg ctt ggc gga gtt gcc   1344
Leu Ser Lys Asp Pro Gly Glu Asn Tyr Asn Leu Leu Gly Gly Val Ala
        435                 440                 445 ggc gct aca cct gaa gtt ctg cag gcc ctg aaa cag ctc cag ctg ctg   1392
Gly Ala Thr Pro Glu Val Leu Gln Ala Leu Lys Gln Leu Gln Leu Leu
    450                 455                 460 aaa gcc cag ctg gac gct gcc gtg aca ttt gga cct agt cag gtg gcc   1440
Lys Ala Gln Leu Asp Ala Ala Val Thr Phe Gly Pro Ser Gln Val Ala
465                 470                 475                 480 aga ggc gag gat cct gct ctg cag atc tgt tgt cac cct ggc tgc aca   1488
Arg Gly Glu Asp Pro Ala Leu Gln Ile Cys Cys His Pro Gly Cys Thr
                485                 490                 495 ccc aga cct gcc tgc tgt cat tgt cct gat cca cac gcc                1527
Pro Arg Pro Ala Cys Cys His Cys Pro Asp Pro His Ala
            500                 505
```

<210> SEQ ID NO 4
<211> LENGTH: 509

```
<212> TYPE: PRT
<213> ORGANISM: Artificial Sequence
<220> FEATURE:
<223> OTHER INFORMATION: Synthetic Construct

<400> SEQUENCE: 4

Met Ser Met Gly Ala Pro Arg Ser Leu Leu Leu Ala Leu Ala Ala Gly
1               5                   10                  15

Leu Ala Val Ala Arg Pro Pro Asn Ile Val Leu Ile Phe Ala Asp Asp
                20                  25                  30

Leu Gly Tyr Gly Asp Leu Gly Cys Tyr Gly His Pro Ser Ser Thr Thr
            35                  40                  45

Pro Asn Leu Asp Gln Leu Ala Ala Gly Gly Leu Arg Phe Thr Asp Phe
        50                  55                  60

Tyr Val Pro Val Ser Leu Cys Thr Pro Ser Arg Ala Ala Leu Leu Thr
65                  70                  75                  80

Gly Arg Leu Pro Val Arg Met Gly Met Tyr Pro Gly Val Leu Val Pro
                85                  90                  95

Ser Ser Arg Gly Gly Leu Pro Leu Glu Val Thr Val Ala Glu Val
                100                 105                 110

Leu Ala Ala Arg Gly Tyr Leu Thr Gly Met Ala Gly Lys Trp His Leu
            115                 120                 125

Gly Val Gly Pro Glu Gly Ala Phe Leu Pro Pro His Gln Gly Phe His
        130                 135                 140

Arg Phe Leu Gly Ile Pro Tyr Ser His Asp Gln Gly Pro Cys Gln Asn
145                 150                 155                 160

Leu Thr Cys Phe Pro Pro Ala Thr Pro Cys Asp Gly Gly Cys Asp Gln
                165                 170                 175

Gly Leu Val Pro Ile Pro Leu Leu Ala Asn Leu Ser Val Glu Ala Gln
            180                 185                 190

Pro Pro Trp Leu Pro Gly Leu Glu Ala Arg Tyr Met Ala Phe Ala His
        195                 200                 205

Asp Leu Met Ala Asp Ala Gln Arg Gln Asp Arg Pro Phe Phe Leu Tyr
        210                 215                 220

Tyr Ala Ser His His Thr His Tyr Pro Gln Phe Ser Gly Gln Ser Phe
225                 230                 235                 240

Ala Glu Arg Ser Gly Arg Gly Pro Phe Gly Asp Ser Leu Met Glu Leu
                245                 250                 255

Asp Ala Ala Val Gly Thr Leu Met Thr Ala Ile Gly Asp Leu Gly Leu
            260                 265                 270

Leu Glu Glu Thr Leu Val Ile Phe Thr Ala Asp Asn Gly Pro Glu Thr
        275                 280                 285

Met Arg Met Ser Arg Gly Gly Cys Ser Gly Leu Leu Arg Cys Gly Lys
        290                 295                 300

Gly Thr Thr Tyr Glu Gly Gly Val Arg Glu Pro Ala Leu Ala Phe Trp
305                 310                 315                 320

Pro Gly His Ile Ala Pro Gly Val Thr His Glu Leu Ala Ser Ser Leu
                325                 330                 335

Asp Leu Leu Pro Thr Leu Ala Ala Leu Ala Gly Ala Pro Leu Pro Asn
            340                 345                 350

Val Thr Leu Asp Gly Phe Asp Leu Ser Pro Leu Leu Leu Gly Thr Gly
        355                 360                 365

Lys Ser Pro Arg Gln Ser Leu Phe Phe Tyr Pro Ser Tyr Pro Asp Glu
        370                 375                 380
```

```
Val Arg Gly Val Phe Ala Val Arg Thr Gly Lys Tyr Lys Ala His Phe
385                 390                 395                 400

Phe Thr Gln Gly Ser Ala His Ser Asp Thr Thr Ala Asp Pro Ala Cys
            405                 410                 415

His Ala Ser Ser Ser Leu Thr Ala His Glu Pro Pro Leu Leu Tyr Asp
            420                 425                 430

Leu Ser Lys Asp Pro Gly Glu Asn Tyr Asn Leu Leu Gly Gly Val Ala
            435                 440                 445

Gly Ala Thr Pro Glu Val Leu Gln Ala Leu Lys Gln Leu Gln Leu Leu
        450                 455                 460

Lys Ala Gln Leu Asp Ala Ala Val Thr Phe Gly Pro Ser Gln Val Ala
465                 470                 475                 480

Arg Gly Glu Asp Pro Ala Leu Gln Ile Cys Cys His Pro Gly Cys Thr
            485                 490                 495

Pro Arg Pro Ala Cys Cys His Cys Pro Asp Pro His Ala
            500                 505
```

```
<210> SEQ ID NO 5
<211> LENGTH: 7141
<212> TYPE: DNA
<213> ORGANISM: Artificial Sequence
<220> FEATURE:
<223> OTHER INFORMATION: Production plasmid for AAV.CB7,CI.hARSAco.RBG
<220> FEATURE:
<221> NAME/KEY: repeat_region
<222> LOCATION: (1)..(130)
<223> OTHER INFORMATION: 5' ITR
<220> FEATURE:
<221> NAME/KEY: promoter
<222> LOCATION: (198)..(579)
<223> OTHER INFORMATION: CMV IE promoter
<220> FEATURE:
<221> NAME/KEY: promoter
<222> LOCATION: (582)..(862)
<223> OTHER INFORMATION: CB promoter
<220> FEATURE:
<221> NAME/KEY: TATA_signal
<222> LOCATION: (836)..(839)
<223> OTHER INFORMATION: TATA
<220> FEATURE:
<221> NAME/KEY: Intron
<222> LOCATION: (956)..(1928)
<223> OTHER INFORMATION: chicken beta-actin intron
<220> FEATURE:
<221> NAME/KEY: misc_feature
<222> LOCATION: (1935)..(3506)
<223> OTHER INFORMATION: Engineered ARSA coding sequence (hARSAco)
<220> FEATURE:
<221> NAME/KEY: polyA_signal
<222> LOCATION: (3539)..(3665)
<223> OTHER INFORMATION: Rabbit globin poly A
<220> FEATURE:
<221> NAME/KEY: repeat_region
<222> LOCATION: (3754)..(3883)
<223> OTHER INFORMATION: 3' ITR
<220> FEATURE:
<221> NAME/KEY: rep_origin
<222> LOCATION: (4060)..(4498)
<223> OTHER INFORMATION: f1 ori
<220> FEATURE:
<221> NAME/KEY: rep_origin
<222> LOCATION: (4527)..(5169)
<223> OTHER INFORMATION: pUC origin of replication
<220> FEATURE:
<221> NAME/KEY: misc_feature
<222> LOCATION: (5844)..(6649)
<223> OTHER INFORMATION: Kan-r

<400> SEQUENCE: 5
ctgcgcgctc gctcgctcac tgaggccgcc cgggcaaagc ccgggcgtcg ggcgaccttt      60
```

```
ggtcgcccgg cctcagtgag cgagcgagcg cgcagagagg gagtggccaa ctccatcact    120 agggggttcct tgtagttaat gattaacccg ccatgctact tatctaccag ggtaatgggg   180
atcctctaga actatagcta gtcgacattg attattgact agttattaat agtaatcaat    240
tacggggtca ttagttcata gcccatatat ggagttccgc gttacataac ttacggtaaa    300
tggcccgcct ggctgaccgc ccaacgaccc ccgcccattg acgtcaataa tgacgtatgt    360
tcccatagta acgccaatag ggactttcca ttgacgtcaa tgggtggagt atttacggta    420
aactgcccac ttggcagtac atcaagtgta tcatatgcca agtacgcccc ctattgacgt    480
caatgacggt aaatggcccg cctggcatta tgcccagtac atgaccttat gggactttcc    540
tacttggcag tacatctacg tattagtcat cgctattacc atggtcgagg tgagccccac    600
gttctgcttc actctcccca tctccccccc ctccccaccc caatttttgt atttatttat    660
tttttaatta ttttgtgcag cgatgggggc ggggggggggg gggggcgcg cgccaggcgg    720 ggcggggcgg ggcgaggggc gggggcgggc gaggcggaga ggtgcggcgg cagccaatca    780
gagcggcgcg ctccgaaagt ttccttttat ggcgaggcgg cggcggcggc ggccctataa    840
aaagcgaagc gcgcggcggg cgggagtcgc tgcgcgctgc cttcgccccg tgccccgctc    900
cgccgccgcc tcgcgccgcc cgccccggct ctgactgacc gcgttactcc cacaggtgag    960
cgggcgggac ggcccttctc ctccgggctg taattagcgc ttggtttaat gacggcttgt   1020
ttcttttctg tggctgcgtg aaagccttga ggggctccgg gagggcccct tgtgcggggg   1080
gagcggctcg gggggtgcgt gcgtgtgtgt gtgcgtgggg agcgccgcgt gcggctccgc   1140
gctgcccggc ggctgtgagc gctgcgggcg cggcgcgggg ctttgtgcgc tccgcagtgt   1200
gcgcgagggg agcgcggccg ggggcggtgc cccgcggtgc ggggggggct gcgaggggaa   1260
caaaggctgc gtgcggggtg tgtgcgtggg ggggtgagca ggggggtgtgg gcgcgtcggt  1320 cgggctgcaa ccccccctgc acccccctcc ccgagttgct gagcacggcc cggcttcggg  1380
tgcggggctc cgtacggggc gtggcgcggg gctcgccgtg ccgggcgggg ggtggcggca   1440
ggtgggggtg ccgggcgggg cggggccgcc tcgggccggg gagggctcgg ggaggggcg    1500 cggcggcccc cggagcgccg gcggctgtcg aggcgcggca agccgcagcc attgcctttt    1560
atggtaatcg tgcgagaggg cgcagggact tcctttgtcc caaatctgtg cggagccgaa    1620
atctgggagg cgccgccgca ccccctctag cgggcgcggg gcgaagcggt gcggcgccgg   1680
caggaaggaa atgggcgggg agggccttcg tgcgtcgccg cgccgccgtc cccttctccc    1740
tctccagcct cggggctgtc cgcggggga cggctgcctt cggggggggac ggggcagggc   1800 ggggttcggc ttctggcgtg tgaccggcgg ctctagagcc tctgctaacc atgttcatgc   1860
cttcttcttt ttcctacagc tcctgggcaa cgtgctggtt attgtgctgt ctcatcattt   1920
tggcaaagaa ttcacgcgtg aattcggtac cacaggccac catgtctatg ggagccccta    1980
gatctctgct gctggctctg gctgctggac tggcagttgc cagacctcct aacatcgtgc    2040
tgatcttcgc cgacgatctc ggctacggcg atctgggctg ttacggacac cccagcagca    2100
ccacacctaa cctggatcaa cttgccgctg gcggcctgag attcaccgat ttctacgtgc    2160
ccgtgtctct gtgcacccct tctagagctg ctctgctgac aggcagactc cctgtgcgga    2220
tgggaatgta tcctggcgtg ctggtgccta gctctagagg cggactgcct ctggaagaag   2280
tgacagttgc cgaagtgctg gccgccagag atatctgac tggcatggcc ggaaagtggc    2340
acctcggagt tggaccagaa ggcgcttttt tgcctcctca ccagggcttc caccggtttc    2400
```

```
tgggcatccc ttactctcac gatcagggcc cctgccagaa cctgacctgt tttcctcctg    2460
ccacaccttg cgacggcggc tgtgatcaag gactggtgcc aattcctctg ctggccaacc    2520
tgagcgtgga agctcaacct ccttggctgc caggactgga agcccggtat atggccttcg    2580
ctcacgacct gatggccgac gctcagagac aggacagacc attcttcctg tactacgcca    2640
gccaccacac acactaccct cagtttagcg gccagagctt cgccgagaga tctggcagag    2700
gacctttcgg cgacagcctg atggaactgg atgccgctgt gggcacactg atgcagcca    2760 tcggagatct gggactgctg aagagacac tggtcatctt caccgccgac aacggccccg    2820
agacaatgag aatgagcaga ggcggctgta gcggcctgct gagatgtggc aagggcacca    2880
catatgaagg cggcgtgaga gaacctgctc tggccttttg gcctggccat attgctccag    2940
gcgtgacaca cgagctggcc tcttctctgg atctgctgcc tacactggca gctcttgctg    3000
gtgctcccct gcctaatgtg acctggatg gcttcgatct gagcccactg ctgctcggca    3060
caggcaagtc tccaagacag agcctgttct tctaccctag ctaccccgac gaagtgcggg    3120
gagtgtttgc cgtgcggacc ggaaagtata aggcccactt cttcacccaa ggcagcgccc    3180
actctgacac cacagctgat cctgcttgtc acgccagctc tagcctgaca gcccatgaac    3240
ctccactgct gtacgacctg agcaaggacc ccggcgagaa ctacaatctg cttggcggag    3300
ttgccggcgc tacacctgaa gttctgcagg ccctgaaaca gctccagctg ctgaaagccc    3360
agctggacgc tgccgtgaca tttggaccta gtcaggtggc cagaggcgag atcctgctc    3420 tgcagatctg ttgtcaccct ggctgcacac ccagacctgc ctgctgtcat tgtcctgatc    3480
cacacgcctg atgaacagcc tgaggctcga ggacggggtg aactacgcct gaggatccga    3540 tcttttccc tctgccaaaa attatgggga catcatgaag ccccttgagc atctgacttc    3600
tggctaataa aggaaattta ttttcattgc aatagtgtgt tggaatttt tgtgtctctc    3660 actcggaagc aattcgttga tctgaatttc gaccacccat aatacccatt accctggtag    3720
ataagtagca tggcgggtta atcattaact acaaggaacc cctagtgatg gagttggcca    3780
ctccctctct gcgcgctcgc tcgctcactg aggccgggcg accaaaggtc gcccgacgcc    3840 cgggcttttgc ccgggcggcc tcagtgagcg agcgagcgcg cagccttaat taacctaatt    3900
cactggccgt cgttttacaa cgtcgtgact gggaaaaccc tggcgttacc caacttaatc    3960
gccttgcagc acatcccct ttcgccagct ggcgtaatag cgaagaggcc cgcaccgatc    4020
gcccttccca acagttgcgc agcctgaatg gcgaatggga cgcgccctgt agcggcgcat    4080
taagcgcggc gggtgtggtg gttacgcgca gcgtgaccgc tacacttgcc agcgccctag    4140
cgcccgctcc tttcgctttc ttcccttcct ttctcgccac gttcgccggc tttccccgtc    4200
aagctctaaa tcgggggctc cctttagggt tccgatttag tgctttacgg cacctcgacc    4260
ccaaaaaact tgattagggt gatggttcac gtagtgggcc atcgccctga tagacggttt    4320
ttcgcccttt gacgttggag tccacgttct ttaatagtgg actcttgttc caaactggaa    4380
caacactcaa ccctatctcg gtctattctt ttgatttata agggattttg ccgatttcgg    4440
cctattggtt aaaaaatgag ctgatttaac aaaaatttaa cgcgaatttt aacaaaatca    4500
tgtgagcaaa aggccagcaa aaggccagga accgtaaaaa ggccgcgttg ctggcgtttt    4560
tccataggct ccgcccccct gacgagcatc acaaaaatcg acgctcaagt cagaggtggc    4620
gaaacccgac aggactataa agataccagg cgtttccccc tggaagctcc ctcgtgcgct    4680
ctcctgttcc gaccctgccg cttaccggat acctgtccgc ctttctccct tcgggaagcg    4740
tggcgctttc tcatagctca cgctgtaggt atctcagttc ggtgtaggtc gttcgctcca    4800
```

```
agctgggctg tgtgcacgaa ccccccgttc agcccgaccg ctgcgcctta tccggtaact   4860
atcgtcttga gtccaacccg gtaagacacg acttatcgcc actggcagca gccactggta   4920
acaggattag cagagcgagg tatgtaggcg gtgctacaga gttcttgaag tggtggccta   4980
actacggcta cactagaaga acagtatttg gtatctgcgc tctgctgaag ccagttacct   5040
tcggaaaaag agttggtagc tcttgatccg gcaaacaaac caccgctggt agcggtggtt   5100
tttttgtttg caagcagcag attacgcgca gaaaaaaagg atctcaagaa gatcctttga   5160
tcttttctac ggggtctgac gctcagtgga acgaaaactc acgttaaggg attttggtca   5220
tgagattatc aaaaaggatc ttcacctaga tccttttgat cctccggcgt tcagcctgtg   5280
ccacagccga caggatggtg accaccattt gccccatatc accgtcggta ctgatcccgt   5340
cgtcaataaa ccgaaccgct acaccctgag catcaaactc ttttatcagt tggatcatgt   5400
cggcggtgtc gcggccaaga cggtcgagct tcttcaccag aatgacatca ccttcctcca   5460
ccttcatcct cagcaaatcc agcccttccc gatctgttga actgccggat gccttgtcgg   5520
taaagatgcg gttagctttt acccctgcat ctttgagcgc tgaggtctgc ctcgtgaaga   5580
aggtgttgct gactcatacc aggcctgaat cgccccatca tccagccaga aagtgaggga   5640
gccacggttg atgagagctt tgttgtaggt ggaccagttg gtgattttga acttttgctt   5700
tgccacggaa cggtctgcgt tgtcgggaag atgcgtgatc tgatccttca actcagcaaa   5760
agttcgattt attcaacaaa gccgccgtcc cgtcaagtca gcgtaatgct ctgccagtgt   5820
tacaaccaat taaccaattc tgattagaaa aactcatcga gcatcaaatg aaactgcaat   5880
ttattcatat caggattatc aataccatat ttttgaaaaa gccgtttctg taatgaagga   5940
gaaaactcac cgaggcagtt ccataggatg gcaagatcct ggtatcggtc tgcgattccg   6000
actcgtccaa catcaataca acctattaat ttcccctcgt caaaaataag gttatcaagt   6060
gagaaatcac catgagtgac gactgaatcc ggtgagaatg gcaaaagctt atgcatttct   6120
ttccagactt gttcaacagg ccagccatta cgctcgtcat caaaatcact cgcatcaacc   6180
aaaccgttat tcattcgtga ttgcgcctga gcgagacgaa atacgcgatc gctgttaaaa   6240
ggacaattac aaacaggaat cgaatgcaac cggcgcagga acactgccag cgcatcaaca   6300
atattttcac ctgaatcagg atattcttct aatacctgga atgctgtttt cccggggatc   6360
gcagtggtga gtaaccatgc atcatcagga gtacggataa aatgcttgat ggtcggaaga   6420
ggcataaatt ccgtcagcca gtttagtctg accatctcat ctgtaacatc attggcaacg   6480
ctacctttgc catgtttcag aaacaactct ggcgcatcgg gcttcccata caatcgatag   6540
attgtcgcac ctgattgccc gacattatcg cgagcccatt tatacccata taaatcagca   6600
tccatgttgg aatttaatcg cggcctcgag caagacgttt cccgttgaat atggctcata   6660
acaccccttg tattactgtt tatgtaagca gacagtttta ttgttcatga tgatatattt   6720
ttatcttgtg caatgtaaca tcagagattt tgagacacca tgttctttcc tgcgttatcc   6780
cctgattctg tggataaccg tattaccgcc tttgagtgag ctgataccgc tcgccgcagc   6840
cgaacgaccg agcgcagcga gtcagtgagc gaggaagcgg aagagcgccc aatacgcaaa   6900
ccgcctctcc ccgcgcgttg gccgattcat taatgcagct ggcacgacag gtttcccgac   6960
tggaaagcgg gcagtgagcg caacgcaatt aatgtgagtt agctcactca ttaggcaccc   7020
caggctttac actttatgct tccggctcgt atgttgtgtg gaattgtgag cggataacaa   7080
tttcacacag gaaacagcta tgaccatgat tacgccagat ttaattaagg ccttaattag   7140
```

```
g                                                              7141

<210> SEQ ID NO 6
<211> LENGTH: 2211
<212> TYPE: DNA
<213> ORGANISM: Artificial Sequence
<220> FEATURE:
<223> OTHER INFORMATION: AAVhu68 vp1
<220> FEATURE:
<221> NAME/KEY: CDS
<222> LOCATION: (1)..(2211)

<400> SEQUENCE: 6 atg gct gcc gat ggt tat ctt cca gat tgg ctc gag gac aac ctc agt    48
Met Ala Ala Asp Gly Tyr Leu Pro Asp Trp Leu Glu Asp Asn Leu Ser
1               5                   10                  15 gaa ggc att cgc gag tgg tgg gct ttg aaa cct gga gcc cct caa ccc    96
Glu Gly Ile Arg Glu Trp Trp Ala Leu Lys Pro Gly Ala Pro Gln Pro
            20                  25                  30 aag gca aat caa caa cat caa gac aac gct cgg ggt ctt gtg ctt ccg   144
Lys Ala Asn Gln Gln His Gln Asp Asn Ala Arg Gly Leu Val Leu Pro
        35                  40                  45 ggt tac aaa tac ctt gga ccc ggc aac gga ctc gac aag ggg gag ccg   192
Gly Tyr Lys Tyr Leu Gly Pro Gly Asn Gly Leu Asp Lys Gly Glu Pro
    50                  55                  60 gtc aac gaa gca gac gcg gcg gcc ctc gag cac gac aag gcc tac gac   240
Val Asn Glu Ala Asp Ala Ala Ala Leu Glu His Asp Lys Ala Tyr Asp
65                  70                  75                  80 cag cag ctc aag gcc gga gac aac ccg tac ctc aag tac aac cac gcc   288
Gln Gln Leu Lys Ala Gly Asp Asn Pro Tyr Leu Lys Tyr Asn His Ala
                85                  90                  95 gac gcc gag ttc cag gag cgg ctc aaa gaa gat acg tct ttt ggg ggc   336
Asp Ala Glu Phe Gln Glu Arg Leu Lys Glu Asp Thr Ser Phe Gly Gly
            100                 105                 110 aac ctc ggg cga gca gtc ttc cag gcc aaa aag agg ctt ctt gaa cct   384
Asn Leu Gly Arg Ala Val Phe Gln Ala Lys Lys Arg Leu Leu Glu Pro
        115                 120                 125 ctt ggt ctg gtt gag gaa gcg gct aag acg gct cct gga aag aag agg   432
Leu Gly Leu Val Glu Glu Ala Ala Lys Thr Ala Pro Gly Lys Lys Arg
    130                 135                 140 cct gta gag cag tct cct cag gaa ccg gac tcc tcc gtg ggt att ggc   480
Pro Val Glu Gln Ser Pro Gln Glu Pro Asp Ser Ser Val Gly Ile Gly
145                 150                 155                 160 aaa tcg ggt gca cag ccc gct aaa aag aga ctc aat ttc ggt cag act   528
Lys Ser Gly Ala Gln Pro Ala Lys Lys Arg Leu Asn Phe Gly Gln Thr
                165                 170                 175 ggc gac aca gag tca gtc ccc gac cct caa cca atc gga gaa cct ccc   576
Gly Asp Thr Glu Ser Val Pro Asp Pro Gln Pro Ile Gly Glu Pro Pro
            180                 185                 190 gca gcc ccc tca ggt gtg gga tct ctt aca atg gct tca ggt ggt ggc   624
Ala Ala Pro Ser Gly Val Gly Ser Leu Thr Met Ala Ser Gly Gly Gly
        195                 200                 205 gca cca gtg gca gac aat aac gaa ggt gcc gat gga gtg ggt agt tcc   672
Ala Pro Val Ala Asp Asn Asn Glu Gly Ala Asp Gly Val Gly Ser Ser
    210                 215                 220 tcg gga aat tgg cat tgc gat tcc caa tgg ctg ggg gac aga gtc atc   720
Ser Gly Asn Trp His Cys Asp Ser Gln Trp Leu Gly Asp Arg Val Ile
225                 230                 235                 240 acc acc agc acc cga acc tgg gcc ctg ccc acc tac aac aat cac ctc   768
Thr Thr Ser Thr Arg Thr Trp Ala Leu Pro Thr Tyr Asn Asn His Leu
                245                 250                 255
```

-continued

| | | |
|---|---|---|
| tac aag caa atc tcc aac agc aca tct gga gga tct tca aat gac aac<br>Tyr Lys Gln Ile Ser Asn Ser Thr Ser Gly Gly Ser Ser Asn Asp Asn<br>260                          265                    270 | 816 |
| gcc tac ttc ggc tac agc acc ccc tgg ggg tat ttt gac ttc aac aga<br>Ala Tyr Phe Gly Tyr Ser Thr Pro Trp Gly Tyr Phe Asp Phe Asn Arg<br>        275                      280                      285 | 864 |
| ttc cac tgc cac ttc tca cca cgt gac tgg caa aga ctc atc aac aac<br>Phe His Cys His Phe Ser Pro Arg Asp Trp Gln Arg Leu Ile Asn Asn<br>290                          295                    300 | 912 |
| aac tgg gga ttc cgg cct aag cga ctc aac ttc aag ctc ttc aac att<br>Asn Trp Gly Phe Arg Pro Lys Arg Leu Asn Phe Lys Leu Phe Asn Ile<br>305                          310                    315                    320 | 960 |
| cag gtc aaa gag gtt acg gac aac aat gga gtc aag acc atc gct aat<br>Gln Val Lys Glu Val Thr Asp Asn Asn Gly Val Lys Thr Ile Ala Asn<br>                  325                      330                    335 | 1008 |
| aac ctt acc agc acg gtc cag gtc ttc acg gac tca gac tat cag ctc<br>Asn Leu Thr Ser Thr Val Gln Val Phe Thr Asp Ser Asp Tyr Gln Leu<br>340                          345                    350 | 1056 |
| ccg tac gtg ctc ggg tcg gct cac gag ggc tgc ctc ccg ccg ttc cca<br>Pro Tyr Val Leu Gly Ser Ala His Glu Gly Cys Leu Pro Pro Phe Pro<br>                  355                      360                    365 | 1104 |
| gcg gac gtt ttc atg att cct cag tac ggg tat cta acg ctt aat gat<br>Ala Asp Val Phe Met Ile Pro Gln Tyr Gly Tyr Leu Thr Leu Asn Asp<br>370                          375                    380 | 1152 |
| gga agc caa gcc gtg ggt cgt tcg tcc ttt tac tgc ctg gaa tat ttc<br>Gly Ser Gln Ala Val Gly Arg Ser Ser Phe Tyr Cys Leu Glu Tyr Phe<br>385                          390                    395                    400 | 1200 |
| ccg tcg caa atg cta aga acg ggt aac aac ttc cag ttc agc tac gag<br>Pro Ser Gln Met Leu Arg Thr Gly Asn Asn Phe Gln Phe Ser Tyr Glu<br>                  405                      410                    415 | 1248 |
| ttt gag aac gta cct ttc cat agc agc tat gct cac agc caa agc ctg<br>Phe Glu Asn Val Pro Phe His Ser Ser Tyr Ala His Ser Gln Ser Leu<br>420                          425                    430 | 1296 |
| gac cga ctc atg aat cca ctc atc gac caa tac ttg tac tat ctc tca<br>Asp Arg Leu Met Asn Pro Leu Ile Asp Gln Tyr Leu Tyr Tyr Leu Ser<br>                  435                      440                    445 | 1344 |
| aag act att aac ggt tct gga cag aat caa caa acg cta aaa ttc agt<br>Lys Thr Ile Asn Gly Ser Gly Gln Asn Gln Gln Thr Leu Lys Phe Ser<br>450                          455                    460 | 1392 |
| gtg gcc gga ccc agc aac atg gct gtc cag gga aga aac tac ata cct<br>Val Ala Gly Pro Ser Asn Met Ala Val Gln Gly Arg Asn Tyr Ile Pro<br>465                          470                    475                    480 | 1440 |
| gga ccc agc tac cga caa caa cgt gtc tca acc act gtg act caa aac<br>Gly Pro Ser Tyr Arg Gln Gln Arg Val Ser Thr Thr Val Thr Gln Asn<br>                  485                      490                    495 | 1488 |
| aac aac agc gaa ttt gct tgg cct gga gct tct tct tgg gct ctc aat<br>Asn Asn Ser Glu Phe Ala Trp Pro Gly Ala Ser Ser Trp Ala Leu Asn<br>500                          505                    510 | 1536 |
| gga cgt aat agc ttg atg aat cct gga cct gct atg gcc agc cac aaa<br>Gly Arg Asn Ser Leu Met Asn Pro Gly Pro Ala Met Ala Ser His Lys<br>                  515                      520                    525 | 1584 |
| gaa gga gag gac cgt ttc ttt cct ttg tct gga tct tta att ttt ggc<br>Glu Gly Glu Asp Arg Phe Phe Pro Leu Ser Gly Ser Leu Ile Phe Gly<br>530                          535                    540 | 1632 |
| aaa caa gga act gga aga gac aac gtg gat gcg gac aaa gtc atg ata<br>Lys Gln Gly Thr Gly Arg Asp Asn Val Asp Ala Asp Lys Val Met Ile<br>545                          550                    555                    560 | 1680 |
| acc aac gaa gaa gaa att aaa act acc aac cca gta gca acg gag tcc<br>Thr Asn Glu Glu Glu Ile Lys Thr Thr Asn Pro Val Ala Thr Glu Ser<br>                  565                      570                    575 | 1728 |

| | | | | | | | | | | | | | | | |
|---|---|---|---|---|---|---|---|---|---|---|---|---|---|---|---|
|tat|gga|caa|gtg|gcc|aca|aac|cac|cag|agt|gcc|caa|gca|cag|gcg|cag|
|Tyr|Gly|Gln|Val|Ala|Thr|Asn|His|Gln|Ser|Ala|Gln|Ala|Gln|Ala|Gln|

1776

```
acc ggc tgg gtt caa aac caa gga ata ctt ccg ggt atg gtt tgg cag    1824
Thr Gly Trp Val Gln Asn Gln Gly Ile Leu Pro Gly Met Val Trp Gln
            595                 600                 605 gac aga gat gtg tac ctg caa gga ccc att tgg gcc aaa att cct cac    1872
Asp Arg Asp Val Tyr Leu Gln Gly Pro Ile Trp Ala Lys Ile Pro His
    610                 615                 620 acg gac ggc aac ttt cac cct tct ccg ctg atg gga ggg ttt gga atg    1920
Thr Asp Gly Asn Phe His Pro Ser Pro Leu Met Gly Gly Phe Gly Met
625                 630                 635                 640 aag cac ccg cct cct cag atc ctc atc aaa aac aca cct gta cct gcg    1968
Lys His Pro Pro Pro Gln Ile Leu Ile Lys Asn Thr Pro Val Pro Ala
                645                 650                 655 gat cct cca acg gct ttc aac aag gac aag ctg aac tct ttc atc acc    2016
Asp Pro Pro Thr Ala Phe Asn Lys Asp Lys Leu Asn Ser Phe Ile Thr
            660                 665                 670 cag tat tct act ggc caa gtc agc gtg gag att gag tgg gag ctg cag    2064
Gln Tyr Ser Thr Gly Gln Val Ser Val Glu Ile Glu Trp Glu Leu Gln
        675                 680                 685 aag gaa aac agc aag cgc tgg aac ccg gag atc cag tac act tcc aac    2112
Lys Glu Asn Ser Lys Arg Trp Asn Pro Glu Ile Gln Tyr Thr Ser Asn
    690                 695                 700 tat tac aag tct aat aat gtt gaa ttt gct gtt aat act gaa ggt gtt    2160
Tyr Tyr Lys Ser Asn Asn Val Glu Phe Ala Val Asn Thr Glu Gly Val
705                 710                 715                 720 tat tct gaa ccc cgc ccc att ggc acc aga tac ctg act cgt aat ctg    2208
Tyr Ser Glu Pro Arg Pro Ile Gly Thr Arg Tyr Leu Thr Arg Asn Leu
                725                 730                 735 taa                                                                 2211
```

<210> SEQ ID NO 7
<211> LENGTH: 736
<212> TYPE: PRT
<213> ORGANISM: Artificial Sequence
<220> FEATURE:
<223> OTHER INFORMATION: Synthetic Construct

<400> SEQUENCE: 7

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140
```

-continued

Pro Val Glu Gln Ser Pro Gln Glu Pro Asp Ser Ser Val Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

-continued

```
Thr Asn Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
        580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 8
<211> LENGTH: 736
<212> TYPE: PRT
<213> ORGANISM: Artificial Sequence
<220> FEATURE:
<223> OTHER INFORMATION: modified hu68vp1
<220> FEATURE:
<221> NAME/KEY: MISC_FEATURE
<222> LOCATION: (23)..(23)
<223> OTHER INFORMATION: Xaa may be W (Trp, tryptophan), or oxidated W.
<220> FEATURE:
<221> NAME/KEY: MISC_FEATURE
<222> LOCATION: (35)..(35)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (57)..(57)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (66)..(66)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (94)..(94)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (97)..(97)
<223> OTHER INFORMATION: Xaa may be D (asp, aspartic acid), or
      isomerized D.
<220> FEATURE:
<221> NAME/KEY: MISC_FEATURE
<222> LOCATION: (107)..(107)
<223> OTHER INFORMATION: Xaa may be D (asp, aspartic acid), or
      isomerized D.
<220> FEATURE:
<221> NAME/KEY: misc_feature
<222> LOCATION: (113)..(113)
<223> OTHER INFORMATION: Xaa can be any naturally occurring amino acid
<220> FEATURE:
```

```
<221> NAME/KEY: MISC_FEATURE
<222> LOCATION: (149)..(149)
<223> OTHER INFORMATION: Xaa may be S (Ser, serine), or Phosphorilated S
<220> FEATURE:
<221> NAME/KEY: MISC_FEATURE
<222> LOCATION: (149)..(149)
<223> OTHER INFORMATION: Xaa may be S (Ser, serine), or Phosphorylated S
<220> FEATURE:
<221> NAME/KEY: MISC_FEATURE
<222> LOCATION: (247)..(247)
<223> OTHER INFORMATION: Xaa may be W (Trp, tryptophan), or oxidated W
      (e.g., kynurenine).
<220> FEATURE:
<221> NAME/KEY: MISC_FEATURE
<222> LOCATION: (253)..(253)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (259)..(259)
<223> OTHER INFORMATION: Xaa represents Q, or Q deamidated to glutamic
      acid (alpha-glutamic acid), gamma-glutamic acid (Glu), or a blend
      of alpha- and gamma-glutamic acid
<220> FEATURE:
<221> NAME/KEY: MISC_FEATURE
<222> LOCATION: (270)..(270)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (297)..(297)
<223> OTHER INFORMATION: Xaa represents D (Asp, aspartic acid) or
      amindated D to N (Asn, asparagine)
<220> FEATURE:
<221> NAME/KEY: MISC_FEATURE
<222> LOCATION: (304)..(304)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (306)..(306)
<223> OTHER INFORMATION: Xaa may be W (Trp, tryptophan), or oxidated W
      (e.g., kynurenine).
<220> FEATURE:
<221> NAME/KEY: MISC_FEATURE
<222> LOCATION: (314)..(314)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (319)..(319)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (329)..(329)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (332)..(332)
<223> OTHER INFORMATION: Xaa may be K (lys, lysine), or acetylated K
<220> FEATURE:
<221> NAME/KEY: MISC_FEATURE
<222> LOCATION: (336)..(336)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (384)..(384)
<223> OTHER INFORMATION: Xaa may be D (asp, aspartic acid), or
      isomerized D.
<220> FEATURE:
<221> NAME/KEY: MISC_FEATURE
<222> LOCATION: (404)..(404)
<223> OTHER INFORMATION: Xaa may be M (Met, Methionine), or oxidated M.
<220> FEATURE:
<221> NAME/KEY: MISC_FEATURE
<222> LOCATION: (409)..(409)
```

```
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (436)..(436)
<223> OTHER INFORMATION: Xaa may be M (Met, Methionine), or oxidated M.
<220> FEATURE:
<221> NAME/KEY: MISC_FEATURE
<222> LOCATION: (452)..(452)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (477)..(477)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (499)..(499)
<223> OTHER INFORMATION: Xaa may be S (Ser, serine), or Phosphorylated S
<220> FEATURE:
<221> NAME/KEY: MISC_FEATURE
<222> LOCATION: (512)..(512)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (515)..(515)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (518)..(518)
<223> OTHER INFORMATION: Xaa may be M (Met, Methionine), or oxidated M.
<220> FEATURE:
<221> NAME/KEY: MISC_FEATURE
<222> LOCATION: (524)..(524)
<223> OTHER INFORMATION: Xaa may be M (Met, Methionine), or oxidated M.
<220> FEATURE:
<221> NAME/KEY: MISC_FEATURE
<222> LOCATION: (559)..(559)
<223> OTHER INFORMATION: Xaa may be M (Met, Methionine), or oxidated M.
<220> FEATURE:
<221> NAME/KEY: MISC_FEATURE
<222> LOCATION: (569)..(569)
<223> OTHER INFORMATION: Xaa may be T (Thr, threonine), or
      Phosphorylated T
<220> FEATURE:
<221> NAME/KEY: MISC_FEATURE
<222> LOCATION: (586)..(586)
<223> OTHER INFORMATION: Xaa may be S (Ser, serine), or Phosphorylated S
<220> FEATURE:
<221> NAME/KEY: MISC_FEATURE
<222> LOCATION: (599)..(599)
<223> OTHER INFORMATION: Xaa represents Q, or Q deamidated to glutamic
      acid (alpha-glutamic acid), gamma-glutamic acid (Glu), or a blend
      of alpha- and gamma-glutamic acid
<220> FEATURE:
<221> NAME/KEY: MISC_FEATURE
<222> LOCATION: (605)..(605)
<223> OTHER INFORMATION: Xaa may be M (Met, Methionine), or oxidated M.
<220> FEATURE:
<221> NAME/KEY: MISC_FEATURE
<222> LOCATION: (619)..(619)
<223> OTHER INFORMATION: Xaa may be W (Trp, tryptophan), or oxidated W
      (e.g., kynurenine).
<220> FEATURE:
<221> NAME/KEY: MISC_FEATURE
<222> LOCATION: (628)..(628)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (640)..(640)
<223> OTHER INFORMATION: Xaa may be M (Met, Methionine), or oxidated M.
<220> FEATURE:
<221> NAME/KEY: MISC_FEATURE
<222> LOCATION: (651)..(651)
<223> OTHER INFORMATION: Xaa may be Asn, or deamidated to Asp, isoAsp,
```

-continued

```
              or Asp/isoAsp
<220> FEATURE:
<221> NAME/KEY: MISC_FEATURE
<222> LOCATION: (663)..(663)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (666)..(666)
<223> OTHER INFORMATION: Xaa may be K (lys, lysine), or acetylated K
<220> FEATURE:
<221> NAME/KEY: MISC_FEATURE
<222> LOCATION: (689)..(689)
<223> OTHER INFORMATION: Xaa may be K (lys, lysine), or acetylated K
<220> FEATURE:
<221> NAME/KEY: MISC_FEATURE
<222> LOCATION: (693)..(693)
<223> OTHER INFORMATION: Xaa may be K (lys, lysine), or acetylated K
<220> FEATURE:
<221> NAME/KEY: MISC_FEATURE
<222> LOCATION: (695)..(695)
<223> OTHER INFORMATION: Xaa may be W (Trp, tryptophan), or oxidated W.
<220> FEATURE:
<221> NAME/KEY: MISC_FEATURE
<222> LOCATION: (709)..(709)
<223> OTHER INFORMATION: Xaa may be Asn, or deamidated to Asp, isoAsp,
      or Asp/isoAsp
<220> FEATURE:
<221> NAME/KEY: MISC_FEATURE
<222> LOCATION: (735)..(735)
<223> OTHER INFORMATION: Xaa may be Asn, or deamidated to Asp, isoAsp,
      or Asp/isoAsp

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Xaa Ala Leu Lys Pro Gly Ala Pro Gln Pro
            20                  25                  30

Lys Ala Xaa Gln Gln His Gln Asp Asn Ala Arg Gly Leu Val Leu Pro
        35                  40                  45

Gly Tyr Lys Tyr Leu Gly Pro Gly Xaa Gly Leu Asp Lys Gly Glu Pro
    50                  55                  60

Val Xaa Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Xaa His Ala
                85                  90                  95

Xaa Ala Glu Phe Gln Glu Arg Leu Lys Glu Xaa Thr Ser Phe Gly Gly
            100                 105                 110

Xaa Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Xaa Pro Gln Glu Pro Asp Ser Ser Val Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240
```

```
Thr Thr Ser Thr Arg Thr Xaa Ala Leu Pro Thr Tyr Xaa Asn His Leu
            245                 250                 255

Tyr Lys Xaa Ile Ser Asn Ser Thr Ser Gly Gly Ser Ser Xaa Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Xaa Trp Gln Arg Leu Ile Asn Xaa
            290                 295                 300

Asn Xaa Gly Phe Arg Pro Lys Arg Leu Xaa Phe Lys Leu Phe Xaa Ile
305                 310                 315                 320

Gln Val Lys Glu Val Thr Asp Asn Xaa Gly Val Xaa Thr Ile Ala Xaa
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Xaa
            370                 375                 380

Gly Ser Gln Ala Val Gly Arg Ser Ser Phe Tyr Cys Leu Glu Tyr Phe
385                 390                 395                 400

Pro Ser Gln Xaa Leu Arg Thr Gly Xaa Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Xaa Asn Pro Leu Ile Asp Gln Tyr Leu Tyr Tyr Leu Ser
            435                 440                 445

Lys Thr Ile Xaa Gly Ser Gly Gln Asn Gln Gln Thr Leu Lys Phe Ser
450                 455                 460

Val Ala Gly Pro Ser Asn Met Ala Val Gln Gly Arg Xaa Tyr Ile Pro
465                 470                 475                 480

Gly Pro Ser Tyr Arg Gln Gln Arg Val Ser Thr Thr Val Thr Gln Asn
            485                 490                 495

Asn Asn Xaa Glu Phe Ala Trp Pro Gly Ala Ser Ser Trp Ala Leu Xaa
            500                 505                 510

Gly Arg Xaa Ser Leu Xaa Asn Pro Gly Pro Ala Xaa Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Xaa Ile
545                 550                 555                 560

Thr Asn Glu Glu Glu Ile Lys Thr Xaa Asn Pro Val Ala Thr Glu Ser
            565                 570                 575

Tyr Gly Gln Val Ala Thr Asn His Gln Xaa Ala Gln Ala Gln Ala Gln
            580                 585                 590

Thr Gly Trp Val Gln Asn Gln Gly Ile Leu Pro Gly Xaa Val Trp Gln
            595                 600                 605

Asp Arg Asp Val Tyr Leu Gln Gly Pro Ile Xaa Ala Lys Ile Pro His
            610                 615                 620

Thr Asp Gly Xaa Phe His Pro Ser Pro Leu Met Gly Gly Phe Gly Xaa
625                 630                 635                 640

Lys His Pro Pro Pro Gln Ile Leu Ile Lys Xaa Thr Pro Val Pro Ala
            645                 650                 655
```

```
Asp Pro Pro Thr Ala Phe Xaa Lys Asp Xaa Leu Asn Ser Phe Ile Thr
            660                 665                 670

Gln Tyr Ser Thr Gly Gln Val Ser Val Glu Ile Glu Trp Glu Leu Gln
        675                 680                 685

Xaa Glu Asn Ser Xaa Arg Xaa Asn Pro Glu Ile Gln Tyr Thr Ser Asn
    690                 695                 700

Tyr Tyr Lys Ser Xaa Asn Val Glu Phe Ala Val Asn Thr Glu Gly Val
705                 710                 715                 720

Tyr Ser Glu Pro Arg Pro Ile Gly Thr Arg Tyr Leu Thr Arg Xaa Leu
                725                 730                 735

<210> SEQ ID NO 9
<211> LENGTH: 2211
<212> TYPE: DNA
<213> ORGANISM: Artificial Sequence
<220> FEATURE:
<223> OTHER INFORMATION: AAV9 vp1 coding sequence

<400> SEQUENCE: 9
```

| | | |
|---|---|---|
| atggctgccg atggttatct tccagattgg ctcgaggaca accttagtga aggaattcgc | | 60 |
| gagtggtggg cttttgaaacc tggagcccct caacccaagg caaatcaaca acatcaagac | | 120 |
| aacgctcgag gtcttgtgct tccgggttac aaataccttg acccggcaa cggactcgac | | 180 |
| aaggggagc cggtcaacgc agcagacgcg gcggccctcg agcacgacaa ggcctacgac | | 240 |
| cagcagctca aggccggaga caacccgtac ctcaagtaca accacgccga cgccgagttc | | 300 |
| caggagcggc tcaaagaaga tacgtctttt gggggcaacc tcgggcgagc agtcttccag | | 360 |
| gccaaaaaga ggcttcttga acctcttggt ctggttgagg aagcggctaa gacggctcct | | 420 |
| ggaaagaaga ggcctgtaga gcagtctcct caggaaccgg actcctccgc gggtattggc | | 480 |
| aaatcgggtg cacagcccgc taaaaagaga ctcaatttcg gtcagactgg cgacacagag | | 540 |
| tcagtcccag accctcaacc aatcggagaa cctcccgcag ccccctcagg tgtgggatct | | 600 |
| cttacaatgg cttcaggtgg tggcgcacca gtggcagaca ataacgaagg tgccgatgga | | 660 |
| gtgggtagtt cctcgggaaa ttggcattgc gattcccaat ggctggggga cagagtcatc | | 720 |
| accaccagca cccgaacctg ggccctgccc acctacaaca atcacctcta caagcaaatc | | 780 |
| tccaacagca catctggagg atcttcaaat gacaacgcct acttcggcta cagcaccccc | | 840 |
| tgggggtatt ttgacttcaa cagattccac tgccacttct caccacgtga ctggcagcga | | 900 |
| ctcatcaaca acaactgggg attccggcct aagcgactca acttcaagct cttcaacatt | | 960 |
| caggtcaaag aggttacgga caacaatgga gtcaagacca tcgccaataa ccttaccagc | | 1020 |
| acggtccagg tcttcacgga ctcagactat cagctcccgt acgtgctcgg tcggctcac | | 1080 |
| gagggctgcc tccgccgttc cccagcggac gttttcatga ttcctcagta cgggtatctg | | 1140 |
| acgcttaatg atggaagcca ggccgtgggt cgttcgtcct tttactgcct ggaatatttc | | 1200 |
| ccgtcgcaaa tgctaagaac gggtaacaac ttccagttca gctacgagtt tgagaacgta | | 1260 |
| cctttccata gcagctacgc tcacagccaa agcctggacc gactaatgaa tccactcatc | | 1320 |
| gaccaatact gtactatctc tcaaagact attaacggtt ctggacagaa tcaacaaacg | | 1380 |
| ctaaaattca gtgtggccgg acccagcaac atggctgtcc agggaagaaa ctacatacct | | 1440 |
| ggacccagct accgacaaca acgtgtctca accactgtga ctcaaaacaa caacagcgaa | | 1500 |
| tttgcttggc ctggagcttc ttcttgggct ctcaatggac gtaatagctt gatgaatcct | | 1560 |
| ggacctgcta tggccagcca caagaaggga gaggaccgtt tctttccttt gtctggatct | | 1620 |

-continued

```
ttaattttg gcaaacaagg aactggaaga gacaacgtgg atgcggacaa agtcatgata    1680
accaacgaag aagaaattaa aactactaac ccggtagcaa cggagtccta tggacaagtg    1740
gccacaaacc accagagtgc ccaagcacag gcgcagaccg gctgggttca aaaccaagga    1800
atacttccgg gtatggtttg gcaggacaga gatgtgtacc tgcaaggacc catttgggcc    1860
aaaattcctc acacggacgg caactttcac ccttctccgc tgatgggagg gtttggaatg    1920
aagcacccgc ctcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa acagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a             2211
```

<210> SEQ ID NO 10
<211> LENGTH: 736
<212> TYPE: PRT
<213> ORGANISM: Artificial Sequence
<220> FEATURE:
<223> OTHER INFORMATION: Encoded AAV9 vp1 amino acid sequence

<400> SEQUENCE: 10

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
```

```
                260                 265                 270
Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685
```

Lys Glu Asn Ser Lys Arg Trp Asn Pro Glu Ile Gln Tyr Thr Ser Asn
    690             695                 700

Tyr Tyr Lys Ser Asn Asn Val Glu Phe Ala Val Asn Thr Glu Gly Val
705             710                 715                 720

Tyr Ser Glu Pro Arg Pro Ile Gly Thr Arg Tyr Leu Thr Arg Asn Leu
            725                 730                 735

<210> SEQ ID NO 11
<211> LENGTH: 2211
<212> TYPE: DNA
<213> ORGANISM: Artificial Sequence
<220> FEATURE:
<223> OTHER INFORMATION: AAVhu31 vp1 coding sequence

<400> SEQUENCE: 11

| | | | | | |
|---|---|---|---|---|---|
| atggctgccg | atggttatct | tccagattgg | ctcgaggaca | accttagtga | aggaattcgc | 60 |
| gagtggtggg | ctttgaaacc | tggagcccct | caacccaagg | caaatcaaca | acatcaagac | 120 |
| aacgctcgag | gtcttgtgct | tccgggttac | aaataccttg | acccggcaa | cggactcgac | 180 |
| aaggggggagc | cggtcaacgc | agcagacgcg | gcggccctcg | agcacgacaa | ggcctacgac | 240 |
| cagcagctca | aggccggaga | caacccgtac | ctcaagtaca | accacgccga | cgccgagttc | 300 |
| caggagcggc | tcaaagaaga | tacgtctttt | gggggcaacc | tcgggcgagc | agtcttccag | 360 |
| gccaaaaaga | ggcttcttga | acctcttggt | ctggttgagg | aagcggctaa | gacggctcct | 420 |
| ggaaagaaga | ggcctgtaga | gcagtctcct | caggaaccgg | actcctccgc | gggtattggc | 480 |
| aaatcgggtg | cacagcccgc | taaaaagaga | ctcaatttcg | gtcagactgg | cgacacagag | 540 |
| tcagtcccag | accctcaacc | aatcggagaa | cctcccgcag | cccctcagg | tgtgggatct | 600 |
| cttacaatgg | cttcaggtgg | tggcgcacca | gtggcagaca | ataacgaagg | tgccgatgga | 660 |
| gtgggtagtt | cctcgggaaa | ttggcattgc | gattcccaat | ggctggggga | cagagtcatc | 720 |
| accaccagca | cccgaacctg | ggccctgccc | acctacaaca | atcacctcta | caagcaaatc | 780 |
| tccaacagca | catctggagg | atcttcaaat | gacaacgcct | acttcggcta | cagcaccccc | 840 |
| tgggggtatt | ttgacttcaa | cagattccac | tgccacttct | caccacgtga | ctggcagcga | 900 |
| ctcatcaaca | acaactgggg | attccggcct | aagcgactca | acttcaagct | cttcaacatt | 960 |
| caggtcaaag | aggttacgga | caacaatgga | gtcaagacca | tcgccaataa | ccttaccagc | 1020 |
| acggtccagg | tcttcacgga | ctcagactat | cagctcccgt | acgtgctcgg | gtcggctcac | 1080 |
| gagggctgcc | tcccgccgtt | cccagcggac | gttttcatga | ttcctcagta | cgggtatctg | 1140 |
| acgcttaatg | atggaagcca | ggccgtgggt | cgttcgtcct | tttactgcct | ggaatatttc | 1200 |
| ccgtcgcaaa | tgctaagaac | gggtaacaac | ttccagttca | gctacgagtt | tgagaacgta | 1260 |
| cctttccata | gcagctacgc | tcacagccaa | agcctggacc | gactaatgaa | tccactcatc | 1320 |
| gaccaatact | tgtactatct | ctcaaagact | attaacggtt | ctggacagaa | tcaacaaacg | 1380 |
| ctaaaattca | gtgtggccgg | acccagcaac | atggctgtcc | aggagaagaa | ctacatacct | 1440 |
| ggacccagct | accgacaaca | acgtgtctca | accactgtga | ctcaaaacaa | caacagcgaa | 1500 |
| tttgcttggc | ctgagcttc | ttcttgggct | ctcaatggac | gtaatagctt | gatgaatcct | 1560 |
| ggacctgcta | tggccagcca | caagaagga | gaggaccgtt | tctttccttt | gtctggatct | 1620 |
| ttaattttg | gcaaacaagg | aactggaaga | acaacgtgg | atgcggacaa | agtcatgata | 1680 |
| accaacgaag | aagaaattaa | aactactaac | ccggtagcaa | cggagtccta | tggacaagtg | 1740 |
| gccacaaacc | accagagtgc | ccaagcacag | gcgcagaccg | gctgggttca | aaaccaagga | 1800 |

-continued

```
atacttccgg gtatggtttg gcaggacaga gatgtgtacc tgcaaggacc catttgggcc    1860
aaaattcctc acacggacgg caactttcac ccttctccgc tgatgggagg gtttggaatg    1920
aagcacccgc ctcctcagat cctcatcaaa aacacacctg tacctgcgga tcctccaacg    1980
gccttcaaca aggacaagct gaactctttc atcacccagt attctactgg ccaagtcagc    2040
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a             2211
```

<210> SEQ ID NO 12
<211> LENGTH: 736
<212> TYPE: PRT
<213> ORGANISM: Artificial Sequence
<220> FEATURE:
<223> OTHER INFORMATION: Encoded AAVhu31 vp1 amino acid sequence

<400> SEQUENCE: 12

```
Met Ala Ala Asp Gly Tyr Leu Pro Asp Trp Leu Glu Asp Thr Leu Ser
1               5                  10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ser Gln Pro Ala Lys Lys Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

-continued

```
Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
370                 375                 380

Gly Gly Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Ser Thr Glu Gly Val
```

| | | | |
|---|---|---|---|
| 705 | 710 | 715 | 720 |

Tyr Ser Glu Pro Arg Pro Ile Gly Thr Arg Tyr Leu Thr Arg Asn Leu
                725                        730                        735

<210> SEQ ID NO 13
<211> LENGTH: 2211
<212> TYPE: DNA
<213> ORGANISM: Artificial Sequence
<220> FEATURE:
<223> OTHER INFORMATION: AAVhu32 vp1 coding sequence

<400> SEQUENCE: 13

| | | | | |
|---|---|---|---|---|
| atggctgccg | atggttatct | tccagattgg | ctcgaggaca | ctctctctga | aggaataaga | 60 |
| cagtggtgga | agctcaaacc | tggcccacca | ccaccaaagc | ccgcagagcg | gcataaggac | 120 |
| gacagcaggg | gtcttgtgct | tcctgggtac | aagtacctcg | acccggcaa | cggactcgac | 180 |
| aaggggagc | cggtcaacgc | agcagacgcg | gcggccctcg | agcacgacaa | ggcctacgac | 240 |
| cagcagctca | aggccggaga | caacccgtac | ctcaagtaca | accacgccga | cgccgagttc | 300 |
| caggagcggc | tcaaagaaga | tacgtctttt | gggggcaacc | tcgggcgagc | agtcttccag | 360 |
| gccaaaaaga | ggcttcttga | acctcttggt | ctggttgagg | aagcggctaa | gacggctcct | 420 |
| ggaaagaaga | ggcctgtaga | gcagtctcct | caggaaccgg | actcctccgc | gggtattggc | 480 |
| aaatcgggtt | cacagcccgc | taaaaagaaa | ctcaatttcg | gtcagactgg | cgacacagag | 540 |
| tcagtccccg | accctcaacc | aatcggagaa | cctcccgcag | cccccctcagg | tgtgggatct | 600 |
| cttacaatgg | cttcaggtgg | tggcgcacca | gtggcagaca | taacgaagg | tgccgatgga | 660 |
| gtgggtagtt | cctcgggaaa | ttggcattgc | gattcccaat | ggctgggga | cagagtcatc | 720 |
| accaccagca | cccgaacctg | gcccctgccc | acctacaaca | atcacctcta | caagcaaatc | 780 |
| tccaacagca | catctggagg | atcttcaaat | gacaacgcct | acttcggcta | cagcacccc | 840 |
| tgggggtatt | ttgacttcaa | cagattccac | tgccacttct | caccacgtga | ctggcagcga | 900 |
| ctcatcaaca | acaactgggg | attccggcct | aagcgactca | acttcaagct | cttcaacatt | 960 |
| caggtcaaag | aggttacgga | caacaatgga | gtcaagacca | tcgccaataa | ccttaccagc | 1020 |
| acggtccagg | tcttcacgga | ctcagactat | cagctcccgt | acgtgctcgg | gtcggctcac | 1080 |
| gagggctgcc | tcccgccgtt | cccagcggac | gttttcatga | ttcctcagta | cgggtatctg | 1140 |
| acgcttaatg | atgggagcca | ggccgtgggt | cgttcgtcct | tttactgcct | ggaatatttc | 1200 |
| ccgtcgcaaa | tgctaagaac | gggtaacaac | ttccagttca | gctacgagtt | tgagaacgta | 1260 |
| cctttccata | gcagctacgc | tcacagccaa | agcctggacc | gactaatgaa | tccactcatc | 1320 |
| gaccaatact | tgtactatct | ctcaaagact | attaacggtt | ctggacagaa | tcaacaaacg | 1380 |
| ctaaaattca | gcgtggccgg | acccagcaac | atggctgtcc | agggaagaaa | ctacatacct | 1440 |
| ggacccagct | accgacaaca | acgtgtctca | accactgtga | ctcaaaacaa | caacagcgaa | 1500 |
| tttgcttggc | ctggagcttc | ttcttgggct | ctcaatggac | gtaatagctt | gatgaatcct | 1560 |
| ggacctgcta | tggccagcca | caaagaagga | gaggaccgtt | tctttccttt | gtctggatct | 1620 |
| ttaattttg | caaacaagg | aactggaaga | gacaacgtgg | atgcggacaa | agtcatgata | 1680 |
| accaacgaag | aagaaattaa | aactactaac | ccggtagcaa | cggagtccta | tggacaagtg | 1740 |
| gccacaaacc | accagagtgc | ccaagcacag | gcgcagaccg | gctgggttca | aaaccaagga | 1800 |
| atacttccgg | gtatggtttg | gcaggacaga | gatgtgtacc | tgcaaggacc | catttgggcc | 1860 |
| aaaattcctc | acacggacgg | caactttcac | ccttctccgc | taatgggagg | gtttggaatg | 1920 |

```
aagcacccgc tcctcagat cctcatcaaa acacacctg tacctgcgga tcctccaacg    1980
gctttcaata aggacaagct gaactctttc atcacccagt attctactgg ccaagtcagc    2040
gtggagattg agtgggagct gcagaaggaa acagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a             2211

<210> SEQ ID NO 14
<211> LENGTH: 736
<212> TYPE: PRT
<213> ORGANISM: Artificial Sequence
<220> FEATURE:
<223> OTHER INFORMATION: Encoded AAVhu32 vp1 amino acid sequence

<400> SEQUENCE: 14

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ser Gln Pro Ala Lys Lys Lys Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320
```

```
Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
                690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 15
<211> LENGTH: 423
<212> TYPE: PRT
<213> ORGANISM: Homo sapiens

<400> SEQUENCE: 15

```
Met Gly Met Tyr Pro Gly Val Leu Val Pro Ser Ser Arg Gly Gly Leu
1               5                   10                  15

Pro Leu Glu Glu Val Thr Val Ala Glu Val Leu Ala Ala Arg Gly Tyr
            20                  25                  30

Leu Thr Gly Met Ala Gly Lys Trp His Leu Gly Val Gly Pro Glu Gly
        35                  40                  45

Ala Phe Leu Pro Pro His Gln Gly Phe His Arg Phe Leu Gly Ile Pro
    50                  55                  60

Tyr Ser His Asp Gln Gly Pro Cys Gln Asn Leu Thr Cys Phe Pro Pro
65                  70                  75                  80

Ala Thr Pro Cys Asp Gly Gly Cys Asp Gln Gly Leu Val Pro Ile Pro
                85                  90                  95

Leu Leu Ala Asn Leu Ser Val Glu Ala Gln Pro Pro Trp Leu Pro Gly
            100                 105                 110

Leu Glu Ala Arg Tyr Met Ala Phe Ala His Asp Leu Met Ala Asp Ala
        115                 120                 125

Gln Arg Gln Asp Arg Pro Phe Phe Leu Tyr Tyr Ala Ser His His Thr
130                 135                 140

His Tyr Pro Gln Phe Ser Gly Gln Ser Phe Ala Glu Arg Ser Gly Arg
145                 150                 155                 160

Gly Pro Phe Gly Asp Ser Leu Met Glu Leu Asp Ala Ala Val Gly Thr
                165                 170                 175

Leu Met Thr Ala Ile Gly Asp Leu Gly Leu Leu Glu Glu Thr Leu Val
            180                 185                 190

Ile Phe Thr Ala Asp Asn Gly Pro Glu Thr Met Arg Met Ser Arg Gly
        195                 200                 205

Gly Cys Ser Gly Leu Leu Arg Cys Gly Lys Gly Thr Thr Tyr Glu Gly
210                 215                 220

Gly Val Arg Glu Pro Ala Leu Ala Phe Trp Pro Gly His Ile Ala Pro
225                 230                 235                 240

Gly Val Thr His Glu Leu Ala Ser Ser Leu Asp Leu Leu Pro Thr Leu
                245                 250                 255

Ala Ala Leu Ala Gly Ala Pro Leu Pro Asn Val Thr Leu Asp Gly Phe
            260                 265                 270

Asp Leu Ser Pro Leu Leu Leu Gly Thr Gly Lys Ser Pro Arg Gln Ser
        275                 280                 285

Leu Phe Phe Tyr Pro Ser Tyr Pro Asp Glu Val Arg Gly Val Phe Ala
    290                 295                 300

Val Arg Thr Gly Lys Tyr Lys Ala His Phe Phe Thr Gln Gly Ser Ala
305                 310                 315                 320

His Ser Asp Thr Thr Ala Asp Pro Ala Cys His Ala Ser Ser Ser Leu
                325                 330                 335

Thr Ala His Glu Pro Pro Leu Leu Tyr Asp Leu Ser Lys Asp Pro Gly
            340                 345                 350

Glu Asn Tyr Asn Leu Leu Gly Gly Val Ala Gly Ala Thr Pro Glu Val
        355                 360                 365

Leu Gln Ala Leu Lys Gln Leu Gln Leu Leu Lys Ala Gln Leu Asp Ala
    370                 375                 380
```

```
Ala Val Thr Phe Gly Pro Ser Gln Val Ala Arg Gly Glu Asp Pro Ala
385                 390                 395                 400

Leu Gln Ile Cys Cys His Pro Gly Cys Thr Pro Arg Pro Ala Cys Cys
            405                 410                 415

His Cys Pro Asp Pro His Ala
            420

<210> SEQ ID NO 16
<211> LENGTH: 666
<212> TYPE: DNA
<213> ORGANISM: Artificial Sequence
<220> FEATURE:
<223> OTHER INFORMATION: chicken beta actin promoter with a
      cytomegalovirus enhancer (CB7)

<400> SEQUENCE: 16
ctagtcgaca ttgattattg actagttatt aatagtaatc aattacgggg tcattagttc      60
atagcccata tatggagttc cgcgttacat aacttacggt aaatggcccg cctggctgac     120
cgcccaacga ccccc gccca ttgacgtcaa taatgacgta tgttcccata gtaacgccaa    180
tagggacttt ccattgacgt caatgggtgg actatttacg gtaaactgcc cacttggcag    240
tacatcaagt gtatcatatg ccaagtacgc ccctattga cgtcaatgac ggtaaatggc     300
ccgcctggca ttatgcccag tacatgacct tatgggactt tcctacttgg cagtacatct    360
acgtattagt catcgctatt accatggtcg aggtgagccc cacgttctgc ttcactctcc    420
ccatctcccc cccctcccca ccccaattt tgtatttatt tattttttaa ttattttgtg    480
cagcgatggg ggcggggggg ggggggggc gcgcgccagg cggggcgggg cggggcgagg    540
ggcggggcgg ggcgaggcgg agaggtgcgg cggcagccaa tcagagcggc gcgctccgaa    600
agtttccttt tatggcgagg cggcggcggc ggcggcccta taaaaagcga agcgcgcggc    660
gggcgg                                                                666

<210> SEQ ID NO 17
<211> LENGTH: 973
<212> TYPE: DNA
<213> ORGANISM: Artificial sequence
<220> FEATURE:
<223> OTHER INFORMATION: chicken beta-actin intron

<400> SEQUENCE: 17
gtgagcgggc gggacggccc ttctcctccg ggctgtaatt agcgcttggt ttaatgacgg      60
cttgtttctt ttctgtggct gcgtgaaagc cttgaggggc tccggagggc ccctttgtgc    120
ggggggagcg gctcgggggg tgcgtgcgtg tgtgtgtgcg tggggagcgc gcgtgcggc     180 tccgcgctgc ccggcggctg tgagcgctgc gggcgcggcg cggggctttg tgcgctccgc    240
agtgtgcgcg aggggagcgc ggccgggggc ggtgccccgc ggtgcggggg gggctgcgag    300
gggaacaaag gctgcgtgcg gggtgtgtgc gtgggggggt gagcagggg tgtgggcgcg    360 tcggtcgggc tgcaacccc cctgcacccc cctccccgag ttgctgagca cggcccggct    420
tcgggtgcgg ggctccgtac ggggcgtggc gcggggctcg ccgtgccggg cggggggtgg    480
cggcaggtgg gggtgccggg cggggcgggg ccgcctcggg ccggggaggg ctcgggggag    540
gggcgcggcg gccccggag cgccggcggc tgtcgaggcg cggcgagccg cagccattgc     600 ctttatggt aatcgtgcga gagggcgcag ggacttcctt tgtcccaaat ctgtgcggag    660
ccgaaatctg ggaggcgccg ccgcaccccc tctagcgggc gcggggcgaa gcggtgcggc    720
```

```
gccggcagga aggaaatggg cggggagggc cttcgtgcgt cgccgcgccg ccgtcccctt    780
ctccctctcc agcctcgggg ctgtccgcgg ggggacggct gccttcgggg gggacggggc    840 agggcgggt tcggcttctg gcgtgtgacc ggcggctcta gagcctctgc taaccatgtt    900
catgccttct tcttttcct acagctcctg ggcaacgtgc tggttattgt gctgtctcat    960
cattttggca aag                                                       973

<210> SEQ ID NO 18
<211> LENGTH: 282
<212> TYPE: DNA
<213> ORGANISM: Artificial sequence
<220> FEATURE:
<223> OTHER INFORMATION: CB promoter

<400> SEQUENCE: 18
tggtcgaggt gagccccacg ttctgcttca ctctccccat ctcccccccc tccccacccc     60
caattttgta tttatttatt ttttaattat tttgtgcagc gatgggggcg ggggggggg    120 ggggcgcgc gccaggcggg gcggggcggg gcgaggggcg gggcggggcg aggcggagag    180
gtgcggcggc agccaatcag agcggcgcgc tccgaaagtt ccttttatg gcgaggcggc    240 ggcggcggcg gccctataaa aagcgaagcg cgcggcgggc gg                      282

<210> SEQ ID NO 19
<211> LENGTH: 382
<212> TYPE: DNA
<213> ORGANISM: Artificial sequence
<220> FEATURE:
<223> OTHER INFORMATION: CMV Immediate early Promoter

<400> SEQUENCE: 19
ctagtcgaca ttgattattg actagttatt aatagtaatc aattacgggg tcattagttc     60
atagcccata tatggagttc cgcgttacat aacttacggt aaatggcccg cctggctgac    120
cgcccaacga ccccgccca ttgacgtcaa taatgacgta tgttcccata gtaacgccaa    180
tagggacttt ccattgacgt caatgggtgg actatttacg gtaaactgcc cacttggcag    240
tacatcaagt gtatcatatg ccaagtacgc ccctattga cgtcaatgac ggtaaatggc    300
ccgcctggca ttatgcccag tacatgacct tatgggactt tcctacttgg cagtacatct    360
acgtattagt catcgctatt ac                                             382

<210> SEQ ID NO 20
<211> LENGTH: 22
<212> TYPE: DNA
<213> ORGANISM: Artificial Sequence
<220> FEATURE:
<223> OTHER INFORMATION: miR183

<400> SEQUENCE: 20
agtgaattct accagtgcca ta                                              22

<210> SEQ ID NO 21
<211> LENGTH: 23
<212> TYPE: DNA
<213> ORGANISM: Artificial Sequence
<220> FEATURE:
<223> OTHER INFORMATION: miRNA target sequence

<400> SEQUENCE: 21
agcaaaaatg tgctagtgcc aaa                                             23
```

```
<210> SEQ ID NO 22
<211> LENGTH: 24
<212> TYPE: DNA
<213> ORGANISM: Artificial Sequence
<220> FEATURE:
<223> OTHER INFORMATION: miRNA target sequence

<400> SEQUENCE: 22
agtgtgagtt ctaccattgc caaa                                              24

<210> SEQ ID NO 23
<211> LENGTH: 23
<212> TYPE: DNA
<213> ORGANISM: Artificial Sequence
<220> FEATURE:
<223> OTHER INFORMATION: miRNA target sequence

<400> SEQUENCE: 23
agggattcct gggaaaactg gac                                               23

<210> SEQ ID NO 24
<211> LENGTH: 16
<212> TYPE: DNA
<213> ORGANISM: Artificial Sequence
<220> FEATURE:
<223> OTHER INFORMATION: Spacer

<400> SEQUENCE: 24
atgacttaaa ccaggt                                                       16
```